United States Patent
Bauer et al.

(10) Patent No.: US 6,436,387 B1
(45) Date of Patent: *Aug. 20, 2002

(54) METHODS OF EX-VIVO EXPANSION OF HEMATOPOIETIC CELLS USING MULTIVARIANT IL-3 HEMATOPOIESIS CHIMERA PROTEINS

(75) Inventors: S. Christopher Bauer, New Haven; Mark Allen Abrams; Sarah Ruth Braford-Goldberg, both of St. Louis; Maire Helena Caparon, Chesterfield; Alan Michael Easton, Maryland Heights; Barbara Kure Klein, St. Louis; John P. McKearn, Glencoe, all of MO (US); Peter O. Olins, Lafayette, CO (US); Kumnan Paik, Wilmette, IL (US); John W. Thomas, Town & Country, MO (US)

(73) Assignee: G.D. Searle & Co., Chicago, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 08/762,227

(22) Filed: Dec. 9, 1996

Related U.S. Application Data

(63) Continuation-in-part of application No. 08/446,872, filed as application No. PCT/US95/01185 on Feb. 4, 1995, which is a continuation-in-part of application No. 08/192,325, filed on Feb. 4, 1994, now Pat. No. 6,057,133, which is a continuation-in-part of application No. 08/411,795, filed as application No. PCT/US93/11197 on Nov. 22, 1993, now Pat. No. 5,604,116, which is a continuation-in-part of application No. 07/981,044, filed on Nov. 24, 1992, now abandoned.

(51) Int. Cl.[7] .......................... A61K 45/00; A61K 38/21; C12N 5/08
(52) U.S. Cl. ..................... 424/85.1; 424/85.2; 424/85.4; 435/372
(58) Field of Search ................... 424/85.1, 85.2, 424/93.21, 93.71, 85.4; 435/372, 372.3

(56) References Cited

U.S. PATENT DOCUMENTS

| | | | | |
|---|---|---|---|---|
| 4,959,455 A | * | 9/1990 | Clark et al. | |
| 5,199,942 A | * | 4/1993 | Gillis et al. | |
| 5,516,512 A | * | 5/1996 | Dorssers et al. | |
| 5,591,427 A | * | 1/1997 | Vadas et al. | 424/85.2 |
| 5,604,116 A | * | 2/1997 | Bauer et al. | |

OTHER PUBLICATIONS

Haylock DN, et al. Blood 80:1405–1412, 1992.*

Brenner M, Cytokines and Molec. Therapy 1:3–9, 1995.*

Dorssers C, et al. J. Biol. Chem. 266:21310–21317, 1991.*

Kaushansky K, et al. J. Clin. Invest. 90:1879–1888, 1992.*

* cited by examiner

Primary Examiner—Gary L. Kunz
Assistant Examiner—Robert S. Landsman
(74) Attorney, Agent, or Firm—S. Christopher Bauer

(57) ABSTRACT

The present invention relates to methods of ex-vivo expansion of hematopoietic cells by culturing hematopoietic cells in a growth medium comprising a chimera protein which comprises a variant of human interleukin-3 (hIL-3) which contains multiple amino acid substitutions and which may have portions of the native hIL-3 molecule deleted and a hematopoietic growth factor. The present invention also relates to the ex-vivo expansion of hematopoietic cells for gene therapy. Additionally, the present invention relates to the use of the expanded hematopoietic cells for treating patients having a hematopoietic disorder.

48 Claims, 5 Drawing Sheets

```
      1              5                 10
ATG GCT CCA ATG ACT CAG ACT ACT TCT CTT AAG ACT TCT
Met Ala Pro Met Thr Gln Thr Thr Ser Leu Lys Thr Ser
         15                20                 25
TGG GTT AAC TGC TCT AAC ATG ATC GAT GAA ATT ATA ACA
Trp Val Asn Cys Ser Asn Met Ile Asp Glu Ile Ile Thr
                 30                 35
CAC TTA AAG CAG CCA CCT TTG CCT TTG CTG GAC TTC AAC
His Leu Lys Gln Pro Pro Leu Pro Leu Leu Asp Phe Asn
         40             45                 50
AAC CTC AAT GGG GAA GAC CAA GAC ATT CTG ATG GAA AAT
Asn Leu Asn Gly Glu Asp Gln Asp Ile Leu Met Glu Asn
                 55                 60
AAC CTT CGA AGG CCA AAC CTG GAG GCA TTC AAC AGG GCT
Asn Leu Arg Arg Pro Asn Leu Glu Ala Phe Asn Arg Ala
65               70                 75
GTC AAG AGT TTA CAG AAT GCA TCA GCA ATT GAG AGC ATT
Val Lys Ser Leu Gln Asn Ala Ser Ala Ile Glu Ser Ile
         80             85                 90
CTT AAA AAT CTC CTG CCA TGT CTG CCC CTG GCC ACG GCC
Leu Lys Asn Leu Leu Pro Cys Leu Pro Leu Ala Thr Ala
                 95                 100
GCA CCC ACG CGA CAT CCA ATC CAT ATC AAG GAC GGT GAC
Ala Pro Thr Arg His Pro Ile His Ile Lys Asp Gly Asp
         105             110                115
TGG AAT GAA TTC CGT CGT AAA CTG ACC TTC TAT CTG AAA
Trp Asn Glu Phe Arg Arg Lys Leu Thr Phe Tyr Leu Lys
                 120                 125
ACC TTG GAG AAC GCG CAG GCT CAA CAG ACC ACT CTG TCG
Thr Leu Glu Asn Ala Gln Ala Gln Gln Thr Thr Leu Ser
130
CTA GCG ATC TTT TAA TAA        (SEQ ID NO: 197)
Leu Ala Ile Phe END END        (SEQ ID NO: 49)
```

FIG. 1

```
     1                         5                              10
ATG  GCT  CCA  ATG  ACT  CAG  ACT  ACT  TCT  CTT  AAG  ACT  TCT
Met  Ala  Pro  Met  Thr  Gln  Thr  Thr  Ser  Leu  Lys  Thr  Ser
               15                      20                      25
TGG  GTT  AAC  TGC  TCT  AAC  ATG  ATC  GAT  GAA  ATT  ATA  ACA
Trp  Val  Asn  Cys  Ser  Asn  Met  Ile  Asp  Glu  Ile  Ile  Thr
                         30                      35
CAC  TTA  AAG  CAG  CCA  CCT  TTG  CCT  TTG  CTG  GAC  TTC  AAC
His  Leu  Lys  Gln  Pro  Pro  Leu  Pro  Leu  Leu  Asp  Phe  Asn
          40                      45                      50
AAC  CTC  AAT  GGG  GAA  GAC  CAA  GAC  ATT  CTG  ATG  GAA  AAT
Asn  Leu  Asn  Gly  Glu  Asp  Gln  Asp  Ile  Leu  Met  Glu  Asn
                    55                      60
AAC  CTT  CGA  AGG  CCA  AAC  CTG  GAG  GCA  TTC  AAC  AGG  GCT
Asn  Leu  Arg  Arg  Pro  Asn  Leu  Glu  Ala  Phe  Asn  Arg  Ala
65                            70                      75
GTC  AAG  AGT  TTA  CAG  AAT  GCA  TCA  GCA  ATT  GAG  AGC  ATT
Val  Lys  Ser  Leu  Gln  Asn  Ala  Ser  Ala  Ile  Glu  Ser  Ile
               80                      85                      90
CTT  AAA  AAT  CTC  CTG  CCA  TGT  CTG  CCC  CTG  GCC  ACG  GCC
Leu  Lys  Asn  Leu  Leu  Pro  Cys  Leu  Pro  Leu  Ala  Thr  Ala
                         95                     100
GCA  CCC  ACG  CGA  CAT  CCA  ATC  CAT  ATC  AAG  GAC  GGT  GAC
Ala  Pro  Thr  Arg  His  Pro  Ile  His  Ile  Lys  Asp  Gly  Asp
     105                           110                          115
TGG  AAT  GAA  TTC  CGT  CGT  AAA  CTG  ACC  TTC  TAT  CTG  AAA
Trp  Asn  Glu  Phe  Arg  Arg  Lys  Leu  Thr  Phe  Tyr  Leu  Lys
                    120                          125
ACC  TTG  GAG  AAC  GCG  CAG  GCT  CAA  CAG  ACC  ACT  CTG  TCG
Thr  Leu  Glu  Asn  Ala  Gln  Ala  Gln  Gln  Thr  Thr  Leu  Ser
130
CTA  GCG  ATC  TTT  TAA  TAA             (SEQ ID NO: 197)
Leu  Ala  Ile  Phe  END  END             (SEQ ID NO: 49)
```

METHODS OF EX-VIVO EXPANSION OF HEMATOPOIETIC CELLS USING MULTIVARIANT IL-3 HEMATOPOIESIS CHIMERA PROTEINS

This is a continuation-in-part of U.S. Ser. No. 08/446,872, filed Jun. 6, 1995, pending, which was filed under 35 USC §371 from PCT/US95/01185, filed Feb. 4, 1995; which is a continuation-in-part of U.S. Ser. No. 08/192,325, filed Feb. 4, 1994, now U.S. Patent No. 6,057,133; which is a continuation-in-part of U.S. Ser. No. 08/411,795, filed Apr. 6, 1995, now U.S. Pat. No. 5,604,116; said Ser. No. 08/411,795 was filed under 35 USC §371 from PCT/US93/11197, filed Nov. 22, 1993; which is a continuation-in-part of U.S. Ser. No. 07/981,044, filed Nov. 24, 1992, now abandoned. The noted applications are incorporated herein by reference.

FIELD OF THE INVENTION

The present invention relates to methods of ex-vivo expansion of hematopoietic cells by culturing hematopoietic cells in a medium which includes a chimera protein comprising a variant of human interleukin-3 (hIL-3) joined with or without a linker to a second colony stimulating factors, cytokines, lymphokines, interleukins, hematopoietic growth factors or IL-3 variants and the use of the expanded hematopoietic cells for treating patients having a hematopoietic disorder.

BACKGROUND OF THE INVENTION

Colony stimulating factors, cytokines, lymphokines, interleukins or hematopoietic growth factors (herein collectively referred to as "hematopoietic growth factors") which stimulate the differentiation and/or proliferation of bone marrow cells have generated much interest because of their therapeutic potential for restoring depressed levels of hematopoietic stem cell-derived cells. Hematopoietic growth factors in both human and murine systems have been identified and distinguished according to their activities. For example, granulocyte-CSF (G-CSF) and macrophage-CSF (M-CSF) stimulate the in vitro formation of neutrophilic granulocyte and macrophage colonies, respectively while GM-CSF and interleukin-3 (IL-3) have broader activities and stimulate the formation of both macrophage, neutrophilic and eosinophilic granulocyte colonies. IL-3 also stimulates the formation of mast, megakaryocyte and pure and mixed erythroid colonies.

Because of its ability to stimulate the proliferation of a number of different cell types and to support the growth and proliferation of progenitor cells, IL-3 has potential for therapeutic use in restoring hematopoietic cells to normal amounts in those cases where the number of cells has been reduced due to diseases or to therapeutic treatments such as radiation and/or chemotherapy.

Interleukin-3 (IL-3) is a hematopoietic growth factor which has the property of being able to promote the survival, growth and differentiation of hematopoietic cells. Among the biological properties of IL-3 are the ability (a) to support the growth and differentiation of progenitor cells committed to all, or virtually all, blood cell lineages; (b) to interact with early multipotential stem cells; (c) to sustain the growth of pluripotent precursor cells; (d) to stimulate proliferation of chronic myelogenous leukemia (CML) cells; (e) to stimulate proliferation of mast cells, eosinophils and basophils; (f) to stimulate DNA synthesis by human acute myelogenous leukemia (AML) cells; (g) to prime cells for production of leukotrienes and histamines; (h) to induce leukocyte chemotaxis; and (i) to induce cell surface molecules needed for leukocyte adhesion.

Mature human interleukin-3 (hIL-3) consists of 133 amino acids. It has one disulfide bridge and two potential glycosylation sites (Yang, et al., CELL 47:3 (1986)).

Murine IL-3 (mIL-3) was first identified by Ihle, et al., J. IMMUNOL. 126:2184 (1981) as a factor which induced expression of a T cell associated enzyme, 20-hydroxysteroid dehydrogenase. The factor was purified to homogeneity and shown to regulate the growth and differentiation of numerous subclasses of early hematopoietic and lymphoid progenitor cells.

In 1984, cDNA clones coding for murine IL-3 were isolated (Fung, et al., NATURE 307:233 (1984) and Yokota, et al., PROC. NATL. ACAD. SCI. USA 81:1070 (1984)). The murine DNA sequence coded for a polypeptide of 166 amino acids including a putative signal peptide.

The gibbon IL-3 sequence was obtained using a gibbon cDNA expression library. The gibbon IL-3 sequence was then used as a probe against a human genomic library to obtain a human IL-3 sequence.

Gibbon and human genomic DNA homologues of the murine IL-3 sequence were disclosed by Yang, et al., CELL 47:3 (1986). The human sequence reported by Yang, et al. included a serine residue at position 8 of the mature protein sequence. Following this finding, others reported isolation of $Pro^8$ hIL-3 cDNAs having proline at position 8 of the protein sequence. Thus it appears that there may be two allelic forms of hIL-3.

Dorssers, et al., GENE 55:115 (1987), found a clone from a human cDNA library which hybridized with mIL-3. This hybridization was the result of the high degree of homology between the 3' noncoding regions of mIL-3 and hIL-3. This cDNA coded for an hIL-3 ($Pro^8$) sequence.

U.S. Pat. Nos. 4,877,729 and 4,959,455 disclose human IL-3 and gibbon IL-3 cDNAs and the protein sequences for which they code. The hIL-3 disclosed has serine rather than proline at position 8 in the protein sequence.

Clark-Lewis, et al., SCIENCE 231:134 (1986) performed a functional analysis of murine IL-3 analogs synthesized with an automated peptide synthesizer. The authors concluded that the stable tertiary structure of the complete molecule was required for full activity. A study on the role of the disulfide bridges showed that replacement of all four cysteines by alanine gave a molecule with 1/500th the activity as the native molecule. Replacement of two of the four Cys residues by Ala($Cys^{79}$, $Cys^{140} \rightarrow Ala^{79}$, $Ala^{140}$) resulted in an increased activity. The authors concluded that in murine IL-3 a single disulfide bridge is required between cysteines 17 and 80 to get biological activity that approximates physiological levels and that this structure probably stabilizes the tertiary structure of the protein to give a conformation that is optimal for function. (Clark-Lewis, et al., PROC. NATL. ACAD. SCI. USA 85:7897 (1988)).

International Patent Application (PCT) WO 88/00598 discloses gibbon- and human-like IL-3. The hIL-3 contains a $Ser^8 \rightarrow Pro^8$ replacement. Suggestions are made to replace Cys by Ser, thereby breaking the disulfide bridge, and to replace one or more amino acids at the glycosylation sites.

EP-A-0275598 (WO 88/04691) illustrates that $Ala^1$ can be deleted while retaining biological activity. Some mutant hIL-3 sequences are provided, e.g., two double mutants, $Ala^1 \rightarrow Asp^1$, $Trp^{13} \rightarrow Arg^{13}$ (pGB/IL-302) and $Ala^1 \rightarrow Asp^1$, $Met^3 \rightarrow Thr^3$ (pGB/IL-304) and one triple mutant $Ala^1 \rightarrow Asp^1$, $Leu^9 \rightarrow Pro^9$, $Trp^{13} \rightarrow Arg^{13}$ (pGB/IL-303).

WO 88/05469 describes how deglycosylation mutants can be obtained and suggests mutants of Arg$^{54}$Arg$^{55}$ and Arg$^{108}$Arg$^{109}$Lys$^{110}$ might avoid proteolysis upon expression in *Saccharomyces cerevisiae* by KEX2 protease. No mutated proteins are disclosed. Glycosylation and the KEX2 protease activity are only important, in this context, upon expression in yeast.

WO 88/06161 mentions various mutants which theoretically may be conformationally and antigenically neutral. The only actually performed mutations are Met$^2$→Ile$^2$ and Ile131→Leu131. It is not disclosed whether the contemplated neutralities were obtained for these two mutations.

WO 91/00350 discloses nonglycosylated hIL-3 analog proteins, for example, hIL-3 (Pro$^8$Asp$^{15}$Asp$^{70}$), Met$^3$ rhuIL-3 (Pro$^8$Asp$^{15}$Asp$^{70}$); Thr$^4$ rhuIL-3 (Pro$^8$Asp$^{15}$Asp$^{70}$) and Thr$^6$ rhuIL-3 (Pro$^8$Asp$^{15}$Asp$^{70}$). It is said that these protein compositions do not exhibit certain adverse side effects associated with native hIL-3 such as urticaria resulting from infiltration of mast cells and lymphocytes into the dermis. The disclosed analog hIL-3 proteins may have N termini at Met$^3$, Thr$^4$, or Thr$^6$.

WO 90/12874 discloses cysteine added variants (CAVs) of IL-3 which have at least one Cys residue substituted for a naturally occurring amino acid residue.

U.S. Pat. No. 4,810,643 discloses the DNA sequence encoding human G-CSF.

WO 91/02754 discloses a fusion protein composed of GM-CSF and IL-3 which has increased biological activity compared to GM-CSF or IL-3 alone. Also disclosed are nonglycosylated IL-3 and GM-CSF analog proteins as components of the fusion.

WO 92/04455 discloses fusion proteins composed of IL-3 fused to a lymphokine selected from the group consisting of IL-3, IL-6, IL-7, IL-9, IL-11, EPO and G-CSF.

WO 92/06006 relates to hematopoietic molecules comprising an early acting factor (IL-3 or GM-CSF) and a late acting factor (EPO, IL-5, G-CSF or M-CSF) and the in vivo use for treating hematopoietic disorders.

Hematopoietic growth factors, such as hIL-3, have been administered alone, co-administered with other hematopoietic growth factors, or in combination with bone marrow transplants subsequent to high dose chemotherapy to treat the neutropenia and thrombocytopenia which are often the result of such treatment. However the period of severe neutropenia and thrombocytopenia may not be totally eliminated. The myeloid lineage, which is comprised of monocytes (macrophages), granulocytes (including neutrophils) and megakaryocytes, is critical in preventing infections and bleeding which can be life-threatening. Neutropenia and thrombocytopenia may also be the result of disease, genetic disorders, drugs, toxins, radiation and many therapeutic treatments such as conventional oncology therapy.

Bone marrow transplants have been used to treat this patient population. However, several problems are associated with the use of bone marrow to reconstitute a compromised hematopoietic system including: 1) the number of stem cells in bone marrow or other is limited, 2) Graft Versus Host Disease, 3) graft rejection and 4) possible contamination with tumor cells. Stem cells make up a very small percentage of the nucleated cells in the bone marrow, spleen and peripheral blood. It is clear that a dose response exits such that a greater number of stem cells will enhance hematopoietic recovery. Therefore, the use of hematopoietic cells that have been expanded ex-vivo should enhance hematopoietic recovery and patient survival. Bone marrow from an allogeneic donor has been used to provide bone marrow for transplant. However, Graft Versus Host Disease and graft rejection limit bone marrow transplantation even in recipients with HLA-matched sibling donors. An alternative to allogenic bone marrow transplants is autologous bone marrow transplants. In autologous bone marrow transplants, some of the patient's own marrow is harvested prior to myeloablative therapy, e.g. high dose chemotherapy, and is transplanted back into the patient afterwards. Autologous transplants eliminate the risk of Graft Versus Host Disease and graft rejection. However, autologous bone marrow transplants still present problems in terms of the limited number of stems cells in the marrow and possible contamination with tumor cells.

The limited number of stem cells may be overcome by ex-vivo expansion of the stem cells. In addition, stem cells can be specifically isolated selected based on the presence of specific surface antigen such as CD34+ in order to decrease tumor cell contamination of the marrow graft.

The following patents contain further details on separating stem cells, CD34+ cells, culturing the cells with hematopoietic growth factors, the use of the cells for the treatment of patients with hematopoietic disorders and the use of hematopoietic factors for cell expansion and gene therapy.

U.S. Pat. No. 5,061,620 relates to compositions comprising human hematopoietic stem cells provided by separating the stem cells from dedicated cells.

U.S. Pat. No. 5,199,942 describes a method for autologous hematopoietic cell transplantation comprising: (1) obtaining hematopoietic progenitor cells from a patient; (2) ex-vivo expansion of cells with a growth factor selected from the group consisting of IL-3, flt3 ligand, c-kit ligand, GM-CSF, IL-1, GM-CSF/IL-3 fusion protein and combinations thereof; (3) administering cellular preparation to a patient.

U.S. Pat. No. 5,240,856 relates to a cell separator that includes apparatus for automatically controlling the cell separation process.

U.S. Pat. No. 5,409,813 describes methods of positive and negative selection of a cell population from a mixture of cell populations utilizing a magnetically stabilized fluidized bed.

U.S. Pat. No. 5,409,825 relates to a method of growing hematopoietic stem cells in a liquid culture medium using mast cell growth factor (MGF) and optionally at least one cytokine selected from the group consisting of IL-3, GM-CSF and IL-3/GM-CSF fusion protein.

U.S. Pat. No. 5,459,069 relates to devices for maintaining and growing human stem cells and/or hematopoietic cells in culture.

U.S. Pat. No. 5,541,103 describes peripheral blood progenitor cells obtained by enriching blood progenitors expressing the cd34 antigen and culture the cells in a growth medium consisting of IL-1, IL-3, IL-6, erythropoietin and stem cell growth factor.

U.S. Pat. No. 5,464,753 describes a method of purifying pluripotent hematopoietic stem cells expressing P-glycoprotein from a mixture of blood or bone marrow cells.

U.S. Pat. No. 5,547,687 relates to a method of enriching CD34 cells from a cell mixture by density centrifugation.

U.S. Pat. No. 5,571,686 depicts the use of megapoietin (c-mpl ligand) for the in vitro expansion of stem cells as a source of platelets for transplantation and for increasing the storage life of platelets.

WO 91/16116 describes devices and methods for selectively isolating and separating target cells from a mixture of cells.

WO 91/18972 describes methods for in vitro culturing of bone marrow, by incubating suspension of bone marrow cells, using a hollow fiber bioreactor.

WO 92/18615 relates to a process for maintaining and expanding bone marrow cells, in a culture medium containing specific mixtures of cytokines, for use in transplants.

WO 93/08268 describes a method for selectively expanding stem cells, comprising the steps of (a) separating CD34+ stem cells from other cells and (b) incubating the separated cells in a selective medium, such that the stem cells are selectively expanded.

WO 93/18136 describes a process for in vitro support of mammalian cells derived from peripheral blood.

WO 93/18648 relates to a composition comprising human neutrophil precursor cells with a high content of myeloblasts and promyelocytes for treating genetic or acquired neutropenia.

WO 94/08039 describes a method of enrichment for human hematopoietic stem cells by selection for cells which express c-kit protein.

WO 94/11493 describes a stem cell population that are CD34+ and small in size, which are isolated using a counterflow elutriation method.

WO 94/27698 relates to a method combining immunoaffinity separation and continuous flow centrifugal separation for the selective separation of a nucleated heterogeneous cell population from a heterogeneous cell mixture.

WO 94/25848 describes a cell separation apparatus for collection and manipulation of target cells.

The long term culturing of highly enriched CD34+ precursors of hematopoietic progenitor cells from human bone marrow in cultures containing IL-1α, IL-3, IL-6 or GM-CSF is discussed in Brandt et al., *J. Clin. Invest.* 86:932–941, 1990.

SUMMARY OF THE INVENTION

The present invention encompasses the use of chimera proteins, comprising a recombinant human interleukin-3 (hIL-3) variant or mutant proteins (muteins) joined with or without a linker to a second colony stimulating factor (CSF), cytokine, lymphokine, interleukin, hematopoietic growth factor (herein collectively referred to as "hematopoietic growth factors") or IL-3 variant, for the ex-vivo expansion of hematopoietic cells. These hIL-3 muteins contain amino acid substitutions and may also have amino acid deletions at either/or both the N- and C-termini. This invention encompasses mixed function hematopoietic growth factors formed from covalently linked polypeptides, each of which may act through a different and specific cell receptor to initiate complementary biological activities.

Novel compounds of this invention are represented by the formulas

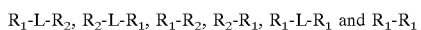

where R1 is a hIL-3 variant which contains multiple amino acid substitutions and which may have portions of the hIL-3 molecule deleted, R2 is an IL-3, IL-3 variant or hematopoietic growth factor with a different but complementary activity. The R1 polypeptide is joined either directly or through a linker segment to the R2 polypeptide. Thus L represents a chemical bond or polypeptide segment to which both R1 and R2 are joined. Preferably, these mutant IL-3 polypeptides of the present invention contain four or more amino acids which differ from the amino acids found at the corresponding positions in the native hIL-3 polypeptide.

These chimera molecules may be characterized by having the usual activity of both of the peptides forming the chimera molecule or it may be further characterized by having a biological or physiological activity greater than simply the additive function of the presence of IL-3 or the second hematopoietic growth factor alone. The chimera molecule may also unexpectedly provide an enhanced effect on the activity or an activity different from that expected by the presence of IL-3 or the second hematopoietic growth factor or IL-3 variant. The chimera molecule may also have an improved activity profile which may include reduction of undesirable biological activities associated with native hIL-3.

The present invention also includes mutants of hIL-3 in which from 1 to 14 amino acids have been deleted from the N-terminus and/or from 1 to 15 amino acids have been deleted from the C-terminus, containing multiple amino acid substitutions, to which a second hematopoietic growth factor or IL-3 variant has been joined. Preferred chimera molecules of the present invention are composed of hIL-3 variants in which amino acids 1 to 14 have been deleted from the N-terminus, amino acids 126 to 133 have been deleted from the C-terminus, and contains from about four to about twenty-six amino acid substitutions in the polypeptide sequence joined to second hematopoietic growth factor or IL-3 variant.

The present invention includes methods for selective ex vivo expansion of stem cells, comprising the steps of; (a) culturing said stem cells with a selected growth medium comprising a chimera protein having the formula selected from the group consisting of:

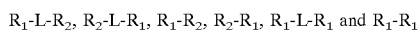

wherein $R_1$ is a human interleukin-3 mutant polypeptide of SEQ ID NO:1
wherein
Xaa at position 17 is Ser, Lys, Gly, Asp, Met, Gln, or Arg;
Xaa at position 18 is Asn, His, Leu, Ile, Phe, Arg, or Gln;
Xaa at position 19 is Met, Phe, Ile, Arg, Gly, Ala, or Cys;
Xaa at position 20 is Ile, Cys, Gln, Glu, Arg, Pro, or Ala;
Xaa at position 21 is Asp, Phe, Lys, Arg, Ala, Gly, Glu, Gln, Asn, Thr, Ser or Val;
Xaa at position 22 is Glu, Trp, Pro, Ser, Ala, His, Asp, Asn, Gln, Leu, Val or Gly;
Xaa at position 23 is Ile, Val, Ala, Leu, Gly, Trp, Lys, Phe, Ser, or Arg;
Xaa at position 24 is Ile, Gly, Val, Arg, Ser, Phe, or Leu;
Xaa at position 25 is Thr, His, Gly, Gln, Arg, Pro, or Ala;
Xaa at position 26 is His, Thr, Phe, Gly, Arg, Ala, or Trp;
Xaa at position 27 is Leu, Gly, Arg, Thr, Ser, or Ala;
Xaa at position 28 is Lys, Arg, Leu, Gln, Gly, Pro, Val or Trp;
Xaa at position 29 is Gln, Asn, Leu, Pro, Arg, or Val;
Xaa at position 30 is Pro, His, Thr, Gly, Asp, Gln, Ser, Leu, or Lys;
Xaa at position 31 is Pro, Asp, Gly, Ala, Arg, Leu, or Gln;
Xaa at position 32 is Leu, Val, Arg, Gln, Asn, Gly, Ala, or Glu;
Xaa at position 33 is Pro, Leu, Gln, Ala, Thr, or Glu;
Xaa at position 34 is Leu, Val, Gly, Ser, Lys, Glu, Gln, Thr, Arg, Ala, Phe, Ile or Met;
Xaa at position 35 is Leu, Ala, Gly, Asn, Pro, Gln, or Val;
Xaa at position 36 is Asp, Leu, or Val;
Xaa at position 37 is Phe, Ser, Pro, Trp, or Ile;
Xaa at position 38 is Asn, or Ala;
Xaa at position 40 is Leu, Trp, or Arg;
Xaa at position 41 is Asn, Cys, Arg, Leu, His, Met, or Pro;
Xaa at position 42 is Gly, Asp, Ser, Cys, Asn, Lys, Thr, Leu, Val, Glu, Phe, Tyr, Ile, Met or Ala;

Xaa at position 43 is Glu, Asn, Tyr, Leu, Phe, Asp, Ala, Cys, Gln, Arg, Thr, Gly or Ser;
Xaa at position 44 is Asp, Ser, Leu, Arg, Lys, Thr, Met, Trp, Glu, Asn, Gln, Ala or Pro;
Xaa at position 45 is Gln, Pro, Phe, Val, Met, Leu, Thr, Lys, Trp, Asp, Asn, Arg, Ser, Ala, Ile, Glu or His;
Xaa at position 46 is Asp, Phe, Ser, Thr, Cys, Glu, Asn, Gln, Lys, His, Ala, Tyr, Ile, Val or Gly;
Xaa at position 47 is Ile, Gly, Val, Ser, Arg, Pro, or His;
Xaa at position 48 is Leu, Ser, Cys, Arg, Ile, His, Phe, Glu, Lys, Thr, Ala, Met, Val or Asn;
Xaa at position 49 is Met, Arg, Ala, Gly, Pro, Asn, His, or Asp;
Xaa at position 50 is Glu, Leu, Thr, Asp, Tyr, Lys, Asn, Ser, Ala, Ile, Val, His, Phe, Met or Gln;
Xaa at position 51 is Asn, Arg, Met, Pro, Ser, Thr, or His;
Xaa at position 52 is Asn, His, Arg, Leu, Gly, Ser, or Thr;
Xaa at position 53 is Leu, Thr, Ala, Gly, Glu, Pro, Lys, Ser, or Met;
Xaa at position 54 is Arg, Asp, Ile, Ser, Val, Thr, Gln, Asn, Lys, His, Ala or Leu;
Xaa at position 55 is Arg, Thr, Val, Ser, Leu, or Gly;
Xaa at position 56 is Pro, Gly, Cys, Ser, Gln, Glu, Arg, His, Thr, Ala, Tyr, Phe, Leu, Val or Lys;
Xaa at position 57 is Asn or Gly;
Xaa at position 58 is Leu, Ser, Asp, Arg, Gln, Val, or Cys;
Xaa at position 59 is Glu, Tyr, His, Leu, Pro, or Arg;
Xaa at position 60 is Ala, Ser, Pro, Tyr, Asn, or Thr;
Xaa at position 61 is Phe, Asn, Glu, Pro, Lys, Arg, or Ser;
Xaa at position 62 is Asn, His, Val, Arg, Pro, Thr, Asp, or Ile;
Xaa at position 63 is Arg, Tyr, Trp, Lys, Ser, His, Pro, or Val;
Xaa at position 64 is Ala, Asn, Pro, Ser, or Lys;
Xaa at position 65 is Val, Thr, Pro, His, Leu, Phe, or Ser;
Xaa at position 66 is Lys, Ile, Arg, Val, Asn, Glu, or Ser;
Xaa at position 67 is Ser, Ala, Phe, Val, Gly, Asn, Ile, Pro, or His;
Xaa at position 68 is Leu, Val, Trp, Ser, Ile, Phe, Thr, or His;
Xaa at position 69 is Gln, Ala, Pro, Thr, Glu, Arg, Trp, Gly, or Leu;
Xaa at position 70 is Asn, Leu, Val, Trp, Pro, or Ala;
Xaa at position 71 is Ala, Met, Leu, Pro, Arg, Glu, Thr, Gln, Trp, or Asn;
Xaa at position 72 is Ser, Glu, Met, Ala, His, Asn, Arg, or Asp;
Xaa at position 73 is Ala, Glu, Asp, Leu, Ser, Gly, Thr, or Arg;
Xaa at position 74 is Ile, Met, Thr, Pro, Arg, Gly, Ala;
Xaa at position 75 is Glu, Lys, Gly, Asp, Pro, Trp, Arg, Ser, Gln, or Leu;
Xaa at position 76 is Ser, Val, Ala, Asn, Trp, Glu, Pro, Gly, or Asp;
Xaa at position 77 is Ile, Ser, Arg, Thr, or Leu;
Xaa at position 78 is Leu, Ala, Ser, Glu, Phe, Gly, or Arg;
Xaa at position 79 is Lys, Thr, Asn, Met, Arg, Ile, Gly, or Asp;
Xaa at position 80 is Asn, Trp, Val, Gly, Thr, Leu, Glu, or Arg;
Xaa at position 81 is Leu, Gln, Gly, Ala, Trp, Arg, Val, or Lys;
Xaa at position 82 is Leu, Gln, Lys, Trp, Arg, Asp, Glu, Asn, His, Thr, Ser, Ala, Tyr, Phe, Ile, Met or Val;
Xaa at position 83 is Pro, Ala, Thr, Trp, Arg, or Met;
Xaa at position 84 is Cys, Glu, Gly, Arg, Met, or Val;
Xaa at position 85 is Leu, Asn, Val, or Gln;
Xaa at position 86 is Pro, Cys, Arg, Ala, or Lys;
Xaa at position 87 is Leu, Ser, Trp, or Gly;
Xaa at position 88 is Ala, Lys, Arg, Val, or Trp;
Xaa at position 89 is Thr, Asp, Cys, Leu, Val, Glu, His, Asn, or Ser;
Xaa at position 90 is Ala, Pro, Ser, Thr, Gly, Asp, Ile, or Met;
Xaa at position 91 is Ala, Pro, Ser, Thr, Phe, Leu, Asp, or His;
Xaa at position 92 is Pro, Phe, Arg, Ser, Lys, His, Ala, Gly, Ile or Leu;
Xaa at position 93 is Thr, Asp, Ser, Asn, Pro, Ala, Leu, or Arg;
Xaa at position 94 is Arg, Ile, Ser, Glu, Leu, Val, Gln, Lys, His, Ala, or Pro;
Xaa at position 95 is His, Gln, Pro, Arg, Val, Leu, Gly, Thr, Asn, Lys, Ser, Ala, Trp, Phe, Ile, or Tyr;
Xaa at position 96 is Pro, Lys, Tyr, Gly, Ile, or Thr;
Xaa at position 97 is Ile, Val, Lys, Ala, or Asn;
Xaa at position 98 is His, Ile, Asn, Leu, Asp, Ala, Thr, Glu, Gln, Ser, Phe, Met, Val, Lys, Arg, Tyr or Pro;
Xaa at position 99 is Ile, Leu, Arg, Asp, Val, Pro, Gln, Gly, Ser, Phe, or His;
Xaa at position 100 is Lys, Tyr, Leu, His, Arg, Ile, Ser, Gln, or Pro;
Xaa at position 101 is Asp, Pro, Met, Lys, His, Thr, Val, Tyr, Glu, Asn, Ser, Ala, Gly, Ile, Leu, or Gln;
Xaa at position 102 is Gly, Leu, Glu, Lys, Ser, Tyr, or Pro;
Xaa at position 103 is Asp, or Ser;
Xaa at position 104 is Trp, Val, Cys, Tyr, Thr, Met, Pro, Leu, Gln, Lys, Ala, Phe, or Gly;
Xaa at position 105 is Asn, Pro, Ala, Phe, Ser, Trp, Gln, Tyr, Leu, Lys, Ile, Asp, or His;
Xaa at position 106 is Glu, Ser, Ala, Lys, Thr, Ile, Gly, or Pro;
Xaa at position 108 is Arg, Lys, Asp, Leu, Thr, Ile, Gln, His, Ser, Ala or Pro;
Xaa at position 109 is Arg, Thr, Pro, Glu, Tyr, Leu, Ser, or Gly;
Xaa at position 110 is Lys, Ala, Asn, Thr, Leu, Arg, Gln, His, Glu, Ser, or Trp;
Xaa at position 111 is Leu, Ile, Arg, Asp, or Met;
Xaa at position 112 is Thr, Val, Gln, Tyr, Glu, His, Ser, or Phe;
Xaa at position 113 is Phe, Ser, Cys, His, Gly, Trp, Tyr, Asp, Lys, Leu, Ile, Val or Asn;
Xaa at position 114 is Tyr, Cys, His, Ser, Trp, Arg, or Leu;
Xaa at position 115 is Leu, Asn, Val, Pro, Arg, Ala, His, Thr, Trp, or Met;
Xaa at position 116 is Lys, Leu, Pro, Thr, Met, Asp, Val, Glu, Arg, Trp, Ser, Asn, His, Ala, Tyr, Phe, Gln, or Ile;
Xaa at position 117 is Thr, Ser, Asn, Ile, Trp, Lys, or Pro;
Xaa at position 118 is Leu, Ser, Pro, Ala, Glu, Cys, Asp, or Tyr;
Xaa at position 119 is Glu, Ser, Lys, Pro, Leu, Thr, Tyr, or Arg;
Xaa at position 120 is Asn, Ala, Pro, Leu, His, Val, or Gln;
Xaa at position 121 is Ala, Ser, Ile, Asn, Pro, Lys, Asp, or Gly;
Xaa at position 122 is Gln, Ser, Met, Trp, Arg, Phe, Pro, His, Ile, Tyr, or Cys;
Xaa at position 123 is Ala, Met, Glu, His, Ser, Pro, Tyr, or Leu;
wherein from 1 to 14 amino acids can be deleted from the N-terminus and/or from 1 to 15 amino acids can be deleted from the C-terminus of said human interleukin-3 mutant polypeptide; and wherein from 4 to 44 of the amino acids designated by Xaa are different from the corresponding amino acids of native (1-133) human interleukin-3;

$R_2$ is a hematopoietic growth factor;

L is a linker capable of Linking $R_1$ to $R_2$; and said chimera protein can additionally be immediately preceded by (methionine$^{-1}$), (alanine$^{-1}$), or (methionine$^{-2}$, alanine$^{-1}$); and (b) harvesting said cultured stem cells.

Additionally, the present invention encompasses methods of ex-vivo expansion of stem cells comprising the steps of (a) separating stem cells from a mixed population of cells; (b) culturing said separated stem cells with a growth medium comprising a chimera protein; (c) harvesting said cultured cells.

The present invention includes methods for treatment of a patient having a hematopoietic disorder, comprising the steps of; (a) removing stem cells from said patient or a blood donor; (b) culturing said stem cells with a growth medium comprising a chimera protein; (c) harvesting said cultured cells; and (d) transplanting said cultured cells into said patient.

The present invention also includes methods for treatment of a patient having a hematopoietic disorder, comprising the steps of; (a) removing stem cells from said patient or a blood donor; (b) separating stem cells from a mixed population of cells; (c) culturing said separated stem cells with a growth medium comprising a chimera protein; (d) harvesting said cultured cells; and (e) transplanting said cultured cells into said patient.

It is also envisioned that a patient could be given a hematopoietic growth factor, preferably a early acting factor, prior to removing stem cells for ex-vivo expansion to increase the number of early progenitors. It is also envisioned that a portion of the stem cells removed from a patient could be frozen and transplanted with the expanded stem cells to provide more early progenitors.

It is envisioned that the present invention includes methods of human gene therapy, comprising the steps of; (a) removing stem cells from a patient or blood donor; (b) culturing said stem cells with a selected growth medium comprising a chimera protein; (c) introducing DNA into said cultured cells; (d) harvesting said transduced cells; and (e) transplanting said transduced cells into said patient.

It is also envisioned that the present invention includes methods of human gene therapy, comprising the steps of; (a) removing stem cells from a patient or blood donor; (b) separating said stem cells from a mixed population of cells; (c) culturing said separated stem cells with a selected growth medium comprising a chimera protein; (d) introducing DNA into said cultured cells; (e) harvesting said transduced cells; and (f) transplanting said transduced cells into said patient.

It is also intended that the present invention includes methods of ex vivo expansion of hematopoietic cells, methods of expanding hematopoietic cells for gene therapy and methods of treating a patient using the expanded cells using the chimeric proteins of the present invention with other hematopoietic growth factors. A non-exclusive list of other appropriate hematopoietic growth factors, colony stimulating factors, cytokines, lymphokines, hematopoietic growth factors and interleukins for simultaneous or serial co-administration with the polypeptides of the present invention includes GM-CSF, CSF-1, G-CSF, G-CSF Ser$^{17}$, c-mpl ligand (MGDF or TPO), c-mpl receptor agonists disclosed in PCT/US96/15938, M-CSF, erythropoietin (EPO), IL-1, IL-4, IL-2, IL-5, IL-6, IL-7, IL-8, IL-9, IL-10, IL-11, IL-12, IL-13, IL-15, IL-16, LIF, flt3 ligand, B-cell growth factor, B-cell differentiation factor and eosinophil differentiation factor, stem cell factor (SCF) also known as steel factor or c-kit ligand, multi-functional hematopoietic receptor agonists disclosed in PCT/US96/15774, or combinations thereof.

BRIEF DESCRIPTION OF THE DRAWINGS

FIG. 1 is the human IL-3 gene for *E. coli* expression (pMON5873), encoding the polypeptide sequence of natural (wild type) human IL-3 (SEQ ID NO:49), plus an initiator methionine, as expressed in *E. coli*, with the amino acids numbered from the N-terminus of the natural hIL-3.

DETAILED DESCRIPTION OF THE INVENTION

Figure 2:
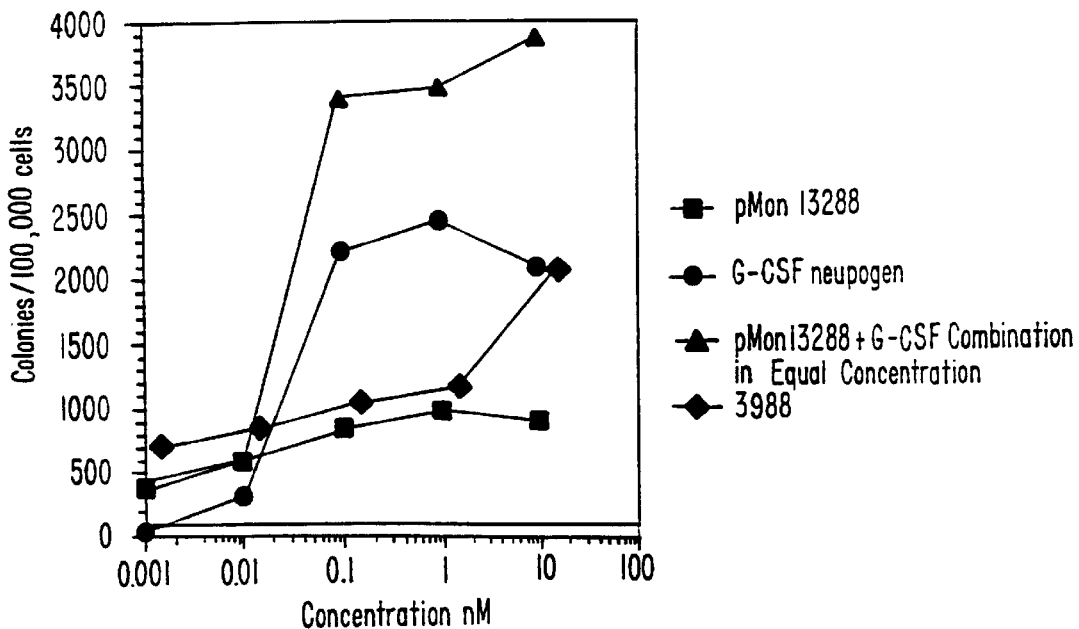
FIG. 2 shows the bioactivity, as measured in the methylcellulose assay, of the polypeptide chimera pMON3988.
Figure 3:
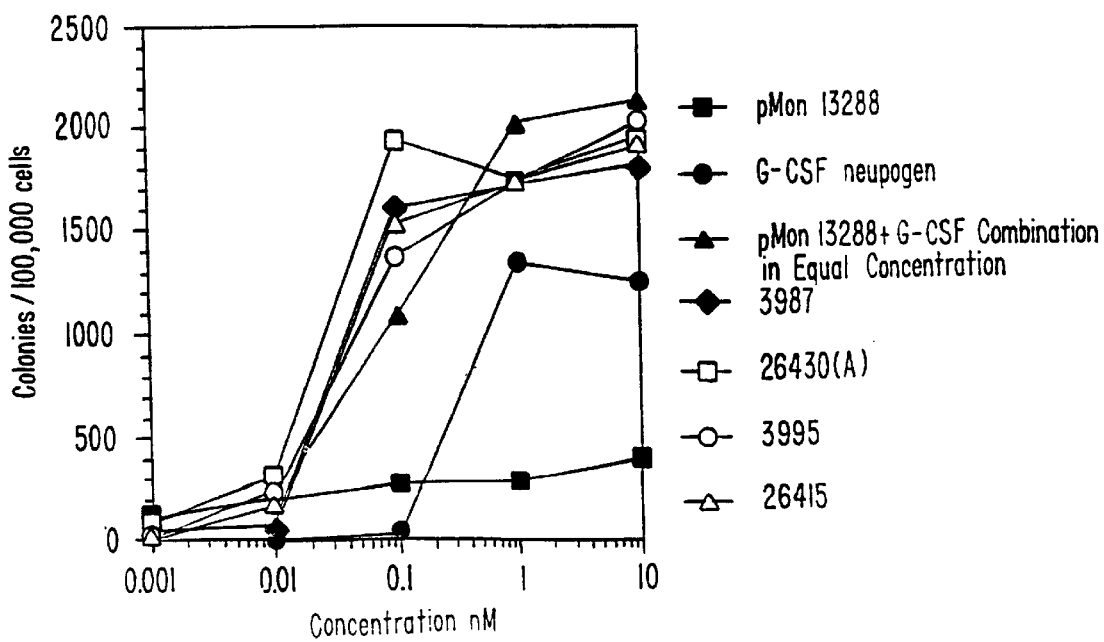
FIG. 3 shows the bioactivity, as measured in the methylcellulose assay, of the polypeptide chimeras pMON3987 and pMON26430, pMON3995 and pMON26415.
Figure 4:
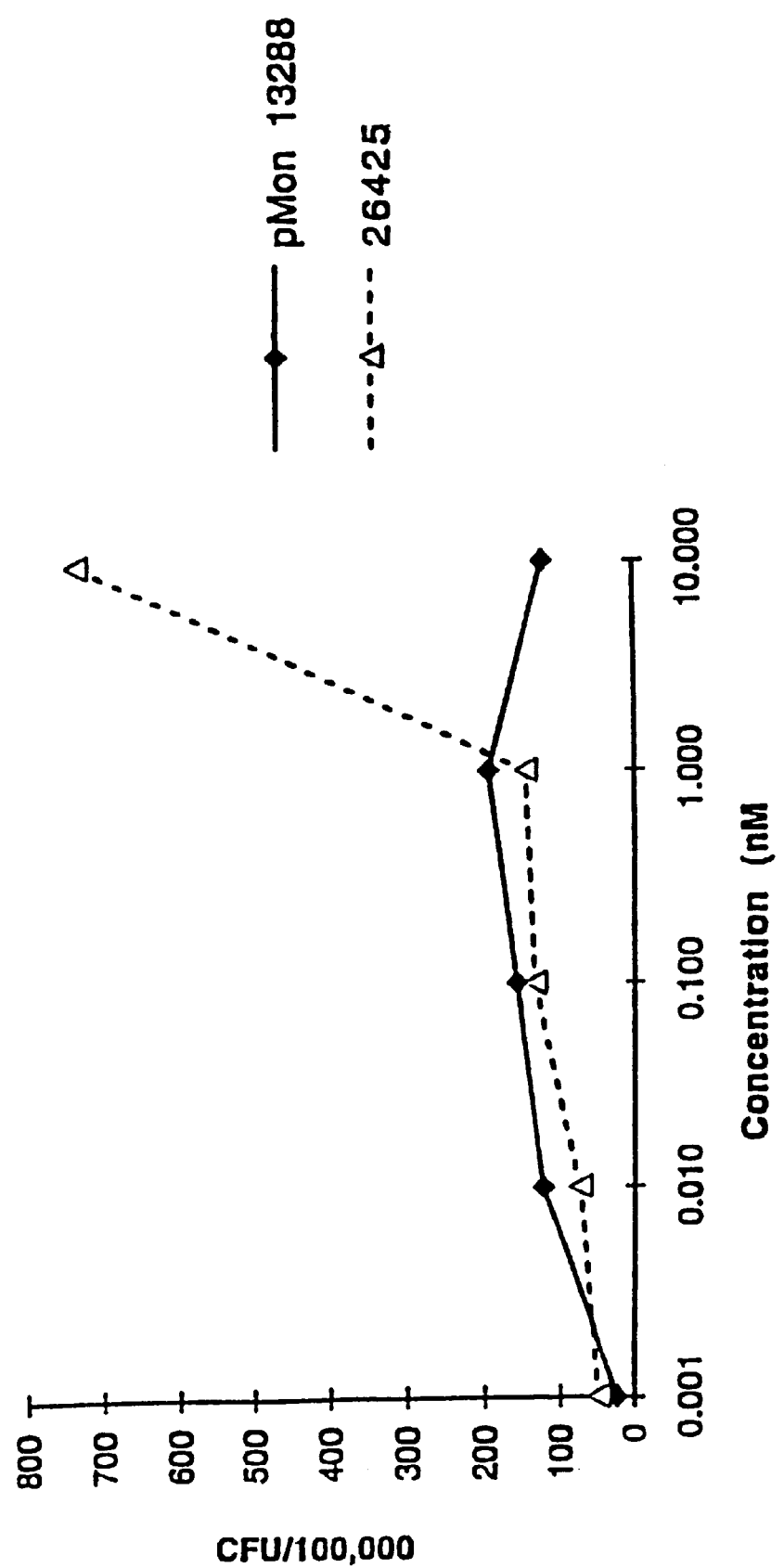
FIG. 4 shows the bioactivity, as measured in the methylcellulose assay, of the polypeptide chimera pMON26425.
Figure 5:
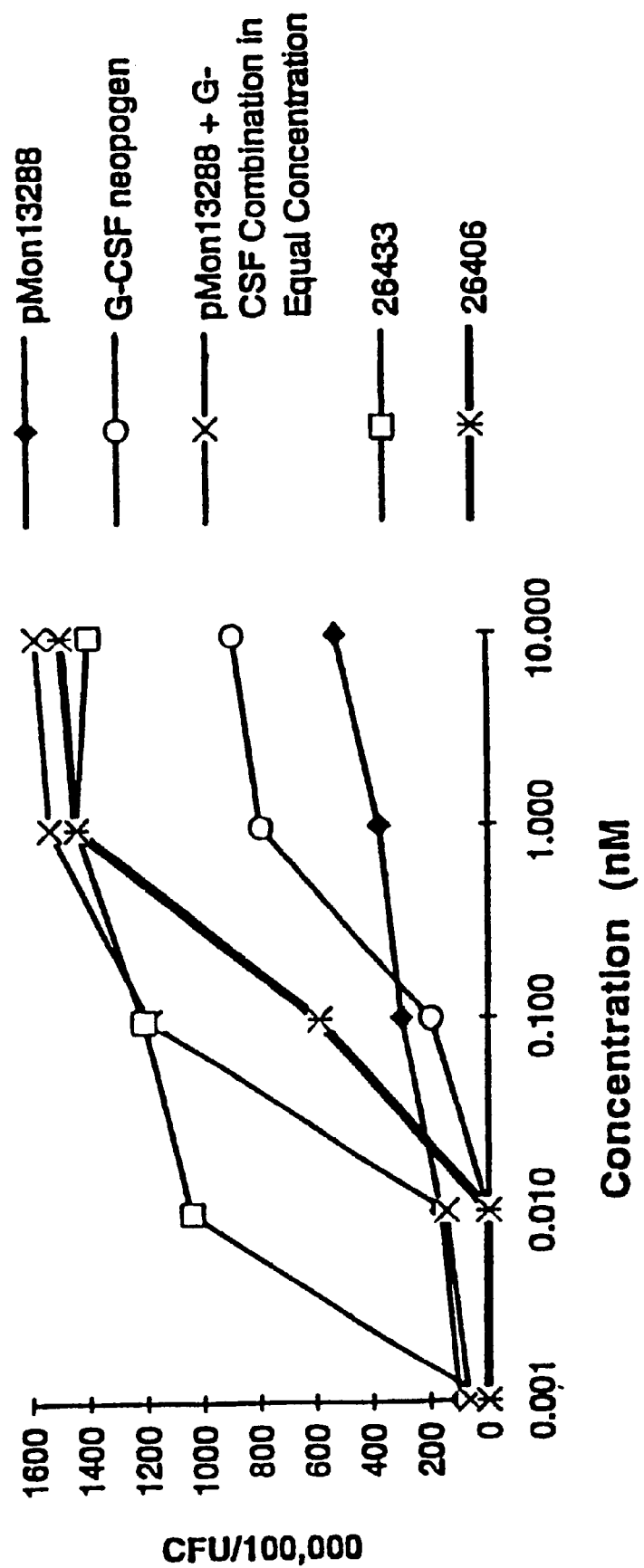
FIG. 5 shows the bioactivity, as measured in the methylcellulose assay, of the polypeptide chimeras pMON26406 and pMON26433.
Figure 6:
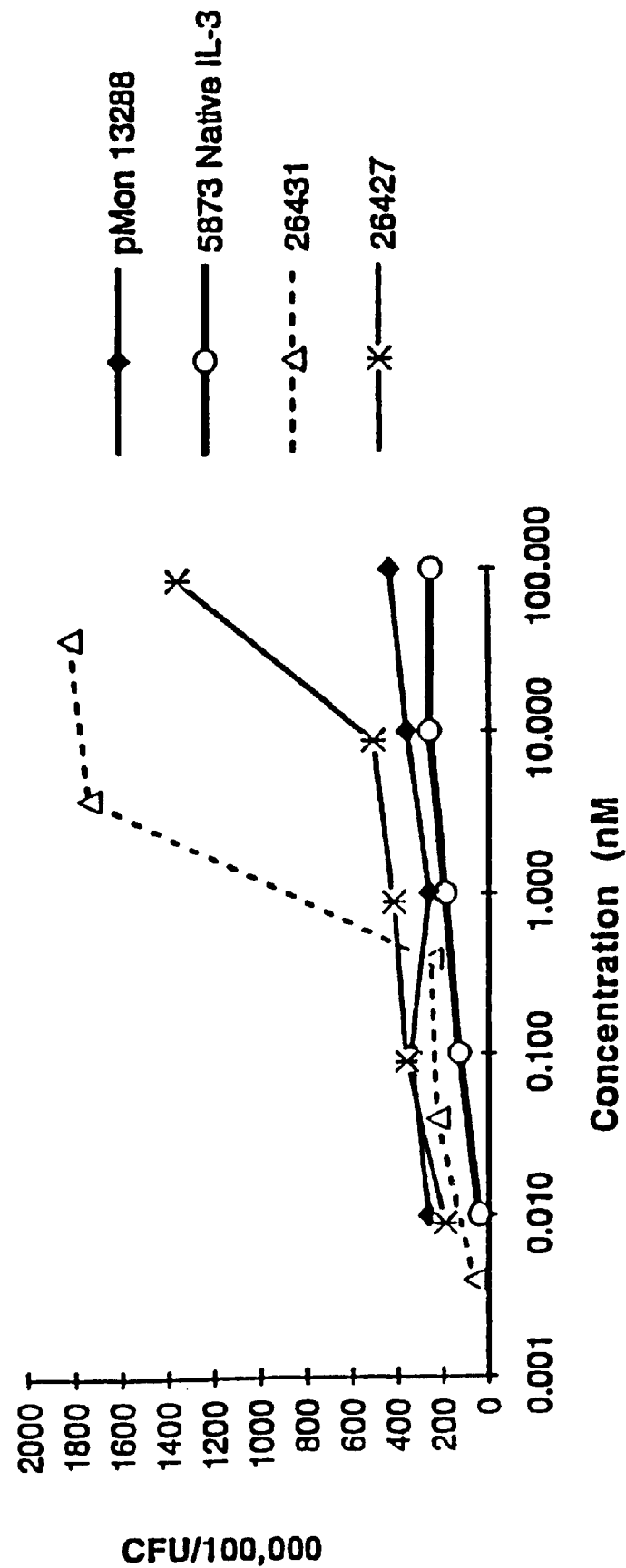
FIG. 6 shows the bioactivity, as measured in the methylcellulose assay, of the polypeptide chimeras pMON26431 and pMON26427.

The present invention encompasses methods of ex-vivo expansion of hematopoietic cells using a chimera protein comprising a recombinant human interleukin-3 (hIL-3) variants or mutant proteins (muteins) joined with or without a linker to a second IL-3 mutein, IL-3 or a second factor including but not limited to colony stimulating factors, cytokines, lymphokines, interleukins, hematopoietic growth factors or IL-3 variants. This invention encompasses the ex-vivo expansion use of these mixed function hematopoietic growth factors (chimera protein) formed from covalently linked polypeptides, each of which may act through a different and specific cell receptor to initiate complementary biological activities.

Hematopoiesis requires a complex series of cellular events in which stem cells generate continuously into large populations of maturing cells in all major lineages. There are currently at least 20 known regulators with hematopoietic proliferative activity. Most of these proliferative regulators can stimulate one or another type of colony formation in vitro, the precise pattern of colony formation stimulated by each regulator is quite distinctive. No two regulators stimulate exactly the same pattern of colony formation, as evaluated by colony numbers or, more importantly, by the lineage and maturation pattern of the cells making up the developing colonies. Proliferative responses can most readily be analyzed in simplified in vitro culture systems. Three quite different parameters can be distinguished: alteration in colony size, alteration in colony numbers and cell lineage. Two or more factors may act on the progenitor cell, inducing the formation of larger number of progeny thereby increasing the colony size. Two or more factors may allow increased number of progenitor cells to proliferate either because distinct subsets of progenitors cells exist that respond exclusively to one factor or because some progenitors require stimulation by two or more factors before being able to respond. Activation of additional receptors on a cell by the use of two or more factors is likely to enhance the mitotic signal because of coalescence of initially differing signal pathways into a common final pathway reaching the nucleus (Metcalf, *Nature* 339:27, 1989). Other mechanisms could explain synergy. For example, if one signaling pathway is limited by an intermediate activation of an additional signaling pathway by a second factor may result in a superadditive response. In some cases, activation of one receptor type can induce a enhanced expression of other receptors (Metcalf, *Blood* 82(12):3515–3523 1993). Two or more factors may result in a different pattern of cell lineages then from a single factor. The use of chimera molecules may have the potential clinical advantage resulting from a proliferative response that is not possible by any single factor.

Hematopoietic and other growth factors can be grouped in to two distinct families of related receptors: (1) tyrosine kinase receptors, including those for epidermal growth factor, M-CSF (Sherr, 1990) and SCF (Yarden et al., *EMBO J* 6:3341, 1987): and (2) hematopoietic receptors, not containing a tyrosine kinase domain, but exhibiting obvious homology in their extracellular domain (Bazan, *Proc. Natl. Acad. Sci. U.S.A.* 87(18):6934–8 1990). Included in this later group are erythropoietin (EPO) (D'Andrea et al., *Cell* 57:277 1989), GM-CSF (Gearing et al., *EMBO J* 8:3667 1989), IL-3 (Kitamura et al., *Cell* 66:1165 1991), G-CSF (Fukunaga et al., *J. Biol. Chem.* 265(23):14008–15 1990), IL-4 (Harada et al., 1990), IL-5 (Takaki et al., *EMBO J* 9:4367 1990), IL-6 (Yamasaki et al., *Science* 241:825 1988), IL-7 (Goodwin et al., *Cell* 60(6):941–51 1990), LIF (Gearing et al., *EMBO J* 10:2839 1991) and IL-2 (Cosman et al., 1987). Most of the later group of receptors exists in high-affinity form as a heterodimers. After ligand binding, the specific α-chains become associated with at least one other receptor chain (β-chain, γ-chain). Many of these factors share a common receptor subunit. The α-chains for GM-CSF, IL-3 and IL-5 share the same β-chain (Kitamura et al., *Cell* 66:1165 1991, Takaki et al., *EMBO. J.* 10(10):2833–8 1991) and receptor complexes for IL-6, LIF and IL-11 share a common β-chain (gp130) (Taga et al., *Cell* 58(3):573–81 1989; Gearing et al., *EMBO J* 10:2839 1992). The receptor complexes of IL-2, IL-4 and IL-7 share a common γ-chain (Kondo et al., *Science* 262:1874 1993; Russell et al., *Science* 262:1880 1993; Noguchi et al., *Science* 262:1877 1993).

The ex-vivo expansion methods of the present invention use chimera proteins of the formula selected from the group consisting of

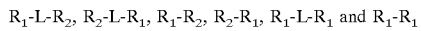

$R_1$-L-$R_2$, $R_2$-L-$R_1$, $R_1$-$R_2$, $R_2$-$R_1$, $R_1$-L-$R_1$ and $R_1$-$R_1$ where R1 is a hIL-3 variant which contains multiple amino acid substitutions and which may have portions of the hIL-3 molecule deleted as is disclosed in WO 94/12638, R2 is a hematopoietic growth factor with a different but complementary activity. By complementary activity is meant activity which enhances or changes the response to another cell modulator. The R1 polypeptide is joined either directly or through a linker segment to the R2 polypeptide. The term "directly" defines chimeras in which the polypeptides are joined without a peptide linker. Thus L represents a chemical bound or polypeptide segment to which both R1 and R2 are joined in frame, most commonly L is a linear peptide to which R1 and R2 are bound by amide bonds linking the carboxy terminus of R1 to the amino terminus of L and carboxy terminus of L to the amino terminus of R2. By "joined in frame" is meant that there is no translation termination or disruption between the reading frames of the DNA sequence encoding R1 and R2. A non-exclusive list of other growth factors, colony stimulating factors, cytokines, lymphokines, interleukins, and hematopoietic growth factors within the definition of R2, which can be joined to a hIL-3 variant of the present invention include GM-CSF, CSF-1, G-CSF, G-CSF Ser17, c-mpl ligand (MGDF or TPO), M-CSF, erythropoietin (EPO), IL-1, IL-4, IL-2, IL-5, IL-6, IL-7, IL-8, IL-9, IL-10, IL-11, IL-12, IL-13, IL-15, IL-16, LIF, flt3 ligand, human growth hormone, B-cell growth factor, B-cell differentiation factor, eosinophil differentiation factor and stem cell factor (SCF) also known as steel factor or c-kit ligand. Additionally, this invention encompasses the use of modified R2 molecules or mutated or modified DNA sequences encoding these R2 molecules. The present invention also includes chimera molecules in which R2 is a hIL-3 variant which means an IL-3 in which has amino acid substitutions and which may have portions of the hIL-3 molecule deleted such as what is disclosed in WO 94/12638 and WO 94/12639 as well as other variants known in the art.

As used herein human interleukin-3 corresponds to the amino acid sequence (1–133) as depicted in FIG. 1 and (15–125) hIL-3 corresponds to the 15 to 125 amino acid sequence of the hIL-3 polypeptide. Naturally occurring variants of hIL-3 polypeptide amino acids are also included in the present invention (for example, the allele in which proline rather than serine is at position 8 in the hIL-3 polypeptide sequence) as are variant hIL-3 molecules which are modified post-translationally (e.g. glycosylation).

"Mutant amino acid sequence," "mutant protein" or "mutant polypeptide" refers to a polypeptide having an amino acid sequence which varies from a native sequence or is encoded by a nucleotide sequence intentionally made variant from a native sequence. "Mutant protein," "variant protein" or "mutein" means a protein comprising a mutant amino acid sequence and includes polypeptides which differ from the amino acid sequence of native hIL-3 due to amino acid deletions, substitutions, or both. "Native sequence" refers to an amino acid or nucleic acid sequence which is identical to a wild-type or native form of a gene or protein.

Human IL-3 can be characterized by its ability to stimulate colony formation by human hematopoietic progenitor cells. The colonies formed include erythroid, granulocyte, megakaryocyte, granulocytic macrophages and mixtures thereof. Human IL-3 has demonstrated an ability to restore bone marrow function and peripheral blood cell populations to therapeutically beneficial levels in studies performed initially in primates and subsequently in humans (Gillio, A. P., et al. *J. Clin. Invest.* 85: 1560 (1990); Ganser, A., et al. *Blood* 76: 666 (1990); Falk, S., et al. *Hematopathology* 95: 355 (1991). Additional activities of hIL-3 include the ability to stimulate leukocyte migration and chemotaxis; the ability to prime human leukocytes to produce high levels of inflammatory mediators like leukotrienes and histamine; the ability to induce cell surface expression of molecules needed for leukocyte adhesion; and the ability to trigger dermal inflammatory responses and fever. Other IL-3-like properties are the interaction with early multipotential stem cells, the sustaining of the growth of pluripotent precursor cells, the ability to stimulate chronic myelogenous leukemia (CML) cell proliferation, the stimulation of proliferation of mast cells, the ability to support the growth of various factor-dependent cell lines, and the ability to trigger immature bone marrow cell progenitors. Other biological properties of IL-3 have been disclosed in the art. Many or all of these biological activities of hIL-3 involve signal transduction and high affinity receptor binding.

Biological activity of hIL-3 and hIL-3 chimera proteins of the present invention is determined by DNA synthesis by human acute myelogenous leukemia cells (AML). The factor-dependent cell line AML 193 was adapted for use in testing biological activity. The biological activity of hIL-3 and hIL-3 chimera proteins of the present invention is also determined by counting the colony forming units in a bone marrow assay.

Other in vitro cell based assays may also be useful to determine the activity of the chimera molecules depending on the hematopoietic growth factors that comprise the chimera. The following are examples of other useful assays.

TF-1 proliferation assay: The TF-1 cell line was derived from bone marrow of a patient with erythroleukemia (Kitamura et al., *J. Cell Physiol.* 140:323–334, 1989). TF-1 cells respond to IL-3, GM-CSF, EPO and IL-5.

32D proliferation assay: 32D is a murine IL-3 dependent cell line which does not respond to human IL-3 but does respond to human G-CSF which is not species restricted. T1165 proliferation assay: T1165 cells are a IL-6 dependent murine cell line (Nordan et al., *Science* 233:566, 1986) which respond to IL-6 and IL-11.

Human Plasma Clot meg-CSF Assay: Used to assay megakaryocyte colony formation activity (Mazur et al., *Blood* 57:277–286 1981).

Compounds of this invention are preferably made by genetic engineering techniques now standard in the art U.S. Pat. No. 4,935,233 and Sambrook et al., "Molecular Cloning. A Laboratory Manual", Cold Spring Harbor Laboratory, 1989. One method of creating the preferred hIL-3 (15–125) mutant genes is cassette mutagenesis (Wells, et al. *Gene,* 34:315–323, 1985) in which a portion of the coding sequence of hIL-3 in a plasmid is replaced with synthetic oligonucleotides that encode the desired amino acid substitutions in a portion of the gene between two restriction sites. In a similar manner amino acid substitutions could be made in the full-length hIL-3 gene, or genes encoding variants of hIL-3 in which from 1 to 14 amino acids have been deleted from the N-terminus and/or from 1 to 15 amino acids have been deleted from the C-terminus. When properly assembled these oligonucleotides would encode hIL-3 variants with the desired amino acid substitutions and/or deletions from the N-terminus and/or C-terminus. These and other mutations could be created by those skilled in the art by other mutagenesis methods including; oligonucleotide-directed mutagenesis (Zoller and Smith *Nucleic Acid Research,* 10:6487–6500, 1982; Zoller and Smith *Methods in Enzymology,* 100:468–500, 1983; Zoller and Smith *DNA,* 3: 479, 1984 Smith M. *Ann. Rev. Genet.,* 19:423–462, 1985; Kunkel *Proc. Natl. Acad. Sci. USA,* 82: 488–492, 1985, Taylor, et al. *Nucl. Acids Res.,* 13:8764–8785 (1985), Deng and Nickoloff, *Anal-Biochem* 200:81–88, 1992) or polymerase chain reaction (PCR) techniques (Saiki, *Science* 230:1350–1354, 1985).

Additional details about recombinant techniques for construction of DNA sequences that encode the chimera proteins, plasmid DNA vectors for use in the expression of these novel chimera molecules, methods for producing the chimera molecules in bacterial cells, mammalian cells, or insect cells and the in-vitro and in-vivo activity of the chimera proteins can be found in WO 95/21254. It is understood that the chimera molecules of the present invention, used for the ex-vivo expansion of hematopoietic cells, can be made by other methods known to those skilled in the art.

Hematopoietic cells that have been expanded ex-vivo using the chimera molecules of the present invention may be useful in the treatment of diseases characterized by a decreased levels of either myeloid, erythroid, lymphoid, or megakaryocyte cells of the hematopoietic system or combinations thereof. In addition, they may be used to activate mature myeloid and/or lymphoid cells. Among conditions susceptible to treatment with hematopoietic cells that have been expanded ex-vivo using the chimera proteins of the present invention is leukopenia, a reduction in the number of circulating leukocytes (white cells) in the peripheral blood. Leukopenia may be induced by exposure to certain viruses or to radiation. It is often a side effect of various forms of cancer therapy, e.g., exposure to chemotherapeutic drugs, radiation and of infection or hemorrhage. Therapeutic treatment of leukopenia with these chimera molecules of the present invention may avoid undesirable side effects caused by treatment with presently available drugs.

Hematopoietic cells that have been expanded ex-vivo using the chimera molecules of the present invention may be useful in the treatment of neutropenia and, for example, in the treatment of such conditions as aplastic anemia, cyclic neutropenia, idiopathic neutropenia, Chediak-Higashi syndrome, systemic lupus erythematosus (SLE), leukemia, myelodysplastic syndrome and myelofibrosis.

Hematopoietic cells that have been expanded ex-vivo using the chimera molecule of the present invention may be useful in the treatment or prevention of thrombocytopenia. Currently the only therapy for thrombocytopenia is platelet transfusions which are costly and carry the significant risks of infection (HIV, HBV) and alloimunization. Treatment involving the transplantation of the hematopoietic cells that have been expanded ex-vivo using chimera proteins of the present invention into a patient, may alleviate or diminish the need for platelet transfusions. Severe thrombocytopenia may result from genetic defects such as Fanconi's Anemia, Wiscott-Aldrich, or May-Hegglin syndromes. Acquired thrombocytopenia may result from auto- or allo-antibodies as in Immune Thrombocytopenia Purpura, Systemic Lupus Erythromatosis, hemolytic anemia, or fetal maternal incompatibility. In addition, splenomegaly, disseminated intravascular coagulation, thrombotic thrombocytopenic purpura, infection or prosthetic heart valves may result in thrombocytopenia. Severe thrombocytopenia may also result from chemotherapy and/or radiation therapy or cancer. Thrombocytopenia may also result from marrow invasion by carcinoma, lymphoma, leukemia or fibrosis.

One aspect of the present invention provides a novel hematopoietic factors for selective ex-vivo expansion of stem cells. The term "stem cell" refers to the totipiotent hematopoietic stem cells as well as early precursors and progenitor cells which can be isolated from bone marrow, spleen or peripheral blood. The term "expanding" refers to the differentiation and proliferation of the cells. The present invention provides a method for selective ex-vivo expansion of stem cells, comprising the steps of; (a) separating stem cells from a mixed population of cells, (b) culturing said separated stem cells with a selected media which contains a chimera protein(s) and (c) harvesting said cultured stems cells.

Stem cells as well as committed progenitor cells destined to become neutrophils, erythrocytes, platelets. etc., may be distinguished from most other cells by the presence or absence of particular progenitor marker antigens, such as CD34, that are present on the surface of these cells and/or by morphological characteristics. The phenotype for a highly enriched human stem cell fraction is reported as CD34+, Thy-1+ and lin-, but it is to be understood that the present invention is not limited to the expansion of this stem cell population. The CD34+ enriched human stem cell fraction can be separated by a number of reported methods, including affinity columns or beads, magnetic beads or flow cytometry using antibodies directed to surface antigens such as the CD34+. Further, physical separation methods such as counterflow elutriation may be used to enrich hematopoietic progenitors. The CD34+ progenitors are heterogeneous, and may be divided into several subpopulations characterized by the presence or absence of coexpression of different lineage associated cell surface associated molecules. The most immature progenitor cells do not express any known lineage-associated markers, such as HLA-DR or CD38, but they may express CD90(thy-1). Other surface antigens such as CD33, CD38, CD41, CD71, HLA-DR or c-kit can also be used to selectively isolate hematopoietic progenitors. The separated cells can be incubated in selected medium in a culture flask, sterile bag or in hollow fibers. Various hematopoietic growth factors may be utilized in order to selectively expand cells. Representative factors that have been utilized for ex-vivo expansion of bone marrow include, c-kit ligand, IL-3, G-CSF, GM-CSF, IL-1, IL-6, IL-11, flt-3 ligand or combinations thereof. The proliferation of the stem cells can be monitored by enumerating the number of stem cells and other cells, by standard techniques (e.g. hemacytometer, CFU, LTCIC) or by flow cytometry prior and subsequent to incubation.

Several methods for ex-vivo expansion of stem cells have been reported utilizing a number of selection methods and expansion using various hematopoietic growth factors including c-kit ligand (Brandt et al., *Blood* 83:1507–1514 (1994), McKenna et al., *Blood* 86:3413–3420 (1995), IL-3 (Brandt et al., *Blood* 83:1507–1514 (1994), Sato et al., *Blood* 82:3600–3609 (1993), G-CSF (Sato et al., *Blood* 82:3600–3609 (1993), GM-CSF (Sato et al., *Blood* 82:3600–3609 (1993), IL-1 (Muench et al., *Blood* 81:3463–3473 (1993), IL-6 (Sato et al., *Blood* 82:3600–3609 (1993), IL-11 (Lemoli et al., *Exp. Hem.* 21:1668–1672 (1993), Sato et al., *Blood* 82:3600–3609 (1993), flt-3 ligand (McKenna et al., *Blood* 86:3413–3420 (1995) and/or combinations thereof (Brandt et al., *Blood* 83:1507–1514 (1994), Haylock et al., *Blood* 80:1405–1412 (1992), Koller et al., *Biotechnology* 11:358–363 (1993), (Lemoli et al., *Exp. Hem.* 21:1668–1672 (1993), McKenna et al., *Blood* 86:3413–3420 (1995), Muench et al., *Blood* 81:3463–3473 (1993), Patchen et al., *Biotherapy* 7:13–26 (1994), Sato et al., *Blood* 82:3600–3609 (1993), Smith et al., *Exp. Hem.* 21:870–877 (1993), Steen et al., *Stem Cells* 12:214–224 (1994), Tsujino et al., *Exp. Hem.* 21:1379–1386 (1993). Among the individual hematopoietic growth factors, hIL-3 has been shown to be one of the most potent in expanding peripheral blood CD34+ cells (Sato et al., *Blood* 82:3600–3609 (1993), Kobayashi et al., *Blood* 73:1836–1841 (1989). However, no single factor has been shown to be as effective as the combination of multiple factors. The present invention provides methods for ex vivo expansion that utilize molecules that are more effective than IL-3 alone.

Another projected clinical use of growth factors has been in the in vitro activation of hematopoietic progenitors and stem cells for gene therapy. Due to the long life-span of hematopoietic progenitor cells and the distribution of their daughter cells throughout the entire body, hematopoietic progenitor cells are good candidates for ex vivo gene transfection. In order to have the gene of interest incorporated into the genome of the hematopoietic progenitor or stem cell one needs to stimulate cell division and DNA replication. Hematopoietic stem cells cycle at a very low frequency which means that growth factors may be useful to promote gene transduction and thereby enhance the clinical prospects for gene therapy. Potential applications of gene therapy (review Crystal, *Science* 270:404–410 (1995) include; 1) the treatment of many congenital metabolic disorders and immunodifiencies (Kay and Woo, *Trends Genet.* 10:253–257 (1994), 2) neurological disorders (Freedmann, *Trends Genet.* 10:210–214 (1994), 3) cancer (Culver and Blaese, *Trends Genet.* 10:174–178 (1994) and 4) infectious diseases (Gilboa and Smith, *Trends Genet.* 10:139–144 (1994). Due to the long life-span of hematopoietic progenitor cells and the distribution of their daughter cells throughout the entire body, hematopoietic progenitor cells are good candidates for ex vivo gene transfection include the treatment of many congenital metabolic disorders and immunodifiencies (Kay and Woo, *Trends Genet.* 10:253–257 (1994) neurological disorders (Freedmann, *Trends Genet.* 10:210–214 (1994), cancer (Culver and Blaese, *Trends Genet.* 10:174–178 (1994) and infectious diseases (Gilboa and Smith, *Trends Genet.* 10:139–144 (1994).

There are a variety of methods, known to those with skill in the art, for introducing genetic material into a host cell. A number of vectors, both viral and non-viral have been developed for transferring therapeutic genes into primary cells. Viral based vectors include; 1) replication-deficient recombinant retrovirus (Boris-Lawrie and Temin, *Curr. Opin. Genet. Dev.* 3:102–109 (1993), Boris-Lawrie and Temin, *Annal. New York Acad. Sci.* 716:59–71 (1994), Miller, *Current Top. Microbiol. Immunol.* 158:1–24 (1992) and replication-deficient recombinant adenovirus (Berkner, *BioTechniques* 6:616–629 (1988), Berkner, *Current Top. Microbiol. Immunol.* 158:39–66 (1992), Brody and Crystal, *Annal. New York Acad. Sci.* 716:90–103 (1994). Non-viral based vectors include protein/DNA complexes (Cristiano et al., *PNAS USA.* 90:2122–2126 (1993), Curiel et al., *PNAS USA* 88:8850–8854 (1991), Curiel, *Annal. New York Acad. Sci.* 716:36–58 (1994), electroporation and liposome mediated delivery such as cationic liposomes (Farhood et al., *Annal. New York Acad. Sci.* 716:23–35 (1994).

The present invention provides an improvement to the existing methods of expanding hematopoietic cells, which new genetic material has been introduced, in that it provides methods utilizing chimera proteins that have improved biological activity, including an activity not seen by any single colony stimulation factor and/or physical properties.

Many drugs may cause bone marrow suppression or hematopoietic deficiencies. Examples of such drugs are AZT, DDI, alkylating agents and anti-metabolites used in chemotherapy, antibiotics such as chloramphenicol, penicillin, gancyclovir, daunomycin and sulfa drugs, phenothiazones, tranquilizers such as meprobamate, analgesics such as aminopyrine and dipyrone, anti convulsants such as phenytoin or carbamazepine, antithyroids such as propylthiouracil and methimazole and diuretics. Hematopoietic cells that have been expanded ex-vivo using the chimera molecules of the present invention may be useful in preventing or treating the bone marrow suppression or hematopoietic deficiencies which often occur in patients treated with these drugs.

Hematopoietic deficiencies may also occur as a result of viral, microbial or parasitic infections and as a result of treatment for renal disease or renal failure, e.g., dialysis. Hematopoietic cells that have been expanded ex-vivo using the chimera molecules of the present invention may be useful in treating such hematopoietic deficiency.

Various immunodeficiencies e.g., in T and/or B lymphocytes, or immune disorders, e.g., rheumatoid arthritis, may also be beneficially affected by treatment with hematopoietic cells that have been expanded ex-vivo using the chimera molecules of the present invention. Immunodeficiencies may be the result of viral infections e.g. HTLVI, HTLVII, HTLVIII, severe exposure to radiation, cancer therapy or the result of other medical treatment. The chimera molecules of the present invention may also be employed, alone or in combination with other hematopoietic growth factors, in the treatment of other blood cell deficiencies, including thrombocytopenia (platelet deficiency), or anemia. Other uses for these novel polypeptides are in the treatment of patients recovering from bone marrow transplants.

As indicated above, the therapeutic method may also include co-administration with other human factors. A non-exclusive list of other appropriate hematopoietic growth factors, colony stimulating factors, cytokines, lymphokines, hematopoietic growth factors and interleukins for simultaneous or serial co-administration with the polypeptides of the present invention includes GM-CSF, CSF-1, G-CSF, G-CSF Ser7, c-mpl ligand (MGDF or TPO), c-mpl receptor agonists disclosed in PCT/US96/15938, M-CSF, erythropoietin (EPO), IL-1, IL-4, IL-2, IL-5, IL-6, IL-7, IL-8, IL-9, IL-10, IL-11, IL-12, IL-13, IL-15, IL-16, LIF, flt3 ligand, B-cell growth factor, B-cell differentiation factor and eosinophil differentiation factor, stem cell factor (SCF) also known as steel factor or c-kit ligand, multi-functional hematopoietic receptor agonists disclosed in PCT/US96/15774, or combinations thereof.

The treatment of hematopoietic deficiency may include removing hematopoietic cell from a patient, culturing the cell in a medium containing the chimera molecules to differentiate and proliferate the cells and returning the cultured cells to the patient following a medical treatment. In addition, hematopoietic cell can be removed from a blood donor, cultured and given to a patient suffering from a hematopoietic disorder.

The present invention is directed to methods of ex-vivo expansion of hematopoietic cells by culturing the cells with a chimeric proteins(s) of the formula:

$R_1$-L-$R_2$, $R_2$-L-$R_1$, $R_1$-$R_2$, $R_2$-$R_1$, $R_1$-L-$R_1$ and $R_1$-$R_1$ wherein $R_1$ is a human interleukin-3 mutant polypeptide of the Formula:

```
                                          (SEQ ID NO:1)
Ala Pro Met Thr Gln Thr Thr Ser Leu Lys Thr Ser
1               5                       10

Trp Val Asn Cys Xaa Xaa Xaa Xaa Xaa Xaa Xaa
        15                  20

Xaa Xaa Xaa Xaa Xaa Xaa Xaa Xaa Xaa Xaa Xaa
25                      30                  35

Xaa Xaa Asn Xaa Xaa Xaa Xaa Xaa Xaa Xaa Xaa
            40                  45

Xaa Xaa Xaa Xaa Xaa Xaa Xaa Xaa Xaa Xaa Xaa
50                      55                  60

Xaa Xaa Xaa Xaa Xaa Xaa Xaa Xaa Xaa Xaa Xaa
                65                  70

Xaa Xaa Xaa Xaa Xaa Xaa Xaa Xaa Xaa Xaa Xaa
        75                  80

Xaa Xaa Xaa Xaa Xaa Xaa Xaa Xaa Xaa Xaa Xaa
85                      90                  95

Xaa Xaa Xaa Xaa Xaa Xaa Xaa Xaa Xaa Phe Xaa
            100                 105

Xaa Xaa Xaa Xaa Xaa Xaa Xaa Xaa Xaa Xaa Xaa
        110                 115                 120

Xaa Xaa Xaa Gln Gln Thr Thr Leu Ser Leu Ala Ile
            125                 130

Phe
``` wherein
Xaa at position 17 is Ser, Lys, Gly, Asp, Met, Gln, or Arg;
Xaa at position 18 is Asn, His, Leu, Ile, Phe, Arg, or Gln;
Xaa at position 19 is Met, Phe, Ile, Arg, Gly, Ala, or Cys;
Xaa at position 20 is Ile, Cys, Gln, Glu, Arg, Pro, or Ala;
Xaa at position 21 is Asp, Phe, Lys, Arg, Ala, Gly, Glu, Gln, Asn, Thr, Ser or Val;
Xaa at position 22 is Glu, Trp, Pro, Ser, Ala, His, Asp, Asn, Gln, Leu, Val or Gly;
Xaa at position 23 is Ile, Val, Ala, Leu, Gly, Trp, Lys, Phe, Ser, or Arg;
Xaa at position 24 is Ile, Gly, Val, Arg, Ser, Phe, or Leu;
Xaa at position 25 is Thr, His, Gly, Gln, Arg, Pro, or Ala;
Xaa at position 26 is His, Thr, Phe, Gly, Arg, Ala, or Trp;
Xaa at position 27 is Leu, Gly, Arg, Thr, Ser, or Ala;
Xaa at position 28 is Lys, Arg, Leu, Gln, Gly, Pro, Val or Trp;
Xaa at position 29 is Gln, Asn, Leu, Pro, Arg, or Val;
Xaa at position 30 is Pro, His, Thr, Gly, Asp, Gln, Ser, Leu, or Lys;
Xaa at position 31 is Pro, Asp, Gly, Ala, Arg, Leu, or Gln;
Xaa at position 32 is Leu, Val, Arg, Gln, Asn, Gly, Ala, or Glu;
Xaa at position 33 is Pro, Leu, Gln, Ala, Thr, or Glu;
Xaa at position 34 is Leu, Val, Gly, Ser, Lys, Glu, Gln, Thr, Arg, Ala, Phe, Ile or Met;
Xaa at position 35 is Leu, Ala, Gly, Asn, Pro, Gln, or Val;
Xaa at position 36 is Asp, Leu, or Val;
Xaa at position 37 is Phe, Ser, Pro, Trp, or Ile;
Xaa at position 38 is Asn, or Ala;
Xaa at position 40 is Leu, Trp, or Arg;
Xaa at position 41 is Asn, Cys, Arg, Leu, His, Met, or Pro;
Xaa at position 42 is Gly, Asp, Ser, Cys, Asn, Lys, Thr, Leu, Val, Glu, Phe, Tyr, Ile, Met or Ala;
Xaa at position 43 is Glu, Asn, Tyr, Leu, Phe, Asp, Ala, Cys, Gln, Arg, Thr, Gly or Ser;
Xaa at position 44 is Asp, Ser, Leu, Arg, Lys, Thr, Met, Trp, Glu, Asn, Gln, Ala or Pro;
Xaa at position 45 is Gln, Pro, Phe, Val, Met, Leu, Thr, Lys, Trp, Asp, Asn, Arg, Ser, Ala, Ile, Glu or His;
Xaa at position 46 is Asp, Phe, Ser, Thr, Cys, Glu, Asn, Gln, Lys, His, Ala, Tyr, Ile, Val or Gly;
Xaa at position 47 is Ile, Gly, Val, Ser, Arg, Pro, or His;
Xaa at position 48 is Leu, Ser, Cys, Arg, Ile, His, Phe, Glu, Lys, Thr, Ala, Met, Val or Asn;
Xaa at position 49 is Met, Arg, Ala, Gly, Pro, Asn, His, or Asp;
Xaa at position 50 is Glu, Leu, Thr, Asp, Tyr, Lys, Asn, Ser, Ala, Ile, Val, His, Phe, Met or Gln;
Xaa at position 51 is Asn, Arg, Met, Pro, Ser, Thr, or His;
Xaa at position 52 is Asn, His, Arg, Leu, Gly, Ser, or Thr;
Xaa at position 53 is Leu, Thr, Ala, Gly, Glu, Pro, Lys, Ser, or Met;
Xaa at position 54 is Arg, Asp, Ile, Ser, Val, Thr, Gln, Asn, Lys, His, Ala or Leu;
Xaa at position 55 is Arg, Thr, Val, Ser, Leu, or Gly;
Xaa at position 56 is Pro, Gly, Cys, Ser, Gln, Glu, Arg, His, Thr, Ala, Tyr, Phe, Leu, Val or Lys;
Xaa at position 57 is Asn or Gly;
Xaa at position 58 is Leu, Ser, Asp, Arg, Gln, Val, or Cys;
Xaa at position 59 is Glu, Tyr, His, Leu, Pro, or Arg;
Xaa at position 60 is Ala, Ser, Pro, Tyr, Asn, or Thr;
Xaa at position 61 is Phe, Asn, Glu, Pro, Lys, Arg, or Ser;
Xaa at position 62 is Asn, His, Val, Arg, Pro, Thr, Asp, or Ile;
Xaa at position 63 is Arg, Tyr, Trp, Lys, Ser, His, Pro, or Val;
Xaa at position 64 is Ala, Asn, Pro, Ser, or Lys;
Xaa at position 65 is Val, Thr, Pro, His, Leu, Phe, or Ser;
Xaa at position 66 is Lys, Ile, Arg, Val, Asn, Glu, or Ser;
Xaa at position 67 is Ser, Ala, Phe, Val, Gly, Asn, Ile, Pro, or His;
Xaa at position 68 is Leu, Val, Trp, Ser, Ile, Phe, Thr, or His;
Xaa at position 69 is Gln, Ala, Pro, Thr, Glu, Arg, Trp, Gly, or Leu;

Xaa at position 70 is Asn, Leu, Val, Trp, Pro, or Ala;
Xaa at position 71 is Ala, Met, Leu, Pro, Arg, Glu, Thr, Gln, Trp, or Asn;
Xaa at position 72 is Ser, Glu, Met, Ala, His, Asn, Arg, or Asp;
Xaa at position 73 is Ala, Glu, Asp, Leu, Ser, Gly, Thr, or Arg;
Xaa at position 74 is Ile, Met, Thr, Pro, Arg, Gly, Ala;
Xaa at position 75 is Glu, Lys, Gly, Asp, Pro, Trp, Arg, Ser, Gln, or Leu;
Xaa at position 76 is Ser, Val, Ala, Asn, Trp, Glu, Pro, Gly, or Asp;
Xaa at position 77 is Ile, Ser, Arg, Thr, or Leu;
Xaa at position 78 is Leu, Ala, Ser, Glu, Phe, Gly, or Arg;
Xaa at position 79 is Lys, Thr, Asn, Met, Arg, Ile, Gly, or Asp;
Xaa at position 80 is Asn, Trp, Val, Gly, Thr, Leu, Glu, or Arg;
Xaa at position 81 is Leu, Gln, Gly, Ala, Trp, Arg, Val, or Lys;
Xaa at position 82 is Leu, Gln, Lys, Trp, Arg, Asp, Glu, Asn, His, Thr, Ser, Ala, Tyr, Phe, Ile, Met or Val;
Xaa at position 83 is Pro, Ala, Thr, Trp, Arg, or Met;
Xaa at position 84 is Cys, Glu, Gly, Arg, Met, or Val;
Xaa at position 85 is Leu, Asn, Val, or Gln;
Xaa at position 86 is Pro, Cys, Arg, Ala, or Lys;
Xaa at position 87 is Leu, Ser, Trp, or Gly;
Xaa at position 88 is Ala, Lys, Arg, Val, or Trp;
Xaa at position 89 is Thr, Asp, Cys, Leu, Val, Glu, His, Asn, or Ser;
Xaa at position 90 is Ala, Pro, Ser, Thr, Gly, Asp, Ile, or Met;
Xaa at position 91 is Ala, Pro, Ser, Thr, Phe, Leu, Asp, or His;
Xaa at position 92 is Pro, Phe, Arg, Ser, Lys, His, Ala, Gly, Ile or Leu;
Xaa at position 93 is Thr, Asp, Ser, Asn, Pro, Ala, Leu, or Arg;
Xaa at position 94 is Arg, Ile, Ser, Glu, Leu, Val, Gln, Lys, His, Ala, or Pro;
Xaa at position 95 is His, Gln, Pro, Arg, Val, Leu, Gly, Thr, Asn, Lys, Ser, Ala, Trp, Phe, Ile, or Tyr;
Xaa at position 96 is Pro, Lys, Tyr, Gly, Ile, or Thr;
Xaa at position 97 is Ile, Val, Lys, Ala, or Asn;
Xaa at position 98 is His, Ile, Asn, Leu, Asp, Ala, Thr, Glu, Gln, Ser, Phe, Met, Val, Lys, Arg, Tyr or Pro;
Xaa at position 99 is Ile, Leu, Arg, Asp, Val, Pro, Gln, Gly, Ser, Phe, or His;
Xaa at position 100 is Lys, Tyr, Leu, His, Arg, Ile, Ser, Gln, or Pro;
Xaa at position 101 is Asp, Pro, Met, Lys, His, Thr, Val, Tyr, Glu, Asn, Ser, Ala, Gly, Ile, Leu, or Gln;
Xaa at position 102 is Gly, Leu, Glu, Lys, Ser, Tyr, or Pro;
Xaa at position 103 is Asp, or Ser;
Xaa at position 104 is Trp, Val, Cys, Tyr, Thr, Met, Pro, Leu, Gln, Lys, Ala, Phe, or Gly;
Xaa at position 105 is Asn, Pro, Ala, Phe, Ser, Trp, Gln, Tyr, Leu, Lys, Ile, Asp, or His;
Xaa at position 106 is Glu, Ser, Ala, Lys, Thr, Ile, Gly, or Pro;
Xaa at position 108 is Arg, Lys, Asp, Leu, Thr, Ile, Gln, His, Ser, Ala or Pro;
Xaa at position 109 is Arg, Thr, Pro, Glu, Tyr, Leu, Ser, or Gly;
Xaa at position 110 is Lys, Ala, Asn, Thr, Leu, Arg, Gln, His, Glu, Ser, or Trp;
Xaa at position 111 is Leu, Ile, Arg, Asp, or Met;
Xaa at position 112 is Thr, Val, Gln, Tyr, Glu, His, Ser, or Phe;
Xaa at position 113 is Phe, Ser, Cys, His, Gly, Trp, Tyr, Asp, Lys, Leu, Ile, Val or Asn;
Xaa at position 114 is Tyr, Cys, His, Ser, Trp, Arg, or Leu;
Xaa at position 115 is Leu, Asn, Val, Pro, Arg, Ala, His, Thr, Trp, or Met;
Xaa at position 116 is Lys, Leu, Pro, Thr, Met, Asp, Val, Glu, Arg, Trp, Ser, Asn, His, Ala, Tyr, Phe, Gln, or Ile;
Xaa at position 117 is Thr, Ser, Asn, Ile, Trp, Lys, or Pro;
Xaa at position 118 is Leu, Ser, Pro, Ala, Glu, Cys, Asp, or Tyr;
Xaa at position 119 is Glu, Ser, Lys, Pro, Leu, Thr, Tyr, or Arg;
Xaa at position 120 is Asn, Ala, Pro, Leu, His, Val, or Gln;
Xaa at position 121 is Ala, Ser, Ile, Asn, Pro, Lys, Asp, or Gly;
Xaa at position 122 is Gln, Ser, Met, Trp, Arg, Phe, Pro, His, Ile, Tyr, or Cys;
Xaa at position 123 is Ala, Met, Glu, His, Ser, Pro, Tyr, or Leu;

wherein from 1 to 14 amino acids can be deleted from the N-terminus and/or from 1 to 15 amino acids can be deleted from the C-terminus; and wherein from 4 to 44 of the amino acids designated by Xaa are different from the corresponding amino acids of native (1–133) human interleukin-3;

$R_2$ is a hematopoietic growth factor;

L is a linker capable of linking $R^1$ and $R^2$; and said chimera protein can additionally be immediately preceded by (methionine$^{-1}$), (alanine$^{-1}$), or (methionine$^{-2}$, alanine$^{-1}$).

In a preferred embodiment, $R^2$ is a hematopoietic growth factor selected from the group consisting of GM-CSF, CSF-1, G-CSF, G-CSF Ser$^7$, c-mpl ligand (MGDF or TPO), M-CSF, erythropoietin (EPO), IL-1, IL-4, IL-2, IL-5, IL-6, IL-7, IL-8, IL-9, IL-10, IL-11, IL-12, IL-13, IL-15, IL-16, LIF, flt3 ligand, human growth hormone, B-cell growth factor, B-cell differentiation factor, eosinophil differentiation factor and stem cell factor (SCF).

The dosage regimen involved in ex-vivo expansion of hematopoietic cells and methods for treating the above-described conditions will be determined by the attending physician considering various factors which modify the action of drugs, e.g. the condition, body weight, sex and diet of the patient, the severity of any infection, time of administration and other clinical factors. Generally, a dosage regimen may be in the range of 1 ng to 100 ng of non-glycosylated IL-3 chimeric protein per mL of culture medium. This dosage regimen is referenced to a standard level of biological activity which recognizes that native IL-3 generally possesses an $EC_{50}$ at or about 10 picoMolar to 100 picoMolar in the AML proliferation assay described herein. Therefore, dosages would be adjusted relative to the activity of a given chimera protein vs. the activity of native (reference) IL-3 and it would not be unreasonable to note that dosage regimens may include doses as low as 0.1 ng and as high as 1 milligram per mL of culture medium. In addition, there may exist specific circumstances where dosages of chimera protein would be adjusted higher or lower. When administered with the chimera proteins of the present invention, other hematopoietic growth factors are used in the range of 1 ng to 100 ng per mL of culture medium. The other hematopoietic growth factors could be used as low as 1 pg/mL and as high as 1 mg/mL depending on the chimeria protein used, the various combination of hematopoietic growth factors used and the nature of the expanded hematopoietic cell population that is desired. Other factors that could effect the dosage of the chimera proteins and other hematopoietic growth factors include; co-administration with chemotherapeutic drugs and/or radiation; the use of glycosylated proteins; and various patient-related issues mentioned earlier in this section.

The following examples will illustrate the invention in greater detail although it will be understood that the invention is not limited to these specific examples.

EXAMPLE 1
Determination of the In Vitro Activity of Chimera Proteins

The protein concentration of the chimera protein can be determined using a sandwich ELISA based on an affinity purified polyclonal antibody. Alternatively the protein concentration can be determined by amino acid composition. The bioactivity of the chimera molecule can be determined in a number of in vitro assays compared with native IL-3, the IL-3 variant or G-CSF alone or together. One such assay is the AML-193 cell proliferation assay. AML-193 cells respond to IL-3 and G-CSF which allows for the combined bioactivity of the IL-3 variant/G-CSF chimera to be determined. In addition other factor dependent cell lines, such as M-NFS-60 (ATCC. CRL 1838) or 32D which are murine IL-3 dependent cell line, may be used. The activity of IL-3 is species specific whereas G-CSF is not, therefor the bioactivity of the G-CSF component of the IL-3 variant/G-CSF chimera can be determined independently. The methylcellulose assay can be used to determine the effect of the IL-3 variant/G-CSF chimera protein on the expansion of the hematopoietic progenitor cells and the pattern of the different types of hematopoietic colonies in vitro. The methylcellulose assay can provide an estimate of precursor frequency since one measures the frequency of progenitors per 100,000 input cells. Long term, stromal dependent cultures have been used to delineate primitive hematopoietic progenitors and stem cells. This assay can be used to determine whether the chimera molecule stimulates the expansion of very primitive progenitors and/or stem cells. In addition, limiting dilution cultures can be performed which will indicate the frequency of primitive progenitors stimulated by the chimera molecule.
Determination of Bioactivity of Chimera Molecules in AML Proliferation Assay The AML assay is useful for determining the activity of chimera molecules that respond to hIL-3, G-CSF and The factor-dependent cell line AML 193 was obtained from the American Type Culture Collection (ATCC, Rockville, Md.). This cell line, established from a patient with acute myelogenous leukemia, is a growth factor dependent cell line which displayed enhanced growth in GM-CSF supplemented medium (Lange, B., et al., *Blood* 70:192, 1987; Valtieri, M., et al., *J. Immunol.* 138:4042, 1987). The ability of AML 193 cells to proliferate in the presence of human IL-3 has also been documented. (Santoli, D., et al., *J. Immunology* 139:348, 1987). A cell line variant was used, AML 193 1.3, which was adapted for long term growth in IL-3 by washing out the growth factors and starving the cytokine dependent AML 193 cells for growth factors for 24 hours. The cells are then replated at $1 \times 10^5$ cells/well in a 24 well plate in media containing 100 U/mL IL-3. It took approximately 2 months for the cells to grow rapidly in IL-3. These cells are maintained as AML 193 1.3 thereafter by supplementing tissue culture medium (see below) with human IL-3.

AML 193 1.3 cells are washed 6 times in cold Hanks balanced salt solution (HBSS, Gibco, Grand Island, N.Y.) by centrifuging cell suspensions at 250×g for 10 minutes followed by decantation of the supernatant. Pelleted cells are resuspended in HBSS and the procedure is repeated until six wash cycles are completed. Cells washed six times by this procedure are resuspended in tissue culture medium at a density ranging from $2 \times 10^5$ to $5 \times 10^5$ viable cells/mL. This medium is prepared by supplementing Iscove's modified Dulbecco's Medium (IMDM, Hazelton, Lenexa, Kans.) with albumin, transferrin, lipids and 2-mercaptoethanol. Bovine albumin (Boehringer-Mannheim, Indianapolis, Ind.) is added at 500 µg/mL; human transferrin (Boehringer-Mannheim, Indianapolis, Ind.) is added at 100 µg/mL; soybean lipid (Boehringer-Mannheim, Indianapolis, Ind.) is added at 50 µg/mL; and 2-mercaptoethanol (Sigma, St. Louis, Mo.) is added at 5×10–5 M.

Serial dilutions of human interleukin-3 or chimera protein (hIL-3 mutein) are made in triplicate series in tissue culture medium supplemented as stated above in 96 well Costar 3596 tissue culture plates. Each well contained 50 µl of medium containing interleukin-3 or chimera protein once serial dilutions are completed. Control wells contained tissue culture medium alone (negative control). AML 193 1.3 cell suspensions prepared as above are added to each well by pipetting 50 µl ($2.5 \times 10^4$ cells) into each well. Tissue culture plates are incubated at 37° C. with 5% $CO_2$ in humidified air for 3 days. On day 3, 0.5 µCi $^3$H-thymidine (2 Ci/mM, New England Nuclear, Boston, Mass.) is added in 50 µl of tissue culture medium. Cultures are incubated at 37° C. with 5% $CO_2$ in humidified air for 18–24 hours. Cellular DNA is harvested onto glass filter mats (Pharmacia LKB, Gaithersburg, Md.) using a TOTED cell harvester (TOMTEC, Orange, Conn.) which utilized a water wash cycle followed by a 70% ethanol wash cycle. Filter mats are allowed to air dry and then placed into sample bags to which scintillation fluid (Scintiverse II, Fisher Scientific, St. Louis, Mo. or BetaPlate Scintillation Fluid, Pharmacia LKB, Gaithersburg, Md.) is added. Beta emissions of samples from individual tissue culture wells are counted in a LKB Betaplate model 1205 scintillation counter (Pharmacia LKB, Gaithersburg, Md.) and data is expressed as counts per minute of $^3$H-thymidine incorporated into cells from each tissue culture well. Activity of each human interleukin-3 preparation or chimera protein preparation is quantitated by measuring cell proliferation ($^3$H-thymidine incorporation) induced by graded concentrations of interleukin-3 or chimera protein. Typically, concentration ranges from 0.05 pM–$10^5$ pM are quantitated in these assays. Activity is determined by measuring the dose of interleukin-3 or chimera molecule which provides 50% of maximal proliferation ($EC_{50}$=0.5×(maximum average counts per minute of $^3$H-thymidine incorporated per well among triplicate cultures of all concentrations of interleukin-3 tested—background proliferation measured by $^3$H-thymidine incorporation observed in triplicate cultures lacking interleukin-3). This $EC_{50}$ value is also equivalent to 1 unit of bioactivity. Every assay is performed with native interleukin-3 as a reference standard so that relative activity levels could be assigned.

Typically, the protein chimeras were tested in a concentration range of 2000 pM to 0.06 pM titrated in serial 2 fold dilutions. Biological activity of the chimera molecules was compared to the following standards as described below.

Protein chimeras comprised in part of G-CSF, pMON3987, pMON3995, pMON3997, pMON26406, pMON26433, pMON26415, pMON26416, and pMON26430, were compared to the dose response curve of equal molar concentrations of hG-CSF and pMON13288 or pMON13416.

Protein chimeras comprised in part of GM-CSF, pMON3989 and pMON3998 were compared to the dose response curve of equal molar concentrations of hGM-CSF and pMON13288. Protein chimeras comprised of dimers of hIL-3 variants, pMON3988, pMON26425, pMON26427, pMON26420, pMON26429 and pMON26431 were compared to the dose response curve of pMON13288 or pMON13416.

Activity for each sample was determined by the concentration which gave 50% of the maximal response by fitting a four-parameter logistic model to the data. It was observed that the upper plateau (maximal response) for the sample and the standard with which it was compared did not differ. Therefore relative potency calculation for each sample was determined from EC50 estimations for the sample and the standard as indicated above. Relative potency (EC50 of standard divided by EC50 of sample) reported in Table 3 is the mean of at least two independent assays unless indicated. AML 193.1.3 cells proliferate in response to hIL-3, hGM-CSF and hG-CSF.

TABLE 3

AML cell proliferation assay

| pMON | $R_1$ | $R_2$ | AML 193.1.3 Bioactivity (relative potency) |
|---|---|---|---|
| pMON3987 | 13288 | G-CSF | 0.35 ± 0.11 |
| pMON3988 | 13288 | 13288 | 0.64 ± 0.13 |
| pMON3989 | 13288 | GM-CSF | 0.6 ± 0.09 |
| pMON3995 | G-CSF | 13288 | 0.41 ± 0.44 |
| pMON3997 | 13288 | G-CSF | 0.26 (n = 1) |
| pMON3998 | 13288 | GM-CSF | 0.21 (n = 1) |
| pMON26406 | 13288 | G-CSF | 0.37 ± 0.30 |
| pMON26433 | G-CSF | 13288 | 0.79 ± 0.35 |
| pMON26415 | 13288 | G-CSF Ser17 | 0.46 ± 0.08 |
| pMON26416 | G-CSF | 13416 | 0.43 ± 0.02 |
| pMON26425 | 13288 | 13288 | 1.32 ± 0.41 |
| pMON26427 | 13288 | 13288 | 1.41 ± 0.91 |
| pMON26420 | 13416 | 13416 | 2.09 ± 0.52 |
| pMON26430 | 13288 | G-CSF | 1.04 ± 0.69 |
| pMON26429 | 13288 | 13288 | 1.88 ± 0.09 |
| pMON26431 | 13288 | 13288 | 0.66 ± 0.26 |

EXAMPLE 2
Determination of Bioactivity of Chimera Molecules in Methylcellulose Assay This assays the ability of hematopoietic growth factors to stimulate normal bone marrow cells to produce different types of hematopoietic colonies in vitro (Bradley et al., *Aust. Exp. Biol. Med. Sci.* 44:287–300 1966; Pluznik et al., *J Cell Comp Physiol* 66:319–324 1965).

Methods

Approximately 30 mL of fresh, normal, healthy bone marrow aspirate are obtained from individuals. Under sterile conditions samples are diluted 1:5 with a 1×PBS (#14040.059 Life Technologies, Gaithersburg, Md.) solution in a 50 mL conical tube (#25339–50 Corning, Corning Md.). Ficoll (Histopaque 1077 Sigma H-8889) is layered under the diluted sample and centrifuged, 300×g for 30 min. The mononuclear cell band is removed and washed two times in 1×PBS and once with 1% BSA PBS (CellPro Co., Bothel, Wash.). Mononuclear cells are counted and CD34+ cells are selected using the Ceprate LC (CD34) Kit (CellPro Co., Bothel, Wash.) column. This fractionation is performed since all stem and progenitor cells within the bone marrow display CD34 surface antigen.

Cultures are set up in triplicate with a final volume of 1.0 mL in a 35×10 mm petri dish (Nunc#174926). Culture medium is purchased from Terry Fox Labs. (HCC-4230 medium (Terry Fox Labs, Vancouver, B. C., Canada) and erythropoietin (Amgen, Thousands Oaks, Calif.) is added to the culture media. 3,000–10,000 CD34+ cells are added per dish. Native IL-3 and chimera molecules are added to give final concentrations ranging from 0.001 nM 10 nM. Native IL-3 and chimera molecules are supplied in house. G-CSF (Neupogen) is from Amgen.

Cultures are resuspended using a 3 cc syringe and 1.0 mL is dispensed per dish. Control (baseline response) cultures received no hematopoietic growth factors. Positive control cultures received conditioned media (PHA stimulated human cells; Terry Fox Lab. H2400). Cultures are incubated at 37° C., 5% $CO_2$ in humidified air. Hematopoietic colonies which are defined as greater than 50 cells are counted on the day of peak response (days 10–11) using a Nikon inverted phase microscope with a 40× objective combination. Groups of cells containing fewer than 50 cells are referred to as clusters. Alternatively colonies can be identified by spreading the colonies on a slide and stained or they can be picked, resuspended and spun onto cytospin slides for staining.

EXAMPLE 3
Determination of Bioactivity of Chimera Molecules in Human Cord Blood Hematopoietic Growth Factor Assay Bone marrow cells are traditionally used for in vitro assays of hematopoietic growth factor activity. However, human bone marrow is not always available, and there is considerable variability between donors. Umbilical cord blood is comparable to bone marrow as a source of hematopoietic stem cells and progenitors (Broxmeyer et al., *Proc. Natl. Acad. Sci. USA*, 89:4109–4113 1992; Mayani et al., *Blood* 81:3252–3258 1993). In contrast to bone marrow, cord blood is more readily available on a regular basis. There is also a potential to reduce assay variability by pooling cells obtained fresh from several donors, or to create a bank of cryopreserved cells for this purpose. By modifying the culture conditions, and/or analyzing for lineage specific markers, it should be possible to assay specifically for granulocyte/macrophage colonies (CFU-GM), for megakaryocyte CSF activity, or for high proliferative potential colony forming cell (HPP-CFC) activity.

Methods

Mononuclear cells (MNC) are isolated from cord blood within 24 hr. of collection, using a standard density gradient (1.077 g/mL Histopaque). Cord blood MNC have been further enriched for stem cells and progenitors by several procedures, including immunomagnetic selection for CD14−, CD34+ cells; panning for SBA−, CD34+ fraction using coated flasks from Applied Immune Science (Santa Clara, Calif.); and CD34+ selection using a CellPro (Bothell, Wash.) avidin column. Either freshly isolated or cryopreserved CD34+ cell enriched fractions are used for the assay. Duplicate cultures for each serial dilution of sample (concentration range from 1 pM to 1204 pM) are prepared with $1×10^4$ cells in 1 ml of 0.9% methylcellulose containing medium without additional growth factors (Methocult H4230 from Stem Cell Technologies, Vancouver, BC.). In some experiments, Methocult H4330 containing erythropoietin (EPO) was used instead of Methocult H4230, or Stem Cell Factor (SCF), 50 ng/mL (Biosource International, Camarillo, Calif.) was added. After culturing for 7–9 days, colonies containing >30 cells are counted. In order to rule out subjective bias in scoring, assays are scored blind.

EXAMPLE 4
Determination of Bioactivity of Chimera Molecules in Megakaryocyte Proliferation Assay Methods 1. Bone Marrow Proliferation Assay a. CD34+ Cell Purification Between 15–20 mL bone marrow aspirates were obtained from normal allogeneic marrow donors after informed consent. Cells were diluted 1:3 in phosphate buffered saline (PBS, Gibco-BRL), 30 mL were layered over 15 mL Histopaque-1077 (Sigma) and centrifuged for 30 minutes at 300 RCF. The mononuclear interface layer was collected and washed in PBS. CD34+ cells were enriched from the mononuclear cell preparation using an affinity column per manufacturers instructions (CellPro, Inc, Bothell Wash.). After enrichment, the purity of CD34+ cells was 70% on average as determined by using flow cytometric analysis using anti CD34 monoclonal antibody conjugated to fluorescein and anti CD38 conjugated to phycoerythrin (Becton Dickinson, San Jose Calif.).

Cells were resuspended at 40,000 cells/mL in X-Vivo 10 media (Bio-Whittaker, Walkersville, Md.) and 1 mL was plated in 12-well tissue culture plates (Costar). The growth factor rhIL-3 was added at 100 ng/mL (pMON5873) was added to some wells. hIL3 variant, pMON13288, was used at 10 ng/mL or 100 ng/mL. Conditioned media from BHK cells transfected with plasmid encoding c-mpl ligand were tested by addition of 100 µl of supernatant added to 1 mL cultures (approximately a 10% dilution). Cells were incubated at 37° C. for 8–14 days at 5% $CO_2$ in a 37° C. humidified incubator.

b. Cell Harvest and Analysis

At the end of the culture period a total cell count was obtained for each condition. For fluorescence analysis and ploidy determination cells were washed in megakaryocyte buffer (MK buffer, 13.6 mM Sodium Citrate, 1 mM Theophylline, 2.2 µm PGE1, 11 mM Glucose, 3% w/v BSA, in PBS, pH 7.4,) (Tomer et al., *Blood* 70(6):1735–1742, 1987) resuspended in 500 µl of MK buffer containing anti-CD41a FITC antibody (1:200, AMAC, Westbrook, Me.) and washed in MK buffer. For DNA analysis cells were permeablized in MK buffer containing 0.5% Tween 20 (Fisher, Fair Lawn N.J.)for 20 min. on ice followed by fixation in 0.5% Tween-20 and 1% paraformaldehyde (Fisher Chemical) for 30 minutes followed by incubation in Propidium Iodide (Calbiochem, La Jolla Calif.) (50 µg/mL) with RNA-ase (400 U/mL) in 55% v/v MK buffer (200 mOsm) for 1–2 hours on ice. Cells were analyzed on a FACScan or Vantage flow cytometer (Becton Dickinson, San Jose, Calif.). Green fluorescence (CD41a-FITC) was collected along with linear and log signals for red fluorescence (PI) to determine DNA ploidy. All cells were collected to determine the percent of cells that were CD41+. Data analysis was performed using software by LYSIS (Becton Dickinson, San Jose, Calif.). Percent of cells expressing the CD41 antigen was obtained from flow cytometry analysis (Percent). Absolute (Abs) number of CD41+ cells/mL was calculated by: (Abs)=(Cell Count)*(Percent)/100.

2. Megakaryocyte Fibrin Clot Assay

CD34+ enriched population were isolated as described above. Cells were suspended at 25,000 cells/mL with/without cytokine(s) in a media consisting of a base Iscoves IMDM media supplemented with 0.3% BSA, 0.4 mg/mL apo-transferrin, 6.67 µM $FeCl_2$, 25 µg/mL $CaCl_2$, 25 µg/mL L-asparagine, 500 µg/mL E-amino-n-caproic acid and Penicillin/Streptomycin. Prior to plating into 35 mm plates, thrombin was added (0.25 Units/mL) to initiate clot formation. Cells were incubated at 37° C. for 13 days at 5% $CO_2$ in a 37° C. humidified incubator.

At the end of the culture period plates were fixed with Methanol:Acetone (1:3), air dried and stored at −200° C. until staining. A peroxidase immunocytochemistry staining procedure was used (Zymed, Histostain-SP. San Francisco, Calif.) using a cocktail of primary monoclonal antibodies consisting of anti CD41a, CD42 and CD61. Colonies were counted after staining and classified as negative, CFU-MK (small colonies, 1–2 foci and less that approx. 25 cells), BFU-MK (large, multi-foci colonies with >25 cells) or mixed colonies (mixture of both positive and negative cells.

EXAMPLE 5

Ex Vivo Expansion of CD34+ Cells from Peripheral Blood Using Chimera Molecules pMON13056 and pMON13148+/−SCF Flow Cytometry Evaluation The percentage of CD34+ cells in the thawed peripheral blood cell population was determined by flow cytometry. Cells were removed from the selected cell population and placed into two centrifuge tube and washed once in 9/1% albumin Phosphate buffer (PAB). Twenty microliters of anti-CD34 monoclonal antibody (8G12-FITC) or mouse monoclonal antibody IgG-FITC control was added to the tube. The tubes were incubated for 15 minutes on ice. The cells were washed once with PAB and resuspended in approximately 0.5 mL PAB. Propidium iodide (2 ug/mL) was added to each tube just prior to the analysis on the FACSort or FACScan. Selected cells that contain greater than 80% CD34+ cells were used to initiate the cultures.

On day 12, cultures were harvested and evaluated with CD41A-FITC (a megakaryocyte marker), CD15-FITC and CD11b-PE (early to late neutrophil marker) and CD34 by flow cytometry, using the same processes of preparation and analysis as described above.

Colony Assay Evaluation

Colony assay evaluation was performed on day 0 with 500–1000 selected CD34+ cells per dish and again on day 12 of culture with 5,000–10,000 cultured cells per dish. The cells were added to a colony assay culture tube containing 3 mL of Terry Fox Iscove's based methylcellulose and the following growth factors: 20 ng/mL SCF, 10 U/mL EPO, 300 U/mL GM-CSF, 300 U/mL G-CSF, 30 U/mL IL3 and 40 ng/mL IL6. Two 35 mm tissue culture dishes containing 1 mL were set up. All dishes were incubated at 37° C., 5% carbon dioxide, 5% oxygen and high humidity for 13–15 days. The dishes were scored for myeloid (CFU-GM), erythroid (BFU-E) or mixed myeloid and erythroid colonies (CFU-mix) using a Nikon SMZU stereoscope.

Cell Morphology Evaluation

On day 12 of culture cells were analyzed for cell morphology after Wright-Giemsa staining. Cultured cells were cytocentrifuged onto slides at 1000 rpm for 4 minutes. Each slide contained approximately 10000–20000 cells. Slides were allowed to air dry before staining with 0.5 mL Wright-Giemsa for 1 minutes and 0.5 mL tap water for 1–2 minutes. Slides were cover-slipped and evaluated using a Microstar light microscope. A differential cell count of neutrophils, megakaryocytes and other blood cells was performed.

Results

CD34+ Selection

Studies were performed on CD34+ cells selected using the Isolex™ 300 magnetic Cell Separator from apheresis products from normal donors mobilized with G-CSF. The selected cells were stored in X-VIVO 10 +12.5%HSA containing 10% DMSO in liquid nitrogen until required. Cultures were initiated as described in the methods section.

Proliferation Index of Cultures At Day 12

The proliferation index of cultures was calculated by diving the cell concentration at day 5–7 by $5 \times 10^4$ and then multiplying it by the cell concentration at day 12 divided by $1 \times 10^5$. A summary of the proliferation index obtained from these CD34+ cell cultures is shown in Table 4.

Flow Cytometry Evaluation of Neutrophil Precursors

The percentage of neutrophil precursors in the CD34+ cell cultures at day 12 was assessed by flow cytometry using the CD15 marker for early to late neutrophil precursors and the CD1b marker found on late neutrophil precursors determined is shown in Table 4.

Flow Cytometry Evaluation of Megakaryocytes

The percentage of Mks in the CD34+ cell cultures was assessed by flow cytometry using the CD41a marker for megakaryocytes. The percentage of Mks observed in the CD34+ cell cultures is shown in Table 4.

Flow Cytometry Evaluation of CD34+ Cells

The percentage of CD34+ cells present in the cultures at day 12 was determined by flow cytometry. The percentage of CD34+ cells still remaining in the cultures at day 12 ranged from 0.103–19.3%, with no significant difference or patterns observed with the different growth factor combinations.

Total Number of Megakaryocytes Generated in Culture

The total number of megakaryocytes present in each culture is calculated by multiplying the total number of cells at day 12 by the percentage of CD15+ cells and is shown in Table 4.

Colony Forming Unit Granulocyte-Macrophage (CFU-GM) Index

CFU-GM index is calculate by dividing the total number of GM-colonies obtained at day 12 by the number of GM-colonies obtained at day 0. A CFU-GM index of 1 indicates that the number of colonies at day 12 is equivalent to the number of colonies at the start of the culture. A summary of the CFU-GM index for these cultures is shown in Table 4.

Colony Forming Unit (CFU) Index

CFU index is calculated by dividing the total number of colonies (CFU-GM, BFU-E and mixed) obtained at day 12 by the total number of colonies obtained at day 0. A CFU index of 1 indicates that the number of colonies at day 12 is equivalent to the number of colonies at the start of the culture. A summary of the CFU index for these cultures is shown in Table 4.

TABLE 4

| | | Ex-vivo Expansion | | | | |
|---|---|---|---|---|---|---|
| Assay | Growth Factor | Donor #1 | Donor #2 | Donor #3 | Donor #4 | Donor #5 |
| Proliferation Index of CD34 + Cell Cultures at Day 12 | pMON13056 | 39.4 | 73.4 | ND | 5.7 | 5.7 |
| | pMON13056 + SCF | 135 | 206 | 37.4 | 17.4 | 6.4 |
| | pMON13148 | 21.4 | 23.8 | ND | ND | ND |
| | pMON13148 + SCF | 88.1 | 117.7 | ND | ND | ND |
| | native hIL-3 | 9 | 4.1 | 10.7 | 1 | 1.4 |
| | native hIL-3 + SCF | 70.5 | 61.3 | 62.3 | 22.6 | 12.2 |
| Percentage CD15 + Cells at Day 12 of CD34 + Cultures | pMON13056 | 57 | 39.6 | 61.1 | 56 | 67.5 |
| | pMON13056 + SCF | 70.8 | 45.4 | 72.7 | 46.3 | 87.4 |
| | pMON13148 | 47.3 | 58.6 | ND | ND | ND |
| | pMON13418 + SCF | 38.7 | 31.7 | ND | ND | ND |
| | native hIL-3 | 25.6 | 10.5 | 43.3 | 26 | 18.2 |
| | native hIL-3 + SCF | 17.7 | 11.5 | 55 | 12.4 | 24.2 |
| Percentage CD41 + Cells at Day 12 of CD34 + Cultures | pMON13056 | 12.6 | 16.5 | 18.2 | 3.4 | 4.6 |
| | pMON13056 + SCF | 7.4 | 8.3 | 5.5 | 4.8 | 1.8 |
| | pMON13148 | 6 | 9.1 | ND | ND | ND |
| | pMON13148 + SCF | 14.1 | 8.3 | ND | ND | ND |
| | native hIL-3 | 18.9 | 14.1 | 13.7 | 4.2 | 5.5 |
| | native hIL-3 + SCF | 15.3 | 10.7 | 12.9 | 7.4 | 15 |
| Total Number of Megakaryoctes (E + 05) In Day 10–12 Cultures | pMON13056 | 20 | 49 | ND | 0.8 | 1 |
| | pMON13056 + SCF | 40 | 68 | 8.2 | 3.4 | 0.5 |
| | pMON13148 | 5.2 | 8.7 | ND | ND | ND |
| | pMON13148 + SCF | 50 | 52 | ND | ND | ND |
| | native hIL-3 | 6.8 | 2.3 | 5.9 | 0.2 | 0.3 |
| | native hIL-3 + SCF | 43 | 26 | 32 | 16 | 7.4 |
| Colony Forming Unit Granulocyte Macrophage (CFU-GM) Index | pMON13056 | 0.9 | 3.2 | ND | 0.2 | 0.1 |
| | pMON13056 + SCF | 1 | 3 | 0.7 | 1.1 | 0.04 |
| | pMON13148 | 0.5 | 0.8 | ND | ND | ND |

TABLE 4-continued

Ex-vivo Expansion

| Assay | Growth Factor | Donor #1 | Donor #2 | Donor #3 | Donor #4 | Donor #5 |
|---|---|---|---|---|---|---|
| | pMON13148 + SCF | 1.2 | 3.2 | ND | ND | ND |
| | native hIL-3 | 0.2 | 0.06 | 0.03 | 0.03 | 0.03 |
| | native hIL-3 + SCF | 1.9 | 1.1 | 0.3 | 0.6 | 0.3 |
| Colony Forning Unit-Index | pMON13056 | 1.4 | 5.1 | ND | 0.2 | 0.2 |
| | pMON13056 + SCF | 1.3 | 4.3 | 0.3 | 1.1 | 0.2 |
| | pMON13148 | 0.7 | 1.1 | ND | ND | ND |
| | PMON13148 + SCF | 1.6 | 5.2 | ND | ND | ND |
| | native hIL-3 | 0.2 | 0.1 | 0.03 | 0.03 | 0.04 |
| | native hIL-3 + SCF | 2.7 | 1.5 | 0.3 | 0.5 | 0.4 |

EXAMPLE 5

Ex Vivo Expansion of CD34+ Cells from Bone Marrow Using pMON13056 vs. Native IL-3+/−G-CSF Cells were cultured as in Example 4 except CD34+ cells were isolated from normal bone marrow. Native IL-3, IL-3 variant (pMON13288) and G-CSF were used at 50 ng/mL and pMON13056 was used at 100 ng/ml of culture medium. Starting cell number for each treatment was 20×10E4. The total cell expansion is shown in Table 5.

TABLE 5

| Treatment | Donor 1 | Donor 2 |
|---|---|---|
| native IL-3 | 42 × 10E4 | 169 × 10E4 |
| pMON13288 | 114 × 10E4 | 259 × 10E4 |
| G-CSF | 14 × 10E4 | 32 × 10E4 |
| pMON13288 and G-CSF | 194 × 10E4 | 609 × 10E4 |
| pMON13056 | 219 × 10E4 | 621 × 10E4 |

Amino acids are shown herein by standard one letter or three letter abbreviations as follows:

| Abbreviated Designation | | Amino Acid |
|---|---|---|
| A | Ala | Alanine |
| C | Cys | Cysteine |
| D | Asp | Aspartic acid |
| E | Glu | Glutamic acid |
| F | Phe | Phenylalanine |
| G | Gly | Glycine |
| H | His | Histidine |
| I | Ile | Isoleucine |
| K | Lys | Lysine |
| L | Leu | Leucine |
| M | Met | Methionine |
| N | Asn | Asparagine |
| P | Pro | Proline |
| Q | Gln | Glutamine |
| R | Arg | Arginine |
| S | Ser | Serine |
| T | Thr | Threonine |
| V | Val | Valine |

-continued

| Abbreviated Designation | | Amino Acid |
|---|---|---|
| W | Trp | Tryptophan |
| Y | Tyr | Tyrosine |

Further details known to those skilled in the art may be found in T. Maniatis, et al., *Molecular Cloning, A Laboratory Manual*, Cold Spring Harbor Laboratory (1982) and references cited therein, incorporated herein by reference; and in J. Sambrook, et al., *Molecular Cloning, A Laboratory Manual*, 2nd edition, Cold Spring Harbor Laboratory (1989) and references cited therein, incorporated herein by reference.

Additional details on the IL-3 variants of the present invention may be found in co-pending U.S. patent application Ser. No. 08/411,795 (WO 94/12638) which is hereby incorporated by reference in its entirety as if written herein.

Additional details on how to make the chimera protein can be found in WO 95/21254, WO 92/04455 and WO 91/02754.

Additional details about the lymphokine and the variants thereof can be found in U.S. Pat. Nos. 4,810,643, and 5,218,092 and E.P. Application 02174004.

All references, patents or applications cited herein are incorporated by reference in their entirety as if written herein.

Various other examples will be apparent to the person skilled in the art after reading the present disclosure without departing from the spirit and scope of the invention. It is intended that all such other examples be included within the scope of the appended claims.

SEQUENCE LISTING (1) GENERAL INFORMATION:

(iii) NUMBER OF SEQUENCES: 196

(2) INFORMATION FOR SEQ ID NO:1:

(i) SEQUENCE CHARACTERISTICS:
       (A) LENGTH: 133 amino acids
       (B) TYPE: amino acid
       (D) TOPOLOGY: linear (ii) MOLECULE TYPE: peptide (ix) FEATURE:
       (A) NAME/KEY: Modified-site
       (B) LOCATION: 1
       (D) OTHER INFORMATION: /note= "Met- may or may not precede the
           amino acid in position 1"

(ix) FEATURE:
       (A) NAME/KEY: Modified-site
       (B) LOCATION: 17
       (D) OTHER INFORMATION: /note= "Xaa at position 17 is Ser,
           Lys, Gly, Asp, Met, Gln, or Arg"

(ix) FEATURE:
       (A) NAME/KEY: Modified-site
       (B) LOCATION: 18
       (D) OTHER INFORMATION: /note= "Xaa at position 18 is Asn,
           His, Leu, Ile, Phe, Arg, or Gln"

(ix) FEATURE:
       (A) NAME/KEY: Modified-site
       (B) LOCATION: 19
       (D) OTHER INFORMATION: /note= "Xaa at positiion 19 is Met,
           Phe, Ile, Arg, Gly, Ala, or Cys"

(ix) FEATURE:
       (A) NAME/KEY: Modified-site
       (B) LOCATION: 20
       (D) OTHER INFORMATION: /note= "Xaa at position 20 is Ile,
           Cys, Gln, Glu, Arg, Pro, or Ala"

(ix) FEATURE:
       (A) NAME/KEY: Modified-site
       (B) LOCATION: 21
       (D) OTHER INFORMATION: /note= "Xaa at position 21 is Asp,
           Phe, Lys, Arg, Ala, Gly, Glu, Gln, Asn, Thr, Ser,
           or Val"

(ix) FEATURE:
       (A) NAME/KEY: Modified-site
       (B) LOCATION: 22
       (D) OTHER INFORMATION: /note= "Xaa at position 22 is Glu,
           Trp, Pro, Ser, Ala, His, Asp, Asn, Gln, Leu, Val,
           or Gly"

(ix) FEATURE:
       (A) NAME/KEY: Modified-site
       (B) LOCATION: 23
       (D) OTHER INFORMATION: /note= "Xaa at position 23 is Ile,
           Val, Ala, Leu, Gly, Trp, Lys, Phe, Ser, or
           Arg"

(ix) FEATURE:
       (A) NAME/KEY: Modified-site
       (B) LOCATION: 24
       (D) OTHER INFORMATION: /note= "Xaa at position 24 is Ile,
           Gly, Val, Arg, Ser, Phe, or Leu"

(ix) FEATURE:
       (A) NAME/KEY: Modified-site
       (B) LOCATION: 25
       (D) OTHER INFORMATION: /note= "Xaa at position 25 is Thr,
           His, Gly, Gln, Arg, Pro, or Ala"

```
(ix) FEATURE:
    (A) NAME/KEY: Modified-site
    (B) LOCATION: 26
    (D) OTHER INFORMATION: /note= "Xaa at position 26 is His,
        Thr, Phe, Gly, Arg, Ala, or Trp"

(ix) FEATURE:
    (A) NAME/KEY: Modified-site
    (B) LOCATION: 27
    (D) OTHER INFORMATION: /note= "Xaa at position 27 is Leu,
        Gly, Arg, Thr, Ser, or Ala"

(ix) FEATURE:
    (A) NAME/KEY: Modified-site
    (B) LOCATION: 28
    (D) OTHER INFORMATION: /note= "Xaa at position 28 is Lys,
        Arg, Leu, Gln, Gly, Pro, Val, or Trp"

(ix) FEATURE:
    (A) NAME/KEY: Modified-site
    (B) LOCATION: 29
    (D) OTHER INFORMATION: /note= "Xaa at position 29 is Gln,
        Asn, Leu, Pro, Arg, or Val"

(ix) FEATURE:
    (A) NAME/KEY: Modified-site
    (B) LOCATION: 30
    (D) OTHER INFORMATION: /note= "Xaa at position 30 is Pro,
        His, Thr, Gly, Asp, Gln, Ser, Leu, or Lys"

(ix) FEATURE:
    (A) NAME/KEY: Modified-site
    (B) LOCATION: 31
    (D) OTHER INFORMATION: /note= "Xaa at position 31 is Pro,
        Asp, Gly, Ala, Arg, Leu, or Gln"

(ix) FEATURE:
    (A) NAME/KEY: Modified-site
    (B) LOCATION: 32
    (D) OTHER INFORMATION: /note= "Xaa at position 32 is Leu,
        Val, Arg, Gln, Asn, Gly, Ala, or Glu"

(ix) FEATURE:
    (A) NAME/KEY: Modified-site
    (B) LOCATION: 33
    (D) OTHER INFORMATION: /note= "Xaa at position 33 is Pro,
        Leu, Gln, Ala, Thr, or Glu"

(ix) FEATURE:
    (A) NAME/KEY: Modified-site
    (B) LOCATION: 34
    (D) OTHER INFORMATION: /note= "Xaa at position 34 is Leu,
        Val, Gly, Ser, Lys, Glu, Gln, Thr, Arg, Ala, Phe,
        Ile, or Met"

(ix) FEATURE:
    (A) NAME/KEY: Modified-site
    (B) LOCATION: 35
    (D) OTHER INFORMATION: /note= "Xaa at position 35 is Leu,
        Ala, Gly, Asn, Pro, Gln, or Val"

(ix) FEATURE:
    (A) NAME/KEY: Modified-site
    (B) LOCATION: 36
    (D) OTHER INFORMATION: /note= "Xaa at position 36 is Asp,
        Leu, or Val"

(ix) FEATURE:
    (A) NAME/KEY: Modified-site
    (B) LOCATION: 37
    (D) OTHER INFORMATION: /note= "Xaa at position 37 is Phe,
        Ser, Pro, Trp, or Ile"

(ix) FEATURE:
    (A) NAME/KEY: Modified-site
    (B) LOCATION: 38
    (D) OTHER INFORMATION: /note= "Xaa at position 38 is Asn,
        or Ala"
```

(ix) FEATURE:
      (A) NAME/KEY: Modified-site
      (B) LOCATION: 40
      (D) OTHER INFORMATION: /note= "Xaa at position 40 is Leu,
          Trp, or Arg"

(ix) FEATURE:
      (A) NAME/KEY: Modified-site
      (B) LOCATION: 41
      (D) OTHER INFORMATION: /note= "Xaa at position 41 is Asn,
          Cys, Arg, Leu, His, Met, or Pro"

(ix) FEATURE:
      (A) NAME/KEY: Modified-site
      (B) LOCATION: 42
      (D) OTHER INFORMATION: /note= "Xaa at position 42 is Gly,
          Asp, Ser, Cys, Asn, Lys, Thr, Leu, Val, Glu, Phe, Tyr,
          Ile, Met, or Ala"

(ix) FEATURE:
      (A) NAME/KEY: Modified-site
      (B) LOCATION: 43
      (D) OTHER INFORMATION: /note= "Xaa at position 43 is Glu,
          Asn, Tyr, Leu, Phe, Asp, Ala, Cys, Gln, Arg, Thr, Gly,
          or Ser"

(ix) FEATURE:
      (A) NAME/KEY: Modified-site
      (B) LOCATION: 44
      (D) OTHER INFORMATION: /note= "Xaa at position 44 is Asp,
          Ser, Leu, Arg, Lys, Thr, Met, Trp, Glu, Asn, Gln, Ala,
          or Pro"

(ix) FEATURE:
      (A) NAME/KEY: Modified-site
      (B) LOCATION: 45
      (D) OTHER INFORMATION: /note= "Xaa at position 45 is Gln,
          Pro, Phe, Val, Met, Leu, Thr, Lys, Trp, Asp, Asn, Arg,
          Ser, Ala, Ile, Glu, or His"

(ix) FEATURE:
      (A) NAME/KEY: Modified-site
      (B) LOCATION: 46
      (D) OTHER INFORMATION: /note= "Xaa at position 46 is Asp,
          Phe, Ser, Thr, Cys, Glu, Asn, Gln, Lys, His, Ala, Tyr,
          Ile, Val, or Gly"

(ix) FEATURE:
      (A) NAME/KEY: Modified-site
      (B) LOCATION: 47
      (D) OTHER INFORMATION: /note= "Xaa at position 47 is Ile,
          Gly, Val, Ser, Arg, Pro, or His"

(ix) FEATURE:
      (A) NAME/KEY: Modified-site
      (B) LOCATION: 48
      (D) OTHER INFORMATION: /note= "Xaa at position 48 is Leu,
          Ser, Cys, Arg, Ile, His, Phe, Glu, Lys, Thr, Ala, Met,
          Val, or Asn"

(ix) FEATURE:
      (A) NAME/KEY: Modified-site
      (B) LOCATION: 49
      (D) OTHER INFORMATION: /note= "Xaa at position 49 is Met,
          Arg, Ala, Gly, Pro, Asn, His, or Asp"

(ix) FEATURE:
      (A) NAME/KEY: Modified-site
      (B) LOCATION: 50
      (D) OTHER INFORMATION: /note= "Xaa at position 50 is Glu,
          Leu, Thr, Asp, Tyr, Lys, Asn, Ser, Ala, Ile, Val, His,
          Phe, Met, or Gln"

(ix) FEATURE:
      (A) NAME/KEY: Modified-site
      (B) LOCATION: 51
      (D) OTHER INFORMATION: /note= "Xaa at position 51 is Asn,
          Arg, Met, Pro, Ser, Thr, or His"

```
(ix) FEATURE:
    (A) NAME/KEY: Modified-site
    (B) LOCATION: 52
    (D) OTHER INFORMATION: /note= "Xaa at position 52 is Asn,
        His, Arg, Leu, Gly, Ser, or Thr"

(ix) FEATURE:
    (A) NAME/KEY: Modified-site
    (B) LOCATION: 53
    (D) OTHER INFORMATION: /note= "Xaa at position 53 is
        Leu, Thr, Ala, Gly, Glu, Pro, Lys, Ser, or Met"

(ix) FEATURE:
    (A) NAME/KEY: Modified-site
    (B) LOCATION: 54
    (D) OTHER INFORMATION: /note= "Xaa at position 54 is Arg,
        Asp, Ile, Ser, Val, Thr, Gln, Asn, Lys, His, Ala,
        or Leu"

(ix) FEATURE:
    (A) NAME/KEY: Modified-site
    (B) LOCATION: 55
    (D) OTHER INFORMATION: /note= "Xaa at position 55 is Arg,
        Thr, Val, Ser, Leu, or Gly"

(ix) FEATURE:
    (A) NAME/KEY: Modified-site
    (B) LOCATION: 56
    (D) OTHER INFORMATION: /note= "Xaa at position 56 is Pro,
        Gly, Cys, Ser, Gln, Glu, Arg, His, Thr, Ala, Tyr,
        Phe, Leu, Val, or Lys"

(ix) FEATURE:
    (A) NAME/KEY: Modified-site
    (B) LOCATION: 57
    (D) OTHER INFORMATION: /note= "Xaa at position 57 is Asn
        or Gly"

(ix) FEATURE:
    (A) NAME/KEY: Modified-site
    (B) LOCATION: 58
    (D) OTHER INFORMATION: /note= "Xaa at position 58 is Leu,
        Ser, Asp, Arg, Gln, Val, or Cys"

(ix) FEATURE:
    (A) NAME/KEY: Modified-site
    (B) LOCATION: 59
    (D) OTHER INFORMATION: /note= "Xaa at position 59 is Glu,
        Tyr, His, Leu, Pro, or Arg"

(ix) FEATURE:
    (A) NAME/KEY: Modified-site
    (B) LOCATION: 60
    (D) OTHER INFORMATION: /note= "Xaa at position 60 is Ala,
        Ser, Pro, Tyr, Asn, or Thr"

(ix) FEATURE:
    (A) NAME/KEY: Modified-site
    (B) LOCATION: 61
    (D) OTHER INFORMATION: /note= "Xaa at position 61 is Phe,
        Asn, Glu, Pro, Lys, Arg, or Ser"

(ix) FEATURE:
    (A) NAME/KEY: Modified-site
    (B) LOCATION: 62
    (D) OTHER INFORMATION: /note= "Xaa at position 62 is Asn,
        His, Val, Arg, Pro, Thr, Asp, or Ile"

(ix) FEATURE:
    (A) NAME/KEY: Modified-site
    (B) LOCATION: 63
    (D) OTHER INFORMATION: /note= "Xaa at position 63 is Arg,
        Tyr, Trp, Lys, Ser, His, Pro, or Val"

(ix) FEATURE:
    (A) NAME/KEY: Modified-site
    (B) LOCATION: 64
    (D) OTHER INFORMATION: /note= "Xaa at position 64 is Ala,
```

```
              Asn, Pro, Ser, or Lys"

(ix) FEATURE:
     (A) NAME/KEY: Modified-site
     (B) LOCATION: 65
     (D) OTHER INFORMATION: /note= "Xaa at position 65 is Val,
              Thr, Pro, His, Leu, Phe, or Ser"

(ix) FEATURE:
     (A) NAME/KEY: Modified-site
     (B) LOCATION: 66
     (D) OTHER INFORMATION: /note= "Xaa at position 66 is Lys,
              Ile, Arg, Val, Asn, Glu, or Ser"

(ix) FEATURE:
     (A) NAME/KEY: Modified-site
     (B) LOCATION: 67
     (D) OTHER INFORMATION: /note= "Xaa at position 67 is Ser,
              Ala, Phe, Val, Gly, Asn, Ile, Pro, or His"

(ix) FEATURE:
     (A) NAME/KEY: Modified-site
     (B) LOCATION: 68
     (D) OTHER INFORMATION: /note= "Xaa at position 68 is Leu,
              Val, Trp, Ser, Ile, Phe, Thr, or His"

(ix) FEATURE:
     (A) NAME/KEY: Modified-site
     (B) LOCATION: 69
     (D) OTHER INFORMATION: /note= "Xaa at position 69 is Gln,
              Ala, Pro, Thr, Glu, Arg, Trp, Gly, or Leu"

(ix) FEATURE:
     (A) NAME/KEY: Modified-site
     (B) LOCATION: 70
     (D) OTHER INFORMATION: /note= "Xaa at position 70 is Asn,
              Leu, Val, Trp, Pro, or Ala"

(ix) FEATURE:
     (A) NAME/KEY: Modified-site
     (B) LOCATION: 71
     (D) OTHER INFORMATION: /note= "Xaa at position 71 is
              Ala, Met, Leu, Pro, Arg, Glu, Thr, Gln, Trp,
              or Asn"

(ix) FEATURE:
     (A) NAME/KEY: Modified-site
     (B) LOCATION: 72
     (D) OTHER INFORMATION: /note= "Xaa at position 72 is Ser,
              Glu, Met, Ala, His, Asn, Arg, or Asp"

(ix) FEATURE:
     (A) NAME/KEY: Modified-site
     (B) LOCATION: 73
     (D) OTHER INFORMATION: /note= "Xaa at position 73 is Ala,
              Glu, Asp, Leu, Ser, Gly, Thr, or Arg"

(ix) FEATURE:
     (A) NAME/KEY: Modified-site
     (B) LOCATION: 74
     (D) OTHER INFORMATION: /note= "Xaa at position 74 is Ile,
              Met, Thr, Pro, Arg, Gly, or Ala"

(ix) FEATURE:
     (A) NAME/KEY: Modified-site
     (B) LOCATION: 75
     (D) OTHER INFORMATION: /note= "Xaa at position 75 is
              Glu, Lys, Gly, Asp, Pro, Trp, Arg, Ser, Gln,
              or Leu"

(ix) FEATURE:
     (A) NAME/KEY: Modified-site
     (B) LOCATION: 76
     (D) OTHER INFORMATION: /note= "Xaa at position 76 is Ser,
              Val, Ala, Asn, Trp, Glu, Pro, Gly, or Asp"

(ix) FEATURE:
     (A) NAME/KEY: Modified-site
     (B) LOCATION: 77
```

```
            (D) OTHER INFORMATION: /note= "Xaa at position 77 is Ile,
                Ser, Arg, Thr, or Leu"

(ix) FEATURE:
            (A) NAME/KEY: Modified-site
            (B) LOCATION: 78
            (D) OTHER INFORMATION: /note= "Xaa at position 78 is Leu,
                Ala, Ser, Glu, Phe, Gly, or Arg"

(ix) FEATURE:
            (A) NAME/KEY: Modified-site
            (B) LOCATION: 79
            (D) OTHER INFORMATION: /note= "Xaa at position 79 is Lys, Thr,
                Asn, Met, Arg, Ile, Gly, or Asp"

(ix) FEATURE:
            (A) NAME/KEY: Modified-site
            (B) LOCATION: 80
            (D) OTHER INFORMATION: /note= "Xaa at position 80 is Asn,
                Trp, Val, Gly, Thr, Leu, Glu, or Arg"

(ix) FEATURE:
            (A) NAME/KEY: Modified-site
            (B) LOCATION: 81
            (D) OTHER INFORMATION: /note= "Xaa at position 81 is Leu,
                Gln, Gly, Ala, Trp, Arg, Val, or Lys"

(ix) FEATURE:
            (A) NAME/KEY: Modified-site
            (B) LOCATION: 82
            (D) OTHER INFORMATION: /note= "Xaa at position 82 is Leu,
                Gln, Lys, Trp, Arg, Asp, Glu, Asn, His, Thr, Ser, Ala,
                Tyr, Phe, Ile, Met, or Val"

(ix) FEATURE:
            (A) NAME/KEY: Modified-site
            (B) LOCATION: 83
            (D) OTHER INFORMATION: /note= "Xaa at position 83 is Pro,
                Ala, Thr, Trp, Arg, or Met"

(ix) FEATURE:
            (A) NAME/KEY: Modified-site
            (B) LOCATION: 84
            (D) OTHER INFORMATION: /note= "Xaa at position 84 is Cys,
                Glu, Gly, Arg, Met, or Val"

(ix) FEATURE:
            (A) NAME/KEY: Modified-site
            (B) LOCATION: 85
            (D) OTHER INFORMATION: /note= "Xaa at position 85 is Leu,
                Asn, Val, or Gln"

(ix) FEATURE:
            (A) NAME/KEY: Modified-site
            (B) LOCATION: 86
            (D) OTHER INFORMATION: /note= "Xaa at position 86 is Pro,
                Cys, Arg, Ala, or Lys"

(ix) FEATURE:
            (A) NAME/KEY: Modified-site
            (B) LOCATION: 87
            (D) OTHER INFORMATION: /note= "Xaa at position 87 is Leu,
                Ser, Trp, or Gly"

(ix) FEATURE:
            (A) NAME/KEY: Modified-site
            (B) LOCATION: 88
            (D) OTHER INFORMATION: /note= "Xaa at position 88 is Ala,
                Lys, Arg, Val, or Trp"

(ix) FEATURE:
            (A) NAME/KEY: Modified-site
            (B) LOCATION: 89
            (D) OTHER INFORMATION: /note= "Xaa at position 89 is Thr,
                Asp, Cys, Leu, Val, Glu, His, Asn, or Ser"

(ix) FEATURE:
            (A) NAME/KEY: Modified-site
            (B) LOCATION: 90
```

(D) OTHER INFORMATION: /note= "Xaa at position 90 is Ala,
               Pro, Ser, Thr, Gly, Asp, Ile, or Met"

(ix) FEATURE:
           (A) NAME/KEY: Modified-site
           (B) LOCATION: 91
           (D) OTHER INFORMATION: /note= "Xaa at position 91 is Ala,
               Pro, Ser, Thr, Phe, Leu, Asp, or His"

(ix) FEATURE:
           (A) NAME/KEY: Modified-site
           (B) LOCATION: 92
           (D) OTHER INFORMATION: /note= "Xaa at position 92 is Pro,
               Phe, Arg, Ser, Lys, His, Ala, Gly, Ile, or Leu"

(ix) FEATURE:
           (A) NAME/KEY: Modified-site
           (B) LOCATION: 93
           (D) OTHER INFORMATION: /note= "Xaa at position 93 is Thr,
               Asp, Ser, Asn, Pro, Ala, Leu, or Arg"

(ix) FEATURE:
           (A) NAME/KEY: Modified-site
           (B) LOCATION: 94
           (D) OTHER INFORMATION: /note= "Xaa at position 94 is Arg,
               Ile, Ser, Glu, Leu, Val, Gln, Lys, His, Ala, or Pro"

(ix) FEATURE:
           (A) NAME/KEY: Modified-site
           (B) LOCATION: 95
           (D) OTHER INFORMATION: /note= "Xaa at position 95 is His,
               Gln, Pro, Arg, Val, Leu, Gly, Thr, Asn, Lys, Ser, Ala,
               Trp, Phe, Ile, or Tyr"

(ix) FEATURE:
           (A) NAME/KEY: Modified-site
           (B) LOCATION: 96
           (D) OTHER INFORMATION: /note= "Xaa at position 96 is Pro,
               Lys, Tyr, Gly, Ile, or Thr"

(ix) FEATURE:
           (A) NAME/KEY: Modified-site
           (B) LOCATION: 97
           (D) OTHER INFORMATION: /note= "Xaa at position 97 is Ile,
               Val, Lys, Ala, or Asn"

(ix) FEATURE:
           (A) NAME/KEY: Modified-site
           (B) LOCATION: 98
           (D) OTHER INFORMATION: /note= "Xaa at position 98 is His,
               Ile, Asn, Leu, Asp, Ala, Thr, Glu, Gln, Ser, Phe, Met,
               Val, Lys, Arg, Tyr, or Pro"

(ix) FEATURE:
           (A) NAME/KEY: Modified-site
           (B) LOCATION: 99
           (D) OTHER INFORMATION: /note= "Xaa at position 99 is Ile,
               Leu, Arg, Asp, Val, Pro, Gln, Gly, Ser, Phe,
               or His"

(ix) FEATURE:
           (A) NAME/KEY: Modified-site
           (B) LOCATION: 100
           (D) OTHER INFORMATION: /note= "Xaa at position 100 is
               Lys, Tyr, Leu, His, Arg, Ile, Ser, Gln, or Pro"

(ix) FEATURE:
           (A) NAME/KEY: Modified-site
           (B) LOCATION: 101
           (D) OTHER INFORMATION: /note= "Xaa at position 101 is
               Asp, Pro, Met, Lys, His, Thr, Val, Tyr, Glu, Asn, Ser,
               Ala, Gly, Ile, Leu, or Gln"

(ix) FEATURE:
           (A) NAME/KEY: Modified-site
           (B) LOCATION: 102
           (D) OTHER INFORMATION: /note= "Xaa at position 102 is Gly,
               Leu, Glu, Lys, Ser, Tyr, or Pro"

-continued

```
(ix) FEATURE:
     (A) NAME/KEY: Modified-site
     (B) LOCATION: 103
     (D) OTHER INFORMATION: /note= "Xaa at position 103 is Asp,
         or Ser"

(ix) FEATURE:
     (A) NAME/KEY: Modified-site
     (B) LOCATION: 104
     (D) OTHER INFORMATION: /note= "Xaa at position 104 is
         Trp, Val, Cys, Tyr, Thr, Met, Pro, Leu, Gln, Lys, Ala,
         Phe, or Gly"

(ix) FEATURE:
     (A) NAME/KEY: Modified-site
     (B) LOCATION: 105
     (D) OTHER INFORMATION: /note= "Xaa at position 105 is
         Asn, Pro, Ala, Phe, Ser, Trp, Gln, Tyr, Leu, Lys, Ile,
         Asp, or His"

(ix) FEATURE:
     (A) NAME/KEY: Modified-site
     (B) LOCATION: 106
     (D) OTHER INFORMATION: /note= "Xaa at position 106 is Glu,
         Ser, Ala, Lys, Thr, Ile, Gly, or Pro"

(ix) FEATURE:
     (A) NAME/KEY: Modified-site
     (B) LOCATION: 108
     (D) OTHER INFORMATION: /note= "Xaa at position 108 is Arg,
         Lys, Asp, Leu, Thr, Ile, Gln, His, Ser, Ala, or Pro"

(ix) FEATURE:
     (A) NAME/KEY: Modified-site
     (B) LOCATION: 109
     (D) OTHER INFORMATION: /note= "Xaa at position 109 is Arg,
         Thr, Pro, Glu, Tyr, Leu, Ser, or Gly"

(ix) FEATURE:
     (A) NAME/KEY: Modified-site
     (B) LOCATION: 110
     (D) OTHER INFORMATION: /note= "Xaa at position 110 is Lys,
         Ala, Asn, Thr, Leu, Arg, Gln, His, Glu, Ser, or Trp"

(ix) FEATURE:
     (A) NAME/KEY: Modified-site
     (B) LOCATION: 111
     (D) OTHER INFORMATION: /note= "Xaa at position 111 is Leu,
         Ile, Arg, Asp, or Met"

(ix) FEATURE:
     (A) NAME/KEY: Modified-site
     (B) LOCATION: 112
     (D) OTHER INFORMATION: /note= "Xaa at position 112 is Thr,
         Val, Gln, Tyr, Glu, His, Ser, or Phe"

(ix) FEATURE:
     (A) NAME/KEY: Modified-site
     (B) LOCATION: 113
     (D) OTHER INFORMATION: /note= "Xaa at position 113 is Phe,
         Ser, Cys, His, Gly, Trp, Tyr, Asp, Lys, Leu, Ile, Val,
         or Asn"

(ix) FEATURE:
     (A) NAME/KEY: Modified-site
     (B) LOCATION: 114
     (D) OTHER INFORMATION: /note= "Xaa at position 114 is Tyr,
         Cys, His, Ser, Trp, Arg, or Leu"

(ix) FEATURE:
     (A) NAME/KEY: Modified-site
     (B) LOCATION: 115
     (D) OTHER INFORMATION: /note= "Xaa at position 115 is
         Leu, Asn, Val, Pro, Arg, Ala, His, Thr, Trp, or
         Met"

(ix) FEATURE:
     (A) NAME/KEY: Modified-site
     (B) LOCATION: 116
```

(D) OTHER INFORMATION: /note= "Xaa at position 116 is Lys, Leu, Pro, Thr, Met, Asp, Val, Glu, Arg, Trp, Ser, Asn, His, Ala, Tyr, Phe, Gln, or Ile"

(ix) FEATURE:
  (A) NAME/KEY: Modified-site
  (B) LOCATION: 117
  (D) OTHER INFORMATION: /note= "Xaa at position 117 is Thr, Ser, Asn, Ile, Trp, Lys, or Pro"

(ix) FEATURE:
  (A) NAME/KEY: Modified-site
  (B) LOCATION: 118
  (D) OTHER INFORMATION: /note= "Xaa at position 118 is Leu, Ser, Pro, Ala, Glu, Cys, Asp, or Tyr"

(ix) FEATURE:
  (A) NAME/KEY: Modified-site
  (B) LOCATION: 119
  (D) OTHER INFORMATION: /note= "Xaa at position 119 is Glu, Ser, Lys, Pro, Leu, Thr, Tyr, or Arg"

(ix) FEATURE:
  (A) NAME/KEY: Modified-site
  (B) LOCATION: 120
  (D) OTHER INFORMATION: /note= "Xaa at position 120 is Asn, Ala, Pro, Leu, His, Val, or Gln"

(ix) FEATURE:
  (A) NAME/KEY: Modified-site
  (B) LOCATION: 121
  (D) OTHER INFORMATION: /note= "Xaa at position 121 is Ala, Ser, Ile, Asn, Pro, Lys, Asp, or Gly"

(ix) FEATURE:
  (A) NAME/KEY: Modified-site
  (B) LOCATION: 122
  (D) OTHER INFORMATION: /note= "Xaa at position 122 is Gln, Ser, Met, Trp, Arg, Phe, Pro, His, Ile, Tyr, or Cys"

(ix) FEATURE:
  (A) NAME/KEY: Modified-site
  (B) LOCATION: 123
  (D) OTHER INFORMATION: /note= "Xaa at position 123 is Ala, Met, Glu, His, Ser, Pro, Tyr, or Leu"

(xi) SEQUENCE DESCRIPTION: SEQ ID NO:1:

```
Ala Pro Met Thr Gln Thr Thr Ser Leu Lys Thr Ser Trp Val Asn Cys
1               5                   10                  15

Xaa Xaa Xaa Xaa Xaa Xaa Xaa Xaa Xaa Xaa Xaa Xaa Xaa Xaa Xaa Xaa
                20                  25                  30

Xaa Xaa Xaa Xaa Xaa Xaa Asn Xaa Xaa Xaa Xaa Xaa Xaa Xaa Xaa Xaa
            35                  40                  45

Xaa Xaa Xaa Xaa Xaa Xaa Xaa Xaa Xaa Xaa Xaa Xaa Xaa Xaa Xaa Xaa
50                  55                  60

Xaa Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa Xaa Xaa Xaa Xaa Xaa Xaa Xaa Xaa
            85                  90                  95

Xaa Xaa Xaa Xaa Xaa Xaa Xaa Xaa Xaa Phe Xaa Xaa Xaa Xaa Xaa
            100                 105                 110

Xaa Xaa Xaa Xaa Xaa Xaa Xaa Xaa Xaa Xaa Xaa Gln Gln Thr Thr Leu
        115                 120                 125

Ser Leu Ala Ile Phe
        130
```

(2) INFORMATION FOR SEQ ID NO:2:

```
    (i) SEQUENCE CHARACTERISTICS:
        (A) LENGTH: 133 amino acids
        (B) TYPE: amino acid
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /note= "Met- may or may not precede
            the amino acid in position 1"

(ix) FEATURE:
        (A) NAME/KEY: Modified-site
        (B) LOCATION: 17
        (D) OTHER INFORMATION: /note= "Xaa at position 17 is Ser,
            Gly, Asp, Met, or Gln"

(ix) FEATURE:
        (A) NAME/KEY: Modified-site
        (B) LOCATION: 18
        (D) OTHER INFORMATION: /note= "Xaa at position 18 is Asn,
            His, or Ile"

(ix) FEATURE:
        (A) NAME/KEY: Modified-site
        (B) LOCATION: 19
        (D) OTHER INFORMATION: /note= "Xaa at position 19 is Met
            or Ile"

(ix) FEATURE:
        (A) NAME/KEY: Modified-site
        (B) LOCATION: 21
        (D) OTHER INFORMATION: /note="Xaa at position 21 is Asp
            or Glu"

(ix) FEATURE:
        (A) NAME/KEY: Modified-site
        (B) LOCATION: 23
        (D) OTHER INFORMATION: /note= "Xaa at position 23 is Ile,
            Ala, Leu, or Gly"

(ix) FEATURE:
        (A) NAME/KEY: Modified-site
        (B) LOCATION: 24
        (D) OTHER INFORMATION: /note= "Xaa at position 24 is Ile,
            Val, or Leu"

(ix) FEATURE:
        (A) NAME/KEY: Modified-site
        (B) LOCATION: 25
        (D) OTHER INFORMATION: /note= "Xaa at position 25 is Thr,
            His, Gln, or Ala"

(ix) FEATURE:
        (A) NAME/KEY: Modified-site
        (B) LOCATION: 26
        (D) OTHER INFORMATION: /note= "Xaa at position 26 is His
            or Ala"

(ix) FEATURE:
        (A) NAME/KEY: Modified-site
        (B) LOCATION: 29
        (D) OTHER INFORMATION: /note= "Xaa at position 29 is Gln,
            Asn, or Val"

(ix) FEATURE:
        (A) NAME/KEY: Modified-site
        (B) LOCATION: 30
        (D) OTHER INFORMATION: /note= "Xaa at position 30 is Pro,
            Gly, or Gln"

(ix) FEATURE:
        (A) NAME/KEY: Modified-site
        (B) LOCATION: 31
        (D) OTHER INFORMATION: /note= "Xaa at position 31 is Pro,
            Asp, Gly, or Gln"
```

-continued

```
(ix) FEATURE:
    (A) NAME/KEY: Modified-site
    (B) LOCATION: 32
    (D) OTHER INFORMATION: /note= "Xaa at position 32 is Leu,
        Arg, Gln, Asn, Gly, Ala, or Glu"

(ix) FEATURE:
    (A) NAME/KEY: Modified-site
    (B) LOCATION: 33
    (D) OTHER INFORMATION: /note= "Xaa at position 33 is Pro
        or Glu"

(ix) FEATURE:
    (A) NAME/KEY: Modified-site
    (B) LOCATION: 34
    (D) OTHER INFORMATION: /note= "Xaa at position 34 is Leu,
        Val, Gly, Ser, Lys, Ala, Arg, Gln, Glu, Ile, Phe,
        Thr, or Met"

(ix) FEATURE:
    (A) NAME/KEY: Modified-site
    (B) LOCATION: 35
    (D) OTHER INFORMATION: /note= "Xaa at position 35 is Leu,
        Ala, Asn, Pro, Gln, or Val"

(ix) FEATURE:
    (A) NAME/KEY: Modified-site
    (B) LOCATION: 37
    (D) OTHER INFORMATION: /note= "Xaa at position 37 is Phe,
        Ser, Pro, or Trp"

(ix) FEATURE:
    (A) NAME/KEY: Modified-site
    (B) LOCATION: 38
    (D) OTHER INFORMATION: /note="Xaa at position 38 is Asn
        or Ala"

(ix) FEATURE:
    (A) NAME/KEY: Modified-site
    (B) LOCATION: 42
    (D) OTHER INFORMATION: /note= "Xaa at position 42 is Gly,
        Asp, Ser, Cys, Ala, Asn, Ile, Leu, Met, Tyr,
        or Arg"

(ix) FEATURE:
    (A) NAME/KEY: Modified-site
    (B) LOCATION: 44
    (D) OTHER INFORMATION: /note="Xaa at position 44 is Asp
        or Glu"

(ix) FEATURE:
    (A) NAME/KEY: Modified-site
    (B) LOCATION: 45
    (D) OTHER INFORMATION: /note= "Xaa at position 45 is Gln,
        Val, Met, Leu, Thr, Ala, Asn, Glu, Ser, or Lys"

(ix) FEATURE:
    (A) NAME/KEY: Modified-site
    (B) LOCATION: 46
    (D) OTHER INFORMATION: /note= "Xaa at position 46 is Asp,
        Phe, Ser, Thr, Ala, Asn, Gln, Glu, His, Ile,
        Lys, Tyr, Val, or Cys"

(ix) FEATURE:
    (A) NAME/KEY: Modified-site
    (B) LOCATION: 50
    (D) OTHER INFORMATION: /note= "Xaa at position 50 is Glu,
        Ala, Asn, Ser, or Asp"

(ix) FEATURE:
    (A) NAME/KEY: Modified-site
    (B) LOCATION: 51
    (D) OTHER INFORMATION: /note= "Xaa at position 51 is Asn,
        Arg, Met, Pro, Ser, Thr, or His"

(ix) FEATURE:
    (A) NAME/KEY: Modified-site
    (B) LOCATION: 54
    (D) OTHER INFORMATION: /note="Xaa at position 54 is Arg
``` or Ala"

(ix) FEATURE:
    (A) NAME/KEY: Modified-site
    (B) LOCATION: 55
    (D) OTHER INFORMATION: /note= "Xaa at position 55 is Arg,
        Thr, Val, Leu, or Gly"

(ix) FEATURE:
    (A) NAME/KEY: Modified-site
    (B) LOCATION: 56
    (D) OTHER INFORMATION: /note= "Xaa at position 56 is Pro,
        Gly, Ser, Gln, Ala, Arg, Asn, Glu, Leu, Thr, Val,
        or Lys"

(ix) FEATURE:
    (A) NAME/KEY: Modified-site
    (B) LOCATION: 60
    (D) OTHER INFORMATION: /note= "Xaa at position 60 is Ala
        or Ser"

(ix) FEATURE:
    (A) NAME/KEY: Modified-site
    (B) LOCATION: 62
    (D) OTHER INFORMATION: /note= "Xaa at position 62 is Asn,
        Pro, Thr, or Ile"

(ix) FEATURE:
    (A) NAME/KEY: Modified-site
    (B) LOCATION: 63
    (D) OTHER INFORMATION: /note= "Xaa at position 63 is Arg
        or Lys"

(ix) FEATURE:
    (A) NAME/KEY: Modified-site
    (B) LOCATION: 64
    (D) OTHER INFORMATION: /note= "Xaa at position 64 is Ala
        or Asn"

(ix) FEATURE:
    (A) NAME/KEY: Modified-site
    (B) LOCATION: 65
    (D) OTHER INFORMATION: /note= "Xaa at position 65 is Val
        or Thr"

(ix) FEATURE:
    (A) NAME/KEY: Modified-site
    (B) LOCATION: 66
    (D) OTHER INFORMATION: /note= "Xaa at position 66 is Lys
        or Arg"

(ix) FEATURE:
    (A) NAME/KEY: Modified-site
    (B) LOCATION: 67
    (D) OTHER INFORMATION: /note= "Xaa at position 67 is Ser
        Phe or His"

(ix) FEATURE:
    (A) NAME/KEY: Modified-site
    (B) LOCATION: 68
    (D) OTHER INFORMATION: /note= "Xaa at position 68 is Leu,
        Ile, Phe, or His"

(ix) FEATURE:
    (A) NAME/KEY: Modified-site
    (B) LOCATION: 69
    (D) OTHER INFORMATION: /note= "Xaa at position 69 is Gln,
        Ala, Pro, Thr, Glu, Arg, or Gly"

(ix) FEATURE:
    (A) NAME/KEY: Modified-site
    (B) LOCATION: 71
    (D) OTHER INFORMATION: /note= "Xaa at position 71 is Ala,
        Pro, or Arg"

(ix) FEATURE:
    (A) NAME/KEY: Modified-site
    (B) LOCATION: 72
    (D) OTHER INFORMATION: /note= "Xaa at position 72 is Ser, Glu, Arg, or Asp"

(ix) FEATURE:
    (A) NAME/KEY: Modified-site
    (B) LOCATION: 73
    (D) OTHER INFORMATION: /note= "Xaa at position 73 is Ala
        or Leu"

(ix) FEATURE:
    (A) NAME/KEY: Modified-site
    (B) LOCATION: 76
    (D) OTHER INFORMATION: /note= "Xaa at position 76 is Ser,
        Val, Ala, Asn, Glu, Pro, or Gly"

(ix) FEATURE:
    (A) NAME/KEY: Modified-site
    (B) LOCATION: 77
    (D) OTHER INFORMATION: /note= "Xaa at position 77 is Ile
        or Leu"

(ix) FEATURE:
    (A) NAME/KEY: Modified-site
    (B) LOCATION: 79
    (D) OTHER INFORMATION: /note= "Xaa at position 79 is
        Lys, Thr, Gly, Asn, Met, Arg, Ile, or Asp"

(ix) FEATURE:
    (A) NAME/KEY: Modified-site
    (B) LOCATION: 80
    (D) OTHER INFORMATION: /note= "Xaa at position 80 is Asn,
        Gly, Glu, or Arg"

(ix) FEATURE:
    (A) NAME/KEY: Modified-site
    (B) LOCATION: 82
    (D) OTHER INFORMATION: /note= "Xaa at position 82 is Leu,
        Gln, Trp, Arg, Asp, Ala, Asn, Glu, His, Ile,
        Met, Phe, Ser, Thr, Tyr, or Val"

(ix) FEATURE:
    (A) NAME/KEY: Modified-site
    (B) LOCATION: 83
    (D) OTHER INFORMATION: /note= "Xaa at position 83 is Pro
        or Thr"

(ix) FEATURE:
    (A) NAME/KEY: Modified-site
    (B) LOCATION: 85
    (D) OTHER INFORMATION: /note= "Xaa at position 85 is Leu
        or Val"

(ix) FEATURE:
    (A) NAME/KEY: Modified-site
    (B) LOCATION: 87
    (D) OTHER INFORMATION: /note= "Xaa at position 87 is Leu
        or Ser"

(ix) FEATURE:
    (A) NAME/KEY: Modified-site
    (B) LOCATION: 88
    (D) OTHER INFORMATION: /note= "Xaa at position 88 is Ala
        or Trp"

(ix) FEATURE:
    (A) NAME/KEY: Modified-site
    (B) LOCATION: 91
    (D) OTHER INFORMATION: /note= "Xaa at position 91 is Ala
        or Pro"

(ix) FEATURE:
    (A) NAME/KEY: Modified-site
    (B) LOCATION: 93
    (D) OTHER INFORMATION: /note= "Xaa at position 93 is Thr,
        Asp, Ser, Pro, Ala, Leu, or Arg"

(ix) FEATURE:
    (A) NAME/KEY: Modified-site
    (B) LOCATION: 95
    (D) OTHER INFORMATION: /note= "Xaa at position 95 is His, Pro, Arg, Val, Leu, Gly, Asn, Phe, Ser, or Thr"

(ix) FEATURE:
    (A) NAME/KEY: Modified-site
    (B) LOCATION: 96
    (D) OTHER INFORMATION: /note= "Xaa at position 96 is Pro
        or Tyr"

(ix) FEATURE:
    (A) NAME/KEY: Modified-site
    (B) LOCATION: 97
    (D) OTHER INFORMATION: /note= "Xaa at position 97 is Ile
        or Val"

(ix) FEATURE:
    (A) NAME/KEY: Modified-site
    (B) LOCATION: 98
    (D) OTHER INFORMATION: /note= "Xaa at position 98 is His,
        Ile, Asn, Leu, Ala, Thr, Arg, Gln, Lys,
        Met, Ser, Tyr, Val, or Pro"

(ix) FEATURE:
    (A) NAME/KEY: Modified-site
    (B) LOCATION: 99
    (D) OTHER INFORMATION: /note= "Xaa at position 99 is Ile,
        Leu, or Val"

(ix) FEATURE:
    (A) NAME/KEY: Modified-site
    (B) LOCATION: 100
    (D) OTHER INFORMATION: /note= "Xaa at position 100 is Lys,
        Arg, Ile, Gln, Pro, or Ser"

(ix) FEATURE:
    (A) NAME/KEY: Modified-site
    (B) LOCATION: 101
    (D) OTHER INFORMATION: /note= "Xaa at position 101 is Asp,
        Pro, Met, Lys, Thr, His, Asn, Ile, Leu, or Tyr"

(ix) FEATURE:
    (A) NAME/KEY: Modified-site
    (B) LOCATION: 104
    (D) OTHER INFORMATION: /note= "Xaa at position 104 is Trp
        or Leu"

(ix) FEATURE:
    (A) NAME/KEY: Modified-site
    (B) LOCATION: 105
    (D) OTHER INFORMATION: /note= "Xaa at position 105 is
        Asn, Pro, Ala, Ser, Trp, Gln, Tyr, Leu, Lys, Ile,
        Asp, or His"

(ix) FEATURE:
    (A) NAME/KEY: Modified-site
    (B) LOCATION: 106
    (D) OTHER INFORMATION: /note= "Xaa at position 106 is Glu
        or Gly"

(ix) FEATURE:
    (A) NAME/KEY: Modified-site
    (B) LOCATION: 108
    (D) OTHER INFORMATION: /note="Xaa at position 108 is Arg,
        Ala, or Ser"

(ix) FEATURE:
    (A) NAME/KEY: Modified-site
    (B) LOCATION: 109
    (D) OTHER INFORMATION: /note= "Xaa at position 109 is Arg,
        Thr, Glu, Leu, or Ser"

(ix) FEATURE:
    (A) NAME/KEY: Modified-site
    (B) LOCATION: 112
    (D) OTHER INFORMATION: /note= "Xaa at position 112 is Thr,
        Val, or Gln"

(ix) FEATURE:
    (A) NAME/KEY: Modified-site
    (B) LOCATION: 114

(D) OTHER INFORMATION: /note= "Xaa at position 114 is Tyr
                or Trp"

(ix) FEATURE:
            (A) NAME/KEY: Modified-site
            (B) LOCATION: 115
            (D) OTHER INFORMATION: /note= "Xaa at position 115 is Leu
                or Ala"

(ix) FEATURE:
            (A) NAME/KEY: Modified-site
            (B) LOCATION: 116
            (D) OTHER INFORMATION: /note= "Xaa at position 116 is Lys,
                Thr, Val, Trp, Ser, Ala, His, Met, Phe, Tyr, or Ile"

(ix) FEATURE:
            (A) NAME/KEY: Modified-site
            (B) LOCATION: 117
            (D) OTHER INFORMATION: /note= "Xaa at position 117 is Thr
                or Ser"

(ix) FEATURE:
            (A) NAME/KEY: Modified-site
            (B) LOCATION: 120
            (D) OTHER INFORMATION: /note= "Xaa at position 120 is Asn,
                Pro, Leu, His, Val, or Gln"

(ix) FEATURE:
            (A) NAME/KEY: Modified-site
            (B) LOCATION: 121
            (D) OTHER INFORMATION: /note= "Xaa at position 121 is Ala,
                Ser, Ile, Asn, Pro, Asp, or Gly"

(ix) FEATURE:
            (A) NAME/KEY: Modified-site
            (B) LOCATION: 122
            (D) OTHER INFORMATION: /note= "Xaa at position 122 is
                Gln, Ser, Met, Trp, Arg, Phe, Pro, His, Ile, Tyr,
                or Cys"

(ix) FEATURE:
            (A) NAME/KEY: Modified-site
            (B) LOCATION: 123
            (D) OTHER INFORMATION: /note= "Xaa at position 123 is Ala,
                Met, Glu, His, Ser, Pro, Tyr, or Leu"

(xi) SEQUENCE DESCRIPTION: SEQ ID NO:2:

Ala Pro Met Thr Gln Thr Thr Ser Leu Lys Thr Ser Trp Val Asn Cys
1               5                   10                  15

Xaa Xaa Xaa Ile Xaa Glu Xaa Xaa Xaa Xaa Leu Lys Xaa Xaa Xaa Xaa
                20                  25                  30

Xaa Xaa Xaa Asp Xaa Xaa Asn Leu Asn Xaa Glu Xaa Xaa Xaa Ile Leu
            35                  40                  45

Met Xaa Xaa Asn Leu Xaa Xaa Xaa Asn Leu Glu Xaa Phe Xaa Xaa Xaa
    50                  55                  60

Xaa Xaa Xaa Xaa Xaa Asn Xaa Xaa Xaa Ile Glu Xaa Xaa Leu Xaa Xaa
65                  70                  75                  80

Leu Xaa Xaa Cys Xaa Pro Xaa Xaa Thr Ala Xaa Pro Xaa Arg Xaa Xaa
            85                  90                  95

Xaa Xaa Xaa Xaa Xaa Gly Asp Xaa Xaa Xaa Phe Xaa Xaa Lys Leu Xaa
                100                 105                 110

Phe Xaa Xaa Xaa Xaa Leu Glu Xaa Xaa Xaa Xaa Gln Gln Thr Thr Leu
        115                 120                 125

Ser Leu Ala Ile Phe
        130

(2) INFORMATION FOR SEQ ID NO:3:

(i) SEQUENCE CHARACTERISTICS:

```
        (A) LENGTH: 133 amino acids
        (B) TYPE: amino acid
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /note= "Met- may or may not precede
            the amino acid in position 1"

(ix) FEATURE:
        (A) NAME/KEY: Modified-site
        (B) LOCATION: 17
        (D) OTHER INFORMATION: /note= "Xaa at position 17 is Ser,
            Gly, Asp, or Gln"

(ix) FEATURE:
        (A) NAME/KEY: Modified-site
        (B) LOCATION: 18
        (D) OTHER INFORMATION: /note= "Xaa at position 18 is Asn,
            His, or Ile"

(ix) FEATURE:
        (A) NAME/KEY: Modified-site
        (B) LOCATION: 23
        (D) OTHER INFORMATION: /note= "Xaa at position 23 is Ile,
            Ala, Leu, or Gly"

(ix) FEATURE:
        (A) NAME/KEY: Modified-site
        (B) LOCATION: 25
        (D) OTHER INFORMATION: /note= "Xaa at position 25 is Thr,
            His, or Gln"

(ix) FEATURE:
        (A) NAME/KEY: Modified-site
        (B) LOCATION: 26
        (D) OTHER INFORMATION: /note= "Xaa at position 26 is His
            or Ala"

(ix) FEATURE:
        (A) NAME/KEY: Modified-site
        (B) LOCATION: 29
        (D) OTHER INFORMATION: /note="Xaa at position 29 is Gln
            or Asn"

(ix) FEATURE:
        (A) NAME/KEY: Modified-site
        (B) LOCATION: 30
        (D) OTHER INFORMATION: /note= "Xaa at position 30 is Pro
            or Gly"

(ix) FEATURE:
        (A) NAME/KEY: Modified-site
        (B) LOCATION: 32
        (D) OTHER INFORMATION: /note= "Xaa at position 32 is Leu,
            Arg, Asn, or Ala"

(ix) FEATURE:
        (A) NAME/KEY: Modified-site
        (B) LOCATION: 34
        (D) OTHER INFORMATION: /note= "Xaa at position 34 is Leu,
            Val, Ser, Ala, Arg, Gln, Glu, Ile, Phe, Thr, or Met"

(ix) FEATURE:
        (A) NAME/KEY: Modified-site
        (B) LOCATION: 35
        (D) OTHER INFORMATION: /note= "Xaa at position 35 is Leu,
            Ala, Asn, or Pro"

(ix) FEATURE:
        (A) NAME/KEY: Modified-site
        (B) LOCATION: 38
        (D) OTHER INFORMATION: /note= "Xaa at position 38 is Asn
            or Ala"

(ix) FEATURE:
```

```
            (A) NAME/KEY: Modified-site
            (B) LOCATION: 42
            (D) OTHER INFORMATION: /note= "Xaa at position 42 is Gly,
                Asp, Ser, Ala, Asn, Ile, Leu, Met, Tyr, or Arg"

(ix) FEATURE:
            (A) NAME/KEY: Modified-site
            (B) LOCATION: 45
            (D) OTHER INFORMATION: /note= "Xaa at position 45 is Gln,
                Val, Met, Leu, Ala, Asn, Glu, or Lys"

(ix) FEATURE:
            (A) NAME/KEY: Modified-site
            (B) LOCATION: 46
            (D) OTHER INFORMATION: /note= "Xaa at position 46 is Asp,
                Phe, Ser, Gln, Glu, His, Val, or Thr"

(ix) FEATURE:
            (A) NAME/KEY: Modified-site
            (B) LOCATION: 50
            (D) OTHER INFORMATION: /note= "Xaa at position 50 is Glu,
                Asn, Ser, or Asp"

(ix) FEATURE:
            (A) NAME/KEY: Modified-site
            (B) LOCATION: 51
            (D) OTHER INFORMATION: /note= "Xaa at position 51 is Asn,
                Arg, Pro, Thr, or His"

(ix) FEATURE:
            (A) NAME/KEY: Modified-site
            (B) LOCATION: 55
            (D) OTHER INFORMATION: /note= "Xaa at position 55 is Arg,
                Leu, or Gly"

(ix) FEATURE:
            (A) NAME/KEY: Modified-site
            (B) LOCATION: 56
            (D) OTHER INFORMATION: /note= "Xaa at position 56 is Pro,
                Gly, Ser, Ala, Asn, Val, Leu, or Gln"

(ix) FEATURE:
            (A) NAME/KEY: Modified-site
            (B) LOCATION: 62
            (D) OTHER INFORMATION: /note= "Xaa at position 62 is Asn,
                Pro, or Thr"

(ix) FEATURE:
            (A) NAME/KEY: Modified-site
            (B) LOCATION: 64
            (D) OTHER INFORMATION: /note= "Xaa at position 64 is Ala
                or Asn"

(ix) FEATURE:
            (A) NAME/KEY: Modified-site
            (B) LOCATION: 65
            (D) OTHER INFORMATION: /note= "Xaa at position 65 is Val
                or Thr"

(ix) FEATURE:
            (A) NAME/KEY: Modified-site
            (B) LOCATION: 67
            (D) OTHER INFORMATION: /note= "Xaa at position 67 is Ser
                or Phe"

(ix) FEATURE:
            (A) NAME/KEY: Modified-site
            (B) LOCATION: 68
            (D) OTHER INFORMATION: /note= "Xaa at position 68 is Leu
                or Phe"

(ix) FEATURE:
            (A) NAME/KEY: Modified-site
            (B) LOCATION: 69
            (D) OTHER INFORMATION: /note= "Xaa at position 69 is Gln,
                Ala, Glu, or Arg"

(ix) FEATURE:
            (A) NAME/KEY: Modified-site
```

```
       (B) LOCATION: 76
       (D) OTHER INFORMATION: /note= "Xaa at position 76 is Ser,
           Val, Asn, Pro, or Gly"

(ix) FEATURE:
       (A) NAME/KEY: Modified-site
       (B) LOCATION: 77
       (D) OTHER INFORMATION: /note= "Xaa at position 77 is Ile
           or Leu"

(ix) FEATURE:
       (A) NAME/KEY: Modified-site
       (B) LOCATION: 79
       (D) OTHER INFORMATION: /note= "Xaa at position 79 is Lys,
           Asn, Met, Arg, Ile, or Gly"

(ix) FEATURE:
       (A) NAME/KEY: Modified-site
       (B) LOCATION: 80
       (D) OTHER INFORMATION: /note= "Xaa at position 80 is Asn,
           Gly, Glu, or Arg"

(ix) FEATURE:
       (A) NAME/KEY: Modified-site
       (B) LOCATION: 82
       (D) OTHER INFORMATION: /note= "Xaa at position 82 is Leu,
           Gln, Trp, Arg, Asp, Asn, Glu, His, Met, Phe, Ser,
           Thr, Tyr, or Val"

(ix) FEATURE:
       (A) NAME/KEY: Modified-site
       (B) LOCATION: 87
       (D) OTHER INFORMATION: /note= "Xaa at position 87 is Leu
           or Ser"

(ix) FEATURE:
       (A) NAME/KEY: Modified-site
       (B) LOCATION: 88
       (D) OTHER INFORMATION: /note= "Xaa at position 88 is Ala
           or Trp"

(ix) FEATURE:
       (A) NAME/KEY: Modified-site
       (B) LOCATION: 91
       (D) OTHER INFORMATION: /note= "Xaa at position 91 is Ala
           or Pro"

(ix) FEATURE:
       (A) NAME/KEY: Modified-site
       (B) LOCATION: 93
       (D) OTHER INFORMATION: /note= "Xaa at position 93 is Thr,
           Asp, or Ala"

(ix) FEATURE:
       (A) NAME/KEY: Modified-site
       (B) LOCATION: 95
       (D) OTHER INFORMATION: /note= "Xaa at position 95 is His,
           Pro, Arg, Val, Gly, Asn, Ser, or Thr"

(ix) FEATURE:
       (A) NAME/KEY: Modified-site
       (B) LOCATION: 98
       (D) OTHER INFORMATION: /note= "Xaa at position 98 is His,
           Ile, Asn, Ala, Thr, Gln, Glu, Lys, Met, Ser, Tyr,
           Val, or Leu"

(ix) FEATURE:
       (A) NAME/KEY: Modified-site
       (B) LOCATION: 99
       (D) OTHER INFORMATION: /note= "Xaa at position 99 is Ile
           or Leu"

(ix) FEATURE:
       (A) NAME/KEY: Modified-site
       (B) LOCATION: 100
       (D) OTHER INFORMATION: /note= "Xaa at position 100 is Lys
           or Arg"

(ix) FEATURE:
```

(A) NAME/KEY: Modified-site
          (B) LOCATION: 101
          (D) OTHER INFORMATION: /note= "Xaa at position 101 is Asp,
              Pro, Met, Lys, Thr, His, Asn, Ile, Leu, or Tyr"

(ix) FEATURE:
          (A) NAME/KEY: Modified-site
          (B) LOCATION: 105
          (D) OTHER INFORMATION: /note= "Xaa at position 105 is Asn,
              Pro, Ser, Ile, or Asp"

(ix) FEATURE:
          (A) NAME/KEY: Modified-site
          (B) LOCATION: 108
          (D) OTHER INFORMATION: /note= "Xaa at position 108 is Arg, Ala,
              or Ser"

(ix) FEATURE:
          (A) NAME/KEY: Modified-site
          (B) LOCATION: 109
          (D) OTHER INFORMATION: /note= "Xaa at position 109 is Arg,
              Thr, Glu, Leu, or Ser"

(ix) FEATURE:
          (A) NAME/KEY: Modified-site
          (B) LOCATION: 112
          (D) OTHER INFORMATION: /note= "Xaa at position 112 is Thr
              or Gln"

(ix) FEATURE:
          (A) NAME/KEY: Modified-site
          (B) LOCATION: 116
          (D) OTHER INFORMATION: /note= "Xaa at position 116 is Lys,
              Val, Trp, Ala, His, Phe, Tyr, or Ile"

(ix) FEATURE:
          (A) NAME/KEY: Modified-site
          (B) LOCATION: 117
          (D) OTHER INFORMATION: /note= "Xaa at position 117 is Thr
              or Ser"

(ix) FEATURE:
          (A) NAME/KEY: Modified-site
          (B) LOCATION: 120
          (D) OTHER INFORMATION: /note= "Xaa at position 120 is Asn,
              Pro, Leu, His, Val, or Gln"

(ix) FEATURE:
          (A) NAME/KEY: Modified-site
          (B) LOCATION: 121
          (D) OTHER INFORMATION: /note= "Xaa at position 121 is Ala,
              Ser, Ile, Pro, or Asp"

(ix) FEATURE:
          (A) NAME/KEY: Modified-site
          (B) LOCATION: 122
          (D) OTHER INFORMATION: /note= "Xaa at position 122 is Gln,
              Met, Trp, Phe, Pro, His, Ile, or Tyr"

(ix) FEATURE:
          (A) NAME/KEY: Modified-site
          (B) LOCATION: 123
          (D) OTHER INFORMATION: /note= "Xaa at position 123 is Ala,
              Met, Glu, Ser, or Leu"

(xi) SEQUENCE DESCRIPTION: SEQ ID NO:3:

Ala Pro Met Thr Gln Thr Thr Ser Leu Lys Thr Ser Trp Val Asn Cys
 1               5                  10                  15

Xaa Xaa Met Ile Asp Glu Xaa Ile Xaa Xaa Leu Lys Xaa Xaa Pro Xaa
                20                  25                  30

Pro Xaa Xaa Asp Phe Xaa Asn Leu Asn Xaa Glu Asp Xaa Xaa Ile Leu
            35                  40                  45

Met Xaa Xaa Asn Leu Arg Xaa Xaa Asn Leu Glu Ala Phe Xaa Arg Xaa
 50                  55                  60

```
Xaa Lys Xaa Xaa Xaa Asn Ala Ser Ala Ile Glu Xaa Xaa Leu Xaa Xaa
 65              70                  75                  80

Leu Xaa Pro Cys Leu Pro Xaa Xaa Thr Ala Xaa Pro Xaa Arg Xaa Pro
             85                  90                  95

Ile Xaa Xaa Xaa Xaa Gly Asp Trp Xaa Glu Phe Xaa Xaa Lys Leu Xaa
            100                 105                 110

Phe Tyr Leu Xaa Xaa Leu Glu Xaa Xaa Xaa Gln Gln Thr Thr Leu
            115                 120                 125

Ser Leu Ala Ile Phe
    130
```

(2) INFORMATION FOR SEQ ID NO:4:

(i) SEQUENCE CHARACTERISTICS:
        (A) LENGTH: 111 amino acids
        (B) TYPE: amino acid
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /note= "Met- or Met-Ala- may or may
            not precede the amino acid in position 1"

(ix) FEATURE:
        (A) NAME/KEY: Modified-site
        (B) LOCATION: 3
        (D) OTHER INFORMATION: /note= "Xaa at position 3 is Ser,
            Lys, Gly, Asp, Met, Gln, or Arg"

(ix) FEATURE:
        (A) NAME/KEY: Modified-site
        (B) LOCATION: 4
        (D) OTHER INFORMATION: /note= "Xaa at position 4 is Asn,
            His, Leu, Ile, Phe, Arg, or Gln"

(ix) FEATURE:
        (A) NAME/KEY: Modified-site
        (B) LOCATION: 5
        (D) OTHER INFORMATION: /note= "Xaa at position 5 is Met,
            Phe, Ile, Arg, Gly, Ala, or Cys"

(ix) FEATURE:
        (A) NAME/KEY: Modified-site
        (B) LOCATION: 6
        (D) OTHER INFORMATION: /note= "Xaa at position 6 is Ile,
            Cys, Gln, Glu, Arg, Pro, or Ala"

(ix) FEATURE:
        (A) NAME/KEY: Modified-site
        (B) LOCATION: 7
        (D) OTHER INFORMATION: /note= "Xaa at position 7 is Asp,
            Phe, Lys, Arg, Ala, Gly, Glu, Gln, Asn, Thr, Ser,
            or Val"

(ix) FEATURE:
        (A) NAME/KEY: Modified-site
        (B) LOCATION: 8
        (D) OTHER INFORMATION: /note= "Xaa at position 8 is Glu,
            Trp, Pro, Ser, Ala, His, Asp, Asn, Gln, Leu, Val,
            or Gly"

(ix) FEATURE:
        (A) NAME/KEY: Modified-site
        (B) LOCATION: 9
        (D) OTHER INFORMATION: /note= "Xaa at position 9 is
            Ile, Val, Ala, Leu, Gly, Trp, Lys, Phe, Ser or Arg"

(ix) FEATURE:
        (A) NAME/KEY: Modified-site
        (B) LOCATION: 10
        (D) OTHER INFORMATION: /note= "Xaa at position 10 is Ile, -continued Gly, Val, Arg, Ser, Phe, or Leu"

(ix) FEATURE:
  (A) NAME/KEY: Modified-site
  (B) LOCATION: 11
  (D) OTHER INFORMATION: /note= "Xaa at position 11 is Thr,
    His, Gly, Gln, Arg, Pro, or Ala"

(ix) FEATURE:
  (A) NAME/KEY: Modified-site
  (B) LOCATION: 12
  (D) OTHER INFORMATION: /note= "Xaa at position 12 is His,
    Thr, Phe, Gly, Arg, Ala, or Trp"

(ix) FEATURE:
  (A) NAME/KEY: Modified-site
  (B) LOCATION: 13
  (D) OTHER INFORMATION: /note= "Xaa at position 13 is Leu,
    Gly, Arg, Thr, Ser, or Ala"

(ix) FEATURE:
  (A) NAME/KEY: Modified-site
  (B) LOCATION: 14
  (D) OTHER INFORMATION: /note= "Xaa at position 14 is Lys,
    Arg, Leu, Gln, Gly, Pro, Val, or Trp"

(ix) FEATURE:
  (A) NAME/KEY: Modified-site
  (B) LOCATION: 15
  (D) OTHER INFORMATION: /note= "Xaa at position 15 is Gln,
    Asn, Leu, Pro, Arg, or Val"

(ix) FEATURE:
  (A) NAME/KEY: Modified-site
  (B) LOCATION: 16
  (D) OTHER INFORMATION: /note= "Xaa at position 16 is Pro,
    His, Thr, Gly, Asp, Gln, Ser, Leu, or Lys"

(ix) FEATURE:
  (A) NAME/KEY: Modified-site
  (B) LOCATION: 17
  (D) OTHER INFORMATION: /note= "Xaa at position 17 is Pro,
    Asp, Gly, Ala, Arg, Leu, or Gln"

(ix) FEATURE:
  (A) NAME/KEY: Modified-site
  (B) LOCATION: 18
  (D) OTHER INFORMATION: /note= "Xaa at position 18 is Leu,
    Val, Arg, Gln, Asn, Gly, Ala, or Glu"

(ix) FEATURE:
  (A) NAME/KEY: Modified-site
  (B) LOCATION: 19
  (D) OTHER INFORMATION: /note= "Xaa at position 19 is Pro,
    Leu, Gln, Ala, Thr, or Glu"

(ix) FEATURE:
  (A) NAME/KEY: Modified-site
  (B) LOCATION: 20
  (D) OTHER INFORMATION: /note= "Xaa at position 20 is Leu,
    Val, Gly, Ser, Lys, Glu, Gln, Thr, Arg, Ala, Phe,
    Ile, or Met"

(ix) FEATURE:
  (A) NAME/KEY: Modified-site
  (B) LOCATION: 21
  (D) OTHER INFORMATION: /note= "Xaa at position 21 is Leu,
    Ala, Gly, Asn, Pro, Gln, or Val"

(ix) FEATURE:
  (A) NAME/KEY: Modified-site
  (B) LOCATION: 22
  (D) OTHER INFORMATION: /note= "Xaa at position 22 is Asp,
    Leu, or Val"

(ix) FEATURE:
  (A) NAME/KEY: Modified-site
  (B) LOCATION: 23
  (D) OTHER INFORMATION: /note= "Xaa at position 23 is Phe,

```
                    Ser, Pro, Trp, or Ile"
(ix) FEATURE:
    (A) NAME/KEY: Modified-site
    (B) LOCATION: 24
    (D) OTHER INFORMATION: /note= "Xaa at position 24 is Asn
        or Ala"

(ix) FEATURE:
    (A) NAME/KEY: Modified-site
    (B) LOCATION: 26
    (D) OTHER INFORMATION: /note= "Xaa at position 26 is Leu,
        Trp, or Arg"

(ix) FEATURE:
    (A) NAME/KEY: Modified-site
    (B) LOCATION: 27
    (D) OTHER INFORMATION: /note= "Xaa at position 27 is Asn,
        Cys, Arg, Leu, His, Met, or Pro"

(ix) FEATURE:
    (A) NAME/KEY: Modified-site
    (B) LOCATION: 28
    (D) OTHER INFORMATION: /note= "Xaa at position 28 is Gly,
        Asp, Ser, Cys, Ala, Lys, Asn, Thr, Leu, Val, Glu,
        Phe, Tyr, Ile, or Met"

(ix) FEATURE:
    (A) NAME/KEY: Modified-site
    (B) LOCATION: 29
    (D) OTHER INFORMATION: /note= "Xaa at position 29 is Glu,
        Asn, Tyr, Leu, Phe, Asp, Ala, Cys, Gln, Arg, Thr,
        Gly, or Ser"

(ix) FEATURE:
    (A) NAME/KEY: Modified-site
    (B) LOCATION: 30
    (D) OTHER INFORMATION: /note= "Xaa at position 30 is Asp,
        Ser, Leu, Arg, Lys, Thr, Met, Trp, Glu, Asn, Gln,
        Ala, or Pro"

(ix) FEATURE:
    (A) NAME/KEY: Modified-site
    (B) LOCATION: 31
    (D) OTHER INFORMATION: /note= "Xaa at position 31 is Gln,
        Pro, Phe, Val, Met, Leu, Thr, Lys, Asp, Asn, Arg,
        Ser, Ala, Ile, Glu, His, or Trp"

(ix) FEATURE:
    (A) NAME/KEY: Modified-site
    (B) LOCATION: 32
    (D) OTHER INFORMATION: /note= "Xaa at position 32 is Asp,
        Phe, Ser, Thr, Cys, Glu, Asn, Gln, Lys, His, Ala,
        Tyr, Ile, Val, or Gly"

(ix) FEATURE:
    (A) NAME/KEY: Modified-site
    (B) LOCATION: 33
    (D) OTHER INFORMATION: /note= "Xaa at position 33 is Ile,
        Gly, Val, Ser, Arg, Pro, or His"

(ix) FEATURE:
    (A) NAME/KEY: Modified-site
    (B) LOCATION: 34
    (D) OTHER INFORMATION: /note= "Xaa at position 34 is Leu,
        Ser, Cys, Arg, Ile, His, Phe, Glu, Lys, Thr, Ala,
        Met, Val, or Asn"

(ix) FEATURE:
    (A) NAME/KEY: Modified-site
    (B) LOCATION: 35
    (D) OTHER INFORMATION: /note= "Xaa at position 35 is Met,
        Arg, Ala, Gly, Pro, Asn, His, or Asp"

(ix) FEATURE:
    (A) NAME/KEY: Modified-site
    (B) LOCATION: 36
    (D) OTHER INFORMATION: /note= "Xaa at position 36 is Glu,
        Leu, Thr, Asp, Tyr, Lys, Asn, Ser, Ala, Ile, Val,
```

His, Phe, Met, or Gln"

(ix) FEATURE:
        (A) NAME/KEY: Modified-site
        (B) LOCATION: 37
        (D) OTHER INFORMATION: /note= "Xaa at position 37 is Asn,
            Arg, Met, Pro, Ser, Thr, or His"

(ix) FEATURE:
        (A) NAME/KEY: Modified-site
        (B) LOCATION: 38
        (D) OTHER INFORMATION: /note= "Xaa at position 38 is Asn,
            His, Arg, Leu, Gly, Ser, or Thr"

(ix) FEATURE:
        (A) NAME/KEY: Modified-site
        (B) LOCATION: 39
        (D) OTHER INFORMATION: /note= "Xaa at position 39 is
            Leu, Thr, Ala, Gly, Glu, Pro, Lys, Ser, or Met"

(ix) FEATURE:
        (A) NAME/KEY: Modified-site
        (B) LOCATION: 40
        (D) OTHER INFORMATION: /note= "Xaa at position 40 is Arg,
            Asp, Ile, Ser, Val, Thr, Gln, Asn, Lys, His,
            Ala, or Leu"

(ix) FEATURE:
        (A) NAME/KEY: Modified-site
        (B) LOCATION: 41
        (D) OTHER INFORMATION: /note= "Xaa at position 41 is Arg,
            Thr, Val, Ser, Leu, or Gly"

(ix) FEATURE:
        (A) NAME/KEY: Modified-site
        (B) LOCATION: 42
        (D) OTHER INFORMATION: /note= "Xaa at position 42 is Pro,
            Gly, Cys, Ser, Gln, Glu, Arg, His, Thr, Ala, Tyr,
            Phe, Leu, Val, or Lys"

(ix) FEATURE:
        (A) NAME/KEY: Modified-site
        (B) LOCATION: 43
        (D) OTHER INFORMATION: /note= "Xaa at position 43 is Asn
            or Gly"

(ix) FEATURE:
        (A) NAME/KEY: Modified-site
        (B) LOCATION: 44
        (D) OTHER INFORMATION: /note= "Xaa at position 44 is Leu,
            Ser, Asp, Arg, Gln, Val, or Cys"

(ix) FEATURE:
        (A) NAME/KEY: Modified-site
        (B) LOCATION: 45
        (D) OTHER INFORMATION: /note= "Xaa at position 45 is Glu,
            Tyr, His, Leu, Pro, or Arg"

(ix) FEATURE:
        (A) NAME/KEY: Modified-site
        (B) LOCATION: 46
        (D) OTHER INFORMATION: /note= "Xaa at position 46 is Ala,
            Ser, Pro, Tyr, Asn, or Thr"

(ix) FEATURE:
        (A) NAME/KEY: Modified-site
        (B) LOCATION: 47
        (D) OTHER INFORMATION: /note= "Xaa at position 47 is Phe,
            Asn, Glu, Pro, Lys, Arg, or Ser"

(ix) FEATURE:
        (A) NAME/KEY: Modified-site
        (B) LOCATION: 48
        (D) OTHER INFORMATION: /note= "Xaa at position 48 is Asn,
            His, Val, Arg, Pro, Thr, Asp, or Ile"

(ix) FEATURE:
        (A) NAME/KEY: Modified-site
        (B) LOCATION: 49

```
              (D) OTHER INFORMATION: /note= "Xaa at position 49 is Arg,
                  Tyr, Trp, Lys, Ser, His, Pro, or Val"

(ix) FEATURE:
              (A) NAME/KEY: Modified-site
              (B) LOCATION: 50
              (D) OTHER INFORMATION: /note= "Xaa at position 50 is Ala,
                  Asn, Pro, Ser, or Lys"

(ix) FEATURE:
              (A) NAME/KEY: Modified-site
              (B) LOCATION: 51
              (D) OTHER INFORMATION: /note= "Xaa at position 51 is Val,
                  Thr, Pro, His, Leu, Phe, or Ser"

(ix) FEATURE:
              (A) NAME/KEY: Modified-site
              (B) LOCATION: 52
              (D) OTHER INFORMATION: /note= "Xaa at position 52 is Lys,
                  Ile, Arg, Val, Asn, Glu, or Ser"

(ix) FEATURE:
              (A) NAME/KEY: Modified-site
              (B) LOCATION: 53
              (D) OTHER INFORMATION: /note= "Xaa at position 53 is Ser,
                  Ala, Phe, Val, Gly, Asn, Ile, Pro, or His"

(ix) FEATURE:
              (A) NAME/KEY: Modified-site
              (B) LOCATION: 54
              (D) OTHER INFORMATION: /note= "Xaa at position 54 is Leu,
                  Val, Trp, Ser, Ile, Phe, Thr, or His"

(ix) FEATURE:
              (A) NAME/KEY: Modified-site
              (B) LOCATION: 55
              (D) OTHER INFORMATION: /note= "Xaa at position 55 is Gln,
                  Ala, Pro, Thr, Glu, Arg, Trp, Gly, or Leu"

(ix) FEATURE:
              (A) NAME/KEY: Modified-site
              (B) LOCATION: 56
              (D) OTHER INFORMATION: /note= "Xaa at position 56 is Asn,
                  Leu, Val, Trp, Pro, or Ala"

(ix) FEATURE:
              (A) NAME/KEY: Modified-site
              (B) LOCATION: 57
              (D) OTHER INFORMATION: /note= "Xaa at position 57 is Ala,
                  Met, Leu, Pro, Arg, Glu, Thr, Gln, Trp, or Asn"

(ix) FEATURE:
              (A) NAME/KEY: Modified-site
              (B) LOCATION: 58
              (D) OTHER INFORMATION: /note= "Xaa at position 58 is Ser,
                  Glu, Met, Ala, His, Asn, Arg, or Asp"

(ix) FEATURE:
              (A) NAME/KEY: Modified-site
              (B) LOCATION: 59
              (D) OTHER INFORMATION: /note= "Xaa at position 59 is Ala,
                  Glu, Asp, Leu, Ser, Gly, Thr, or Arg"

(ix) FEATURE:
              (A) NAME/KEY: Modified-site
              (B) LOCATION: 60
              (D) OTHER INFORMATION: /note= "Xaa at position 60 is Ile,
                  Met, Thr, Pro, Arg, Gly, Ala"

(ix) FEATURE:
              (A) NAME/KEY: Modified-site
              (B) LOCATION: 61
              (D) OTHER INFORMATION: /note= "Xaa at position 61 is
                  Glu, Lys, Gly, Asp, Pro, Trp, Arg, Ser, Gln,
                  or Leu"

(ix) FEATURE:
              (A) NAME/KEY: Modified-site
              (B) LOCATION: 62
```

(D) OTHER INFORMATION: /note= "Xaa at position 62 is Ser,
                Val, Ala, Asn, Trp, Glu, Pro, Gly, or Asp"

(ix) FEATURE:
            (A) NAME/KEY: Modified-site
            (B) LOCATION: 63
            (D) OTHER INFORMATION: /note= "Xaa at position 63 is Ile,
                Ser, Arg, Thr, or Leu"

(ix) FEATURE:
            (A) NAME/KEY: Modified-site
            (B) LOCATION: 64
            (D) OTHER INFORMATION: /note= "Xaa at position 64 is Leu,
                Ala, Ser, Glu, Phe, Gly, or Arg"

(ix) FEATURE:
            (A) NAME/KEY: Modified-site
            (B) LOCATION: 65
            (D) OTHER INFORMATION: /note= "Xaa at position 65 is Lys,
                Thr, Gly, Asn, Met, Arg, Ile, or Asp"

(ix) FEATURE:
            (A) NAME/KEY: Modified-site
            (B) LOCATION: 66
            (D) OTHER INFORMATION: /note= "Xaa at position 66 is Asn,
                Trp, Val, Gly, Thr, Leu, Glu, or Arg"

(ix) FEATURE:
            (A) NAME/KEY: Modified-site
            (B) LOCATION: 67
            (D) OTHER INFORMATION: /note= "Xaa at position 67 is Leu,
                Gln, Gly, Ala, Trp, Arg, Val, or Lys"

(ix) FEATURE:
            (A) NAME/KEY: Modified-site
            (B) LOCATION: 68
            (D) OTHER INFORMATION: /note= "Xaa at position 68 is Leu,
                Gln, Lys, Trp, Arg, Asp, Glu, Asn, His, Thr, Ser, Ala,
                Tyr, Phe, Ile, Met, or Val"

(ix) FEATURE:
            (A) NAME/KEY: Modified-site
            (B) LOCATION: 69
            (D) OTHER INFORMATION: /note= "Xaa at position 69 is Pro,
                Ala, Thr, Trp, Arg, or Met"

(ix) FEATURE:
            (A) NAME/KEY: Modified-site
            (B) LOCATION: 70
            (D) OTHER INFORMATION: /note= "Xaa at position 70 is Cys,
                Glu, Gly, Arg, Met, or Val"

(ix) FEATURE:
            (A) NAME/KEY: Modified-site
            (B) LOCATION: 71
            (D) OTHER INFORMATION: /note= "Xaa at position 71 is Leu,
                Asn, Val, or Gln"

(ix) FEATURE:
            (A) NAME/KEY: Modified-site
            (B) LOCATION: 72
            (D) OTHER INFORMATION: /note= "Xaa at position 72 is Pro,
                Cys, Arg, Ala, or Lys"

(ix) FEATURE:
            (A) NAME/KEY: Modified-site
            (B) LOCATION: 73
            (D) OTHER INFORMATION: /note= "Xaa at position 73 is Leu,
                Ser, Trp, or Gly"

(ix) FEATURE:
            (A) NAME/KEY: Modified-site
            (B) LOCATION: 74
            (D) OTHER INFORMATION: /note= "Xaa at position 74 is Ala,
                Lys, Arg, Val, or Trp"

(ix) FEATURE:
            (A) NAME/KEY: Modified-site
            (B) LOCATION: 75

```
        (D) OTHER INFORMATION: /note= "Xaa at position 75 is Thr,
            Asp, Cys, Leu, Val, Glu, His, Asn, or Ser"

(ix) FEATURE:
        (A) NAME/KEY: Modified-site
        (B) LOCATION: 76
        (D) OTHER INFORMATION: /note= "Xaa at position 76 is Ala,
            Pro, Ser, Thr, Gly, Asp, Ile, or Met"

(ix) FEATURE:
        (A) NAME/KEY: Modified-site
        (B) LOCATION: 77
        (D) OTHER INFORMATION: /note= "Xaa at position 77 is Ala,
            Pro, Ser, Thr, Phe, Leu, Asp, or His"

(ix) FEATURE:
        (A) NAME/KEY: Modified-site
        (B) LOCATION: 78
        (D) OTHER INFORMATION: /note= "Xaa at position 78 is Pro,
            Phe, Arg, Ser, Lys, His, Ala, Gly, Ile, or Leu"

(ix) FEATURE:
        (A) NAME/KEY: Modified-site
        (B) LOCATION: 79
        (D) OTHER INFORMATION: /note= "Xaa at position 79 is Thr,
            Asp, Ser, Asn, Pro, Ala, Leu, or Arg"

(ix) FEATURE:
        (A) NAME/KEY: Modified-site
        (B) LOCATION: 80
        (D) OTHER INFORMATION: /note= "Xaa at position 80 is Arg,
            Ile, Ser, Glu, Leu, Val, Gln, Lys, His, Ala, or Pro"

(ix) FEATURE:
        (A) NAME/KEY: Modified-site
        (B) LOCATION: 81
        (D) OTHER INFORMATION: /note= "Xaa at position 81 is His,
            Gln, Pro, Arg, Val, Leu, Gly, Thr, Asn, Lys, Ser,
            Ala, Trp, Phe, Ile, or Tyr"

(ix) FEATURE:
        (A) NAME/KEY: Modified-site
        (B) LOCATION: 82
        (D) OTHER INFORMATION: /note= "Xaa at position 82 is Pro,
            Lys, Tyr, Gly, Ile, or Thr"

(ix) FEATURE:
        (A) NAME/KEY: Modified-site
        (B) LOCATION: 83
        (D) OTHER INFORMATION: /note= "Xaa at position 83 is Ile,
            Val, Lys, Ala, or Asn"

(ix) FEATURE:
        (A) NAME/KEY: Modified-site
        (B) LOCATION: 84
        (D) OTHER INFORMATION: /note= "Xaa at position 84 is His,
            Ile, Asn, Leu, Asp, Ala, Thr, Glu, Gln, Ser,
            Phe, Met, Val, Lys, Arg, Tyr, or Pro"

(ix) FEATURE:
        (A) NAME/KEY: Modified-site
        (B) LOCATION: 85
        (D) OTHER INFORMATION: /note= "Xaa at position 85 is
            Ile, Leu, Arg, Asp, Val, Pro, Gln, Gly, Ser,
            Phe, or His"

(ix) FEATURE:
        (A) NAME/KEY: Modified-site
        (B) LOCATION: 86
        (D) OTHER INFORMATION: /note= "Xaa at position 86 is
            Lys, Tyr, Leu, His, Arg, Ile, Ser, Gln, or Pro"

(ix) FEATURE:
        (A) NAME/KEY: Modified-site
        (B) LOCATION: 87
        (D) OTHER INFORMATION: /note= "Xaa at position 87 is
            Asp, Pro, Met, Lys, His, Thr, Val, Tyr, Glu, Asn,
            Ser, Ala, Gly, Ile, Leu, or Gln"
```

```
(ix) FEATURE:
    (A) NAME/KEY: Modified-site
    (B) LOCATION: 88
    (D) OTHER INFORMATION: /note= "Xaa at position 88 Gly,
        Leu, Glu, Lys, Ser, Tyr, or Pro"

(ix) FEATURE:
    (A) NAME/KEY: Modified-site
    (B) LOCATION: 89
    (D) OTHER INFORMATION: /note= "Xaa at position 89 is Asp
        or Ser"

(ix) FEATURE:
    (A) NAME/KEY: Modified-site
    (B) LOCATION: 90
    (D) OTHER INFORMATION: /note= "Xaa at position 90 is
        Trp, Val, Cys, Tyr, Thr, Met, Pro, Leu, Gln, Lys,
        Ala, Phe, or Gly"

(ix) FEATURE:
    (A) NAME/KEY: Modified-site
    (B) LOCATION: 91
    (D) OTHER INFORMATION: /note= "Xaa at position 91 is
        Asn, Pro, Ala, Phe, Ser, Trp, Gln, Tyr, Leu, Lys,
        Ile, Asp, or His"

(ix) FEATURE:
    (A) NAME/KEY: Modified-site
    (B) LOCATION: 92
    (D) OTHER INFORMATION: /note= "Xaa at position 92 is Glu,
        Ser, Ala, Lys, Thr, Ile, Gly, or Pro"

(ix) FEATURE:
    (A) NAME/KEY: Modified-site
    (B) LOCATION: 94
    (D) OTHER INFORMATION: /note= "Xaa at position 94 is Arg,
        Lys, Asp, Leu, Thr, Ile, Gln, His, Ser, Ala, or Pro"

(ix) FEATURE:
    (A) NAME/KEY: Modified-site
    (B) LOCATION: 95
    (D) OTHER INFORMATION: /note= "Xaa at position 95 is Arg,
        Thr, Pro, Glu, Tyr, Leu, Ser, or Gly"

(ix) FEATURE:
    (A) NAME/KEY: Modified-site
    (B) LOCATION: 96
    (D) OTHER INFORMATION: /note= "Xaa at position 96 is Lys,
        Asn, Thr, Leu, Gln, Arg, His, Glu, Ser, Ala,
        or Trp"

(ix) FEATURE:
    (A) NAME/KEY: Modified-site
    (B) LOCATION: 97
    (D) OTHER INFORMATION: /note= "Xaa at position 97 is Leu,
        Ile, Arg, Asp, or Met"

(ix) FEATURE:
    (A) NAME/KEY: Modified-site
    (B) LOCATION: 98
    (D) OTHER INFORMATION: /note= "Xaa at position 98 is Thr,
        Val, Gln, Tyr, Glu, His, Ser, or Phe"

(ix) FEATURE:
    (A) NAME/KEY: Modified-site
    (B) LOCATION: 99
    (D) OTHER INFORMATION: /note= "Xaa at position 99 is Phe,
        Ser, Cys, His, Gly, Trp, Tyr, Asp, Lys, Leu, Ile,
        Val, or Asn"

(ix) FEATURE:
    (A) NAME/KEY: Modified-site
    (B) LOCATION: 100
    (D) OTHER INFORMATION: /note= "Xaa at position 100 is Tyr,
        Cys, His, Ser, Trp, Arg, or Leu"

(ix) FEATURE:
    (A) NAME/KEY: Modified-site
    (B) LOCATION: 101
```

(D) OTHER INFORMATION: /note= "Xaa at position 101 is Leu, Asn, Val, Pro, Arg, Ala, His, Thr, Trp, or Met"

(ix) FEATURE:
  (A) NAME/KEY: Modified-site
  (B) LOCATION: 102
  (D) OTHER INFORMATION: /note= "Xaa at position 102 is Lys, Leu, Pro, Thr, Met, Asp, Val, Glu, Arg, Trp, Ser, Asn, His, Ala, Tyr, Phe, Gln, or Ile"

(ix) FEATURE:
  (A) NAME/KEY: Modified-site
  (B) LOCATION: 103
  (D) OTHER INFORMATION: /note= "Xaa at position 103 is Thr, Ser, Asn, Ile, Trp, Lys, or Pro"

(ix) FEATURE:
  (A) NAME/KEY: Modified-site
  (B) LOCATION: 104
  (D) OTHER INFORMATION: /note= "Xaa at position 104 is Leu, Ser, Pro, Ala, Glu, Cys, Asp, or Tyr"

(ix) FEATURE:
  (A) NAME/KEY: Modified-site
  (B) LOCATION: 105
  (D) OTHER INFORMATION: /note= "Xaa at position 105 is Glu, Ser, Lys, Pro, Leu, Thr, Tyr, or Arg"

(ix) FEATURE:
  (A) NAME/KEY: Modified-site
  (B) LOCATION: 106
  (D) OTHER INFORMATION: /note= "Xaa at position 106 is Asn, Ala, Pro, Leu, His, Val or Gln"

(ix) FEATURE:
  (A) NAME/KEY: Modified-site
  (B) LOCATION: 107
  (D) OTHER INFORMATION: /note= "Xaa at position 107 is Ala, Ser, Ile, Asn, Pro, Lys, Asp, or Gly"

(ix) FEATURE:
  (A) NAME/KEY: Modified-site
  (B) LOCATION: 108
  (D) OTHER INFORMATION: /note= "Xaa at position 108 is Gln, Ser, Met, Trp, Arg, Phe, Pro, His, Ile, Tyr, or Cys"

(ix) FEATURE:
  (A) NAME/KEY: Modified-site
  (B) LOCATION: 109
  (D) OTHER INFORMATION: /note= "Xaa at position 109 is Ala, Met, Glu, His, Ser, Pro, Tyr, or Leu"

(xi) SEQUENCE DESCRIPTION: SEQ ID NO:4:

```
Asn Cys Xaa Xaa Xaa Xaa Xaa Xaa Xaa Xaa Xaa Xaa Xaa Xaa Xaa Xaa
 1               5                  10                  15

Xaa Xaa Xaa Xaa Xaa Xaa Xaa Xaa Asn Xaa Xaa Xaa Xaa Xaa Xaa Xaa
            20                  25                  30

Xaa Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Xaa Xaa Xaa Xaa Xaa Xaa Xaa Xaa Xaa Xaa Xaa
 50                  55                  60

Xaa Xaa Xaa Xaa Xaa Xaa Xaa Xaa Xaa Xaa Xaa Xaa Xaa Xaa Xaa Xaa
 65                  70                  75                  80

Xaa Xaa Xaa Xaa Xaa Xaa Xaa Xaa Xaa Xaa Xaa Phe Xaa Xaa Xaa
            85                  90                  95

Xaa Xaa Xaa Xaa Xaa Xaa Xaa Xaa Xaa Xaa Xaa Xaa Xaa Gln Gln
        100                 105                 110
```

(2) INFORMATION FOR SEQ ID NO:5:

```
    (i) SEQUENCE CHARACTERISTICS:
        (A) LENGTH: 111 amino acids
        (B) TYPE: amino acid
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /note= "Met- or Met-Ala- may or may
            not precede the amino acid in position 1"

(ix) FEATURE:
        (A) NAME/KEY: Modified-site
        (B) LOCATION: 3
        (D) OTHER INFORMATION: /note= "Xaa at position 3 is Ser,
            Gly, Asp, Met, or Gln"

(ix) FEATURE:
        (A) NAME/KEY: Modified-site
        (B) LOCATION: 4
        (D) OTHER INFORMATION: /note= "Xaa at position 4 is Asn,
            His, or Ile"

(ix) FEATURE:
        (A) NAME/KEY: Modified-site
        (B) LOCATION: 5
        (D) OTHER INFORMATION: /note= "Xaa at position 5 is Met
            or Ile"

(ix) FEATURE:
        (A) NAME/KEY: Modified-site
        (B) LOCATION: 7
        (C) OTHER INFORMATION: /note= "Xaa at position 7 is Asp or
            Glu"

(ix) FEATURE:
        (A) NAME/KEY: Modified-site
        (B) LOCATION: 9
        (D) OTHER INFORMATION: /note= "Xaa at position 9 is Ile,
            Ala, Leu, or Gly"

(ix) FEATURE:
        (A) NAME/KEY: Modified-site
        (B) LOCATION: 10
        (D) OTHER INFORMATION: /note= "Xaa at position 10 is Ile,
            Val, or Leu"

(ix) FEATURE:
        (A) NAME/KEY: Modified-site
        (B) LOCATION: 11
        (D) OTHER INFORMATION: /note= "Xaa at position 11 is Thr,
            His, Gln, or Ala"

(ix) FEATURE:
        (A) NAME/KEY: Modified-site
        (B) LOCATION: 12
        (D) OTHER INFORMATION: /note= "Xaa at position 12 is His
            or Ala"

(ix) FEATURE:
        (A) NAME/KEY: Modified-site
        (B) LOCATION: 15
        (D) OTHER INFORMATION: /note= "Xaa at position 15 is Gln,
            Asn, or Val"

(ix) FEATURE:
        (A) NAME/KEY: Modified-site
        (B) LOCATION: 16
        (D) OTHER INFORMATION: /note= "Xaa at position 16 is Pro,
            Gly, or Gln"

(ix) FEATURE:
        (A) NAME/KEY: Modified-site
        (B) LOCATION: 17
        (D) OTHER INFORMATION: /note= "Xaa at position 17 is Pro,
            Asp, Gly, or Gln"
```

```
(ix) FEATURE:
    (A) NAME/KEY: Modified-site
    (B) LOCATION: 18
    (D) OTHER INFORMATION: /note= "Xaa at position 18 is Leu,
        Arg, Gln, Asn, Gly, Ala, or Glu"

(ix) FEATURE:
    (A) NAME/KEY: Modified-site
    (B) LOCATION: 19
    (D) OTHER INFORMATION: /note= "Xaa at position 19 is Pro
        or Glu"

(ix) FEATURE:
    (A) NAME/KEY: Modified-site
    (B) LOCATION: 20
    (D) OTHER INFORMATION: /note= "Xaa at position 20 is Leu,
        Val, Gly, Ser, Lys, Ala, Arg, Gln, Glu, Ile, Phe,
        Thr, or Met"

(ix) FEATURE:
    (A) NAME/KEY: Modified-site
    (B) LOCATION: 21
    (D) OTHER INFORMATION: /note= "Xaa at position 21 is Leu,
        Ala, Asn, Pro, Gln, or Val"

(ix) FEATURE:
    (A) NAME/KEY: Modified-site
    (B) LOCATION: 23
    (D) OTHER INFORMATION: /note= "Xaa at position 23 is Phe,
        Ser, Pro, or Trp"

(ix) FEATURE:
    (A) NAME/KEY: Modified-site
    (B) LOCATION: 24
    (D) OTHER INFORMATION: /note= "Xaa at position 24 is Asn
        or Ala"

(ix) FEATURE:
    (A) NAME/KEY: Modified-site
    (B) LOCATION: 28
    (D) OTHER INFORMATION: /note= "Xaa at position 28 is Gly,
        Asp, Ser, Cys, Ala, Asn, Ile, Leu, Met, Tyr, or Arg"

(ix) FEATURE:
    (A) NAME/KEY: Modified-site
    (B) LOCATION: 30
    (D) OTHER INFORMATION: /note= "Xaa at position 30 is Asp
        or Glu"

(ix) FEATURE:
    (A) NAME/KEY: Modified-site
    (B) LOCATION: 31
    (D) OTHER INFORMATION: /note= "Xaa at position 31 is Gln,
        Val, Met, Leu, Thr, Ala, Asn, Glu, Ser, or Lys"

(ix) FEATURE:
    (A) NAME/KEY: Modified-site
    (B) LOCATION: 32
    (D) OTHER INFORMATION: /note= "Xaa at position 32 is Asp,
        Phe, Ser, Thr, Ala, Asn, Gln, Glu, His, Ile, Lys,
        Tyr, Val, or Cys"

(ix) FEATURE:
    (A) NAME/KEY: Modified-site
    (B) LOCATION: 36
    (D) OTHER INFORMATION: /note= "Xaa at position 36 is Glu,
        Ala, Asn, Ser, or Asp"

(ix) FEATURE:
    (A) NAME/KEY: Modified-site
    (B) LOCATION: 37
    (D) OTHER INFORMATION: /note= "Xaa at position 37 is Asn,
        Arg, Met, Pro, Ser, Thr, or His"

(ix) FEATURE:
    (A) NAME/KEY: Modified-site
    (B) LOCATION: 40
    (D) OTHER INFORMATION: /note= "Xaa at position 40 is Arg
        or Ala"
```

```
(ix) FEATURE:
    (A) NAME/KEY: Modified-site
    (B) LOCATION: 41
    (D) OTHER INFORMATION: /note= "Xaa at position 41 is Arg,
        Thr, Val, Leu, or Gly"

(ix) FEATURE:
    (A) NAME/KEY: Modified-site
    (B) LOCATION: 42
    (D) OTHER INFORMATION: /note= "Xaa at position 42 is Pro,
        Gly, Ser, Gln, Ala, Arg, Asn, Glu, Leu, Thr, Val,
        or Lys"

(ix) FEATURE:
    (A) NAME/KEY: Modified-site
    (B) LOCATION: 46
    (D) OTHER INFORMATION: /note= "Xaa at position 46 is Ala
        or Ser"

(ix) FEATURE:
    (A) NAME/KEY: Modified-site
    (B) LOCATION: 48
    (D) OTHER INFORMATION: /note= "Xaa at position 48 is Asn,
        Pro, Thr, or Ile"

(ix) FEATURE:
    (A) NAME/KEY: Modified-site
    (B) LOCATION: 49
    (D) OTHER INFORMATION: /note= "Xaa at position 49 is Arg
        or Lys"

(ix) FEATURE:
    (A) NAME/KEY: Modified-site
    (B) LOCATION: 50
    (D) OTHER INFORMATION: /note= "Xaa at position 50 is Ala
        or Asn"

(ix) FEATURE:
    (A) NAME/KEY: Modified-site
    (B) LOCATION: 51
    (D) OTHER INFORMATION: /note= "Xaa at position 51 is Val
        or Thr"

(ix) FEATURE:
    (A) NAME/KEY: Modified-site
    (B) LOCATION: 52
    (D) OTHER INFORMATION: /note= "Xaa at position 52 is Lys
        or Arg"

(ix) FEATURE:
    (A) NAME/KEY: Modified-site
    (B) LOCATION: 53
    (D) OTHER INFORMATION: /note= "Xaa at position 53 is Ser,
        Phe, or His"

(ix) FEATURE:
    (A) NAME/KEY: Modified-site
    (B) LOCATION: 54
    (D) OTHER INFORMATION: /note= "Xaa at position 54 is Leu,
        Ile, Phe, or His"

(ix) FEATURE:
    (A) NAME/KEY: Modified-site
    (B) LOCATION: 55
    (D) OTHER INFORMATION: /note= "Xaa at position 55 is Gln,
        Ala, Pro, Thr, Glu, Arg, or Gly"

(ix) FEATURE:
    (A) NAME/KEY: Modified-site
    (B) LOCATION: 57
    (D) OTHER INFORMATION: /note= "Xaa at position 57 is Ala,
        Pro, or Arg"

(ix) FEATURE:
    (A) NAME/KEY: Modified-site
    (B) LOCATION: 58
    (D) OTHER INFORMATION: /note= "Xaa at position 58 is Ser,
        Glu, Arg, or Asp"
```

```
(ix) FEATURE:
    (A) NAME/KEY: Modified-site
    (B) LOCATION: 59
    (D) OTHER INFORMATION: /note= "Xaa at position 59 is Ala
        or Leu"

(ix) FEATURE:
    (A) NAME/KEY: Modified-site
    (B) LOCATION: 62
    (D) OTHER INFORMATION: /note= "Xaa at position 62 is Ser,
        Val, Ala, Asn, Glu, Pro, or Gly"

(ix) FEATURE:
    (A) NAME/KEY: Modified-site
    (B) LOCATION: 63
    (D) OTHER INFORMATION: /note= "Xaa at position 63 is Ile
        or Leu"

(ix) FEATURE:
    (A) NAME/KEY: Modified-site
    (B) LOCATION: 65
    (D) OTHER INFORMATION: /note= "Xaa at position 65 is Lys,
        Thr, Gly, Asn, Met, Arg, Ile, or Asp"

(ix) FEATURE:
    (A) NAME/KEY: Modified-site
    (B) LOCATION: 66
    (D) OTHER INFORMATION: /note= "Xaa at position 66 is Asn,
        Gly, Glu, or Arg"

(ix) FEATURE:
    (A) NAME/KEY: Modified-site
    (B) LOCATION: 68
    (D) OTHER INFORMATION: /note= "Xaa at position 68 is Leu,
        Gln, Trp, Arg, Asp, Ala, Asn, Glu, His, Ile, Met,
        Phe, Ser, Thr, Tyr, or Val"

(ix) FEATURE:
    (A) NAME/KEY: Modified-site
    (B) LOCATION: 69
    (D) OTHER INFORMATION: /note= "Xaa at position 69 is Pro
        or Thr"

(ix) FEATURE:
    (A) NAME/KEY: Modified-site
    (B) LOCATION: 71
    (D) OTHER INFORMATION: /note= "Xaa at position 71 is Leu
        or Val"

(ix) FEATURE:
    (A) NAME/KEY: Modified-site
    (B) LOCATION: 73
    (D) OTHER INFORMATION: /note= "Xaa at position 73 is Leu
        or Ser"

(ix) FEATURE:
    (A) NAME/KEY: Modified-site
    (B) LOCATION: 74
    (D) OTHER INFORMATION: /note= "Xaa at position 74 is Ala
        or Trp"

(ix) FEATURE:
    (A) NAME/KEY: Modified-site
    (B) LOCATION: 77
    (D) OTHER INFORMATION: /note= "Xaa at position 77 is Ala
        or Pro"

(ix) FEATURE:
    (A) NAME/KEY: Modified-site
    (B) LOCATION: 79
    (D) OTHER INFORMATION: /note= "Xaa at position 79 is Thr,
        Asp, Ser, Pro, Ala, Leu, or Arg"

(ix) FEATURE:
    (A) NAME/KEY: Modified-site
    (B) LOCATION: 81
    (D) OTHER INFORMATION: /note= "Xaa at position 81 is His,
        Pro, Arg, Val, Leu, Gly, Asn, Phe, Ser, or Thr"
```

-continued

```
(ix) FEATURE:
     (A) NAME/KEY: Modified-site
     (B) LOCATION: 82
     (D) OTHER INFORMATION: /note= "Xaa at position 82 is Pro
         or Tyr"

(ix) FEATURE:
     (A) NAME/KEY: Modified-site
     (B) LOCATION: 83
     (D) OTHER INFORMATION: /note= "Xaa at position 83 is Ile
         or Val"

(ix) FEATURE:
     (A) NAME/KEY: Modified-site
     (B) LOCATION: 84
     (D) OTHER INFORMATION: /note= "Xaa at position 84 is His,
         Ile, Asn, Leu, Ala, Thr, Arg, Gln, Lys,
         Met, Ser, Tyr, Val, or Pro"

(ix) FEATURE:
     (A) NAME/KEY: Modified-site
     (B) LOCATION: 85
     (D) OTHER INFORMATION: /note= "Xaa at position 85 is Ile,
         Leu, or Val"

(ix) FEATURE:
     (A) NAME/KEY: Modified-site
     (B) LOCATION: 86
     (D) OTHER INFORMATION: /note= "Xaa at position 86 is Lys,
         Arg, Ile, Gln, Pro, or Ser"

(ix) FEATURE:
     (A) NAME/KEY: Modified-site
     (B) LOCATION: 87
     (D) OTHER INFORMATION: /note= "Xaa at position 87 is Asp,
         Pro, Met, Lys, His, Thr, Asn, Ile, Leu, or Tyr"

(ix) FEATURE:
     (A) NAME/KEY: Modified-site
     (B) LOCATION: 90
     (D) OTHER INFORMATION: /note= "Xaa at position 90 is Trp
         or Leu"

(ix) FEATURE:
     (A) NAME/KEY: Modified-site
     (B) LOCATION: 91
     (D) OTHER INFORMATION: /note="Xaa at position 91 is Asn,
         Pro, Ala, Ser, Trp, Gln, Tyr, Leu, Lys, Ile, Asp,
         or His"

(ix) FEATURE:
     (A) NAME/KEY: Modified-site
     (B) LOCATION: 92
     (D) OTHER INFORMATION: /note= "Xaa at position 92 is Glu
         or Gly"

(ix) FEATURE:
     (A) NAME/KEY: Modified-site
     (B) LOCATION: 94
     (C) OTHER INFORMATION: /note= "Xaa at position 94 is Arg,
         Ala, or Ser"

(ix) FEATURE:
     (A) NAME/KEY: Modified-site
     (B) LOCATION: 95
     (D) OTHER INFORMATION: /note= "Xaa at position 95 is Arg,
         Thr, Glu, Leu, or Ser"

(ix) FEATURE:
     (A) NAME/KEY: Modified-site
     (B) LOCATION: 98
     (D) OTHER INFORMATION: /note= "Xaa at position 98 is Thr,
         Val, or Gln"

(ix) FEATURE:
     (A) NAME/KEY: Modified-site
     (B) LOCATION: 100
     (D) OTHER INFORMATION: /note= "Xaa at position 100 is Tyr
``` or Trp"

(ix) FEATURE:
        (A) NAME/KEY: Modified-site
        (B) LOCATION: 101
        (D) OTHER INFORMATION: /note= "Xaa at position 101 is Leu
            or Ala"

(ix) FEATURE:
        (A) NAME/KEY: Modified-site
        (B) LOCATION: 102
        (D) OTHER INFORMATION: /note= "Xaa at position 102 is Lys,
            Thr, Val, Trp, Ser, Ala, His, Met, Phe, Tyr, or Ile"

(ix) FEATURE:
        (A) NAME/KEY: Modified-site
        (B) LOCATION: 103
        (D) OTHER INFORMATION: /note= "Xaa at position 103 is Thr
            or Ser"

(ix) FEATURE:
        (A) NAME/KEY: Modified-site
        (B) LOCATION: 106
        (D) OTHER INFORMATION: /note= "Xaa at position 106 is Asn,
            Pro, Leu, His, Val, or Gln"

(ix) FEATURE:
        (A) NAME/KEY: Modified-site
        (B) LOCATION: 107
        (D) OTHER INFORMATION: /note= "Xaa at position 107 is Ala,
            Ser, Ile, Asn, Pro, Asp, or Gly"

(ix) FEATURE:
        (A) NAME/KEY: Modified-site
        (B) LOCATION: 108
        (D) OTHER INFORMATION: /note= "Xaa at position 108 is Gln,
            Ser, Met, Trp, Arg, Phe, Pro, His, Ile, Tyr, or Cys"

(ix) FEATURE:
        (A) NAME/KEY: Modified-site
        (B) LOCATION: 109
        (D) OTHER INFORMATION: /note= "Xaa at position 109 is Ala,
            Met, Glu, His, Ser, Pro, Tyr, or Leu"

(xi) SEQUENCE DESCRIPTION: SEQ ID NO:5:

Asn Cys Xaa Xaa Xaa Ile Xaa Glu Xaa Xaa Xaa Xaa Leu Lys Xaa Xaa
1               5                   10                  15

Xaa Xaa Xaa Xaa Xaa Asp Xaa Xaa Asn Leu Asn Xaa Glu Xaa Xaa Xaa
            20                  25                  30

Ile Leu Met Xaa Xaa Asn Leu Xaa Xaa Xaa Asn Leu Glu Xaa Phe Xaa
        35                  40                  45

Xaa Xaa Xaa Xaa Xaa Xaa Xaa Asn Xaa Xaa Xaa Ile Glu Xaa Xaa Leu
    50                  55                  60

Xaa Xaa Leu Xaa Xaa Cys Xaa Pro Xaa Xaa Thr Ala Xaa Pro Xaa Arg
65              70                  75                  80

Xaa Xaa Xaa Xaa Xaa Xaa Xaa Gly Asp Xaa Xaa Xaa Phe Xaa Xaa Lys
                85                  90                  95

Leu Xaa Phe Xaa Xaa Xaa Xaa Leu Glu Xaa Xaa Xaa Xaa Gln Gln
            100                 105                 110

(2) INFORMATION FOR SEQ ID NO:6:

(i) SEQUENCE CHARACTERISTICS:
        (A) LENGTH: 111 amino acids
        (B) TYPE: amino acid
        (D) TOPOLOGY: linear (ii) MOLECULE TYPE: peptide (ix) FEATURE:
        (A) NAME/KEY: Modified-site

```
        (B) LOCATION: 1
        (D) OTHER INFORMATION: /note= "Met- or Met-Ala- may or may
            not precede the amino acid in position 1"

(ix) FEATURE:
        (A) NAME/KEY: Modified-site
        (B) LOCATION: 3
        (D) OTHER INFORMATION: /note= "Xaa at position 3 is Ser,
            Gly, Asp, or Gln"

(ix) FEATURE:
        (A) NAME/KEY: Modified-site
        (B) LOCATION: 4
        (D) OTHER INFORMATION: /note= "Xaa at position 4 is Asn,
            His, or Ile"

(ix) FEATURE:
        (A) NAME/KEY: Modified-site
        (B) LOCATION: 9
        (D) OTHER INFORMATION: /note= "Xaa at position 9 is Ile,
            Ala, Leu, or Gly"

(ix) FEATURE:
        (A) NAME/KEY: Modified-site
        (B) LOCATION: 11
        (D) OTHER INFORMATION: /note= "Xaa at position 11 is Thr,
            His, or Gln"

(ix) FEATURE:
        (A) NAME/KEY: Modified-site
        (B) LOCATION: 12
        (D) OTHER INFORMATION: /note= "Xaa at position 12 is His
            or Ala"

(ix) FEATURE:
        (A) NAME/KEY: Modified-site
        (B) LOCATION: 15
        (D) OTHER INFORMATION: /note= "Xaa at position 15 is Gln
            or Asn"

(ix) FEATURE:
        (A) NAME/KEY: Modified-site
        (B) LOCATION: 16
        (D) OTHER INFORMATION: /note= "Xaa at position 16 is Pro
            or Gly"

(ix) FEATURE:
        (A) NAME/KEY: Modified-site
        (B) LOCATION: 18
        (D) OTHER INFORMATION: /note= "Xaa at position 18 is Leu,
            Arg, Asn, or Ala"

(ix) FEATURE:
        (A) NAME/KEY: Modified-site
        (B) LOCATION: 20
        (D) OTHER INFORMATION: /note= "Xaa at position 20 is Leu,
            Val, Ser, Ala, Arg, Gln, Glu, Ile, Phe, Thr, or Met"

(ix) FEATURE:
        (A) NAME/KEY: Modified-site
        (B) LOCATION: 21
        (D) OTHER INFORMATION: /note= "Xaa at position 21 is Leu,
            Ala, Asn, or Pro"

(ix) FEATURE:
        (A) NAME/KEY: Modified-site
        (B) LOCATION: 24
        (D) OTHER INFORMATION: /note= "Xaa at position 24 is Asn
            or Ala"

(ix) FEATURE:
        (A) NAME/KEY: Modified-site
        (B) LOCATION: 28
        (D) OTHER INFORMATION: /note= "Xaa at position 28 is Gly,
            Asp, Ser, Ala, Asn, Ile, Leu, Met, Tyr, or Arg"

(ix) FEATURE:
        (A) NAME/KEY: Modified-site
        (B) LOCATION: 31
```

```
          (D) OTHER INFORMATION: /note= "Xaa at position 31 is Gln,
              Val, Met, Leu, Ala, Asn, Glu, or Lys"

(ix) FEATURE:
          (A) NAME/KEY: Modified-site
          (B) LOCATION: 32
          (D) OTHER INFORMATION: /note= "Xaa at position 32 is Asp,
              Phe, Ser, Ala, Gln, Glu, His, Val, or Thr"

(ix) FEATURE:
          (A) NAME/KEY: Modified-site
          (B) LOCATION: 36
          (D) OTHER INFORMATION: /note= "Xaa at position 36 is Glu,
              Asn, Ser, or Asp"

(ix) FEATURE:
          (A) NAME/KEY: Modified-site
          (B) LOCATION: 37
          (D) OTHER INFORMATION: /note= "Xaa at position 37 is Asn,
              Arg, Pro, Thr, or His"

(ix) FEATURE:
          (A) NAME/KEY: Modified-site
          (B) LOCATION: 41
          (D) OTHER INFORMATION: /note= "Xaa at position 41 is Arg,
              Leu, or Gly"

(ix) FEATURE:
          (A) NAME/KEY: Modified-site
          (B) LOCATION: 42
          (D) OTHER INFORMATION: /note= "Xaa at position 42 is Pro,
              Gly, Ser, Ala, Asn, Val, Leu, or Gln"

(ix) FEATURE:
          (A) NAME/KEY: Modified-site
          (B) LOCATION: 48
          (D) OTHER INFORMATION: /note= "Xaa at position 48 is Asn,
              Pro, or Thr"

(ix) FEATURE:
          (A) NAME/KEY: Modified-site
          (B) LOCATION: 50
          (D) OTHER INFORMATION: /note= "Xaa at position 50 is Ala
              or Asn"

(ix) FEATURE:
          (A) NAME/KEY: Modified-site
          (B) LOCATION: 51
          (D) OTHER INFORMATION: /note= "Xaa at position 51 is Val
              or Thr"

(ix) FEATURE:
          (A) NAME/KEY: Modified-site
          (B) LOCATION: 53
          (D) OTHER INFORMATION: /note= "Xaa at position 53 is Ser
              or Phe"

(ix) FEATURE:
          (A) NAME/KEY: Modified-site
          (B) LOCATION: 54
          (D) OTHER INFORMATION: /note= "Xaa at position 54 is Leu
              or Phe"

(ix) FEATURE:
          (A) NAME/KEY: Modified-site
          (B) LOCATION: 55
          (D) OTHER INFORMATION: /note= "Xaa at position 55 is Gln,
              Ala, Glu, or Arg"

(ix) FEATURE:
          (A) NAME/KEY: Modified-site
          (B) LOCATION: 62
          (D) OTHER INFORMATION: /note= "Xaa at position 62 is Ser,
              Val, Asn, Pro, or Gly"

(ix) FEATURE:
          (A) NAME/KEY: Modified-site
          (B) LOCATION: 63
          (D) OTHER INFORMATION: /note= "Xaa at position 63 is Ile
``` or Leu"

(ix) FEATURE:
      (A) NAME/KEY: Modified-site
      (B) LOCATION: 65
      (D) OTHER INFORMATION: /note= "Xaa at position 65 is Lys,
          Asn, Met, Arg, Ile, or Gly"

(ix) FEATURE:
      (A) NAME/KEY: Modified-site
      (B) LOCATION: 66
      (D) OTHER INFORMATION: /note= "Xaa at position 66 is Asn,
          Gly, Glu, or Arg"

(ix) FEATURE:
      (A) NAME/KEY: Modified-site
      (B) LOCATION: 68
      (D) OTHER INFORMATION: /note= "Xaa at position 68 is Leu,
          Gln, Trp, Arg, Asp, Asn, Glu, His, Met, Phe, Ser,
          Thr, Tyr, or Val"

(ix) FEATURE:
      (A) NAME/KEY: Modified-site
      (B) LOCATION: 73
      (D) OTHER INFORMATION: /note= "Xaa at position 73 is Leu
          or Ser"

(ix) FEATURE:
      (A) NAME/KEY: Modified-site
      (B) LOCATION: 74
      (D) OTHER INFORMATION: /note= "Xaa at position 74 is Ala
          or Trp"

(ix) FEATURE:
      (A) NAME/KEY: Modified-site
      (B) LOCATION: 77
      (D) OTHER INFORMATION: /note= "Xaa at position 77 is Ala
          or Pro"

(ix) FEATURE:
      (A) NAME/KEY: Modified-site
      (B) LOCATION: 79
      (D) OTHER INFORMATION: /note= "Xaa at position 79 is Thr,
          Asp, or Ala"

(ix) FEATURE:
      (A) NAME/KEY: Modified-site
      (B) LOCATION: 81
      (D) OTHER INFORMATION: /note= "Xaa at position 81 is His,
          Pro, Arg, Val, Gly, Asn, Ser, or Thr"

(ix) FEATURE:
      (A) NAME/KEY: Modified-site
      (B) LOCATION: 84
      (D) OTHER INFORMATION: /note= "Xaa at position 84 is His,
          Ile, Asn, Leu, Ala, Thr, Arg, Gln, Glu, Lys, Met,
          Ser, Tyr, or Val"

(ix) FEATURE:
      (A) NAME/KEY: Modified-site
      (B) LOCATION: 85
      (D) OTHER INFORMATION: /note= "Xaa at position 85 is Ile
          or Leu"

(ix) FEATURE:
      (A) NAME/KEY: Modified-site
      (B) LOCATION: 86
      (D) OTHER INFORMATION: /note= "Xaa at position 86 is Lys
          or Arg"

(ix) FEATURE:
      (A) NAME/KEY: Modified-site
      (B) LOCATION: 87
      (D) OTHER INFORMATION: /note= "Xaa at position 87 is Asp,
          Pro, Met, Lys, His, Pro, Asn, Ile, Leu, or Tyr"

(ix) FEATURE:
      (A) NAME/KEY: Modified-site
      (B) LOCATION: 91

(D) OTHER INFORMATION: /note= "Xaa at position 91 is Asn,
            Pro, Ser, Ile, or Asp"

(ix) FEATURE:
        (A) NAME/KEY: Modified-site
        (B) LOCATION: 94
        (D) OTHER INFORMATION: /note="Xaa at position 94 is Arg,
            Ala, or Ser"

(ix) FEATURE:
        (A) NAME/KEY: Modified-site
        (B) LOCATION: 95
        (D) OTHER INFORMATION: /note= "Xaa at position 95 is Arg,
            Thr, Glu, Leu, or Ser"

(ix) FEATURE:
        (A) NAME/KEY: Modified-site
        (B) LOCATION: 98
        (D) OTHER INFORMATION: /note= "Xaa at position 98 is Thr
            or Gln"

(ix) FEATURE:
        (A) NAME/KEY: Modified-site
        (B) LOCATION: 102
        (D) OTHER INFORMATION: /note= "Xaa at position 102 is Lys,
            Val, Trp, or Ile"

(ix) FEATURE:
        (A) NAME/KEY: Modified-site
        (B) LOCATION: 103
        (D) OTHER INFORMATION: /note= "Xaa at position 103 is Thr,
            Ala, His, Phe, Tyr, or Ser"

(ix) FEATURE:
        (A) NAME/KEY: Modified-site
        (B) LOCATION: 106
        (D) OTHER INFORMATION: /note= "Xaa at position 106 is Asn,
            Pro, Leu, His, Val, or Gln"

(ix) FEATURE:
        (A) NAME/KEY: Modified-site
        (B) LOCATION: 107
        (D) OTHER INFORMATION: /note= "Xaa at position 107 is Ala,
            Ser, Ile, Pro, or Asp"

(ix) FEATURE:
        (A) NAME/KEY: Modified-site
        (B) LOCATION: 108
        (D) OTHER INFORMATION: /note= "Xaa at position 108 is Gln,
            Met, Trp, Phe, Pro, His, Ile, or Tyr"

(ix) FEATURE:
        (A) NAME/KEY: Modified-site
        (B) LOCATION: 109
        (D) OTHER INFORMATION: /note= "Xaa at position 109 is Ala,
            Met, Glu, Ser, or Leu"

(xi) SEQUENCE DESCRIPTION: SEQ ID NO:6:

Asn Cys Xaa Xaa Met Ile Asp Glu Xaa Ile Xaa Xaa Leu Lys Xaa Xaa
1               5                   10                  15

Pro Xaa Pro Xaa Xaa Asp Phe Xaa Asn Leu Asn Xaa Glu Asp Xaa Xaa
            20                  25                  30

Ile Leu Met Xaa Xaa Asn Leu Arg Xaa Xaa Asn Leu Glu Ala Phe Xaa
        35                  40                  45

Arg Xaa Xaa Lys Xaa Xaa Xaa Asn Ala Ser Ala Ile Glu Xaa Xaa Leu
    50                  55                  60

Xaa Xaa Leu Xaa Pro Cys Leu Pro Xaa Xaa Thr Ala Xaa Pro Xaa Arg
65                  70                  75                  80

Xaa Pro Ile Xaa Xaa Xaa Xaa Gly Asp Trp Xaa Glu Phe Xaa Xaa Lys
            85                  90                  95

Leu Xaa Phe Tyr Leu Xaa Xaa Leu Glu Xaa Xaa Xaa Xaa Gln Gln
            100                 105                 110

(2) INFORMATION FOR SEQ ID NO:7:

(i) SEQUENCE CHARACTERISTICS:
        (A) LENGTH: 133 amino acids
        (B) TYPE: amino acid
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /note= "Met- may or may not precede
            the amino acid in position 1"

(ix) FEATURE:
        (A) NAME/KEY: Modified-site
        (B) LOCATION: 18
        (D) OTHER INFORMATION: /note= "Xaa at position 18 is Asn
            or Ile"

(ix) FEATURE:
        (A) NAME/KEY: Modified-site
        (B) LOCATION: 19
        (D) OTHER INFORMATION: /note= "Xaa at position 19 is Met,
            Ala, or Ile"

(ix) FEATURE:
        (A) NAME/KEY: Modified-site
        (B) LOCATION: 20
        (D) OTHER INFORMATION: /note= "Xaa at position 20 is Ile,
            Pro, or Leu"

(ix) FEATURE:
        (A) NAME/KEY: Modified-site
        (B) LOCATION: 23
        (D) OTHER INFORMATION: /note= "Xaa at position 23 is Ile,
            Ala, or Leu"

(ix) FEATURE:
        (A) NAME/KEY: Modified-site
        (B) LOCATION: 25
        (D) OTHER INFORMATION: /note= "Xaa at position 25 is Thr
            or His"

(ix) FEATURE:
        (A) NAME/KEY: Modified-site
        (B) LOCATION: 29
        (D) OTHER INFORMATION: /note= "Xaa at position 29 is Gln,
            Arg, Val, or Ile"

(ix) FEATURE:
        (A) NAME/KEY: Modified-site
        (B) LOCATION: 32
        (D) OTHER INFORMATION: /note= "Xaa at position 32 is Leu,
            Ala, Asn, or Arg"

(ix) FEATURE:
        (A) NAME/KEY: Modified-site
        (B) LOCATION: 34
        (D) OTHER INFORMATION: /note= "Xaa at position 34 is Leu
            or Ser"

(ix) FEATURE:
        (A) NAME/KEY: Modified-site
        (B) LOCATION: 37
        (D) OTHER INFORMATION: /note= "Xaa at position 37 is Phe,
            Pro, or Ser"

(ix) FEATURE:
        (A) NAME/KEY: Modified-site
        (B) LOCATION:; 38
        (D) OTHER INFORMATION: /note= "Xaa at position 38 is Asn
            or Ala"

(ix) FEATURE:
        (A) NAME/KEY: Modified-site

```
         (B) LOCATION: 42
         (D) OTHER INFORMATION: /note= "Xaa at position 42 is Gly,
             Ala, Ser, Asp, or Asn"

(ix) FEATURE:
         (A) NAME/KEY: Modified-site
         (B) LOCATION: 45
         (D) OTHER INFORMATION: /note= "Xaa at position 45 is Gln,
             Val, or Met"

(ix) FEATURE:
         (A) NAME/KEY: Modified-site
         (B) LOCATION: 46
         (D) OTHER INFORMATION: /note= "Xaa at position 46 is Asp
             or Ser"

(ix) FEATURE:
         (A) NAME/KEY: Modified-site
         (B) LOCATION: 49
         (D) OTHER INFORMATION: /note= "Xaa at position 49 is Met,
             Ile, Leu, or Asp"

(ix) FEATURE:
         (A) NAME/KEY: Modified-site
         (B) LOCATION: 50
         (D) OTHER INFORMATION: /note= "Xaa at position 50 is Glu
             or Asp"

(ix) FEATURE:
         (A) NAME/KEY: Modified-site
         (B) LOCATION: 51
         (D) OTHER INFORMATION: /note= "Xaa at position 51 is Asn,
             Arg, or Ser"

(ix) FEATURE:
         (A) NAME/KEY: Modified-site
         (B) LOCATION: 55
         (D) OTHER INFORMATION: /note= "Xaa at position 55 is Arg,
             Leu, or Thr"

(ix) FEATURE:
         (A) NAME/KEY: Modified-site
         (B) LOCATION: 56
         (D) OTHER INFORMATION: /note= "Xaa at position 56 is Pro
             or Ser"

(ix) FEATURE:
         (A) NAME/KEY: Modified-site
         (B) LOCATION: 59
         (D) OTHER INFORMATION: /note= "Xaa at position 59 is Glu
             or Leu"

(ix) FEATURE:
         (A) NAME/KEY: Modified-site
         (B) LOCATION: 60
         (D) OTHER INFORMATION: /note= "Xaa at position 60 is Ala
             or Ser"

(ix) FEATURE:
         (A) NAME/KEY: Modified-site
         (B) LOCATION: 62
         (D) OTHER INFORMATION: /note= "Xaa at position 62 is Asn
             Val, or Pro"

(ix) FEATURE:
         (A) NAME/KEY: Modified-site
         (B) LOCATION: 63
         (D) OTHER INFORMATION: /note= "Xaa at position 63 is Arg
             or His"

(ix) FEATURE:
         (A) NAME/KEY: Modified-site
         (B) LOCATION: 65
         (D) OTHER INFORMATION: /note= "Xaa at position 65 is Val
             or Ser"

(ix) FEATURE:
         (A) NAME/KEY: Modified-site
         (B) LOCATION: 67
```

```
          (D) OTHER INFORMATION: /note= "Xaa at position 67 is Ser,
              Asn, His, or Gln"

(ix) FEATURE:
          (A) NAME/KEY: Modified-site
          (B) LOCATION: 69
          (D) OTHER INFORMATION: /note= "Xaa at position 69 is Gln
              or Glu"

(ix) FEATURE:
          (A) NAME/KEY: Modified-site
          (B) LOCATION: 73
          (D) OTHER INFORMATION: /note= "Xaa at position 73 is Ala
              or Gly"

(ix) FEATURE:
          (A) NAME/KEY: Modified-site
          (B) LOCATION: 76
          (D) OTHER INFORMATION: /note= "Xaa at position 76 is Ser,
              Ala, or Pro"

(ix) FEATURE:
          (A) NAME/KEY: Modified-site
          (B) LOCATION: 79
          (D) OTHER INFORMATION: /note= "Xaa at position 79 is Lys,
              Arg, or Ser"

(ix) FEATURE:
          (A) NAME/KEY: Modified-site
          (B) LOCATION: 82
          (D) OTHER INFORMATION: /note= "Xaa at position 82 is Leu,
              Glu, Val, or Trp"

(ix) FEATURE:
          (A) NAME/KEY: Modified-site
          (B) LOCATION: 85
          (D) OTHER INFORMATION: /note= "Xaa at position 85 is Leu
              or Val"

(ix) FEATURE:
          (A) NAME/KEY: Modified-site
          (B) LOCATION: 87
          (D) OTHER INFORMATION: /note= "Xaa at position 87 is Leu,
              Ser, or Tyr"

(ix) FEATURE:
          (A) NAME/KEY: Modified-site
          (B) LOCATION: 88
          (D) OTHER INFORMATION: /note= "Xaa at position 88 is Ala
              or Trp"

(ix) FEATURE:
          (A) NAME/KEY: Modified-site
          (B) LOCATION: 91
          (D) OTHER INFORMATION: /note= "Xaa at position 91 is Ala
              or Pro"

(ix) FEATURE:
          (A) NAME/KEY: Modified-site
          (B) LOCATION: 93
          (D) OTHER INFORMATION: /note= "Xaa at position 93 is Pro
              or Ser"

(ix) FEATURE:
          (A) NAME/KEY: Modified-site
          (B) LOCATION: 95
          (D) OTHER INFORMATION: /note= "Xaa at position 95 is His
              or Thr"

(ix) FEATURE:
          (A) NAME/KEY: Modified-site
          (B) LOCATION: 98
          (D) OTHER INFORMATION: /note= "Xaa at position 98 is His,
              Ile, or Thr"

(ix) FEATURE:
          (A) NAME/KEY: Modified-site
          (B) LOCATION: 100
          (D) OTHER INFORMATION: /note= "Xaa at position 100 is Lys
``` or Arg"

(ix) FEATURE:
            (A) NAME/KEY: Modified-site
            (B) LOCATION: 101
            (D) OTHER INFORMATION: /note= "Xaa at position 101 is Asp,
                Ala, or Met"

(ix) FEATURE:
            (A) NAME/KEY: Modified-site
            (B) LOCATION: 105
            (D) OTHER INFORMATION: /note= "Xaa at position 105 is Asn
                or Glu"

(ix) FEATURE:
            (A) NAME/KEY: Modified-site
            (B) LOCATION: 109
            (D) OTHER INFORMATION: /note= "Xaa at position 109 is Arg,
                Glu, or Leu"

(ix) FEATURE:
            (A) NAME/KEY: Modified-site
            (B) LOCATION: 112
            (D) OTHER INFORMATION: /note= "Xaa at position 112 is Thr
                or Gln"

(ix) FEATURE:
            (A) NAME/KEY: Modified-site
            (B) LOCATION: 116
            (D) OTHER INFORMATION: /note= "Xaa at position 116 is Lys,
                Val, Trp, or Ser"

(ix) FEATURE:
            (A) NAME/KEY: Modified-site
            (B) LOCATION: 117
            (D) OTHER INFORMATION: /note= "Xaa at position 117 is Thr
                or Ser"

(ix) FEATURE:
            (A) NAME/KEY: Modified-site
            (B) LOCATION: 120
            (D) OTHER INFORMATION: /note= "Xaa at position 120 is Asn,
                Gln, or His"

(ix) FEATURE:
            (A) NAME/KEY: Modified-site
            (B) LOCATION: 123
            (D) OTHER INFORMATION: /note= "Xaa at position 123 is Ala
                or Glu"

(xi) SEQUENCE DESCRIPTION: SEQ ID NO:7:

Ala Pro Met Thr Gln Thr Thr Ser Leu Lys Thr Ser Trp Val Asn Cys
1               5                   10                  15

Ser Xaa Xaa Xaa Asp Glu Xaa Ile Xaa His Leu Lys Xaa Pro Pro Xaa
            20                  25                  30

Pro Xaa Leu Asp Xaa Xaa Asn Leu Asn Xaa Glu Asp Xaa Xaa Ile Leu
        35                  40                  45

Xaa Xaa Xaa Asn Leu Arg Xaa Xaa Asn Leu Xaa Xaa Phe Xaa Xaa Ala
    50                  55                  60

Xaa Lys Xaa Leu Xaa Asn Ala Ser Xaa Ile Glu Xaa Ile Leu Xaa Asn
65                  70                  75                  80

Leu Xaa Pro Cys Xaa Pro Xaa Xaa Thr Ala Xaa Pro Xaa Arg Xaa Pro
        85                  90                  95

Ile Xaa Ile Xaa Xaa Gly Asp Trp Xaa Glu Phe Arg Xaa Lys Leu Xaa
        100                 105                 110

Phe Tyr Leu Xaa Xaa Leu Glu Xaa Ala Gln Xaa Gln Gln Thr Thr Leu
        115                 120                 125

Ser Leu Ala Ile Phe
130

(2) INFORMATION FOR SEQ ID NO:8:

(i) SEQUENCE CHARACTERISTICS:
        (A) LENGTH: 111 amino acids
        (B) TYPE: amino acid
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /note= "Met- or Met-Ala may or may
            not precede the amino acid in position 1"

(ix) FEATURE:
        (A) NAME/KEY: Modified-site
        (B) LOCATION: 4
        (D) OTHER INFORMATION: /note= "Xaa at position 4 is Asn or
            Ile"

(ix) FEATURE:
        (A) NAME/KEY: Modified-site
        (B) LOCATION: 5
        (D) OTHER INFORMATION: /note= "Xaa at position 5 is Met,
            Ala, or Ile"

(ix) FEATURE:
        (A) NAME/KEY: Modified-site
        (B) LOCATION: 6
        (D) OTHER INFORMATION: /note= "Xaa at position 6 is Ile,
            Pro, or Leu"

(ix) FEATURE:
        (A) NAME/KEY: Modified-site
        (B) LOCATION: 9
        (D) OTHER INFORMATION: /note= "Xaa at position 9 is Ile,
            Ala, or Leu"

(ix) FEATURE:
        (A) NAME/KEY: Modified-site
        (B) LOCATION: 11
        (D) OTHER INFORMATION: /note= "Xaa at position 11 is Thr
            or His"

(ix) FEATURE:
        (A) NAME/KEY: Modified-site
        (B) LOCATION: 15
        (D) OTHER INFORMATION: /note= "Xaa at position 15 is Gln,
            Arg, Val, or Ile"

(ix) FEATURE:
        (A) NAME/KEY: Modified-site
        (B) LOCATION: 18
        (D) OTHER INFORMATION: /note= "Xaa at position 18 is Leu,
            Ala, Asn, or Arg"

(ix) FEATURE:
        (A) NAME/KEY: Modified-site
        (B) LOCATION: 20
        (D) OTHER INFORMATION: /note= "Xaa at position 20 is Leu
            or Ser"

(ix) FEATURE:
        (A) NAME/KEY: Modified-site
        (B) LOCATION: 23
        (D) OTHER INFORMATION: /note= "Xaa at position 23 is Phe,
            Pro, or Ser"

(ix) FEATURE:
        (A) NAME/KEY: Modified-site
        (B) LOCATION: 24
        (D) OTHER INFORMATION: /note= "Xaa at position 24 is Asn
            or Ala"

(ix) FEATURE:
        (A) NAME/KEY: Modified-site
        (B) LOCATION: 28

(D) OTHER INFORMATION: /note= "Xaa at position 28 is Gly,
                    Ala, Ser, Asp, or Asn"

(ix) FEATURE:
                (A) NAME/KEY: Modified-site
                (B) LOCATION: 31
                (D) OTHER INFORMATION: /note= "Xaa at position 31 is Gln,
                    Val, or Met"

(ix) FEATURE:
                (A) NAME/KEY: Modified-site
                (B) LOCATION: 32
                (D) OTHER INFORMATION: /note= "Xaa at position 32 is Asp
                    or Ser"

(ix) FEATURE:
                (A) NAME/KEY: Modified-site
                (B) LOCATION: 35
                (D) OTHER INFORMATION: /note= "Xaa at position 35 is Met,
                    Ile, or Asp"

(ix) FEATURE:
                (A) NAME/KEY: Modified-site
                (B) LOCATION: 36
                (D) OTHER INFORMATION: /note= "Xaa at position 36 is Glu
                    or Asp"

(ix) FEATURE:
                (A) NAME/KEY: Modified-site
                (B) LOCATION: 37
                (D) OTHER INFORMATION: /note= "Xaa at position 37 is Asn,
                    Arg, or Ser"

(ix) FEATURE:
                (A) NAME/KEY: Modified-site
                (B) LOCATION: 41
                (D) OTHER INFORMATION: /note= "Xaa at position 41 is Arg,
                    Leu, or Thr"

(ix) FEATURE:
                (A) NAME/KEY: Modified-site
                (B) LOCATION: 42
                (D) OTHER INFORMATION: /note= "Xaa at position 42 is Pro
                    or Ser"

(ix) FEATURE:
                (A) NAME/KEY: Modified-site
                (B) LOCATION: 45
                (D) OTHER INFORMATION: /note= "Xaa at position 45 is Glu
                    or Leu"

(ix) FEATURE:
                (A) NAME/KEY: Modified-site
                (B) LOCATION: 46
                (D) OTHER INFORMATION: /note= "Xaa at position 46 is Ala
                    or Ser"

(ix) FEATURE:
                (A) NAME/KEY: Modified-site
                (B) LOCATION: 48
                (D) OTHER INFORMATION: /note= "Xaa at position 48 is Asn,
                    Val, or Pro"

(ix) FEATURE:
                (A) NAME/KEY: Modified-site
                (B) LOCATION: 49
                (D) OTHER INFORMATION: /note= "Xaa at position 49 is Arg
                    or His"

(ix) FEATURE:
                (A) NAME/KEY: Modified-site
                (B) LOCATION: 51
                (D) OTHER INFORMATION: /note= "Xaa at position 51 is Val
                    or Ser"

(ix) FEATURE:
                (A) NAME/KEY: Modified-site
                (B) LOCATION: 53
                (D) OTHER INFORMATION: /note= "Xaa at position 53 is Ser,

```
            Asn, His, or Gln"

(ix) FEATURE:
    (A) NAME/KEY: Modified-site
    (B) LOCATION: 55
    (D) OTHER INFORMATION: /note= "Xaa at position 55 is Gln
        or Glu"

(ix) FEATURE:
    (A) NAME/KEY: Modified-site
    (B) LOCATION: 59
    (D) OTHER INFORMATION: /note= "Xaa at position 59 is Ala
        or Gly"

(ix) FEATURE:
    (A) NAME/KEY: Modified-site
    (B) LOCATION: 62
    (D) OTHER INFORMATION: /note= "Xaa at position 62 is Ser,
        Ala, or Pro"

(ix) FEATURE:
    (A) NAME/KEY: Modified-site
    (B) LOCATION: 65
    (D) OTHER INFORMATION: /note= "Xaa at position 65 is Lys,
        Arg, or Ser"

(ix) FEATURE:
    (A) NAME/KEY: Modified-site
    (B) LOCATION: 67
    (D) OTHER INFORMATION: /note= "Xaa at position 67 is Leu,
        Glu, or Val"

(ix) FEATURE:
    (A) NAME/KEY: Modified-site
    (B) LOCATION: 68
    (D) OTHER INFORMATION: /note= "Xaa at position 68 is Leu,
        Glu, Val, or Trp"

(ix) FEATURE:
    (A) NAME/KEY: Modified-site
    (B) LOCATION: 71
    (D) OTHER INFORMATION: /note= "Xaa at position 71 is Leu
        or Val"

(ix) FEATURE:
    (A) NAME/KEY: Modified-site
    (B) LOCATION: 73
    (D) OTHER INFORMATION: /note= "Xaa at position 73 is Leu,
        Ser, or Tyr"

(ix) FEATURE:
    (A) NAME/KEY: Modified-site
    (B) LOCATION: 74
    (D) OTHER INFORMATION: /note= "Xaa at position 74 is Ala
        or Trp"

(ix) FEATURE:
    (A) NAME/KEY: Modified-site
    (B) LOCATION: 77
    (D) OTHER INFORMATION: /note= "Xaa at position 77 is Ala
        or Pro"

(ix) FEATURE:
    (A) NAME/KEY: Modified-site
    (B) LOCATION: 79
    (D) OTHER INFORMATION: /note= "Xaa at position 79 is Pro
        or Ser"

(ix) FEATURE:
    (A) NAME/KEY: Modified-site
    (B) LOCATION: 81
    (D) OTHER INFORMATION: /note= "Xaa at position 81 is His
        or Thr"

(ix) FEATURE:
    (A) NAME/KEY: Modified-site
    (B) LOCATION: 84
    (D) OTHER INFORMATION: /note= "Xaa at position 84 is His,
        Ile, or Thr"
```

```
    (ix) FEATURE:
         (A) NAME/KEY: Modified-site
         (B) LOCATION: 86
         (D) OTHER INFORMATION: /note= "Xaa at position 86 is Lys
             or Arg"

(ix) FEATURE:
         (A) NAME/KEY: Modified-site
         (B) LOCATION: 87
         (D) OTHER INFORMATION: /note= "Xaa at position 87 is Asp,
             Ala, or Met"

(ix) FEATURE:
         (A) NAME/KEY: Modified-site
         (B) LOCATION: 91
         (D) OTHER INFORMATION: /note= "Xaa at position 91 is Asn
             or Glu"

(ix) FEATURE:
         (A) NAME/KEY: Modified-site
         (B) LOCATION: 95
         (D) OTHER INFORMATION: /note= "Xaa at position 95 is Arg,
             Glu, or Leu"

(ix) FEATURE:
         (A) NAME/KEY: Modified-site
         (B) LOCATION: 98
         (D) OTHER INFORMATION: /note= "Xaa at position 98 is Thr
             or Gln"

(ix) FEATURE:
         (A) NAME/KEY: Modified-site
         (B) LOCATION: 102
         (D) OTHER INFORMATION: /note= "Xaa at position 102 is Lys,
             Val, Trp, or Ser"

(ix) FEATURE:
         (A) NAME/KEY: Modified-site
         (B) LOCATION: 103
         (D) OTHER INFORMATION: /note= "Xaa at position 103 is Thr
             or Ser"

(ix) FEATURE:
         (A) NAME/KEY: Modified-site
         (B) LOCATION: 106
         (D) OTHER INFORMATION: /note= "Xaa at position 106 is Asn,
             Gln, or His"

(ix) FEATURE:
         (A) NAME/KEY: Modified-site
         (B) LOCATION: 109
         (D) OTHER INFORMATION: /note= "Xaa at position 109 is Ala
             or Glu"

(xi) SEQUENCE DESCRIPTION: SEQ ID NO:8:

Asn Cys Ser Xaa Xaa Xaa Asp Glu Xaa Ile Xaa His Leu Lys Xaa Pro
1               5                  10                 15

Pro Xaa Pro Xaa Leu Asp Xaa Xaa Asn Leu Asn Xaa Glu Asp Xaa Xaa
            20                 25                 30

Ile Leu Xaa Xaa Xaa Asn Leu Arg Xaa Xaa Asn Leu Xaa Xaa Phe Xaa
            35                 40                 45

Xaa Ala Xaa Lys Xaa Leu Xaa Asn Ala Ser Xaa Ile Glu Xaa Ile Leu
    50              55                 60

Xaa Asn Xaa Xaa Pro Cys Xaa Pro Xaa Xaa Thr Ala Xaa Pro Xaa Arg
65              70                 75                     80

Xaa Pro Ile Xaa Ile Xaa Xaa Gly Asp Trp Xaa Glu Phe Arg Xaa Lys
            85                 90                     95

Leu Xaa Phe Tyr Leu Xaa Xaa Leu Glu Xaa Ala Gln Xaa Gln Gln
        100                 105                110
```

(2) INFORMATION FOR SEQ ID NO:9:

(i) SEQUENCE CHARACTERISTICS:
        (A) LENGTH: 111 amino acids
        (B) TYPE: amino acid
        (D) TOPOLOGY: linear (ii) MOLECULE TYPE: peptide (xi) SEQUENCE DESCRIPTION: SEQ ID NO:9:

```
Asn Cys Ser Ile Met Ile Asp Glu Ile Ile His His Leu Lys Arg Pro
 1               5                  10                  15

Pro Ala Pro Leu Leu Asp Pro Asn Asn Leu Asn Ala Glu Asp Val Asp
                20                  25                  30

Ile Leu Met Glu Asn Asn Leu Arg Arg Pro Asn Leu Glu Ala Phe Asn
            35                  40                  45

Arg Ala Val Lys Ser Leu Gln Asn Ala Ser Ala Ile Glu Ser Ile Leu
         50                  55                  60

Lys Asn Leu Leu Pro Cys Leu Pro Leu Ala Thr Ala Ala Pro Thr Arg
 65                  70                  75                  80

His Pro Ile His Ile Lys Asp Gly Asp Trp Asn Glu Phe Arg Arg Lys
                85                  90                  95

Leu Thr Phe Tyr Leu Lys Thr Leu Glu Asn Ala Gln Ala Gln Gln
                100                 105                 110
```

(2) INFORMATION FOR SEQ ID NO:10:

(i) SEQUENCE CHARACTERISTICS:
        (A) LENGTH: 111 amino acids
        (B) TYPE: amino acid
        (D) TOPOLOGY: linear (ii) MOLECULE TYPE: peptide (xi) SEQUENCE DESCRIPTION: SEQ ID NO:10:

```
Asn Cys Ser Ile Met Ile Asp Glu Ile Ile His His Leu Lys Arg Pro
 1               5                  10                  15

Pro Asn Pro Leu Leu Asp Pro Asn Asn Leu Asn Ser Glu Asp Met Asp
                20                  25                  30

Ile Leu Met Glu Asn Asn Leu Arg Arg Pro Asn Leu Glu Ala Phe Asn
            35                  40                  45

Arg Ala Val Lys Ser Leu Gln Asn Ala Ser Ala Ile Glu Ser Ile Leu
         50                  55                  60

Lys Asn Leu Leu Pro Cys Leu Pro Leu Ala Thr Ala Ala Pro Thr Arg
 65                  70                  75                  80

His Pro Ile His Ile Lys Asp Gly Asp Trp Asn Glu Phe Arg Arg Lys
                85                  90                  95

Leu Thr Phe Tyr Leu Lys Thr Leu Glu Asn Ala Gln Ala Gln Gln
                100                 105                 110
```

(2) INFORMATION FOR SEQ ID NO:11:

(i) SEQUENCE CHARACTERISTICS:
        (A) LENGTH: 111 amino acids
        (B) TYPE: amino acid
        (D) TOPOLOGY: linear (ii) MOLECULE TYPE: peptide (xi) SEQUENCE DESCRIPTION: SEQ ID NO:11:

```
Asn Cys Ser Ile Met Ile Asp Glu Ile Ile His His Leu Lys Val Pro
 1               5                  10                  15
```

```
Pro Ala Pro Leu Leu Asp Ser Asn Asn Leu Asn Ser Glu Asp Met Asp
            20                  25                  30

Ile Leu Met Glu Asn Asn Leu Arg Arg Pro Asn Leu Glu Ala Phe Asn
        35                  40                  45

Arg Ala Val Lys Ser Leu Gln Asn Ala Ser Ala Ile Glu Ser Ile Leu
    50                  55                  60

Lys Asn Leu Leu Pro Cys Leu Pro Leu Ala Thr Ala Ala Pro Thr Arg
65                      70                  75                  80

His Pro Ile His Ile Lys Asp Gly Asp Trp Asn Glu Phe Arg Arg Lys
                85                  90                  95

Leu Thr Phe Tyr Leu Lys Thr Leu Glu Asn Ala Gln Ala Gln Gln
                100                 105                 110
```

(2) INFORMATION FOR SEQ ID NO:12:

(i) SEQUENCE CHARACTERISTICS:
        (A) LENGTH: 111 amino acids
        (B) TYPE: amino acid
        (D) TOPOLOGY: linear (ii) MOLECULE TYPE: peptide (xi) SEQUENCE DESCRIPTION: SEQ ID NO:12:

```
Asn Cys Ser Asn Met Ile Asp Glu Ile Ile Thr His Leu Lys Gln Pro
1               5                   10                  15

Pro Leu Pro Leu Leu Asp Phe Asn Asn Leu Asn Gly Glu Asp Gln Asp
            20                  25                  30

Ile Leu Met Glu Arg Asn Leu Arg Leu Pro Asn Leu Leu Ala Phe Val
        35                  40                  45

Arg Ala Val Lys Asn Leu Glu Asn Ala Ser Ala Ile Glu Ser Ile Leu
    50                  55                  60

Lys Asn Leu Leu Pro Cys Leu Pro Leu Ala Thr Ala Ala Pro Thr Arg
65                      70                  75                  80

His Pro Ile His Ile Lys Asp Gly Asp Trp Asn Glu Phe Arg Arg Lys
                85                  90                  95

Leu Thr Phe Tyr Leu Lys Thr Leu Glu Asn Ala Gln Ala Gln Gln
                100                 105                 110
```

(2) INFORMATION FOR SEQ ID NO:13:

(i) SEQUENCE CHARACTERISTICS:
        (A) LENGTH: 111 amino acids
        (B) TYPE: amino acid
        (D) TOPOLOGY: linear (ii) MOLECULE TYPE: peptide (xi) SEQUENCE DESCRIPTION: SEQ ID NO:13:

```
Asn Cys Ser Asn Met Ile Asp Glu Ile Ile Thr His Leu Lys Gln Pro
1               5                   10                  15

Pro Leu Pro Leu Leu Asp Phe Asn Asn Leu Asn Gly Glu Asp Gln Asp
            20                  25                  30

Ile Leu Met Glu Arg Asn Leu Arg Leu Pro Asn Leu Glu Ser Phe Val
        35                  40                  45

Arg Ala Val Lys Asn Leu Glu Asn Ala Ser Ala Ile Glu Ser Ile Leu
    50                  55                  60

Lys Asn Leu Leu Pro Cys Leu Pro Leu Ala Thr Ala Ala Pro Thr Arg
65                      70                  75                  80
```

```
His Pro Ile His Ile Lys Asp Gly Asp Trp Asn Glu Phe Arg Arg Lys
                85                  90                  95
Leu Thr Phe Tyr Leu Lys Thr Leu Glu Asn Ala Gln Ala Gln Gln
            100                 105                 110
```

(2) INFORMATION FOR SEQ ID NO:14:

(i) SEQUENCE CHARACTERISTICS:
        (A) LENGTH: 111 amino acids
        (B) TYPE: amino acid
        (D) TOPOLOGY: linear (ii) MOLECULE TYPE: peptide (xi) SEQUENCE DESCRIPTION: SEQ ID NO:14:

```
Asn Cys Ser Asn Met Ile Asp Glu Ile Ile Thr His Leu Lys Gln Pro
1               5                   10                  15
Pro Leu Pro Leu Leu Asp Phe Asn Asn Leu Asn Gly Glu Asp Gln Asp
            20                  25                  30
Ile Leu Met Glu Arg Asn Leu Arg Thr Pro Asn Leu Leu Ala Phe Val
            35                  40                  45
Arg Ala Val Lys His Leu Glu Asn Ala Ser Ala Ile Glu Ser Ile Leu
        50                  55                  60
Lys Asn Leu Leu Pro Cys Leu Pro Leu Ala Thr Ala Ala Pro Thr Arg
65                  70                  75                  80
His Pro Ile His Ile Lys Asp Gly Asp Trp Asn Glu Phe Arg Arg Lys
                85                  90                  95
Leu Thr Phe Tyr Leu Lys Thr Leu Glu Asn Ala Gln Ala Gln Gln
            100                 105                 110
```

(2) INFORMATION FOR SEQ ID NO:15:

(i) SEQUENCE CHARACTERISTICS:
        (A) LENGTH: 111 amino acids
        (B) TYPE: amino acid
        (D) TOPOLOGY: linear (ii) MOLECULE TYPE: peptide (xi) SEQUENCE DESCRIPTION: SEQ ID NO:15:

```
Asn Cys Ser Asn Met Ile Asp Glu Ile Ile Thr His Leu Lys Gln Pro
1               5                   10                  15
Pro Leu Pro Leu Leu Asp Phe Asn Asn Leu Asn Gly Glu Asp Gln Asp
            20                  25                  30
Ile Leu Met Glu Asn Asn Leu Arg Arg Pro Asn Leu Glu Ala Phe Asn
            35                  40                  45
Arg Ala Val Lys Ser Leu Gln Asn Ala Ser Gly Ile Glu Ala Ile Leu
        50                  55                  60
Arg Asn Leu Gln Pro Cys Leu Pro Ser Ala Thr Ala Ala Pro Ser Arg
65                  70                  75                  80
His Pro Ile Ile Ile Lys Ala Gly Asp Trp Gln Glu Phe Arg Arg Lys
                85                  90                  95
Leu Thr Phe Tyr Leu Lys Thr Leu Glu Asn Ala Gln Ala Gln Gln
            100                 105                 110
```

(2) INFORMATION FOR SEQ ID NO:16:

(i) SEQUENCE CHARACTERISTICS:
        (A) LENGTH: 111 amino acids
        (B) TYPE: amino acid
        (D) TOPOLOGY: linear (ii) MOLECULE TYPE: peptide (xi) SEQUENCE DESCRIPTION: SEQ ID NO:16:

```
Asn Cys Ser Asn Met Ile Asp Glu Ile Ile Thr His Leu Lys Gln Pro
1               5                   10                  15

Pro Leu Pro Leu Leu Asp Phe Asn Asn Leu Asn Gly Glu Asp Gln Asp
            20                  25                  30

Ile Leu Met Glu Asn Asn Leu Arg Arg Pro Asn Leu Glu Ala Phe Asn
            35                  40                  45

Arg Ala Val Lys Ser Leu Gln Asn Ala Ser Gly Ile Glu Ala Ile Leu
        50                  55                  60

Arg Asn Leu Val Pro Cys Leu Pro Ser Ala Thr Ala Ala Pro Ser Arg
65                  70                  75                  80

His Pro Ile Thr Ile Lys Ala Gly Asp Trp Gln Glu Phe Arg Arg Lys
                85                  90                  95

Leu Thr Phe Tyr Leu Lys Thr Leu Glu Asn Ala Gln Ala Gln Gln
                100                 105                 110
```

(2) INFORMATION FOR SEQ ID NO:17:

(i) SEQUENCE CHARACTERISTICS:
        (A) LENGTH: 111 amino acids
        (B) TYPE: amino acid
        (D) TOPOLOGY: linear (ii) MOLECULE TYPE: peptide (xi) SEQUENCE DESCRIPTION: SEQ ID NO:17:

```
Asn Cys Ser Asn Met Ile Asp Glu Ile Ile Thr His Leu Lys Gln Pro
1               5                   10                  15

Pro Leu Pro Leu Leu Asp Phe Asn Asn Leu Asn Gly Glu Asp Gln Asp
            20                  25                  30

Ile Leu Met Glu Asn Asn Leu Arg Arg Pro Asn Leu Glu Ala Phe Asn
            35                  40                  45

Arg Ala Val Lys Ser Leu Gln Asn Ala Ser Ala Ile Glu Ser Ile Leu
        50                  55                  60

Lys Asn Leu Leu Pro Cys Leu Pro Leu Ala Thr Ala Ala Pro Thr Arg
65                  70                  75                  80

His Pro Ile His Ile Lys Asp Gly Asp Trp Asn Glu Phe Arg Glu Lys
                85                  90                  95

Leu Thr Phe Tyr Leu Val Thr Leu Glu Gln Ala Gln Glu Gln Gln
                100                 105                 110
```

(2) INFORMATION FOR SEQ ID NO:18:

(i) SEQUENCE CHARACTERISTICS:
        (A) LENGTH: 111 amino acids
        (B) TYPE: amino acid
        (D) TOPOLOGY: linear (ii) MOLECULE TYPE: peptide (xi) SEQUENCE DESCRIPTION: SEQ ID NO:18:

```
Asn Cys Ser Asn Met Ile Asp Glu Ile Ile Thr His Leu Lys Gln Pro
1               5                   10                  15

Pro Leu Pro Leu Leu Asp Phe Asn Asn Leu Asn Gly Glu Asp Gln Asp
            20                  25                  30

Ile Leu Met Glu Asn Asn Leu Arg Arg Pro Asn Leu Glu Ala Phe Asn
            35                  40                  45
```

```
Arg Ala Val Lys Ser Leu Gln Asn Ala Ser Ala Ile Glu Ser Ile Leu
    50                  55                  60

Lys Asn Leu Leu Pro Cys Leu Pro Leu Ala Thr Ala Ala Pro Thr Arg
65                  70                  75                  80

His Pro Ile His Ile Lys Asp Gly Asp Trp Asn Glu Phe Arg Glu Lys
                85                  90                  95

Leu Thr Phe Tyr Leu Val Ser Leu Glu His Ala Gln Glu Gln Gln
                100                 105                 110
```

(2) INFORMATION FOR SEQ ID NO:19:

(i) SEQUENCE CHARACTERISTICS:
        (A) LENGTH: 111 amino acids
        (B) TYPE: amino acid
        (D) TOPOLOGY: linear (ii) MOLECULE TYPE: peptide (xi) SEQUENCE DESCRIPTION: SEQ ID NO:19:

```
Asn Cys Ser Asn Met Ile Asp Glu Ile Ile Thr His Leu Lys Gln Pro
1               5                   10                  15

Pro Leu Pro Leu Leu Asp Phe Asn Asn Leu Asn Gly Glu Asp Gln Asp
                20                  25                  30

Ile Leu Met Glu Asn Asn Leu Arg Arg Pro Asn Leu Glu Ala Phe Asn
                35                  40                  45

Arg Ala Val Lys Ser Leu Gln Asn Ala Ser Gly Ile Glu Ala Ile Leu
    50                  55                  60

Arg Asn Leu Gln Pro Cys Leu Pro Ser Ala Thr Ala Ala Pro Ser Arg
65                  70                  75                  80

His Pro Ile Ile Ile Lys Ala Gly Asp Trp Gln Glu Phe Arg Glu Lys
                85                  90                  95

Leu Thr Phe Tyr Leu Val Thr Leu Glu Gln Ala Gln Glu Gln Gln
                100                 105                 110
```

(2) INFORMATION FOR SEQ ID NO:20:

(i) SEQUENCE CHARACTERISTICS:
        (A) LENGTH: 111 amino acids
        (B) TYPE: amino acid
        (D) TOPOLOGY: linear (ii) MOLECULE TYPE: peptide (xi) SEQUENCE DESCRIPTION: SEQ ID NO:20:

```
Asn Cys Ser Asn Met Ile Asp Glu Ile Ile Thr His Leu Lys Gln Pro
1               5                   10                  15

Pro Leu Pro Leu Leu Asp Phe Asn Asn Leu Asn Gly Glu Asp Gln Asp
                20                  25                  30

Ile Leu Met Glu Asn Asn Leu Arg Arg Pro Asn Leu Glu Ala Phe Asn
                35                  40                  45

Arg Ala Val Lys Ser Leu Gln Asn Ala Ser Gly Ile Glu Ala Ile Leu
    50                  55                  60

Arg Asn Leu Val Pro Cys Leu Pro Ser Ala Thr Ala Ala Pro Ser Arg
65                  70                  75                  80

His Pro Ile Thr Ile Lys Ala Gly Asp Trp Gln Glu Phe Arg Glu Lys
                85                  90                  95

Leu Thr Phe Tyr Leu Val Thr Leu Glu Gln Ala Gln Glu Gln Gln
                100                 105                 110
```

(2) INFORMATION FOR SEQ ID NO:21:

(i) SEQUENCE CHARACTERISTICS:
        (A) LENGTH: 111 amino acids
        (B) TYPE: amino acid
        (D) TOPOLOGY: linear (ii) MOLECULE TYPE: peptide (xi) SEQUENCE DESCRIPTION: SEQ ID NO:21:

Asn Cys Ser Asn Met Ile Asp Glu Ile Ile Thr His Leu Lys Gln Pro
1               5                   10                  15

Pro Leu Pro Leu Leu Asp Phe Asn Asn Leu Asn Gly Glu Asp Gln Asp
            20                  25                  30

Ile Leu Met Glu Asn Asn Leu Arg Arg Pro Asn Leu Glu Ala Phe Asn
                35                  40                  45

Arg Ala Val Lys Ser Leu Gln Asn Ala Ser Gly Ile Glu Ala Ile Leu
50                      55                  60

Arg Asn Leu Val Pro Cys Leu Pro Ser Ala Thr Ala Ala Pro Ser Arg
65                      70                  75                  80

His Pro Ile Thr Ile Lys Ala Gly Asp Trp Gln Glu Phe Arg Glu Lys
                85                  90                  95

Leu Thr Phe Tyr Leu Val Ser Leu Glu His Ala Gln Glu Gln Gln
                100                 105                 110

(2) INFORMATION FOR SEQ ID NO:22:

(i) SEQUENCE CHARACTERISTICS:
        (A) LENGTH: 111 amino acids
        (B) TYPE: amino acid
        (D) TOPOLOGY: linear (ii) MOLECULE TYPE: peptide (xi) SEQUENCE DESCRIPTION: SEQ ID NO:22:

Asn Cys Ser Ile Met Ile Asp Glu Ile Ile His His Leu Lys Arg Pro
1               5                   10                  15

Pro Ala Pro Leu Leu Asp Pro Asn Asn Leu Asn Ala Glu Asp Val Asp
            20                  25                  30

Ile Leu Met Glu Arg Asn Leu Arg Leu Pro Asn Leu Glu Ser Phe Val
                35                  40                  45

Arg Ala Val Lys Asn Leu Glu Asn Ala Ser Ala Ile Glu Ser Ile Leu
50                      55                  60

Lys Asn Leu Leu Pro Cys Leu Pro Leu Ala Thr Ala Ala Pro Thr Arg
65                      70                  75                  80

His Pro Ile His Ile Lys Asp Gly Asp Trp Asn Glu Phe Arg Arg Lys
                85                  90                  95

Leu Thr Phe Tyr Leu Lys Thr Leu Glu Asn Ala Gln Ala Gln Gln
                100                 105                 110

(2) INFORMATION FOR SEQ ID NO:23:

(i) SEQUENCE CHARACTERISTICS:
        (A) LENGTH: 111 amino acids
        (B) TYPE: amino acid
        (D) TOPOLOGY: linear (ii) MOLECULE TYPE: peptide (xi) SEQUENCE DESCRIPTION: SEQ ID NO:23:

Asn Cys Ser Ile Met Ile Asp Glu Ile Ile His His Leu Lys Arg Pro

-continued

```
1               5                   10                  15
Pro Asn Pro Leu Leu Asp Pro Asn Asn Leu Asn Ser Glu Asp Met Asp
                20                  25                  30
Ile Leu Met Glu Arg Asn Leu Arg Thr Pro Asn Leu Leu Ala Phe Val
                35                  40                  45
Arg Ala Val Lys His Leu Glu Asn Ala Ser Ala Ile Glu Ser Ile Leu
 50                  55                  60
Lys Asn Leu Leu Pro Cys Leu Pro Leu Ala Thr Ala Ala Pro Thr Arg
 65                  70                  75                  80
His Pro Ile His Ile Lys Asp Gly Asp Trp Asn Glu Phe Arg Arg Lys
                85                  90                  95
Leu Thr Phe Tyr Leu Lys Thr Leu Glu Asn Ala Gln Ala Gln Gln
                100                 105                 110
```

(2) INFORMATION FOR SEQ ID NO:24:

(i) SEQUENCE CHARACTERISTICS:
        (A) LENGTH: 111 amino acids
        (B) TYPE: amino acid
        (D) TOPOLOGY: linear (ii) MOLECULE TYPE: peptide (xi) SEQUENCE DESCRIPTION: SEQ ID NO:24:

```
Asn Cys Ser Ile Met Ile Asp Glu Ile Ile His His Leu Lys Val Pro
 1               5                   10                  15
Pro Ala Pro Leu Leu Asp Ser Asn Asn Leu Asn Ser Glu Asp Met Asp
                20                  25                  30
Ile Leu Met Glu Arg Asn Leu Arg Leu Pro Asn Leu Leu Ala Phe Val
                35                  40                  45
Arg Ala Val Lys Asn Leu Glu Asn Ala Ser Ala Ile Glu Ser Ile Leu
 50                  55                  60
Lys Asn Leu Leu Pro Cys Leu Pro Leu Ala Thr Ala Ala Pro Thr Arg
 65                  70                  75                  80
His Pro Ile His Ile Lys Asp Gly Asp Trp Asn Glu Phe Arg Arg Lys
                85                  90                  95
Leu Thr Phe Tyr Leu Lys Thr Leu Glu Asn Ala Gln Ala Gln Gln
                100                 105                 110
```

(2) INFORMATION FOR SEQ ID NO:25:

(i) SEQUENCE CHARACTERISTICS:
        (A) LENGTH: 113 amino acids
        (B) TYPE: amino acid
        (D) TOPOLOGY: linear (ii) MOLECULE TYPE: peptide (xi) SEQUENCE DESCRIPTION: SEQ ID NO:25:

```
Met Ala Asn Cys Ser Asn Met Ile Asp Glu Ile Ile Thr His Leu Lys
 1               5                   10                  15
Gln Pro Pro Leu Pro Leu Leu Asp Phe Asn Asn Leu Asn Gly Glu Asp
                20                  25                  30
Gln Asp Ile Leu Met Glu Asn Asn Leu Arg Arg Pro Asn Leu Glu Ala
                35                  40                  45
Phe Asn Arg Ala Val Lys Ser Leu Gln Asn Ala Ser Gly Ile Glu Ala
 50                  55                  60
Ile Leu Arg Asn Leu Gln Pro Cys Leu Pro Ser Ala Thr Ala Ala Pro
 65                  70                  75                  80
```

Ser Arg His Pro Ile Ile Ile Lys Ala Gly Asp Trp Gln Glu Phe Arg
                85                  90                  95

Glu Lys Leu Thr Phe Tyr Leu Val Thr Leu Glu Gln Ala Gln Glu Gln
                100                 105                 110

Gln (2) INFORMATION FOR SEQ ID NO:26:

(i) SEQUENCE CHARACTERISTICS:
        (A) LENGTH: 113 amino acids
        (B) TYPE: amino acid
        (D) TOPOLOGY: linear (ii) MOLECULE TYPE: peptide (xi) SEQUENCE DESCRIPTION: SEQ ID NO:26:

Met Ala Asn Cys Ser Asn Met Ile Asp Glu Ile Ile Thr His Leu Lys
1               5                   10                  15

Gln Pro Pro Leu Pro Leu Leu Asp Phe Asn Asn Leu Asn Gly Glu Asp
                20                  25                  30

Gln Asp Ile Leu Met Glu Asn Asn Leu Arg Arg Pro Asn Leu Glu Ala
            35                  40                  45

Phe Asn Arg Ala Val Lys Ser Leu Gln Asn Ala Ser Gly Ile Glu Ala
    50                  55                  60

Ile Leu Arg Asn Leu Val Pro Cys Leu Pro Ser Ala Thr Ala Ala Pro
65                  70                  75                  80

Ser Arg His Pro Ile Thr Ile Lys Ala Gly Asp Trp Gln Glu Phe Arg
                85                  90                  95

Glu Lys Leu Thr Phe Tyr Leu Val Thr Leu Glu Gln Ala Gln Glu Gln
                100                 105                 110

Gln (2) INFORMATION FOR SEQ ID NO:27:

(i) SEQUENCE CHARACTERISTICS:
        (A) LENGTH: 113 amino acids
        (B) TYPE: amino acid
        (D) TOPOLOGY: linear (ii) MOLECULE TYPE: peptide (xi) SEQUENCE DESCRIPTION: SEQ ID NO:27:

Met Ala Asn Cys Ser Asn Met Ile Asp Glu Ile Ile Thr His Leu Lys
1               5                   10                  15

Gln Pro Pro Leu Pro Leu Leu Asp Phe Asn Asn Leu Asn Gly Glu Asp
                20                  25                  30

Gln Asp Ile Leu Met Glu Asn Asn Leu Arg Arg Pro Asn Leu Glu Ala
            35                  40                  45

Phe Asn Arg Ala Val Lys Ser Leu Gln Asn Ala Ser Gly Ile Glu Ala
    50                  55                  60

Ile Leu Arg Asn Leu Val Pro Cys Leu Pro Ser Ala Thr Ala Ala Pro
65                  70                  75                  80

Ser Arg His Pro Ile Thr Ile Lys Ala Gly Asp Trp Gln Glu Phe Arg
                85                  90                  95

Glu Lys Leu Thr Phe Tyr Leu Val Ser Leu Glu His Ala Gln Glu Gln
                100                 105                 110

Gln (2) INFORMATION FOR SEQ ID NO:28:

(i) SEQUENCE CHARACTERISTICS:
        (A) LENGTH: 113 amino acids
        (B) TYPE: amino acid
        (D) TOPOLOGY: linear (ii) MOLECULE TYPE: peptide (xi) SEQUENCE DESCRIPTION: SEQ ID NO:28:

```
Met Ala Asn Cys Ser Ile Met Ile Asp Glu Ile Ile His His Leu Lys
1               5                   10                  15

Arg Pro Pro Ala Pro Leu Leu Asp Pro Asn Asn Leu Asn Ala Glu Asp
            20                  25                  30

Val Asp Ile Leu Met Glu Arg Asn Leu Arg Leu Pro Asn Leu Glu Ser
        35                  40                  45

Phe Val Arg Ala Val Lys Asn Leu Glu Asn Ala Ser Ala Ile Glu Ser
    50                  55                  60

Ile Leu Lys Asn Leu Leu Pro Cys Leu Pro Leu Ala Thr Ala Ala Pro
65                  70                  75                  80

Thr Arg His Pro Ile His Ile Lys Asp Gly Asp Trp Asn Glu Phe Arg
                85                  90                  95

Arg Lys Leu Thr Phe Tyr Leu Lys Thr Leu Glu Asn Ala Gln Ala Gln
                100                 105                 110

Gln
```

(2) INFORMATION FOR SEQ ID NO:29:

(i) SEQUENCE CHARACTERISTICS:
        (A) LENGTH: 113 amino acids
        (B) TYPE: amino acid
        (D) TOPOLOGY: linear (ii) MOLECULE TYPE: peptide (xi) SEQUENCE DESCRIPTION: SEQ ID NO:29:

```
Met Ala Asn Cys Ser Ile Met Ile Asp Glu Ile Ile His His Leu Lys
1               5                   10                  15

Arg Pro Pro Asn Pro Leu Leu Asp Pro Asn Asn Leu Asn Ser Glu Asp
            20                  25                  30

Met Asp Ile Leu Met Glu Arg Asn Leu Arg Thr Pro Asn Leu Leu Ala
        35                  40                  45

Phe Val Arg Ala Val Lys His Leu Glu Asn Ala Ser Ala Ile Glu Ser
    50                  55                  60

Ile Leu Lys Asn Leu Leu Pro Cys Leu Pro Leu Ala Thr Ala Ala Pro
65                  70                  75                  80

Thr Arg His Pro Ile His Ile Lys Asp Gly Asp Trp Asn Glu Phe Arg
                85                  90                  95

Arg Lys Leu Thr Phe Tyr Leu Lys Thr Leu Glu Asn Ala Gln Ala Gln
                100                 105                 110

Gln
```

(2) INFORMATION FOR SEQ ID NO:30:

(i) SEQUENCE CHARACTERISTICS:
        (A) LENGTH: 113 amino acids
        (B) TYPE: amino acid
        (D) TOPOLOGY: linear (ii) MOLECULE TYPE: peptide (xi) SEQUENCE DESCRIPTION: SEQ ID NO:30:

Met Ala Asn Cys Ser Ile Met Ile Asp Glu Ile Ile His His Leu Lys
1               5                   10                  15

Val Pro Pro Ala Pro Leu Leu Asp Ser Asn Asn Leu Asn Ser Glu Asp
                20                  25                  30

Met Asp Ile Leu Met Glu Arg Asn Leu Arg Leu Pro Asn Leu Leu Ala
            35                  40                  45

Phe Val Arg Ala Val Lys Asn Leu Glu Asn Ala Ser Ala Ile Glu Ser
    50                  55                  60

Ile Leu Lys Asn Leu Leu Pro Cys Leu Pro Leu Ala Thr Ala Ala Pro
65                  70                  75                  80

Thr Arg His Pro Ile His Ile Lys Asp Gly Asp Trp Asn Glu Phe Arg
                85                  90                  95

Arg Lys Leu Thr Phe Tyr Leu Lys Thr Leu Glu Asn Ala Gln Ala Gln
            100                 105                 110

Gln (2) INFORMATION FOR SEQ ID NO:31:

(i) SEQUENCE CHARACTERISTICS:
        (A) LENGTH: 113 amino acids
        (B) TYPE: amino acid
        (D) TOPOLOGY: linear (ii) MOLECULE TYPE: peptide (xi) SEQUENCE DESCRIPTION: SEQ ID NO:31:

Met Ala Asn Cys Ser Ile Met Ile Asp Glu Ile Ile His His Leu Lys
1               5                   10                  15

Arg Pro Pro Ala Pro Leu Leu Asp Pro Asn Asn Leu Asn Ala Glu Asp
                20                  25                  30

Val Asp Ile Leu Met Glu Arg Asn Leu Arg Leu Pro Asn Leu Glu Ser
            35                  40                  45

Phe Val Arg Ala Val Lys Asn Leu Glu Asn Ala Ser Gly Ile Glu Ala
    50                  55                  60

Ile Leu Arg Asn Leu Gln Pro Cys Leu Pro Ser Ala Thr Ala Ala Pro
65                  70                  75                  80

Ser Arg His Pro Ile Ile Ile Lys Ala Gly Asp Trp Gln Glu Phe Arg
                85                  90                  95

Glu Lys Leu Thr Phe Tyr Leu Val Thr Leu Glu Gln Ala Gln Glu Gln
            100                 105                 110

Gln (2) INFORMATION FOR SEQ ID NO:32:

(i) SEQUENCE CHARACTERISTICS:
        (A) LENGTH: 113 amino acids
        (B) TYPE: amino acid
        (D) TOPOLOGY: linear (ii) MOLECULE TYPE: peptide (xi) SEQUENCE DESCRIPTION: SEQ ID NO:32:

Met Ala Asn Cys Ser Ile Met Ile Asp Glu Ile Ile His His Leu Lys
1               5                   10                  15

Arg Pro Pro Asn Pro Leu Leu Asp Pro Asn Asn Leu Asn Ser Glu Asp
                20                  25                  30

```
Met Asp Ile Leu Met Glu Arg Asn Leu Arg Thr Pro Asn Leu Leu Ala
        35                  40                  45

Phe Val Arg Ala Val Lys His Leu Glu Asn Ala Ser Gly Ile Glu Ala
        50                  55                  60

Ile Leu Arg Asn Leu Gln Pro Cys Leu Pro Ser Ala Thr Ala Ala Pro
 65                  70                  75                  80

Ser Arg His Pro Ile Ile Ile Lys Ala Gly Asp Trp Gln Glu Phe Arg
                 85                  90                  95

Glu Lys Leu Thr Phe Tyr Leu Val Thr Leu Glu Gln Ala Gln Glu Gln
            100                 105                 110

Gln
```

(2) INFORMATION FOR SEQ ID NO:33:

(i) SEQUENCE CHARACTERISTICS:
        (A) LENGTH: 113 amino acids
        (B) TYPE: amino acid
        (D) TOPOLOGY: linear (ii) MOLECULE TYPE: peptide (xi) SEQUENCE DESCRIPTION: SEQ ID NO:33:

```
Met Ala Asn Cys Ser Ile Met Ile Asp Glu Ile Ile His His Leu Lys
 1               5                  10                  15

Val Pro Pro Ala Pro Leu Leu Asp Ser Asn Asn Leu Asn Ser Glu Asp
                20                  25                  30

Met Asp Ile Leu Met Glu Arg Asn Leu Arg Leu Pro Asn Leu Leu Ala
        35                  40                  45

Phe Val Arg Ala Val Lys Asn Leu Glu Asn Ala Ser Gly Ile Glu Ala
        50                  55                  60

Ile Leu Arg Asn Leu Gln Pro Cys Leu Pro Ser Ala Thr Ala Ala Pro
 65                  70                  75                  80

Ser Arg His Pro Ile Ile Ile Lys Ala Gly Asp Trp Gln Glu Phe Arg
                 85                  90                  95

Glu Lys Leu Thr Phe Tyr Leu Val Thr Leu Glu Gln Ala Gln Glu Gln
            100                 105                 110

Gln
```

(2) INFORMATION FOR SEQ ID NO:34:

(i) SEQUENCE CHARACTERISTICS:
        (A) LENGTH: 113 amino acids
        (B) TYPE: amino acid
        (D) TOPOLOGY: linear (ii) MOLECULE TYPE: peptide (xi) SEQUENCE DESCRIPTION: SEQ ID NO:34:

```
Met Ala Asn Cys Ser Ile Met Ile Asp Glu Ile Ile His His Leu Lys
 1               5                  10                  15

Arg Pro Pro Ala Pro Leu Leu Asp Pro Asn Asn Leu Asn Ala Glu Asp
                20                  25                  30

Val Asp Ile Leu Met Glu Arg Asn Leu Arg Leu Pro Asn Leu Glu Ser
        35                  40                  45

Phe Val Arg Ala Val Lys Asn Leu Glu Asn Ala Ser Gly Ile Glu Ala
        50                  55                  60

Ile Leu Arg Asn Leu Val Pro Cys Leu Pro Ser Ala Thr Ala Ala Pro
 65                  70                  75                  80
```

```
Ser Arg His Pro Ile Thr Ile Lys Ala Gly Asp Trp Gln Glu Phe Arg
                85                  90                  95

Glu Lys Leu Thr Phe Tyr Leu Val Thr Leu Glu Gln Ala Gln Glu Gln
            100                 105                 110

Gln
```

(2) INFORMATION FOR SEQ ID NO:35:

(i) SEQUENCE CHARACTERISTICS:
        (A) LENGTH: 113 amino acids
        (B) TYPE: amino acid
        (D) TOPOLOGY: linear (ii) MOLECULE TYPE: peptide (xi) SEQUENCE DESCRIPTION: SEQ ID NO:35:

```
Met Ala Asn Cys Ser Ile Met Ile Asp Glu Ile Ile His His Leu Lys
1               5                   10                  15

Val Pro Pro Ala Pro Leu Leu Asp Ser Asn Asn Leu Asn Ser Glu Asp
            20                  25                  30

Met Asp Ile Leu Met Glu Arg Asn Leu Arg Leu Pro Asn Leu Leu Ala
            35                  40                  45

Phe Val Arg Ala Val Lys Asn Leu Glu Asn Ala Ser Gly Ile Glu Ala
        50                  55                  60

Ile Leu Arg Asn Leu Val Pro Cys Leu Pro Ser Ala Thr Ala Ala Pro
65                  70                  75                  80

Ser Arg His Pro Ile Thr Ile Lys Ala Gly Asp Trp Gln Glu Phe Arg
                85                  90                  95

Glu Lys Leu Thr Phe Tyr Leu Val Thr Leu Glu Gln Ala Gln Glu Gln
            100                 105                 110

Gln
```

(2) INFORMATION FOR SEQ ID NO:36:

(i) SEQUENCE CHARACTERISTICS:
        (A) LENGTH: 113 amino acids
        (B) TYPE: amino acid
        (D) TOPOLOGY: linear (ii) MOLECULE TYPE: peptide (xi) SEQUENCE DESCRIPTION: SEQ ID NO:36:

```
Met Ala Asn Cys Ser Ile Met Ile Asp Glu Ile Ile His His Leu Lys
1               5                   10                  15

Arg Pro Pro Asn Pro Leu Leu Asp Pro Asn Asn Leu Asn Ser Glu Asp
            20                  25                  30

Met Asp Ile Leu Met Glu Arg Asn Leu Arg Thr Pro Asn Leu Leu Ala
            35                  40                  45

Phe Val Arg Ala Val Lys His Leu Glu Asn Ala Ser Gly Ile Glu Ala
        50                  55                  60

Ile Leu Arg Asn Leu Val Pro Cys Leu Pro Ser Ala Thr Ala Ala Pro
65                  70                  75                  80

Ser Arg His Pro Ile Thr Ile Lys Ala Gly Asp Trp Gln Glu Phe Arg
                85                  90                  95

Glu Lys Leu Thr Phe Tyr Leu Val Ser Leu Glu His Ala Gln Glu Gln
            100                 105                 110

Gln
```

(2) INFORMATION FOR SEQ ID NO:37:

(i) SEQUENCE CHARACTERISTICS:
        (A) LENGTH: 113 amino acids
        (B) TYPE: amino acid
        (D) TOPOLOGY: linear (ii) MOLECULE TYPE: peptide (xi) SEQUENCE DESCRIPTION: SEQ ID NO:37:

```
Met Ala Asn Cys Ser Ile Met Ile Asp Glu Ile Ile His His Leu Lys
1               5                   10                  15

Val Pro Pro Ala Pro Leu Leu Asp Ser Asn Asn Leu Asn Ser Glu Asp
            20                  25                  30

Met Asp Ile Leu Met Glu Arg Asn Leu Arg Leu Pro Asn Leu Leu Ala
        35                  40                  45

Phe Val Arg Ala Val Lys Asn Leu Glu Asn Ala Ser Gly Ile Glu Ala
    50                  55                  60

Ile Leu Arg Asn Leu Val Pro Cys Leu Pro Ser Ala Thr Ala Ala Pro
65                  70                  75                  80

Ser Arg His Pro Ile Thr Ile Lys Ala Gly Asp Trp Gln Glu Phe Arg
                85                  90                  95

Glu Lys Leu Thr Phe Tyr Leu Val Ser Leu Glu His Ala Gln Glu Gln
            100                 105                 110

Gln
```

(2) INFORMATION FOR SEQ ID NO:38:

(i) SEQUENCE CHARACTERISTICS:
        (A) LENGTH: 113 amino acids
        (B) TYPE: amino acid
        (D) TOPOLOGY: linear (ii) MOLECULE TYPE: peptide (xi) SEQUENCE DESCRIPTION: SEQ ID NO:38:

```
Met Ala Asn Cys Ser Ile Met Ile Asp Glu Ile Ile His His Leu Lys
1               5                   10                  15

Arg Pro Pro Asn Pro Leu Leu Asp Pro Asn Asn Leu Asn Ser Glu Asp
            20                  25                  30

Met Asp Ile Leu Met Glu Arg Asn Leu Arg Thr Pro Asn Leu Leu Ala
        35                  40                  45

Phe Val Arg Ala Val Lys His Leu Glu Asn Ala Ser Gly Ile Glu Ala
    50                  55                  60

Ile Leu Arg Asn Leu Val Pro Cys Leu Pro Ser Ala Thr Ala Ala Pro
65                  70                  75                  80

Ser Arg His Pro Ile Thr Ile Lys Ala Gly Asp Trp Gln Glu Phe Arg
                85                  90                  95

Glu Lys Leu Thr Phe Tyr Leu Val Thr Leu Glu Gln Ala Gln Glu Gln
            100                 105                 110

Gln
```

(2) INFORMATION FOR SEQ ID NO:39:

(i) SEQUENCE CHARACTERISTICS:
        (A) LENGTH: 113 amino acids
        (B) TYPE: amino acid
        (D) TOPOLOGY: linear (ii) MOLECULE TYPE: peptide -continued (xi) SEQUENCE DESCRIPTION: SEQ ID NO:39:

Met Ala Asn Cys Ser Ile Met Ile Asp Glu Ile Ile His His Leu Lys
1               5                   10                  15

Arg Pro Pro Ala Pro Leu Leu Asp Pro Asn Asn Leu Asn Ala Glu Asp
            20                  25                  30

Val Asp Ile Leu Met Glu Arg Asn Leu Arg Leu Pro Asn Leu Glu Ser
        35                  40                  45

Phe Val Arg Ala Val Lys Asn Leu Glu Asn Ala Ser Gly Ile Glu Ala
    50                  55                  60

Ile Leu Arg Asn Leu Val Pro Cys Leu Pro Ser Ala Thr Ala Ala Pro
65                  70                  75                  80

Ser Arg His Pro Ile Thr Ile Lys Ala Gly Asp Trp Gln Glu Phe Arg
                85                  90                  95

Glu Lys Leu Thr Phe Tyr Leu Val Ser Leu Glu His Ala Gln Glu Gln
            100                 105                 110

Gln (2) INFORMATION FOR SEQ ID NO:40:

(i) SEQUENCE CHARACTERISTICS:
        (A) LENGTH: 113 amino acids
        (B) TYPE: amino acid
        (D) TOPOLOGY: linear (ii) MOLECULE TYPE: peptide (xi) SEQUENCE DESCRIPTION: SEQ ID NO:40:

Met Ala Asn Cys Ser Ile Met Ile Asp Glu Ile Ile His His Leu Lys
1               5                   10                  15

Arg Pro Pro Ala Pro Leu Leu Asp Pro Asn Asn Leu Asn Ala Glu Asp
            20                  25                  30

Val Asp Ile Leu Met Asp Arg Asn Leu Arg Leu Ser Asn Leu Glu Ser
        35                  40                  45

Phe Val Arg Ala Val Lys Asn Leu Glu Asn Ala Ser Gly Ile Glu Ala
    50                  55                  60

Ile Leu Arg Asn Leu Gln Pro Cys Leu Pro Ser Ala Thr Ala Ala Pro
65                  70                  75                  80

Ser Arg His Pro Ile Ile Ile Lys Ala Gly Asp Trp Gln Glu Phe Arg
                85                  90                  95

Glu Lys Leu Thr Phe Tyr Leu Val Thr Leu Glu Gln Ala Gln Glu Gln
            100                 105                 110

Gln (2) INFORMATION FOR SEQ ID NO:41:

(i) SEQUENCE CHARACTERISTICS:
        (A) LENGTH: 113 amino acids
        (B) TYPE: amino acid
        (D) TOPOLOGY: linear (ii) MOLECULE TYPE: peptide (xi) SEQUENCE DESCRIPTION: SEQ ID NO:41:

Met Ala Asn Cys Ser Ile Met Ile Asp Glu Ala Ile His His Leu Lys
1               5                   10                  15

Arg Pro Pro Ala Pro Ser Leu Asp Pro Asn Asn Leu Asn Asp Glu Asp
            20                  25                  30

Met Ser Ile Leu Met Glu Arg Asn Leu Arg Leu Pro Asn Leu Glu Ser

```
              35                  40                  45
Phe Val Arg Ala Val Lys Asn Leu Glu Asn Ala Ser Gly Ile Glu Ala
 50                  55                  60

Ile Leu Arg Asn Leu Gln Pro Cys Leu Pro Ser Ala Thr Ala Ala Pro
 65                  70                  75                  80

Ser Arg His Pro Ile Ile Ile Lys Ala Gly Asp Trp Gln Glu Phe Arg
                 85                  90                  95

Glu Lys Leu Thr Phe Tyr Leu Val Thr Leu Glu Gln Ala Gln Glu Gln
                100                 105                 110

Gln (2) INFORMATION FOR SEQ ID NO:42:

(i) SEQUENCE CHARACTERISTICS:
        (A) LENGTH: 113 amino acids
        (B) TYPE: amino acid
        (D) TOPOLOGY: linear (ii) MOLECULE TYPE: peptide (xi) SEQUENCE DESCRIPTION: SEQ ID NO:42:

Met Ala Asn Cys Ser Ile Met Ile Asp Glu Ile Ile His His Leu Lys
 1               5                  10                  15

Arg Pro Pro Ala Pro Leu Leu Asp Pro Asn Asn Leu Asn Asp Glu Asp
                 20                  25                  30

Met Ser Ile Leu Met Glu Arg Asn Leu Arg Leu Pro Asn Leu Glu Ser
                 35                  40                  45

Phe Val Arg Ala Val Lys Asn Leu Glu Asn Ala Ser Gly Ile Glu Ala
 50                  55                  60

Ile Leu Arg Asn Leu Gln Pro Cys Leu Pro Ser Ala Thr Ala Ala Pro
 65                  70                  75                  80

Ser Arg His Pro Ile Ile Ile Lys Ala Gly Asp Trp Gln Glu Phe Arg
                 85                  90                  95

Glu Lys Leu Thr Phe Tyr Leu Val Thr Leu Glu Gln Ala Gln Glu Gln
                100                 105                 110

Gln (2) INFORMATION FOR SEQ ID NO:43:

(i) SEQUENCE CHARACTERISTICS:
        (A) LENGTH: 113 amino acids
        (B) TYPE: amino acid
        (D) TOPOLOGY: linear (ii) MOLECULE TYPE: peptide (xi) SEQUENCE DESCRIPTION: SEQ ID NO:43:

Met Ala Asn Cys Ser Ile Met Ile Asp Glu Ile Ile His His Leu Lys
 1               5                  10                  15

Arg Pro Pro Ala Pro Leu Leu Asp Pro Asn Asn Leu Asn Ala Glu Asp
                 20                  25                  30

Val Asp Ile Leu Met Asp Arg Asn Leu Arg Leu Pro Asn Leu Glu Ser
                 35                  40                  45

Phe Val Arg Ala Val Lys Asn Leu Glu Asn Ala Ser Gly Ile Glu Ala
 50                  55                  60

Ile Leu Arg Asn Leu Gln Pro Cys Leu Pro Ser Ala Thr Ala Ala Pro
 65                  70                  75                  80

Ser Arg His Pro Ile Ile Ile Lys Ala Gly Asp Trp Gln Glu Phe Arg
```

```
                    85                  90                  95
Glu Lys Leu Thr Phe Tyr Leu Val Thr Leu Glu Gln Ala Gln Glu Gln
                100                 105                 110
Gln
```

(2) INFORMATION FOR SEQ ID NO:44:

(i) SEQUENCE CHARACTERISTICS:
        (A) LENGTH: 113 amino acids
        (B) TYPE: amino acid
        (D) TOPOLOGY: linear (ii) MOLECULE TYPE: peptide (xi) SEQUENCE DESCRIPTION: SEQ ID NO:44:

```
Met Ala Asn Cys Ser Ile Met Ile Asp Glu Ile Ile His His Leu Lys
1               5                   10                  15
Arg Pro Pro Ala Pro Leu Leu Asp Pro Asn Asn Leu Asn Asp Glu Asp
                20                  25                  30
Val Ser Ile Leu Met Glu Arg Asn Leu Arg Leu Pro Asn Leu Glu Ser
            35                  40                  45
Phe Val Arg Ala Val Lys Asn Leu Glu Asn Ala Ser Gly Ile Glu Ala
        50                  55                  60
Ile Leu Arg Asn Leu Gln Pro Cys Leu Pro Ser Ala Thr Ala Ala Pro
65                  70                  75                  80
Ser Arg His Pro Ile Ile Ile Lys Ala Gly Asp Trp Gln Glu Phe Arg
                85                  90                  95
Glu Lys Leu Thr Phe Tyr Leu Val Thr Leu Glu Gln Ala Gln Glu Gln
                100                 105                 110
Gln
```

(2) INFORMATION FOR SEQ ID NO:45:

(i) SEQUENCE CHARACTERISTICS:
        (A) LENGTH: 113 amino acids
        (B) TYPE: amino acid
        (D) TOPOLOGY: linear (ii) MOLECULE TYPE: peptide (xi) SEQUENCE DESCRIPTION: SEQ ID NO:45:

```
Met Ala Asn Cys Ser Ile Met Ile Asp Glu Ile Ile His His Leu Lys
1               5                   10                  15
Arg Pro Pro Ala Pro Leu Leu Asp Pro Asn Asn Leu Asn Asp Glu Asp
                20                  25                  30
Met Ser Ile Leu Met Glu Arg Asn Leu Arg Leu Pro Asn Leu Glu Ser
            35                  40                  45
Phe Val Arg Ala Val Lys Asn Leu Glu Asn Ala Ser Gly Ile Glu Ala
        50                  55                  60
Ile Leu Arg Asn Leu Gln Pro Cys Leu Pro Ser Ala Thr Ala Ala Pro
65                  70                  75                  80
Ser Arg His Pro Ile Ile Ile Lys Ala Gly Asp Trp Gln Glu Phe Arg
                85                  90                  95
Glu Lys Leu Thr Phe Tyr Leu Val Thr Leu Glu Gln Ala Gln Glu Gln
                100                 105                 110
Gln
```

(2) INFORMATION FOR SEQ ID NO:46:

(i) SEQUENCE CHARACTERISTICS:
    (A) LENGTH: 125 amino acids
    (B) TYPE: amino acid
    (D) TOPOLOGY: linear (ii) MOLECULE TYPE: peptide (xi) SEQUENCE DESCRIPTION: SEQ ID NO:46:

```
Met Ala Tyr Pro Glu Thr Asp Tyr Lys Asp Asp Asp Lys Asn Cys
1               5                   10                  15

Ser Ile Met Ile Asp Glu Ile Ile His His Leu Lys Arg Pro Pro Ala
            20                  25                  30

Pro Leu Leu Asp Pro Asn Asn Leu Asn Ala Glu Asp Val Asp Ile Leu
            35                  40                  45

Met Glu Arg Asn Leu Arg Leu Pro Asn Leu Glu Ser Phe Val Arg Ala
    50                  55                  60

Val Lys Asn Leu Glu Asn Ala Ser Gly Ile Glu Ala Ile Leu Arg Asn
65                  70                  75                  80

Leu Gln Pro Cys Leu Pro Ser Ala Thr Ala Ala Pro Ser Arg His Pro
                85                  90                  95

Ile Ile Ile Lys Ala Gly Asp Trp Gln Glu Phe Arg Glu Lys Leu Thr
                100                 105                 110

Phe Tyr Leu Val Thr Leu Glu Gln Ala Gln Glu Gln Gln
        115                 120                 125
```

(2) INFORMATION FOR SEQ ID NO:47:

(i) SEQUENCE CHARACTERISTICS:
        (A) LENGTH: 125 amino acids
        (B) TYPE: amino acid
        (D) TOPOLOGY: linear (ii) MOLECULE TYPE: peptide (xi) SEQUENCE DESCRIPTION: SEQ ID NO:47:

```
Met Ala Tyr Pro Glu Thr Asp Tyr Lys Asp Asp Asp Lys Asn Cys
1               5                   10                  15

Ser Ile Met Ile Asp Glu Ile Ile His His Leu Lys Arg Pro Pro Asn
            20                  25                  30

Pro Leu Leu Asp Pro Asn Asn Leu Asn Ser Glu Asp Met Asp Ile Leu
            35                  40                  45

Met Glu Arg Asn Leu Arg Thr Pro Asn Leu Leu Ala Phe Val Arg Ala
    50                  55                  60

Val Lys His Leu Glu Asn Ala Ser Gly Ile Glu Ala Ile Leu Arg Asn
65                  70                  75                  80

Leu Gln Pro Cys Leu Pro Ser Ala Thr Ala Ala Pro Ser Arg His Pro
                85                  90                  95

Ile Ile Ile Lys Ala Gly Asp Trp Gln Glu Phe Arg Glu Lys Leu Thr
                100                 105                 110

Phe Tyr Leu Val Thr Leu Glu Gln Ala Gln Glu Gln Gln
        115                 120                 125
```

(2) INFORMATION FOR SEQ ID NO:48:

(i) SEQUENCE CHARACTERISTICS:
        (A) LENGTH: 113 amino acids
        (B) TYPE: amino acid
        (D) TOPOLOGY: linear (ii) MOLECULE TYPE: peptide (xi) SEQUENCE DESCRIPTION: SEQ ID NO:48:

Met Ala Asn Cys Ser Ile Met Ile Asp Glu Leu Ile His His Leu Lys
1               5                   10                  15

Ile Pro Pro Asn Pro Ser Leu Asp Ser Ala Asn Leu Asn Ser Glu Asp
                20                  25                  30

Val Ser Ile Leu Met Glu Arg Asn Leu Arg Thr Pro Asn Leu Leu Ala
            35                  40                  45

Phe Val Arg Ala Val Lys His Leu Glu Asn Ala Ser Gly Ile Glu Ala
        50                  55                  60

Ile Leu Arg Asn Leu Gln Pro Cys Leu Pro Ser Ala Thr Ala Ala Pro
65                  70                  75                  80

Ser Arg His Pro Ile Ile Lys Ala Gly Asp Trp Gln Glu Phe Arg
                85                  90                  95

Glu Lys Leu Thr Phe Tyr Leu Val Thr Leu Glu Gln Ala Gln Glu Gln
                100                 105                 110

Gln (2) INFORMATION FOR SEQ ID NO:49:

(i) SEQUENCE CHARACTERISTICS:
        (A) LENGTH: 134 amino acids
        (B) TYPE: amino acid
        (D) TOPOLOGY: linear (ii) MOLECULE TYPE: peptide (xi) SEQUENCE DESCRIPTION: SEQ ID NO:49:

Met Ala Pro Met Thr Gln Thr Thr Ser Leu Lys Thr Ser Trp Val Asn
1               5                   10                  15

Cys Ser Asn Met Ile Asp Glu Ile Ile Thr His Leu Lys Gln Pro Pro
                20                  25                  30

Leu Pro Leu Leu Asp Phe Asn Asn Leu Asn Gly Glu Asp Gln Asp Ile
            35                  40                  45

Leu Met Glu Asn Asn Leu Arg Arg Pro Asn Leu Glu Ala Phe Asn Arg
        50                  55                  60

Ala Val Lys Ser Leu Gln Asn Ala Ser Ala Ile Glu Ser Ile Leu Lys
65                  70                  75                  80

Asn Leu Leu Pro Cys Leu Pro Leu Ala Thr Ala Ala Pro Thr Arg His
                85                  90                  95

Pro Ile His Ile Lys Asp Gly Asp Trp Asn Glu Phe Arg Arg Lys Leu
                100                 105                 110

Thr Phe Tyr Leu Lys Thr Leu Glu Asn Ala Gln Ala Gln Gln Thr Thr
            115                 120                 125

Leu Ser Leu Ala Ile Phe
            130

(2) INFORMATION FOR SEQ ID NO:50:

(i) SEQUENCE CHARACTERISTICS:
        (A) LENGTH: 36 amino acids
        (B) TYPE: amino acid
        (D) TOPOLOGY: linear (ii) MOLECULE TYPE: peptide (xi) SEQUENCE DESCRIPTION: SEQ ID NO:50:

Gly Gly Gly Ser Gly Gly Gly Ser Gly Gly Ser Glu Gly Gly Gly
1               5                   10                  15

Ser Glu Gly Gly Gly Ser Glu Gly Gly Gly Ser Glu Gly Gly Gly Ser
            20                  25                  30

Gly Gly Gly Ser
       35

(2) INFORMATION FOR SEQ ID NO:51:

(i) SEQUENCE CHARACTERISTICS:
        (A) LENGTH: 24 amino acids
        (B) TYPE: amino acid
        (D) TOPOLOGY: linear (ii) MOLECULE TYPE: peptide (xi) SEQUENCE DESCRIPTION: SEQ ID NO:51:

Ile Ser Glu Pro Ser Gly Pro Ile Ser Thr Ile Asn Pro Ser Pro Pro
1               5                   10                  15

Ser Lys Glu Ser His Lys Ser Pro
            20

(2) INFORMATION FOR SEQ ID NO:52:

(i) SEQUENCE CHARACTERISTICS:
        (A) LENGTH: 28 amino acids
        (B) TYPE: amino acid
        (D) TOPOLOGY: linear (ii) MOLECULE TYPE: peptide (xi) SEQUENCE DESCRIPTION: SEQ ID NO:52:

Ile Glu Gly Arg Ile Ser Glu Pro Ser Gly Pro Ile Ser Thr Ile Asn
1               5                   10                  15

Pro Ser Pro Pro Ser Lys Glu Ser His Lys Ser Pro
            20                  25

(2) INFORMATION FOR SEQ ID NO:53:

(i) SEQUENCE CHARACTERISTICS:
        (A) LENGTH: 906 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:53:

```
ATGGCTAACT GCTCTATAAT GATCGATGAA ATTATACATC ACTTAAAGAG ACCACCTAAC      60

CCTTTGCTGG ACCCGAACAA CCTCAATTCT GAAGACATGG ATATCCTGAT GGAACGAAAC     120

CTTCGAACTC CAAACCTGCT CGCATTCGTA AGGGCTGTCA AGCACTTAGA AAATGCATCA     180

GGTATTGAGG CAATTCTTCG TAATCTCCAA CCATGTCTGC CCTCTGCCAC GGCCGCACCC     240

TCTCGACATC CAATCATCAT CAAGGCAGGT GACTGGCAAG AATTCCGGGA AAAACTGACG     300

TTCTATCTGG TTACCCTTGA GCAAGCGCAG GAACAACAGT ACGTAATCGA GGGAAGGATT     360

TCCCCGGGTG GTGGTTCTGG CGGCGGCTCC AACATGGCTA CACCATTAGG CCCTGCCAGC     420

TCCCTGCCCC AGAGCTTCCT GCTCAAGTGC TTAGAGCAAG TGAGGAAGAT CCAGGGCGAT     480

GGCGCAGCGC TCCAGGAGAA GCTGTGTGCC ACCTACAAGC TGTGCCACCC CGAGGAGCTG     540

GTGCTGCTCG ACACTCTCT GGGCATCCCC TGGGCTCCCC TGAGCTCCTG CCCCAGCCAG     600

GCCCTGCAGC TGGCAGGCTG CTTGAGCCAA CTCCATAGCG GCCTTTTCCT CTACCAGGGG     660

CTCCTGCAGG CCCTGGAAGG GATATCCCCC GAGTTGGGTC CCACCTTGGA CACACTGCAG     720
```

```
CTGGACGTCG CCGACTTTGC CACCACCATC TAACTGGGAA TGGCCCCTGC CCTGCAGCCC      780

ACCCAGGGTG CCATGCCGGC CTTCGCCTCT GCTTTCCAGC GCCGGGCAGG AGGGGTCCTG      840

GTTGCTAGCC ATCTGCAGAG CTTCCTGGAG GTGTCGTACC GCGTTCTACG CCACCTTGCG      900

CAGCCC                                                                906

(2) INFORMATION FOR SEQ ID NO:54:

(i) SEQUENCE CHARACTERISTICS:
        (A) LENGTH: 732 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:54:

ATGGCTAACT GCTCTATAAT GATCGATGAA ATTATACATC ACTTAAAGAG ACCACCTAAC       60

CCTTTGCTGG ACCCGAACAA CCTCAATTCT GAAGACATGG ATATCCTGAT GGAACGAAAC      120

CTTCGAACTC CAAACCTGCT CGCATTCGTA AGGGCTGTCA AGCACTTAGA AAATGCATCA      180

GGTATTGAGG CAATTCTTCG TAATCTCCAA CCATGTCTGC CCTCTGCCAC GGCCGCACCC      240

TCTCGACATC CAATCATCAT CAAGGCAGGT GACTGGCAAG AATTCCGGGA AAAACTGACG      300

TTCTATCTGG TTACCCTTGA GCAAGCGCAG GAACAACAGT ACGTAATCGA GGGAAGGATT      360

TCCCCGGGTG GTGGTTCTGG CGGCGGCTCC AACATGGCTA ACTGCTCTAT AATGATCGAT      420

GAAATTATAC ATCACTTAAA GAGACCACCT AACCCTTTGC TGGACCCGAA CAACCTCAAT      480

TCTGAAGACA TGGATATCCT GATGGAACGA AACCTTCGAA CTCCAAACCT GCTCGCATTC      540

GTAAGGGCTG TCAAGCACTT AGAAAATGCA TCAGGTATTG AGGCAATTCT TCGTAATCTC      600

CAACCATGTC TGCCCTCTGC CACGGCCGCA CCCTCTCGAC ATCCAATCAT CATCAAGGCA      660

GGTGACTGGC AAGAATTCCG GGAAAAACTG ACGTTCTATC TGGTTACCCT TGAGCAAGCG      720

CAGGAACAAC AG                                                         732

(2) INFORMATION FOR SEQ ID NO:55:

(i) SEQUENCE CHARACTERISTICS:
        (A) LENGTH: 777 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:55:

ATGGCTAACT GCTCTATAAT GATCGATGAA ATTATACATC ACTTAAAGAG ACCACCTAAC       60

CCTTTGCTGG ACCCGAACAA CCTCAATTCT GAAGACATGG ATATCCTGAT GGAACGAAAC      120

CTTCGAACTC CAAACCTGCT CGCATTCGTA AGGGCTGTCA AGCACTTAGA AAATGCATCA      180

GGTATTGAGG CAATTCTTCG TAATCTCCAA CCATGTCTGC CCTCTGCCAC GGCCGCACCC      240

TCTCGACATC CAATCATCAT CAAGGCAGGT GACTGGCAAG AATTCCGGGA AAAACTGACG      300

TTCTATCTGG TTACCCTTGA GCAAGCGCAG GAACAACAGT ACGTAATCGA GGGAAGGATT      360

TCCCCGGGTG GTGGTTCTGG CGGCGGCTCC AACATGGCAC CGGCTCGTTC CCCGTCCCCG      420

TCTACCCAGC CGTGGGAACA CGTGAATGCC ATCCAGGAGG CCCGGCGTCT CCTGAACCTG      480

AGTAGAGACA CTGCTGCTGA GATGAATGAA ACAGTAGAAG TGATATCAGA AATGTTTGAC      540
```

-continued

```
CTCCAGGAGC CGACTTGCCT ACAGACCCGC CTGGAGCTGT ACAAGCAGGG CCTGCGGGGC    600

AGCCTCACCA AGCTCAAGGG CCCCTTGACC ATGATGGCCA GCCACTACAA GCAGCACTGC    660

CCTCCAACCC CGGAAACTTC CTGTGCAACC CAGATTATCA CCTTTGAAAG TTTCAAAGAG    720

AACCTGAAGG ACTTCCTGCT TGTCATCCCC TTTGACTGCT GGGAGCCAGT CCAGGAG       777
```

(2) INFORMATION FOR SEQ ID NO:56:

(i) SEQUENCE CHARACTERISTICS:
        (A) LENGTH: 921 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:56:

```
ATGGCTAACT GCTCTATAAT GATCGATGAA ATTATACATC ACTTAAAGAG ACCACCTAAC     60

CCTTTGCTGG ACCCGAACAA CCTCAATTCT GAAGACATGG ATATCCTGAT GGAACGAAAC    120

CTTCGAACTC CAAACCTGCT CGCATTCGTA AGGGCTGTCA AGCACTTAGA AAATGCATCA    180

GGTATTGAGG CAATTCTTCG TAATCTCCAA CCATGTCTGC CCTCTGCCAC GGCCGCACCC    240

TCTCGACATC CAATCATCAT CAAGGCAGGT GACTGGCAAG AATTCCGGGA AAAACTGACG    300

TTCTATCTGG TTACCCTTGA GCAAGCGCAG GAACAACAGT ACGTAATCGA GGGAAGGATT    360

TCCCCGGGTG GTGGTTCTGG CGGCGGCTCC AACATGGCTA CACCATTGGG CCCTGCCAGC    420

TCCCTGCCCC AGAGCTTCCT GCTCAAGTCT TTAGAGCAAG TGAGGAAGAT CCAGGGCGAT    480

GGCGCAGCGC TCCAGGAGAA GCTGTGTGCC ACCTACAAGC TGTGCCACCC CGAGGAGCTG    540

GTGCTGCTCG ACACTCTCT GGGCATCCCC TGGGCTCCCC TGAGCTCCTG CCCCAGCCAG     600

GCCCTGCAGC TGGCAGGCTG CTTGAGCCAA CTCCATAGCG GCCTTTTCCT CTACCAGGGG    660

CTCCTGCAGG CCCTGGAAGG GATATCCCCC GAGTTGGGTC CCACCTTGGA CACACTGCAG    720

CTGGACGTCG CCGACTTTGC CACCACCATC TGGCAGCAGA TGGAAGAACT GGGAATGGCC    780

CCTGCCCTGC AGCCCACCCA GGGTGCCATG CCGGCCTTCG CCTCTGCTTT CCAGCGCCGG    840

GCAGGAGGGG TCCTGGTTGC TAGCCATCTG CAGAGCTTCC TGGAGGTGTC GTACCGCGTT    900

CTACGCCACC TTGCGCAGCC C                                              921
```

(2) INFORMATION FOR SEQ ID NO:57:

(i) SEQUENCE CHARACTERISTICS:
        (A) LENGTH: 951 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:57:

```
ATGGCTAACT GCTCTATAAT GATCGATGAA ATTATACATC ACTTAAAGAG ACCACCTAAC     60

CCTTTGCTGG ACCCGAACAA CCTCAATTCT GAAGACATGG ATATCCTGAT GGAACGAAAC    120

CTTCGAACTC CAAACCTGCT CGCATTCGTA AGGGCTGTCA AGCACTTAGA AAATGCATCA    180

GGTATTGAGG CAATTCTTCG TAATCTCCAA CCATGTCTGC CCTCTGCCAC GGCCGCACCC    240

TCTCGACATC CAATCATCAT CAAGGCAGGT GACTGGCAAG AATTCCGGGA AAAACTGACG    300

TTCTATCTGG TTACCCTTGA GCAAGCGCAG GAACAACAGT ACGTAATCGA GGGAAGGATT    360

TCCCCGGGTG GTGGTTCTGG CGGCGGCTCC AACATGGCTC CAGTACCACC AGGTGAAGAT    420
```

```
TCCAAAGATG TGGCCGCCCC ACACAGACAG CCACTCACCT CTTCAGAACG AATTGACAAA      480

CAAATTCGGT ACATCCTCGA CGGGATATCA GCCCTGAGAA AGGAGACATG TAACAAGAGT      540

AACATGTGTG AAAGCAGCAA AGAGGCGCTA GCAGAAAACA ACCTGAACCT TCCAAAGATG      600

GCTGAAAAAG ATGGATGCTT CCAATCCGGA TTCAATGAGG AGACTTGCCT GGTGAAAATC      660

ATCACTGGTC TTTTGGAGTT TGAGGTATAC CTCGAGTACC TCCAGAACAG ATTTGAGAGT      720

AGTGAGGAAC AAGCCAGAGC TGTGCAGATG TCGACAAAAG TCCTGATCCA GTTCCTGCAG      780

AAAAAGGCAA AGAATCTAGA TGCAATAACC ACCCCTGACC CAACCACAAA TGCATCCCTG      840

CTGACGAAGC TGCAGGCACA GAACCAGTGG CTGCAGGACA TGACAACTCA TCTCATTCTG      900

CGCAGCTTTA AGGAGTTCCT GCAGTCCAGC CTGAGGGCTC TTCGGCAAAT G              951

(2) INFORMATION FOR SEQ ID NO:58:

(i) SEQUENCE CHARACTERISTICS:
        (A) LENGTH: 732 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:58:

ATGGCTAACT GCTCTATAAT GATCGATGAA ATTATACATC ACTTAAAGAG ACCACCTAAC       60

CCTTTGCTGG ACCCGAACAA CCTCAATTCT GAAGACATGG ATATCCTGAT GGAACGAAAC      120

CTTCGAACTC CAAACCTGCT CGCATTCGTA AGGGCTGTCA AGCACTTAGA AAATGCATCA      180

GGTATTGAGG CAATTCTTCG TAATCTCCAA CCATGTCTGC CCTCTGCCAC GGCCGCACCC      240

TCTCGACATC CAATCATCAT CAAGGCAGGT GACTGGCAAG AATTCCGGGA AAAACTGACG      300

TTCTATCTGG TTACCCTTGA GCAAGCGCAG GAACAACAGT ACGTAATCGA GGGAAAGATT      360

TCCCCGGGTG GTGGTTCTGG CGGCGGCTCC AACATGGCTA ACTGCTCTAT AATGATCGAT      420

GAAATTATAC ATCACTTAAA GAGACCACCT AACCCTTTGC TGGACCCGAA CAACCTCAAT      480

TCTGAAGACA TGGATATCCT GATGGAACGA AACCTTCGAA CTCCAAACCT GCTCGCATTC      540

GTAAGGGCTG TCAAGCACTT AGAAAATGCA TCAGGTATTG AGGCAATTCT TCGTAATCTC      600

CAACCATGTC TGCCCTCTGC CACGGCCGCA CCCTCTCGAC ATCCAATCAT CATCAAGGCA      660

GGTGACTGGC AAGAATTCCG GGAAAAACTG ACGTTCTATC TGGTTACCCT TGAGCAAGCG      720

CAGGAACAAC AG                                                          732

(2) INFORMATION FOR SEQ ID NO:59:

(i) SEQUENCE CHARACTERISTICS:
        (A) LENGTH: 921 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:59:

ATGGCTAACT GCTCTATAAT GATCGATGAA ATTATACATC ACTTAAAGAG ACCACCTAAC       60

CCTTTGCTGG ACCCGAACAA CCTCAATTCT GAAGACATGG ATATCCTGAT GGAACGAAAC      120

CTTCGAACTC CAAACCTGCT CGCATTCGTA AGGGCTGTCA AGCACTTAGA AAATGCATCA      180

GGTATTGAGG CAATTCTTCG TAATCTCCAA CCATGTCTGC CCTCTGCCAC GGCCGCACCC      240
```

```
TCTCGACATC CAATCATCAT CAAGGCAGGT GACTGGCAAG AATTCCGGGA AAAACTGACG      300

TTCTATCTGG TTACCCTTGA GCAAGCGCAG GAACAACAGT ACGTAATCGA GGGAAAGATT      360

TCCCCGGGTG GTGGTTCTGG CGGCGGCTCC AACATGGCTA CACCATTGGG CCCTGCCAGC      420

TCCCTGCCCC AGAGCTTCCT GCTCAAGTCT TTAGAGCAAG TGAGGAAGAT CCAGGGCGAT      480

GGCGCAGCGC TCCAGGAGAA GCTGTGTGCC ACCTACAAGC TGTGCCACCC CGAGGAGCTG      540

GTGCTGCTCG GACACTCTCT GGGCATCCCC TGGGCTCCCC TGAGCTCCTG CCCCAGCCAG      600

GCCCTGCAGC TGGCAGGCTG CTTGAGCCAA CTCCATAGCG GCCTTTTCCT CTACCAGGGG      660

CTCCTGCAGG CCCTGGAAGG GATATCCCCC GAGTTGGGTC CCACCTTGGA CACACTGCAG      720

CTGGACGTCG CCGACTTTGC CACCACCATC TGGCAGCAGA TGGAAGAACT GGGAATGGCC      780

CCTGCCCTGC AGCCCACCCA GGGTGCCATG CCGGCCTTCG CCTCTGCTTT CCAGCGCCGG      840

GCAGGAGGGG TCCTGGTTGC TAGCCATCTG CAGAGCTTCC TGGAGGTGTC GTACCGCGTT      900

CTACGCCACC TTGCGCAGCC C                                                 921
```

(2) INFORMATION FOR SEQ ID NO:60:

(i) SEQUENCE CHARACTERISTICS:
        (A) LENGTH: 921 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:60:

```
ATGGCTAACT GCTCTATAAT GATCGATGAA ATTATACATC ACTTAAAGAG ACCACCTAAC       60

CCTTTGCTGG ACCCGAACAA CCTCAATTCT GAAGACATGG ATATCCTGAT GGAACGAAAC      120

CTTCGAACTC CAAACCTGCT CGCATTCGTA AGGGCTGTCA AGCACTTAGA AAATGCATCA      180

GGTATTGAGG CAATTCTTCG TAATCTCCAA CCATGTCTGC CCTCTGCCAC GGCCGCACCC      240

TCTCGACATC CAATCATCAT CAAGGCAGGT GACTGGCAAG AATTCCGGGA AAAACTGACG      300

TTCTATCTGG TTACCCTTGA GCAAGCGCAG GAACAACAGT ACGTAGAGGG CGGTGGAGGC      360

TCCCCGGGTG GTGGTTCTGG CGGCGGCTCC AACATGGCTA CACCATTGGG CCCTGCCAGC      420

TCCCTGCCCC AGAGCTTCCT GCTCAAGTCT TTAGAGCAAG TGAGGAAGAT CCAGGGCGAT      480

GGCGCAGCGC TCCAGGAGAA GCTGTGTGCC ACCTACAAGC TGTGCCACCC CGAGGAGCTG      540

GTGCTGCTCG GACACTCTCT GGGCATCCCC TGGGCTCCCC TGAGCTCCTG CCCCAGCCAG      600

GCCCTGCAGC TGGCAGGCTG CTTGAGCCAA CTCCATAGCG GCCTTTTCCT CTACCAGGGG      660

CTCCTGCAGG CCCTGGAAGG GATATCCCCC GAGTTGGGTC CCACCTTGGA CACACTGCAG      720

CTGGACGTCG CCGACTTTGC CACCACCATC TGGCAGCAGA TGGAAGAACT GGGAATGGCC      780

CCTGCCCTGC AGCCCACCCA GGGTGCCATG CCGGCCTTCG CCTCTGCTTT CCAGCGCCGG      840

GCAGGAGGGG TCCTGGTTGC TAGCCATCTG CAGAGCTTCC TGGAGGTGTC GTACCGCGTT      900

CTACGCCACC TTGCGCAGCC C                                                 921
```

(2) INFORMATION FOR SEQ ID NO:61:

(i) SEQUENCE CHARACTERISTICS:
        (A) LENGTH: 732 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:61:

| | |
|---|---|
| ATGGCTAACT GCTCTATAAT GATCGATGAA ATTATACATC ACTTAAAGAG ACCACCTAAC | 60 |
| CCTTTGCTGG ACCCGAACAA CCTCAATTCT GAAGACATGG ATATCCTGAT GGAACGAAAC | 120 |
| CTTCGAACTC CAAACCTGCT CGCATTCGTA AGGGCTGTCA AGCACTTAGA AAATGCATCA | 180 |
| GGTATTGAGG CAATTCTTCG TAATCTCCAA CCATGTCTGC CCTCTGCCAC GGCCGCACCC | 240 |
| TCTCGACATC CAATCATCAT CAAGGCAGGT GACTGGCAAG AATTCCGGGA AAAACTGACG | 300 |
| TTCTATCTGG TTACCCTTGA GCAAGCGCAG GAACAACAGT ACGTAGAGGG CGGTGGAGGC | 360 |
| TCCCCGGGTG GTGGTTCTGG CGGCGGCTCC AACATGGCTA ACTGCTCTAT AATGATCGAT | 420 |
| GAAATTATAC ATCACTTAAA GAGACCACCT AACCCTTTGC TGGACCCGAA CAACCTCAAT | 480 |
| TCTGAAGACA TGGATATCCT GATGGAACGA AACCTTCGAA CTCCAAACCT GCTCGCATTC | 540 |
| GTAAGGGCTG TCAAGCACTT AGAAAATGCA TCAGGTATTG AGGCAATTCT TCGTAATCTC | 600 |
| CAACCATGTC TGCCCTCTGC CACGGCCGCA CCCTCTCGAC ATCCAATCAT CATCAAGGCA | 660 |
| GGTGACTGGC AAGAATTCCG GGAAAAACTG ACGTTCTATC TGGTTACCCT TGAGCAAGCG | 720 |
| CAGGAACAAC AG | 732 |

(2) INFORMATION FOR SEQ ID NO:62:

(i) SEQUENCE CHARACTERISTICS:
        (A) LENGTH: 777 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:62:

| | |
|---|---|
| ATGGCTAACT GCTCTATAAT GATCGATGAA ATTATACATC ACTTAAAGAG ACCACCTAAC | 60 |
| CCTTTGCTGG ACCCGAACAA CCTCAATTCT GAAGACATGG ATATCCTGAT GGAACGAAAC | 120 |
| CTTCGAACTC CAAACCTGCT CGCATTCGTA AGGGCTGTCA AGCACTTAGA AAATGCATCA | 180 |
| GGTATTGAGG CAATTCTTCG TAATCTCCAA CCATGTCTGC CCTCTGCCAC GGCCGCACCC | 240 |
| TCTCGACATC CAATCATCAT CAAGGCAGGT GACTGGCAAG AATTCCGGGA AAAACTGACG | 300 |
| TTCTATCTGG TTACCCTTGA GCAAGCGCAG GAACAACAGT ACGTAATCGA GGGAAGGATT | 360 |
| TCCCCGGGTG AACCGTCTGG TCCAATCTCT ACTATCAACC CGTCTCCTCC GTCTAAAGAA | 420 |
| TCTCATAAAT CTCCAAACAT GGCTAACTGC TCTATAATGA TCGATGAAAT TATACATCAC | 480 |
| TTAAAGAGAC CACCTAACCC TTTGCTGGAC CCGAACAACC TCAATTCTGA AGACATGGAT | 540 |
| ATCCTGATGG AACGAAACCT TCGAACTCCA AACCTGCTCG CATTCGTAAG GCTGTCAAG | 600 |
| CACTTAGAAA ATGCATCAGG TATTGAGGCA ATTCTTCGTA ATCTCCAACC ATGTCTGCCC | 660 |
| TCTGCCACGG CCGCACCCTC TCGACATCCA ATCATCATCA AGGCAGGTGA CTGGCAAGAA | 720 |
| TTCCGGGAAA AACTGACGTT CTATCTGGTT ACCCTTGAGC AAGCGCAGGA ACAACAG | 777 |

(2) INFORMATION FOR SEQ ID NO:63:

(i) SEQUENCE CHARACTERISTICS:
        (A) LENGTH: 777 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:63:

```
ATGGCTAACT GCTCTATAAT GATCGATGAA ATTATACATC ACTTAAAGAG ACCACCTAAC      60
CCTTTGCTGG ACCCGAACAA CCTCAATTCT GAAGACATGG ATATCCTGAT GGAACGAAAC     120
CTTCGAACTC CAAACCTGCT CGCATTCGTA AGGGCTGTCA AGCACTTAGA AAATGCATCA     180
GGTATTGAGG CAATTCTTCG TAATCTCCAA CCATGTCTGC CCTCTGCCAC GGCCGCACCC     240
TCTCGACATC CAATCATCAT CAAGGCAGGT GACTGGCAAG AATTCCGGGA AAAACTGACG     300
TTCTATCTGG TTACCCTTGA GCAAGCGCAG GAACAACAGT ACGTAATCGA GGGAAAGATT     360
TCCCCGGGTG AACCGTCTGG TCCAATCTCT ACTATCAACC CGTCTCCTCC GTCTAAAGAA     420
TCTCATAAAT CTCCAAACAT GGCTAACTGC TCTATAATGA TCGATGAAAT TATACATCAC     480
TTAAAGAGAC CACCTAACCC TTTGCTGGAC CCGAACAACC TCAATTCTGA AGACATGGAT     540
ATCCTGATGG AACGAAACCT TCGAACTCCA AACCTGCTCG CATTCGTAAG GGCTGTCAAG     600
CACTTAGAAA ATGCATCAGG TATTGAGGCA ATTCTTCGTA ATCTCCAACC ATGTCTGCCC     660
TCTGCCACGG CCGCACCCTC TCGACATCCA ATCATCATCA AGGCAGGTGA CTGGCAAGAA     720
TTCCGGGAAA AACTGACGTT CTATCTGGTT ACCCTTGAGC AAGCGCAGGA ACAACAG       777
```

(2) INFORMATION FOR SEQ ID NO:64:

(i) SEQUENCE CHARACTERISTICS:
        (A) LENGTH: 777 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:64:

```
ATGGCTAACT GCTCTATAAT GATCGATGAA ATTATACATC ACTTAAAGAG ACCACCTAAC      60
CCTTTGCTGG ACCCGAACAA CCTCAATTCT GAAGACATGG ATATCCTGAT GGAACGAAAC     120
CTTCGAACTC CAAACCTGCT CGCATTCGTA AGGGCTGTCA AGCACTTAGA AAATGCATCA     180
GGTATTGAGG CAATTCTTCG TAATCTCCAA CCATGTCTGC CCTCTGCCAC GGCCGCACCC     240
TCTCGACATC CAATCATCAT CAAGGCAGGT GACTGGCAAG AATTCCGGGA AAAACTGACG     300
TTCTATCTGG TTACCCTTGA GCAAGCGCAG GAACAACAGT ACGTAGAGGG CGGTGGAGGC     360
TCCCCGGGTG AACCGTCTGG TCCAATCTCT ACTATCAACC CGTCTCCTCC GTCTAAAGAA     420
TCTCATAAAT CTCCAAACAT GGCTAACTGC TCTATAATGA TCGATGAAAT TATACATCAC     480
TTAAAGAGAC CACCTAACCC TTTGCTGGAC CCGAACAACC TCAATTCTGA AGACATGGAT     540
ATCCTGATGG AACGAAACCT TCGAACTCCA AACCTGCTCG CATTCGTAAG GGCTGTCAAG     600
CACTTAGAAA ATGCATCAGG TATTGAGGCA ATTCTTCGTA ATCTCCAACC ATGTCTGCCC     660
TCTGCCACGG CCGCACCCTC TCGACATCCA ATCATCATCA AGGCAGGTGA CTGGCAAGAA     720
TTCCGGGAAA AACTGACGTT CTATCTGGTT ACCCTTGAGC AAGCGCAGGA ACAACAG       777
```

(2) INFORMATION FOR SEQ ID NO:65:

(i) SEQUENCE CHARACTERISTICS:
        (A) LENGTH: 1047 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:65:

```
ATGGCTAACT GCTCTATAAT GATCGATGAA ATTATACATC ACTTAAAGAG ACCACCTAAC      60

CCTTTGCTGG ACCCGAACAA CCTCAATTCT GAAGACATGG ATATCCTGAT GGAACGAAAC     120

CTTCGAACTC CAAACCTGCT CGCATTCGTA AGGGCTGTCA AGCACTTAGA AAATGCATCA     180

GGTATTGAGG CAATTCTTCG TAATCTCCAA CCATGTCTGC CCTCTGCCAC GGCCGCACCC     240

TCTCGACATC CAATCATCAT CAAGGCAGGT GACTGGCAAG AATTCCGGGA AAAACTGACG     300

TTCTATCTGG TTACCCTTGA GCAAGCGCAG GAACAACAGT ACGTAATCGA GGGAAGGATT     360

TCCCCCGGGC CTCCTGTCAA TGCTGGCGGC GGCTCTGGTG GTGGTTCTGG TGGCGGCTCT     420

GAGGGTGGCG GCTCTGAGGG TGGCGGTTCT GAGGGTGGCG GCTCTGAGGG TGGCGGTTCC     480

GGTGGCGGCT CCGGTTCCGG TGATTTTGAT TATGAAAACA TGGCTACACC ATTGGGCCCT     540

GCCAGCTCCC TGCCCCAGAG CTTCCTGCTC AAGTCTTTAG AGCAAGTGAG GAAGATCCAG     600

GGCGATGGCG CAGCGCTCCA GGAGAAGCTG TGTGCCACCT ACAAGCTGTG CCACCCCGAG     660

GAGCTGGTGC TGCTCGGACA CTCTCTGGGC ATCCCCTGGG CTCCCCTGAG CTCCTGCCCC     720

AGCCAGGCCC TGCAGCTGGC AGGCTGCTTG AGCCAACTCC ATAGCGGCCT TTTCCTCTAC     780

CAGGGGCTCC TGCAGGCCCT GGAAGGGATA TCCCCCGAGT TGGGTCCCAC CTTGGACACA     840

CTGCAGCTGG ACGTCGCCGA CTTTGCCACC ACCATCTGGC AGCAGATGGA AGAACTGGGA     900

ATGGCCCCTG CCCTGCAGCC CACCCAGGGT GCCATGCCGG CCTTCGCCTC TGCTTTCCAG     960

CGCCGGGCAG GAGGGGTCCT GGTTGCTAGC CATCTGCAGA GCTTCCTGGA GGTGTCGTAC    1020

CGCGTTCTAC GCCACCTTGC GCAGCCC                                        1047

(2) INFORMATION FOR SEQ ID NO:66:

(i) SEQUENCE CHARACTERISTICS:
        (A) LENGTH: 903 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:66:

ATGGCTAACT GCTCTATAAT GATCGATGAA ATTATACATC ACTTAAAGAG ACCACCTAAC      60

CCTTTGCTGG ACCCGAACAA CCTCAATTCT GAAGACATGG ATATCCTGAT GGAACGAAAC     120

CTTCGAACTC CAAACCTGCT CGCATTCGTA AGGGCTGTCA AGCACTTAGA AAATGCATCA     180

GGTATTGAGG CAATTCTTCG TAATCTCCAA CCATGTCTGC CCTCTGCCAC GGCCGCACCC     240

TCTCGACATC CAATCATCAT CAAGGCAGGT GACTGGCAAG AATTCCGGGA AAAACTGACG     300

TTCTATCTGG TTACCCTTGA GCAAGCGCAG GAACAACAGT ACGTAATCGA GGGAAGGATT     360

TCCCCCGGGC CTCCTGTCAA TGCTGGCGGC GGCTCTGGTG GTGGTTCTGG TGGCGGCTCT     420

GAGGGTGGCG GCTCTGAGGG TGGCGGTTCT GAGGGTGGCG GCTCTGAGGG TGGCGGTTCC     480

GGTGGCGGCT CCGGTTCCGG TGATTTTGAT TATGAAAACA TGGCACCGGC TCGTTCCCCG     540

TCCCCGTCTA CCCAGCCGTG GGAACACGTG AATGCCATCC AGGAGGCCCG GCGTCTCCTG     600

AACCTGAGTA GAGACACTGC TGCTGAGATG AATGAAACAG TAGAAGTGAT ATCAGAAATG     660

TTTGACCTCC AGGAGCCGAC TTGCCTACAG ACCCGCCTGG AGCTGTACAA GCAGGGCCTG     720

CGGGGCAGCC TCACCAAGCT CAAGGGCCCC TTGACCATGA TGGCCAGCCA CTACAAGCAG     780

CACTGCCCTC CAACCCCGGA AACTTCCTGT GCAACCCAGA TTATCACCTT TGAAAGTTTC     840

AAAGAGAACC TGAAGGACTT CCTGCTTGTC ATCCCCTTTG ACTGCTGGGA GCCAGTCCAG     900
```

GAG                                                                                 903

(2) INFORMATION FOR SEQ ID NO:67:

(i) SEQUENCE CHARACTERISTICS:
        (A) LENGTH: 1017 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:67:

```
ATGGCTAACT GCTCTATAAT GATCGATGAA ATTATACATC ACTTAAAGAG ACCACCTAAC     60
CCTTTGCTGG ACCCGAACAA CCTCAATTCT GAAGACATGG ATATCCTGAT GGAACGAAAC    120
CTTCGAACTC CAAACCTGCT CGCATTCGTA AGGGCTGTCA AGCACTTAGA AAATGCATCA    180
GGTATTGAGG CAATTCTTCG TAATCTCCAA CCATGTCTGC CCTCTGCCAC GGCCGCACCC    240
TCTCGACATC CAATCATCAT CAAGGCAGGT GACTGGCAAG AATTCCGGGA AAAACTGACG    300
TTCTATCTGG TTACCCTTGA GCAAGCGCAG GAACAACAGT ACGTAATCGA GGGAAGGATT    360
TCCCCCGGTG GCGGCGGCTC TGGTGGTGGT TCTGGTGGCG GCTCTGAGGG TGGCGGCTCT    420
GAGGGTGGCG GTTCTGAGGG TGGCGGCTCT GAGGGTGGCG GTTCCGGTGG CGGCTCCGGT    480
TCCGGTAACA TGGCTACACC ATTAGGCCCT GCCAGCTCCC TGCCCCAGAG CTTCCTGCTC    540
AAGTGCTTAG AGCAAGTGAG GAAGATCCAG GGCGATGGCG CAGCGCTCCA GGAGAAGCTG    600
TGTGCCACCT ACAAGCTGTG CCACCCCGAG GAGCTGGTGC TGCTCGGACA CTCTCTGGGC    660
ATCCCCTGGG CTCCCCTGAG CTCCTGCCCC AGCCAGGCCC TGCAGCTGGC AGGCTGCTTG    720
AGCCAACTCC ATAGCGGCCT TTTCCTCTAC CAGGGGCTCC TGCAGGCCCT GGAAGGGATA    780
TCCCCCGAGT TGGGTCCCAC CTTGGACACA CTGCAGCTGG ACGTCGCCGA CTTTGCCACC    840
ACCATCTGGC AGCAGATGGA AGAACTGGGA ATGGCCCCTG CCCTGCAGCC CACCCAGGGT    900
GCCATGCCGG CCTTCGCCTC TGCTTTCCAG CGCCGGGCAG GAGGGGTCCT GGTTGCTAGC    960
CATCTGCAGA GCTTCCTGGA GGTGTCGTAC CGCGTTCTAC GCCACCTTGC GCAGCCC     1017
```

(2) INFORMATION FOR SEQ ID NO:68:

(i) SEQUENCE CHARACTERISTICS:
        (A) LENGTH: 966 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:68:

```
ATGGCTAACT GCTCTATAAT GATCGATGAA ATTATACATC ACTTAAAGAG ACCACCTAAC     60
CCTTTGCTGG ACCCGAACAA CCTCAATTCT GAAGACATGG ATATCCTGAT GGAACGAAAC    120
CTTCGAACTC CAAACCTGCT CGCATTCGTA AGGGCTGTCA AGCACTTAGA AAATGCATCA    180
GGTATTGAGG CAATTCTTCG TAATCTCCAA CCATGTCTGC CCTCTGCCAC GGCCGCACCC    240
TCTCGACATC CAATCATCAT CAAGGCAGGT GACTGGCAAG AATTCCGGGA AAAACTGACG    300
TTCTATCTGG TTACCCTTGA GCAAGCGCAG GAACAACAGT ACGTAATCGA GGGAAGGATT    360
TCCCCGGGTG AACCGTCTGG TCCAATCTCT ACTATCAACC CGTCTCCTCC GTCTAAAGAA    420
TCTCATAAAT CTCCAAACAT GGCTACACCA TTAGGCCCTG CCAGCTCCCT GCCCCAGAGC    480
```

```
TTCCTGCTCA AGTGCTTAGA GCAAGTGAGG AAGATCCAGG GCGATGGCGC AGCGCTCCAG    540

GAGAAGCTGT GTGCCACCTA CAAGCTGTGC CACCCCGAGG AGCTGGTGCT GCTCGGACAC    600

TCTCTGGGCA TCCCCTGGGC TCCCCTGAGC TCCTGCCCCA GCCAGGCCCT GCAGCTGGCA    660

GGCTGCTTGA GCCAACTCCA TAGCGGCCTT TTCCTCTACC AGGGGCTCCT GCAGGCCCTG    720

GAAGGGATAT CCCCCGAGTT GGGTCCCACC TTGGACACAC TGCAGCTGGA CGTCGCCGAC    780

TTTGCCACCA CCATCTGGCA GCAGATGGAA GAACTGGGAA TGGCCCCTGC CCTGCAGCCC    840

ACCCAGGGTG CCATGCCGGC CTTCGCCTCT GCTTTCCAGC GCCGGGCAGG AGGGGTCCTG    900

GTTGCTAGCC ATCTGCAGAG CTTCCTGGAG GTGTCGTACC GCGTTCTACG CCACCTTGCG    960

CAGCCC                                                                966
```

(2) INFORMATION FOR SEQ ID NO:69:

(i) SEQUENCE CHARACTERISTICS:
        (A) LENGTH: 822 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:69:

```
ATGGCTAACT GCTCTATAAT GATCGATGAA ATTATACATC ACTTAAAGAG ACCACCTAAC     60

CCTTTGCTGG ACCCGAACAA CCTCAATTCT GAAGACATGG ATATCCTGAT GGAACGAAAC    120

CTTCGAACTC CAAACCTGCT CGCATTCGTA AGGGCTGTCA AGCACTTAGA AAATGCATCA    180

GGTATTGAGG CAATTCTTCG TAATCTCCAA CCATGTCTGC CCTCTGCCAC GGCCGCACCC    240

TCTCGACATC CAATCATCAT CAAGGCAGGT GACTGGCAAG AATTCCGGGA AAAACTGACG    300

TTCTATCTGG TTACCCTTGA GCAAGCGCAG GAACAACAGT ACGTAATCGA GGGAAGGATT    360

TCCCCGGGTG AACCGTCTGG TCCAATCTCT ACTATCAACC CGTCTCCTCC GTCTAAAGAA    420

TCTCATAAAT CTCCAAACAT GGCACCGGCT CGTTCCCCGT CCCCGTCTAC CCAGCCGTGG    480

GAACACGTGA ATGCCATCCA GGAGGCCCGG CGTCTCCTGA ACTGAGTAG  AGACACTGCT    540

GCTGAGATGA ATGAAACAGT AGAAGTGATA TCAGAAATGT TTGACCTCCA GGAGCCGACT    600

TGCCTACAGA CCCGCCTGGA GCTGTACAAG CAGGGCCTGC GGGGCAGCCT CACCAAGCTC    660

AAGGGCCCCT TGACCATGAT GGCCAGCCAC TACAAGCAGC ACTGCCCTCC AACCCCGGAA    720

ACTTCCTGTG CAACCCAGAT TATCACCTTT GAAAGTTTCA AGAGAACCT  GAAGGACTTC    780

CTGCTTGTCA TCCCCTTTGA CTGCTGGGAG CCAGTCCAGG AG                       822
```

(2) INFORMATION FOR SEQ ID NO:70:

(i) SEQUENCE CHARACTERISTICS:
        (A) LENGTH: 966 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:70:

```
ATGGCTAACT GCTCTATAAT GATCGATGAA ATTATACATC ACTTAAAGAG ACCACCTAAC     60

CCTTTGCTGG ACCCGAACAA CCTCAATTCT GAAGACATGG ATATCCTGAT GGAACGAAAC    120

CTTCGAACTC CAAACCTGCT CGCATTCGTA AGGGCTGTCA AGCACTTAGA AAATGCATCA    180

GGTATTGAGG CAATTCTTCG TAATCTCCAA CCATGTCTGC CCTCTGCCAC GGCCGCACCC    240
```

```
TCTCGACATC CAATCATCAT CAAGGCAGGT GACTGGCAAG AATTCCGGGA AAAACTGACG      300

TTCTATCTGG TTACCCTTGA GCAAGCGCAG GAACAACAGT ACGTAATCGA GGGAAAGATT      360

TCCCCGGGTG AACCGTCTGG TCCAATCTCT ACTATCAACC CGTCTCCTCC GTCTAAAGAA      420

TCTCATAAAT CTCCAAACAT GGCTACACCA TTAGGCCCTG CCAGCTCCCT GCCCCAGAGC      480

TTCCTGCTCA AGTGCTTAGA GCAAGTGAGG AAGATCCAGG GCGATGGCGC AGCGCTCCAG      540

GAGAAGCTGT GTGCCACCTA CAAGCTGTGC CACCCCGAGG AGCTGGTGCT GCTCGGACAC      600

TCTCTGGGCA TCCCCTGGGC TCCCCTGAGC TCCTGCCCCA GCCAGGCCCT GCAGCTGGCA      660

GGCTGCTTGA GCCAACTCCA TAGCGGCCTT TTCCTCTACC AGGGGCTCCT GCAGGCCCTG      720

GAAGGGATAT CCCCCGAGTT GGGTCCCACC TTGGACACAC TGCAGCTGGA CGTCGCCGAC      780

TTTGCCACCA CCATCTGGCA GCAGATGGAA GAACTGGGAA TGGCCCCTGC CCTGCAGCCC      840

ACCCAGGGTG CCATGCCGGC CTTCGCCTCT GCTTTCCAGC GCCGGGCAGG AGGGGTCCTG      900

GTTGCTAGCC ATCTGCAGAG CTTCCTGGAG GTGTCGTACC GCGTTCTACG CCACCTTGCG      960

CAGCCC                                                                 966

(2) INFORMATION FOR SEQ ID NO:71:

(i) SEQUENCE CHARACTERISTICS:
        (A) LENGTH: 966 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:71:

ATGGCTAACT GCTCTATAAT GATCGATGAA ATTATACATC ACTTAAAGAG ACCACCTAAC       60

CCTTTGCTGG ACCCGAACAA CCTCAATTCT GAAGACATGG ATATCCTGAT GGAACGAAAC      120

CTTCGAACTC CAAACCTGCT CGCATTCGTA AGGGCTGTCA AGCACTTAGA AAATGCATCA      180

GGTATTGAGG CAATTCTTCG TAATCTCCAA CCATGTCTGC CCTCTGCCAC GGCCGCACCC      240

TCTCGACATC CAATCATCAT CAAGGCAGGT GACTGGCAAG AATTCCGGGA AAAACTGACG      300

TTCTATCTGG TTACCCTTGA GCAAGCGCAG GAACAACAGT ACGTAGAGGG CGGTGGAGGC      360

TCCCCGGGTG AACCGTCTGG TCCAATCTCT ACTATCAACC CGTCTCCTCC GTCTAAAGAA      420

TCTCATAAAT CTCCAAACAT GGCTACACCA TTAGGCCCTG CCAGCTCCCT GCCCCAGAGC      480

TTCCTGCTCA AGTGCTTAGA GCAAGTGAGG AAGATCCAGG GCGATGGCGC AGCGCTCCAG      540

GAGAAGCTGT GTGCCACCTA CAAGCTGTGC CACCCCGAGG AGCTGGTGCT GCTCGGACAC      600

TCTCTGGGCA TCCCCTGGGC TCCCCTGAGC TCCTGCCCCA GCCAGGCCCT GCAGCTGGCA      660

GGCTGCTTGA GCCAACTCCA TAGCGGCCTT TTCCTCTACC AGGGGCTCCT GCAGGCCCTG      720

GAAGGGATAT CCCCCGAGTT GGGTCCCACC TTGGACACAC TGCAGCTGGA CGTCGCCGAC      780

TTTGCCACCA CCATCTGGCA GCAGATGGAA GAACTGGGAA TGGCCCCTGC CCTGCAGCCC      840

ACCCAGGGTG CCATGCCGGC CTTCGCCTCT GCTTTCCAGC GCCGGGCAGG AGGGGTCCTG      900

GTTGCTAGCC ATCTGCAGAG CTTCCTGGAG GTGTCGTACC GCGTTCTACG CCACCTTGCG      960

CAGCCC                                                                 966

(2) INFORMATION FOR SEQ ID NO:72:

(i) SEQUENCE CHARACTERISTICS:
        (A) LENGTH: 921 base pairs
```

(B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:72:

```
ATGGCTACAC CATTAGGCCC TGCCAGCTCC CTGCCCCAGA GCTTCCTGCT CAAGTGCTTA      60

GAGCAAGTGA GGAAGATCCA GGGCGATGGC GCAGCGCTCC AGGAGAAGCT GTGTGCCACC     120

TACAAGCTGT GCCACCCCGA GGAGCTGGTG CTGCTCGGAC ACTCTCTGGG CATCCCCTGG     180

GCTCCCCTGA GCTCCTGCCC CAGCCAGGCC CTGCAGCTGG CAGGCTGCTT GAGCCAACTC     240

CATAGCGGCC TTTTCCTCTA CCAGGGGCTC CTGCAGGCCC TGGAAGGGAT ATCCCCCGAG     300

TTGGGTCCCA CCTTGGACAC ACTGCAGCTG GACGTCGCCG ACTTTGCCAC CACCATCTGG     360

CAGCAGATGG AAGAACTGGG AATGGCCCCT GCCCTGCAGC CCACCCAGGG TGCCATGCCG     420

GCCTTCGCCT CTGCTTTCCA GCGCCGGGCA GGAGGGGTCC TGGTTGCTAG CCATCTGCAG     480

AGCTTCCTGG AGGTGTCGTA CCGCGTTCTA CGCCACCTTG CGCAGCCCTA CGTAATCGAG     540

GGAAGGATTT CCCCGGGTGG TGGTTCTGGC GGCGGCTCCA ACATGGCTAA CTGCTCTATA     600

ATGATCGATG AAATTATACA TCACTTAAAG AGACCACCTA ACCCTTTGCT GGACCCGAAC     660

AACCTCAATT CTGAAGACAT GGATATCCTG ATGGAACGAA ACCTTCGAAC TCCAAACCTG     720

CTCGCATTCG TAAGGGCTGT CAAGCACTTA GAAAATGCAT CAGGTATTGA GGCAATTCTT     780

CGTAATCTCC AACCATGTCT GCCCTCTGCC ACGGCCGCAC CCTCTCGACA TCCAATCATC     840

ATCAAGGCAG GTGACTGGCA AGAATTCCGG GAAAAACTGA CGTTCTATCT GGTTACCCTT     900

GAGCAAGCGC AGGAACAACA G                                             921
```

(2) INFORMATION FOR SEQ ID NO:73:

(i) SEQUENCE CHARACTERISTICS:
        (A) LENGTH: 966 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:73:

```
ATGGCTACAC CATTAGGCCC TGCCAGCTCC CTGCCCCAGA GCTTCCTGCT CAAGTGCTTA      60

GAGCAAGTGA GGAAGATCCA GGGCGATGGC GCAGCGCTCC AGGAGAAGCT GTGTGCCACC     120

TACAAGCTGT GCCACCCCGA GGAGCTGGTG CTGCTCGGAC ACTCTCTGGG CATCCCCTGG     180

GCTCCCCTGA GCTCCTGCCC CAGCCAGGCC CTGCAGCTGG CAGGCTGCTT GAGCCAACTC     240

CATAGCGGCC TTTTCCTCTA CCAGGGGCTC CTGCAGGCCC TGGAAGGGAT ATCCCCCGAG     300

TTGGGTCCCA CCTTGGACAC ACTGCAGCTG GACGTCGCCG ACTTTGCCAC CACCATCTGG     360

CAGCAGATGG AAGAACTGGG AATGGCCCCT GCCCTGCAGC CCACCCAGGG TGCCATGCCG     420

GCCTTCGCCT CTGCTTTCCA GCGCCGGGCA GGAGGGGTCC TGGTTGCTAG CCATCTGCAG     480

AGCTTCCTGG AGGTGTCGTA CCGCGTTCTA CGCCACCTTG CGCAGCCCTA CGTAATCGAG     540

GGAAGGATTT CCCCGGGTGA ACCGTCTGGT CCAATCTCTA CTATCAACCC GTCTCCTCCG     600

TCTAAAGAAT CTCATAAATC TCCAAACATG GCTAACTGCT CTATAATGAT CGATGAAATT     660

ATACATCACT TAAAGAGACC ACCTAACCCT TTGCTGGACC CGAACAACCT CAATTCTGAA     720

GACATGGATA TCCTGATGGA ACGAAACCTT CGAACTCCAA ACCTGCTCGC ATTCGTAAGG     780
```

| | | |
|---|---|---|
| GCTGTCAAGC ACTTAGAAAA TGCATCAGGT ATTGAGGCAA TTCTTCGTAA TCTCCAACCA | 840 | |
| TGTCTGCCCT CTGCCACGGC CGCACCCTCT CGACATCCAA TCATCATCAA GGCAGGTGAC | 900 | |
| TGGCAAGAAT TCCGGGAAAA ACTGACGTTC TATCTGGTTA CCCTTGAGCA AGCGCAGGAA | 960 | |
| CAACAG | 966 | |

(2) INFORMATION FOR SEQ ID NO:74:

(i) SEQUENCE CHARACTERISTICS:
        (A) LENGTH: 1047 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:74:

| | |
|---|---|
| ATGGCTACAC CATTAGGCCC TGCCAGCTCC CTGCCCCAGA GCTTCCTGCT CAAGTGCTTA | 60 |
| GAGCAAGTGA GGAAGATCCA GGGCGATGGC GCAGCGCTCC AGGAGAAGCT GTGTGCCACC | 120 |
| TACAAGCTGT GCCACCCCGA GGAGCTGGTG CTGCTCGGAC ACTCTCTGGG CATCCCCTGG | 180 |
| GCTCCCCTGA GCTCCTGCCC CAGCCAGGCC CTGCAGCTGG CAGGCTGCTT GAGCCAACTC | 240 |
| CATAGCGGCC TTTTCCTCTA CCAGGGGCTC CTGCAGGCCC TGGAAGGGAT ATCCCCCGAG | 300 |
| TTGGGTCCCA CCTTGGACAC ACTGCAGCTG GACGTCGCCG ACTTTGCCAC CACCATCTGG | 360 |
| CAGCAGATGG AAGAACTGGG AATGGCCCCT GCCCTGCAGC CCACCCAGGG TGCCATGCCG | 420 |
| GCCTTCGCCT CTGCTTTCCA GCGCCGGGCA GGAGGGGTCC TGGTTGCTAG CCATCTGCAG | 480 |
| AGCTTCCTGG AGGTGTCGTA CCGCGTTCTA CGCCACCTTG CGCAGCCCTA CGTAATCGAG | 540 |
| GGAAGGATTT CCCCCGGGCC TCCTGTCAAT GCTGGCGGCG GCTCTGGTGG TGGTTCTGGT | 600 |
| GGCGGCTCTG AGGGTGGCGG CTCTGAGGGT GGCGGTTCTG AGGGTGGCGG CTCTGAGGGT | 660 |
| GGCGGTTCCG GTGGCGGCTC CGGTTCCGGT GATTTTGATT ATGAAAACAT GGCTAACTGC | 720 |
| TCTATAATGA TCGATGAAAT TATACATCAC TTAAAGAGAC CACCTAACCC TTTGCTGGAC | 780 |
| CCGAACAACC TCAATTCTGA AGACATGGAT ATCCTGATGG AACGAAACCT TCGAACTCCA | 840 |
| AACCTGCTCG CATTCGTAAG GGCTGTCAAG CACTTAGAAA ATGCATCAGG TATTGAGGCA | 900 |
| ATTCTTCGTA ATCTCCAACC ATGTCTGCCC TCTGCCACGG CCGCACCCTC TCGACATCCA | 960 |
| ATCATCATCA AGGCAGGTGA CTGGCAAGAA TTCCGGGAAA ACTGACGTT CTATCTGGTT | 1020 |
| ACCCTTGAGC AAGCGCAGGA ACAACAG | 1047 |

(2) INFORMATION FOR SEQ ID NO:75:

(i) SEQUENCE CHARACTERISTICS:
        (A) LENGTH: 921 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:75:

| | |
|---|---|
| ATGGCTACAC CATTAGGCCC TGCCAGCTCC CTGCCCCAGA GCTTCCTGCT CAAGTGCTTA | 60 |
| GAGCAAGTGA GGAAGATCCA GGGCGATGGC GCAGCGCTCC AGGAGAAGCT GTGTGCCACC | 120 |
| TACAAGCTGT GCCACCCCGA GGAGCTGGTG CTGCTCGGAC ACTCTCTGGG CATCCCCTGG | 180 |
| GCTCCCCTGA GCTCCTGCCC CAGCCAGGCC CTGCAGCTGG CAGGCTGCTT GAGCCAACTC | 240 |
| CATAGCGGCC TTTTCCTCTA CCAGGGGCTC CTGCAGGCCC TGGAAGGGAT ATCCCCCGAG | 300 |

| | |
|---|---:|
| TTGGGTCCCA CCTTGGACAC ACTGCAGCTG GACGTCGCCG ACTTTGCCAC CACCATCTGG | 360 |
| CAGCAGATGG AAGAACTGGG AATGGCCCCT GCCCTGCAGC CCACCCAGGG TGCCATGCCG | 420 |
| GCCTTCGCCT CTGCTTTCCA GCGCCGGGCA GGAGGGGTCC TGGTTGCTAG CCATCTGCAG | 480 |
| AGCTTCCTGG AGGTGTCGTA CCGCGTTCTA CGCCACCTTG CGCAGCCCTA CGTAATCGAG | 540 |
| GGAAGGATTT CCCCGGGTGG TGGTTCTGGC GGCGGCTCCA ACATGGCTAA CTGCTCTATA | 600 |
| ATGATCGATG AAATTATACA TCACTTAAAG AGACCACCTG CACCTTTGCT GGACCCGAAC | 660 |
| AACCTCAATG ACGAAGACGT CTCTATCCTG ATGGAACGAA ACCTTCGACT TCCAAACCTG | 720 |
| GAGAGCTTCG TAAGGGCTGT CAAGAACTTA GAAAATGCAT CAGGTATTGA GGCAATTCTT | 780 |
| CGTAATCTCC AACCATGTCT GCCCTCTGCC ACGGCCGCAC CCTCTCGACA TCCAATCATC | 840 |
| ATCAAGGCAG GTGACTGGCA AGAATTCCGG GAAAAACTGA CGTTCTATCT GGTTACCCTT | 900 |
| GAGCAAGCGC AGGAACAACA G | 921 |

(2) INFORMATION FOR SEQ ID NO:76:

(i) SEQUENCE CHARACTERISTICS:
        (A) LENGTH: 1047 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:76:

| | |
|---|---:|
| ATGGCTACAC CATTAGGCCC TGCCAGCTCC CTGCCCCAGA GCTTCCTGCT CAAGTGCTTA | 60 |
| GAGCAAGTGA GGAAGATCCA GGGCGATGGC GCAGCGCTCC AGGAGAAGCT GTGTGCCACC | 120 |
| TACAAGCTGT GCCACCCCGA GGAGCTGGTG CTGCTCGGAC ACTCTCTGGG CATCCCCTGG | 180 |
| GCTCCCCTGA GCTCCTGCCC CAGCCAGGCC CTGCAGCTGG CAGGCTGCTT GAGCCAACTC | 240 |
| CATAGCGGCC TTTTCCTCTA CCAGGGGCTC CTGCAGGCCC TGGAAGGGAT ATCCCCCGAG | 300 |
| TTGGGTCCCA CCTTGGACAC ACTGCAGCTG GACGTCGCCG ACTTTGCCAC CACCATCTGG | 360 |
| CAGCAGATGG AAGAACTGGG AATGGCCCCT GCCCTGCAGC CCACCCAGGG TGCCATGCCG | 420 |
| GCCTTCGCCT CTGCTTTCCA GCGCCGGGCA GGAGGGGTCC TGGTTGCTAG CCATCTGCAG | 480 |
| AGCTTCCTGG AGGTGTCGTA CCGCGTTCTA CGCCACCTTG CGCAGCCCTA CGTAATCGAG | 540 |
| GGAAGGATTT CCCCCGGGCC TCCTGTCAAT GCTGGCGGCG GCTCTGGTGG TGGTTCTGGT | 600 |
| GGCGGCTCTG AGGGTGGCGG CTCTGAGGGT GGCGGTTCTG AGGGTGGCGG CTCTGAGGGT | 660 |
| GGCGGTTCCG GTGGCGGCTC CGGTTCCGGT GATTTTGATT ATGAAAACAT GGCTAACTGC | 720 |
| TCTATAATGA TCGATGAAAT TATACATCAC TTAAAGAGAC CACCTGCACC TTTGCTGGAC | 780 |
| CCGAACAACC TCAATGACGA AGACGTCTCT ATCCTGATGG AACGAAACCT TCGACTTCCA | 840 |
| AACCTGGAGA GCTTCGTAAG GGCTGTCAAG AACTTAGAAA ATGCATCAGG TATTGAGGCA | 900 |
| ATTCTTCGTA ATCTCCAACC ATGTCTGCCC TCTGCCACGG CCGCACCCTC TCGACATCCA | 960 |
| ATCATCATCA AGGCAGGTGA CTGGCAAGAA TTCCGGGAAA AACTGACGTT CTATCTGGTT | 1020 |
| ACCCTTGAGC AAGCGCAGGA ACAACAG | 1047 |

(2) INFORMATION FOR SEQ ID NO:77:

(i) SEQUENCE CHARACTERISTICS:
        (A) LENGTH: 966 base pairs
        (B) TYPE: nucleic acid
        (C) STRANDEDNESS: double

```
           (D) TOPOLOGY: linear (ii) MOLECULE TYPE: DNA (genomic)

(xi) SEQUENCE DESCRIPTION: SEQ ID NO:77:

ATGGCTACAC CATTAGGCCC TGCCAGCTCC CTGCCCCAGA GCTTCCTGCT CAAGTGCTTA      60

GAGCAAGTGA GGAAGATCCA GGGCGATGGC GCAGCGCTCC AGGAGAAGCT GTGTGCCACC     120

TACAAGCTGT GCCACCCCGA GGAGCTGGTG CTGCTCGGAC ACTCTCTGGG CATCCCCTGG     180

GCTCCCCTGA GCTCCTGCCC CAGCCAGGCC CTGCAGCTGG CAGGCTGCTT GAGCCAACTC     240

CATAGCGGCC TTTTCCTCTA CCAGGGGCTC CTGCAGGCCC TGGAAGGGAT ATCCCCCGAG     300

TTGGGTCCCA CCTTGGACAC ACTGCAGCTG GACGTCGCCG ACTTTGCCAC CACCATCTGG     360

CAGCAGATGG AAGAACTGGG AATGGCCCCT GCCCTGCAGC CCACCCAGGG TGCCATGCCG     420

GCCTTCGCCT CTGCTTTCCA GCGCCGGGCA GGAGGGGTCC TGGTTGCTAG CCATCTGCAG     480

AGCTTCCTGG AGGTGTCGTA CCGCGTTCTA CGCCACCTTG CGCAGCCCTA CGTAATCGAG     540

GGAAGGATTT CCCCGGGTGA ACCGTCTGGT CCAATCTCTA CTATCAACCC GTCTCCTCCG     600

TCTAAAGAAT CTCATAAATC TCCAAACATG GCTAACTGCT CTATAATGAT CGATGAAATT     660

ATACATCACT TAAAGAGACC ACCTGCACCT TTGCTGGACC CGAACAACCT CAATGACGAA     720

GACGTCTCTA TCCTGATGGA ACGAAACCTT CGACTTCCAA ACCTGGAGAG CTTCGTAAGG     780

GCTGTCAAGA ACTTAGAAAA TGCATCAGGT ATTGAGGCAA TTCTTCGTAA TCTCCAACCA     840

TGTCTGCCCT CTGCCACGGC CGCACCCTCT CGACATCCAA TCATCATCAA GGCAGGTGAC     900

TGGCAAGAAT TCCGGGAAAA ACTGACGTTC TATCTGGTTA CCCTTGAGCA AGCGCAGGAA     960

CAACAG                                                               966

(2) INFORMATION FOR SEQ ID NO:78:

(i) SEQUENCE CHARACTERISTICS:
           (A) LENGTH: 921 base pairs
           (B) TYPE: nucleic acid
           (C) STRANDEDNESS: double
           (D) TOPOLOGY: linear (ii) MOLECULE TYPE: DNA (genomic)

(xi) SEQUENCE DESCRIPTION: SEQ ID NO:78:

ATGGCTACAC CATTAGGCCC TGCCAGCTCC CTGCCCCAGA GCTTCCTGCT CAAGTGCTTA      60

GAGCAAGTGA GGAAGATCCA GGGCGATGGC GCAGCGCTCC AGGAGAAGCT GTGTGCCACC     120

TACAAGCTGT GCCACCCCGA GGAGCTGGTG CTGCTCGGAC ACTCTCTGGG CATCCCCTGG     180

GCTCCCCTGA GCTCCTGCCC CAGCCAGGCC CTGCAGCTGG CAGGCTGCTT GAGCCAACTC     240

CATAGCGGCC TTTTCCTCTA CCAGGGGCTC CTGCAGGCCC TGGAAGGGAT ATCCCCCGAG     300

TTGGGTCCCA CCTTGGACAC ACTGCAGCTG GACGTCGCCG ACTTTGCCAC CACCATCTGG     360

CAGCAGATGG AAGAACTGGG AATGGCCCCT GCCCTGCAGC CCACCCAGGG TGCCATGCCG     420

GCCTTCGCCT CTGCTTTCCA GCGCCGGGCA GGAGGGGTCC TGGTTGCTAG CCATCTGCAG     480

AGCTTCCTGG AGGTGTCGTA CCGCGTTCTA CGCCACCTTG CGCAGCCCTA CGTAGAGGGC     540

GGTGGAGGCT CCCCGGGTGG TGGTTCTGGC GGCGGCTCCA ACATGGCTAA CTGCTCTATA     600

ATGATCGATG AAATTATACA TCACTTAAAG AGACCACCTG CACCTTTGCT GGACCCGAAC     660

AACCTCAATG ACGAAGACGT CTCTATCCTG ATGGAACGAA ACCTTCGACT TCCAAACCTG     720

GAGAGCTTCG TAAGGGCTGT CAAGAACTTA GAAAATGCAT CAGGTATTGA GGCAATTCTT     780
```

```
CGTAATCTCC AACCATGTCT GCCCTCTGCC ACGGCCGCAC CCTCTCGACA TCCAATCATC        840

ATCAAGGCAG GTGACTGGCA AGAATTCCGG GAAAAACTGA CGTTCTATCT GGTTACCCTT        900

GAGCAAGCGC AGGAACAACA G                                                 921
```

(2) INFORMATION FOR SEQ ID NO:79:

(i) SEQUENCE CHARACTERISTICS:
        (A) LENGTH: 966 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:79:

```
ATGGCTACAC CATTAGGCCC TGCCAGCTCC CTGCCCCAGA GCTTCCTGCT CAAGTGCTTA         60

GAGCAAGTGA GGAAGATCCA GGGCGATGGC GCAGCGCTCC AGGAGAAGCT GTGTGCCACC        120

TACAAGCTGT GCCACCCCGA GGAGCTGGTG CTGCTCGGAC ACTCTCTGGG CATCCCCTGG        180

GCTCCCCTGA GCTCCTGCCC CAGCCAGGCC CTGCAGCTGG CAGGCTGCTT GAGCCAACTC        240

CATAGCGGCC TTTTCCTCTA CCAGGGGCTC CTGCAGGCCC TGGAAGGGAT ATCCCCCGAG        300

TTGGGTCCCA CCTTGGACAC ACTGCAGCTG GACGTCGCCG ACTTTGCCAC CACCATCTGG        360

CAGCAGATGG AAGAACTGGG AATGGCCCCT GCCCTGCAGC CCACCCAGGG TGCCATGCCG        420

GCCTTCGCCT CTGCTTTCCA GCGCCGGGCA GGAGGGGTCC TGGTTGCTAG CCATCTGCAG        480

AGCTTCCTGG AGGTGTCGTA CCGCGTTCTA CGCCACCTTG CGCAGCCCTA CGTAGAGGGC        540

GGTGGAGGCT CCCCGGGTGA ACCGTCTGGT CCAATCTCTA CTATCAACCC GTCTCCTCCG        600

TCTAAAGAAT CTCATAAATC TCCAAACATG GCTAACTGCT CTATAATGAT CGATGAAATT        660

ATACATCACT TAAAGAGACC ACCTGCACCT TTGCTGGACC CGAACAACCT CAATGACGAA        720

GACGTCTCTA TCCTGATGGA ACGAAACCTT CGACTTCCAA ACCTGGAGAG CTTCGTAAGG        780

GCTGTCAAGA ACTTAGAAAA TGCATCAGGT ATTGAGGCAA TTCTTCGTAA TCTCCAACCA        840

TGTCTGCCCT CTGCCACGGC CGCACCCTCT CGACATCCAA TCATCATCAA GGCAGGTGAC        900

TGGCAAGAAT TCCGGGAAAA ACTGACGTTC TATCTGGTTA CCCTTGAGCA AGCGCAGGAA        960

CAACAG                                                                  966
```

(2) INFORMATION FOR SEQ ID NO:80:

(i) SEQUENCE CHARACTERISTICS:
        (A) LENGTH: 921 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:80:

```
ATGGCTACAC CATTGGGCCC TGCCAGCTCC CTGCCCCAGA GCTTCCTGCT CAAGTCTTTA         60

GAGCAAGTGA GGAAGATCCA GGGCGATGGC GCAGCGCTCC AGGAGAAGCT GTGTGCCACC        120

TACAAGCTGT GCCACCCCGA GGAGCTGGTG CTGCTCGGAC ACTCTCTGGG CATCCCCTGG        180

GCTCCCCTGA GCTCCTGCCC CAGCCAGGCC CTGCAGCTGG CAGGCTGCTT GAGCCAACTC        240

CATAGCGGCC TTTTCCTCTA CCAGGGGCTC CTGCAGGCCC TGGAAGGGAT ATCCCCCGAG        300

TTGGGTCCCA CCTTGGACAC ACTGCAGCTG GACGTCGCCG ACTTTGCCAC CACCATCTGG        360

CAGCAGATGG AAGAACTGGG AATGGCCCCT GCCCTGCAGC CCACCCAGGG TGCCATGCCG        420
```

```
GCCTTCGCCT CTGCTTTCCA GCGCCGGGCA GGAGGGGTCC TGGTTGCTAG CCATCTGCAG      480

AGCTTCCTGG AGGTGTCGTA CCGCGTTCTA CGCCACCTTG CGCAGCCCTA CGTAGAGGGC      540

GGTGGAGGCT CCCCGGGTGG TGGTTCTGGC GGCGGCTCCA ACATGGCTAA CTGCTCTATA      600

ATGATCGATG AAATTATACA TCACTTAAAG AGACCACCTG CACCTTTGCT GGACCCGAAC      660

AACCTCAATG ACGAAGACGT CTCTATCCTG ATGGAACGAA ACCTTCGACT TCCAAACCTG      720

GAGAGCTTCG TAAGGGCTGT CAAGAACTTA GAAAATGCAT CAGGTATTGA GGCAATTCTT      780

CGTAATCTCC AACCATGTCT GCCCTCTGCC ACGGCCGCAC CCTCTCGACA TCCAATCATC      840

ATCAAGGCAG GTGACTGGCA AGAATTCCGG GAAAAACTGA CGTTCTATCT GGTTACCCTT      900

GAGCAAGCGC AGGAACAACA G                                                921
```

(2) INFORMATION FOR SEQ ID NO:81:

(i) SEQUENCE CHARACTERISTICS:
        (A) LENGTH: 966 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:81:

```
ATGGCTACAC CATTGGGCCC TGCCAGCTCC CTGCCCCAGA GCTTCCTGCT CAAGTCTTTA       60

GAGCAAGTGA GGAAGATCCA GGGCGATGGC GCAGCGCTCC AGGAGAAGCT GTGTGCCACC      120

TACAAGCTGT GCCACCCCGA GGAGCTGGTG CTGCTCGGAC ACTCTCTGGG CATCCCCTGG      180

GCTCCCCTGA GCTCCTGCCC CAGCCAGGCC CTGCAGCTGG CAGGCTGCTT GAGCCAACTC      240

CATAGCGGCC TTTTCCTCTA CCAGGGGCTC CTGCAGGCCC TGGAAGGGAT ATCCCCCGAG      300

TTGGGTCCCA CCTTGGACAC ACTGCAGCTG ACGTCGCCG ACTTTGCCAC CACCATCTGG      360

CAGCAGATGG AAGAACTGGG AATGGCCCCT GCCCTGCAGC CCACCCAGGG TGCCATGCCG      420

GCCTTCGCCT CTGCTTTCCA GCGCCGGGCA GGAGGGGTCC TGGTTGCTAG CCATCTGCAG      480

AGCTTCCTGG AGGTGTCGTA CCGCGTTCTA CGCCACCTTG CGCAGCCCTA CGTAGAGGGC      540

GGTGGAGGCT CCCCGGGTGA ACCGTCTGGT CCAATCTCTA CTATCAACCC GTCTCCTCCG      600

TCTAAAGAAT CTCATAAATC TCCAAACATG GCTAACTGCT CTATAATGAT CGATGAAATT      660

ATACATCACT TAAAGAGACC ACCTGCACCT TTGCTGGACC CGAACAACCT CAATGACGAA      720

GACGTCTCTA TCCTGATGGA ACGAAACCTT CGACTTCCAA ACCTGGAGAG CTTCGTAAGG      780

GCTGTCAAGA ACTTAGAAAA TGCATCAGGT ATTGAGGCAA TTCTTCGTAA TCTCCAACCA      840

TGTCTGCCCT CTGCCACGGC CGCACCCTCT CGACATCCAA TCATCATCAA GGCAGGTGAC      900

TGGCAAGAAT TCCGGGAAAA ACTGACGTTC TATCTGGTTA CCCTTGAGCA AGCGCAGGAA      960

CAACAG                                                                966
```

(2) INFORMATION FOR SEQ ID NO:82:

(i) SEQUENCE CHARACTERISTICS:
        (A) LENGTH: 777 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:82:

-continued

```
ATGGCTAACT GCTCTATAAT GATCGATGAA ATTATACATC ACTTAAAGAG ACCACCTGCA        60

CCTTTGCTGG ACCCGAACAA CCTCAATGAC GAAGACGTCT CTATCCTGAT GGAACGAAAC       120

CTTCGACTTC CAAACCTGGA GAGCTTCGTA AGGGCTGTCA AGAACTTAGA AAATGCATCA       180

GGTATTGAGG CAATTCTTCG TAATCTCCAA CCATGTCTGC CCTCTGCCAC GGCCGCACCC       240

TCTCGACATC CAATCATCAT CAAGGCAGGT GACTGGCAAG AATTCCGGGA AAAACTGACG       300

TTCTATCTGG TTACCCTTGA GCAAGCGCAG GAACAACAGT ACGTAATCGA GGGAAGGATT       360

TCCCCGGGTG AACCGTCTGG TCCAATCTCT ACTATCAACC CGTCTCCTCC GTCTAAAGAA       420

TCTCATAAAT CTCCAAACAT GGCTAACTGC TCTATAATGA TCGATGAAAT TATACATCAC       480

TTAAAGAGAC CACCTGCACC TTTGCTGGAC CCGAACAACC TCAATGACGA AGACGTCTCT       540

ATCCTGATGG AACGAAACCT TCGACTTCCA AACCTGGAGA GCTTCGTAAG GGCTGTCAAG       600

AACTTAGAAA ATGCATCAGG TATTGAGGCA ATTCTTCGTA ATCTCCAACC ATGTCTGCCC       660

TCTGCCACGG CCGCACCCTC TCGACATCCA ATCATCATCA AGGCAGGTGA CTGGCAAGAA       720

TTCCGGGAAA AACTGACGTT CTATCTGGTT ACCCTTGAGC AAGCGCAGGA ACAACAG         777
```

(2) INFORMATION FOR SEQ ID NO:83:

(i) SEQUENCE CHARACTERISTICS:
        (A) LENGTH: 984 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:83:

```
ATGGCTAACT GCTCTATAAT GATCGATGAA ATTATACATC ACTTAAAGAG ACCACCTGCA        60

CCTTTGCTGG ACCCGAACAA CCTCAATGAC GAAGACGTCT CTATCCTGAT GGAACGAAAC       120

CTTCGACTTC CAAACCTGGA GAGCTTCGTA AGGGCTGTCA AGAACTTAGA AAATGCATCA       180

GGTATTGAGG CAATTCTTCG TAATCTCCAA CCATGTCTGC CCTCTGCCAC GGCCGCACCC       240

TCTCGACATC CAATCATCAT CAAGGCAGGT GACTGGCAAG AATTCCGGGA AAAACTGACG       300

TTCTATCTGG TTACCCTTGA GCAAGCGCAG GAACAACAGT ACGTAATCGA GGGAAGGATT       360

TCCCCGGGTG AACCGTCTGG TCCAATCTCT ACTATCAACC CGTCTCCTCC GTCTAAAGAA       420

TCTCATAAAT CTCCAAACAT GGCTACACCA TTGGGCCCTG CCAGCTCCCT GCCCCAGAGC       480

TTCCTGCTCA AGTCTTTAGA GCAAGTGAGG AAGATCCAGG GCGATGGCGC AGCGCTCCAG       540

GAGAAGCTGT GTGCCACCTA CAAGCTGTGC CACCCCGAGG AGCTGGTGCT GCTCGGACAC       600

TCTCTGGGCA TCCCCTGGGC TCCCCTGAGC TCCTGCCCCA GCCAGGCCCT GCAGCTGGCA       660

GGCTGCTTGA GCCAACTCCA TAGCGGCCTT TTCCTCTACC AGGGGCTCCT GCAGGCCCTG       720

GAAGGGATAT CCCCCGAGTT GGGTCCCACC TTGGACACAC TGCAGCTGGA CGTCGCCGAC       780

TTTGCCACCA CCATCTGGCA GCAGATGGAA GAACTGGGAA TGGCCCCTGC CCTGCAGCCC       840

ACCCAGGGTG CCATGCCGGC CTTCGCCTCT GCTTTCCAGC GCCGGGCAGG AGGGGTCCTG       900

GTTGCTAGCC ATCTGCAGAG CTTCCTGGAG GTGTCGTACC GCGTTCTACG CCACCTTGCG       960

CAGCCCTGAT AAGGATCCGA ATTC                                             984
```

(2) INFORMATION FOR SEQ ID NO:84:

(i) SEQUENCE CHARACTERISTICS:
        (A) LENGTH: 921 base pairs
        (B) TYPE: nucleic acid (C) STRANDEDNESS: double
        (D) TOPOLOGY: linear (ii) MOLECULE TYPE: DNA (genomic)

(xi) SEQUENCE DESCRIPTION: SEQ ID NO:84:

```
ATGGCTAACT GCTCTATAAT GATCGATGAA ATTATACATC ACTTAAAGAG ACCACCTGCA      60

CCTTTGCTGG ACCCGAACAA CCTCAATGAC GAAGACGTCT CTATCCTGAT GGAACGAAAC     120

CTTCGACTTC CAAACCTGGA GAGCTTCGTA AGGGCTGTCA AGAACTTAGA AAATGCATCA     180

GGTATTGAGG CAATTCTTCG TAATCTCCAA CCATGTCTGC CCTCTGCCAC GGCCGCACCC     240

TCTCGACATC CAATCATCAT CAAGGCAGGT GACTGGCAAG AATTCCGGGA AAAACTGACG     300

TTCTATCTGG TTACCCTTGA GCAAGCGCAG GAACAACAGT ACGTAATCGA GGGAAGGATT     360

TCCCCGGGTG GTGGTTCTGG CGGCGGCTCC AACATGGCTA CACCATTAGG CCCTGCCAGC     420

TCCCTGCCCC AGAGCTTCCT GCTCAAGTGC TTAGAGCAAG TGAGGAAGAT CCAGGGCGAT     480

GGCGCAGCGC TCCAGGAGAA GCTGTGTGCC ACCTACAAGC TGTGCCACCC CGAGGAGCTG     540

GTGCTGCTCG ACACTCTCT GGGCATCCCC TGGGCTCCCC TGAGCTCCTG CCCCAGCCAG     600

GCCCTGCAGC TGGCAGGCTG CTTGAGCCAA CTCCATAGCG GCCTTTTCCT CTACCAGGGG     660

CTCCTGCAGG CCCTGGAAGG GATATCCCCC GAGTTGGGTC CCACCTTGGA CACACTGCAG     720

CTGGACGTCG CCGACTTTGC CACCACCATC TGGCAGCAGA TGGAAGAACT GGGAATGGCC     780

CCTGCCCTGC AGCCCACCCA GGGTGCCATG CCGGCCTTCG CCTCTGCTTT CCAGCGCCGG     840

GCAGGAGGGG TCCTGGTTGC TAGCCATCTG CAGAGCTTCC TGGAGGTGTC GTACCGCGTT     900

CTACGCCACC TTGCGCAGCC C                                              921
```

(2) INFORMATION FOR SEQ ID NO:85:

(i) SEQUENCE CHARACTERISTICS:
        (A) LENGTH: 921 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:85:

```
ATGGCTAACT GCTCTATAAT GATCGATGAA ATTATACATC ACTTAAAGAG ACCACCTGCA      60

CCTTTGCTGG ACCCGAACAA CCTCAATGAC GAAGACGTCT CTATCCTGAT GGAACGAAAC     120

CTTCGACTTC CAAACCTGGA GAGCTTCGTA AGGGCTGTCA AGAACTTAGA AAATGCATCA     180

GGTATTGAGG CAATTCTTCG TAATCTCCAA CCATGTCTGC CCTCTGCCAC GGCCGCACCC     240

TCTCGACATC CAATCATCAT CAAGGCAGGT GACTGGCAAG AATTCCGGGA AAAACTGACG     300

TTCTATCTGG TTACCCTTGA GCAAGCGCAG GAACAACAGT ACGTAATCGA GGGAAGGATT     360

TCCCCGGGTG GTGGTTCTGG CGGCGGCTCC AACATGGCTA CACCATTGGG CCCTGCCAGC     420

TCCCTGCCCC AGAGCTTCCT GCTCAAGTCT TTAGAGCAAG TGAGGAAGAT CCAGGGCGAT     480

GGCGCAGCGC TCCAGGAGAA GCTGTGTGCC ACCTACAAGC TGTGCCACCC CGAGGAGCTG     540

GTGCTGCTCG ACACTCTCT GGGCATCCCC TGGGCTCCCC TGAGCTCCTG CCCCAGCCAG     600

GCCCTGCAGC TGGCAGGCTG CTTGAGCCAA CTCCATAGCG GCCTTTTCCT CTACCAGGGG     660

CTCCTGCAGG CCCTGGAAGG GATATCCCCC GAGTTGGGTC CCACCTTGGA CACACTGCAG     720

CTGGACGTCG CCGACTTTGC CACCACCATC TGGCAGCAGA TGGAAGAACT GGGAATGGCC     780

CCTGCCCTGC AGCCCACCCA GGGTGCCATG CCGGCCTTCG CCTCTGCTTT CCAGCGCCGG     840
```

| | |
|---|---:|
| GCAGGAGGGG TCCTGGTTGC TAGCCATCTG CAGAGCTTCC TGGAGGTGTC GTACCGCGTT | 900 |
| CTACGCCACC TTGCGCAGCC C | 921 |

(2) INFORMATION FOR SEQ ID NO:86:

(i) SEQUENCE CHARACTERISTICS:
        (A) LENGTH: 732 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:86:

| | |
|---|---:|
| ATGGCTAACT GCTCTATAAT GATCGATGAA ATTATACATC ACTTAAAGAG ACCACCTGCA | 60 |
| CCTTTGCTGG ACCCGAACAA CCTCAATGAC GAAGACGTCT CTATCCTGAT GGAACGAAAC | 120 |
| CTTCGACTTC CAAACCTGGA GAGCTTCGTA AGGGCTGTCA AGAACTTAGA AAATGCATCA | 180 |
| GGTATTGAGG CAATTCTTCG TAATCTCCAA CCATGTCTGC CCTCTGCCAC GGCCGCACCC | 240 |
| TCTCGACATC CAATCATCAT CAAGGCAGGT GACTGGCAAG AATTCCGGGA AAAACTGACG | 300 |
| TTCTATCTGG TTACCCTTGA GCAAGCGCAG GAACAACAGT ACGTAATCGA GGGAAGGATT | 360 |
| TCCCCGGGTG GTGGTTCTGG CGGCGGCTCC AACATGGCTA ACTGCTCTAT AATGATCGAT | 420 |
| GAAATTATAC ATCACTTAAA GAGACCACCT GCACCTTTGC TGGACCCGAA CAACCTCAAT | 480 |
| GACGAAGACG TCTCTATCCT GATGGAACGA AACCTTCGAC TTCCAAACCT GGAGAGCTTC | 540 |
| GTAAGGGCTG TCAAGAACTT AGAAAATGCA TCAGGTATTG AGGCAATTCT TCGTAATCTC | 600 |
| CAACCATGTC TGCCCTCTGC CACGGCCGCA CCCTCTCGAC ATCCAATCAT CATCAAGGCA | 660 |
| GGTGACTGGC AAGAATTCCG GGAAAAACTG ACGTTCTATC TGGTTACCCT TGAGCAAGCG | 720 |
| CAGGAACAAC AG | 732 |

(2) INFORMATION FOR SEQ ID NO:87:

(i) SEQUENCE CHARACTERISTICS:
        (A) LENGTH: 921 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:87:

| | |
|---|---:|
| ATGGCTAACT GCTCTATAAT GATCGATGAA ATTATACATC ACTTAAAGAG ACCACCTGCA | 60 |
| CCTTTGCTGG ACCCGAACAA CCTCAATGAC GAAGACGTCT CTATCCTGAT GGAACGAAAC | 120 |
| CTTCGACTTC CAAACCTGGA GAGCTTCGTA AGGGCTGTCA AGAACTTAGA AAATGCATCA | 180 |
| GGTATTGAGG CAATTCTTCG TAATCTCCAA CCATGTCTGC CCTCTGCCAC GGCCGCACCC | 240 |
| TCTCGACATC CAATCATCAT CAAGGCAGGT GACTGGCAAG AATTCCGGGA AAAACTGACG | 300 |
| TTCTATCTGG TTACCCTTGA GCAAGCGCAG GAACAACAGT ACGTAGAGGG CGGTGGAGGC | 360 |
| TCCCCGGGTG GTGGTTCTGG CGGCGGCTCC AACATGGCTA CACCATTGGG CCCTGCCAGC | 420 |
| TCCCTGCCCC AGAGCTTCCT GCTCAAGTCT TTAGAGCAAG TGAGGAAGAT CCAGGGCGAT | 480 |
| GGCGCAGCGC TCCAGGAGAA GCTGTGTGCC ACCTACAAGC TGTGCCACCC CGAGGAGCTG | 540 |
| GTGCTGCTCG GACACTCTCT GGGCATCCCC TGGGCTCCCC TGAGCTCCTG CCCCAGCCAG | 600 |
| GCCCTGCAGC TGGCAGGCTG CTTGAGCCAA CTCCATAGCG GCCTTTTCCT CTACCAGGGG | 660 |

| | |
|---|---|
| CTCCTGCAGG CCCTGGAAGG GATATCCCCC GAGTTGGGTC CCACCTTGGA CACACTGCAG | 720 |
| CTGGACGTCG CCGACTTTGC CACCACCATC TGGCAGCAGA TGGAAGAACT GGGAATGGCC | 780 |
| CCTGCCCTGC AGCCCACCCA GGGTGCCATG CCGGCCTTCG CCTCTGCTTT CCAGCGCCGG | 840 |
| GCAGGAGGGG TCCTGGTTGC TAGCCATCTG CAGAGCTTCC TGGAGGTGTC GTACCGCGTT | 900 |
| CTACGCCACC TTGCGCAGCC C | 921 |

(2) INFORMATION FOR SEQ ID NO:88:

(i) SEQUENCE CHARACTERISTICS:
        (A) LENGTH: 732 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:88:

| | |
|---|---|
| ATGGCTAACT GCTCTATAAT GATCGATGAA ATTATACATC ACTTAAAGAG ACCACCTGCA | 60 |
| CCTTTGCTGG ACCCGAACAA CCTCAATGAC GAAGACGTCT CTATCCTGAT GGAACGAAAC | 120 |
| CTTCGACTTC CAAACCTGGA GAGCTTCGTA AGGGCTGTCA AGAACTTAGA AAATGCATCA | 180 |
| GGTATTGAGG CAATTCTTCG TAATCTCCAA CCATGTCTGC CCTCTGCCAC GGCCGCACCC | 240 |
| TCTCGACATC CAATCATCAT CAAGGCAGGT GACTGGCAAG AATTCCGGGA AAAACTGACG | 300 |
| TTCTATCTGG TTACCCTTGA GCAAGCGCAG GAACAACAGT ACGTAGAGGG CGGTGGAGGC | 360 |
| TCCCCGGGTG GTGGTTCTGG CGGCGGCTCC AACATGGCTA ACTGCTCTAT AATGATCGAT | 420 |
| GAAATTATAC ATCACTTAAA GAGACCACCT GCACCTTTGC TGGACCCGAA CAACCTCAAT | 480 |
| GACGAAGACG TCTCTATCCT GATGGAACGA AACCTTCGAC TTCCAAACCT GGAGAGCTTC | 540 |
| GTAAGGGCTG TCAAGAACTT AGAAAATGCA TCAGGTATTG AGGCAATTCT TCGTAATCTC | 600 |
| CAACCATGTC TGCCCTCTGC CACGGCCGCA CCCTCTCGAC ATCCAATCAT CATCAAGGCA | 660 |
| GGTGACTGGC AAGAATTCCG GGAAAAACTG ACGTTCTATC TGGTTACCCT TGAGCAAGCG | 720 |
| CAGGAACAAC AG | 732 |

(2) INFORMATION FOR SEQ ID NO:89:

(i) SEQUENCE CHARACTERISTICS:
        (A) LENGTH: 966 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:89:

| | |
|---|---|
| ATGGCTAACT GCTCTATAAT GATCGATGAA ATTATACATC ACTTAAAGAG ACCACCTGCA | 60 |
| CCTTTGCTGG ACCCGAACAA CCTCAATGAC GAAGACGTCT CTATCCTGAT GGAACGAAAC | 120 |
| CTTCGACTTC CAAACCTGGA GAGCTTCGTA AGGGCTGTCA AGAACTTAGA AAATGCATCA | 180 |
| GGTATTGAGG CAATTCTTCG TAATCTCCAA CCATGTCTGC CCTCTGCCAC GGCCGCACCC | 240 |
| TCTCGACATC CAATCATCAT CAAGGCAGGT GACTGGCAAG AATTCCGGGA AAAACTGACG | 300 |
| TTCTATCTGG TTACCCTTGA GCAAGCGCAG GAACAACAGT ACGTAGAGGG CGGTGGAGGC | 360 |
| TCCCCGGGTG AACCGTCTGG TCCAATCTCT ACTATCAACC CGTCTCCTCC GTCTAAAGAA | 420 |
| TCTCATAAAT CTCCAAACAT GGCTACACCA TTGGCCCTG CCAGCTCCCT GCCCCAGAGC | 480 |
| TTCCTGCTCA GTCTTTAGA GCAAGTGAGG AAGATCCAGG GCGATGGCGC AGCGCTCCAG | 540 |

```
GAGAAGCTGT GTGCCACCTA CAAGCTGTGC CACCCCGAGG AGCTGGTGCT GCTCGGACAC      600

TCTCTGGGCA TCCCCTGGGC TCCCCTGAGC TCCTGCCCCA GCCAGGCCCT GCAGCTGGCA      660

GGCTGCTTGA GCCAACTCCA TAGCGGCCTT TTCCTCTACC AGGGGCTCCT GCAGGCCCTG      720

GAAGGGATAT CCCCCGAGTT GGGTCCCACC TTGGACACAC TGCAGCTGGA CGTCGCCGAC      780

TTTGCCACCA CCATCTGGCA GCAGATGGAA GAACTGGGAA TGGCCCCTGC CCTGCAGCCC      840

ACCCAGGGTG CCATGCCGGC CTTCGCCTCT GCTTTCCAGC GCCGGGCAGG AGGGGTCCTG      900

GTTGCTAGCC ATCTGCAGAG CTTCCTGGAG GTGTCGTACC GCGTTCTACG CCACCTTGCG      960

CAGCCC                                                                966
```

(2) INFORMATION FOR SEQ ID NO:90:

(i) SEQUENCE CHARACTERISTICS:
        (A) LENGTH: 777 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:90:

```
ATGGCTAACT GCTCTATAAT GATCGATGAA ATTATACATC ACTTAAAGAG ACCACCTGCA       60

CCTTTGCTGG ACCCGAACAA CCTCAATGAC GAAGACGTCT CTATCCTGAT GGAACGAAAC      120

CTTCGACTTC CAAACCTGGA GAGCTTCGTA AGGGCTGTCA AGAACTTAGA AAATGCATCA      180

GGTATTGAGG CAATTCTTCG TAATCTCCAA CCATGTCTGC CCTCTGCCAC GGCCGCACCC      240

TCTCGACATC CAATCATCAT CAAGGCAGGT GACTGGCAAG AATTCCGGGA AAAACTGACG      300

TTCTATCTGG TTACCCTTGA GCAAGCGCAG GAACAACAGT ACGTAGAGGG CGGTGGAGGC      360

TCCCCGGGTG AACCGTCTGG TCCAATCTCT ACTATCAACC CGTCTCCTCC GTCTAAAGAA      420

TCTCATAAAT CTCCAAACAT GGCTAACTGC TCTATAATGA TCGATGAAAT TATACATCAC      480

TTAAAGAGAC CACCTGCACC TTTGCTGGAC CCGAACAACC TCAATGACGA AGACGTCTCT      540

ATCCTGATGG AACGAAACCT TCGACTTCCA AACCTGGAGA GCTTCGTAAG GGCTGTCAAG      600

AACTTAGAAA ATGCATCAGG TATTGAGGCA ATTCTTCGTA ATCTCCAACC ATGTCTGCCC      660

TCTGCCACGG CCGCACCCTC TCGACATCCA ATCATCATCA AGGCAGGTGA CTGGCAAGAA      720

TTCCGGGAAA AACTGACGTT CTATCTGGTT ACCCTTGAGC AAGCGCAGGA ACAACAG        777
```

(2) INFORMATION FOR SEQ ID NO:91:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA"

(xi) SEQUENCE DESCRIPTION: SEQ ID NO:91:

```
AATTCCGGGA AAAACTGACG TTCTATCTGG TTACCCTTGA G                           41
```

(2) INFORMATION FOR SEQ ID NO:92:

(i) SEQUENCE CHARACTERISTICS:
        (A) LENGTH: 46 base pairs
        (B) TYPE: nucleic acid
        (C) STRANDEDNESS: single

```
        (D) TOPOLOGY: linear (ii) MOLECULE TYPE: other nucleic acid
        (A) DESCRIPTION: /desc = "synthetic DNA"

(xi) SEQUENCE DESCRIPTION: SEQ ID NO:92:

CTGCGCTTGC TCAAGGGTAA CCAGATAGAA CGTCAGTTTT TCCCGG                46

(2) INFORMATION FOR SEQ ID NO:93:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA"

(xi) SEQUENCE DESCRIPTION: SEQ ID NO:93:

CAAGCGCAGG AACAACAGTA CGTAATCGAG GGAAGGATT                        39

(2) INFORMATION FOR SEQ ID NO:94:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA"

(xi) SEQUENCE DESCRIPTION: SEQ ID NO:94:

ACCCGGGGAA ATCCTTCCCT CGATTACGTA CTGTTGTTC                        39

(2) INFORMATION FOR SEQ ID NO:95:

(i) SEQUENCE CHARACTERISTICS:
        (A) LENGTH: 63 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA"

(xi) SEQUENCE DESCRIPTION: SEQ ID NO:95:

TCCCCGGGTG GTGGTTCTGG CGGCGGCTCC AACATGTAAG GTACCGCATG CAAGCTTAGA    60

TCT                                                                 63

(2) INFORMATION FOR SEQ ID NO:96:

(i) SEQUENCE CHARACTERISTICS:
        (A) LENGTH: 58 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA"

(xi) SEQUENCE DESCRIPTION: SEQ ID NO:96:

AGCTAGATCT AAGCTTGCAT GCGGTACCTT ACATGTTGGA GCCGCCGCCA GAACCACC      58

(2) INFORMATION FOR SEQ ID NO:97:

(i) SEQUENCE CHARACTERISTICS:
```

(A) LENGTH: 74 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA"

(xi) SEQUENCE DESCRIPTION: SEQ ID NO:97:

CCGGGTGAAC CGTCTGGTCC AATCTCTACT ATCAACCCGT CTCCTCCGTC TAAAGAATCT    60

CATAAATCTC CAAA    74

(2) INFORMATION FOR SEQ ID NO:98:

(i) SEQUENCE CHARACTERISTICS:
        (A) LENGTH: 74 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA"

(xi) SEQUENCE DESCRIPTION: SEQ ID NO:98:

CATGTTTGGA GATTTATGAG ATTCTTTAGA CGGAGGAGAC GGGTTGATAG TAGAGATTGG    60

ACCAGACGGT TCAC    74

(2) INFORMATION FOR SEQ ID NO:99:

(i) SEQUENCE CHARACTERISTICS:
        (A) LENGTH: 68 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA"

(xi) SEQUENCE DESCRIPTION: SEQ ID NO:99:

CTAGCCATCT GCAGAGCTTC CTGGAGGTGT CGTACCGCGT TCTACGCCAC CTTGCGCAGC    60

CCTACGTA    68

(2) INFORMATION FOR SEQ ID NO:100:

(i) SEQUENCE CHARACTERISTICS:
        (A) LENGTH: 68 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA"

(xi) SEQUENCE DESCRIPTION: SEQ ID NO:100:

AGCTTACGTA GGGCTGCGCA AGGTGGCGTA GAACGCGGTA CGACACCTCC AGGAAGCTCT    60

GCAGATGG    68

(2) INFORMATION FOR SEQ ID NO:101:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA"

(xi) SEQUENCE DESCRIPTION: SEQ ID NO:101:

GTAATCGAGG GAAAGATTTC C                                21

(2) INFORMATION FOR SEQ ID NO:102:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA"

(xi) SEQUENCE DESCRIPTION: SEQ ID NO:102:

CCGGGGAAAT CTTTCCCTCG ATTAC                            25

(2) INFORMATION FOR SEQ ID NO:103:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA"

(xi) SEQUENCE DESCRIPTION: SEQ ID NO:103:

GTAGAGGGCG GTGGAGGCTC C                                21

(2) INFORMATION FOR SEQ ID NO:104:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA"

(xi) SEQUENCE DESCRIPTION: SEQ ID NO:104:

CCGGGGAGCC TCCACCGCCC TCTAC                            25

(2) INFORMATION FOR SEQ ID NO:105:

(i) SEQUENCE CHARACTERISTICS:
        (A) LENGTH: 58 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "sythetic DNA"

(xi) SEQUENCE DESCRIPTION: SEQ ID NO:105:

CATGGCACCA GCAAGATCAC CATCACCATC AACTCAACCT TGGGAACATG TGAATGCC       58

(2) INFORMATION FOR SEQ ID NO:106:

(i) SEQUENCE CHARACTERISTICS:
        (A) LENGTH: 52 base pairs
        (B) TYPE: nucleic acid
        (C) STRANDEDNESS: single
        (D) TOPOLOGY: linear (ii) MOLECULE TYPE: other nucleic acid (A) DESCRIPTION: /desc = "synthetic DNA"

(xi) SEQUENCE DESCRIPTION: SEQ ID NO:106:

CATTCACATG TTCCCAAGGT TGAGTTGATG GTGATGGTGA TCTTGCTGGT GC        52

(2) INFORMATION FOR SEQ ID NO:107:

(i) SEQUENCE CHARACTERISTICS:
        (A) LENGTH: 66 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA"

(xi) SEQUENCE DESCRIPTION: SEQ ID NO:107:

CTGCCAGCTC CCTGCCCCAG AGCTTCCTGC TCAAGTCTTT AGAGCAAGTG AGGAAGATCC        60

AGGGCG        66

(2) INFORMATION FOR SEQ ID NO:108:

(i) SEQUENCE CHARACTERISTICS:
        (A) LENGTH: 66 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA"

(xi) SEQUENCE DESCRIPTION: SEQ ID NO:108:

CTGGATCTTC CTCACTTGCT CTAAAGACTT GAGCAGGAAG CTCTGGGGCA GGGAGCTGGC        60

AGGGCC        66

(2) INFORMATION FOR SEQ ID NO:109:

(i) SEQUENCE CHARACTERISTICS:
        (A) LENGTH: 48 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA"

(xi) SEQUENCE DESCRIPTION: SEQ ID NO:109:

AGCTTACCTG CCATGGCTCC AGTACCACCA GGTGAAGATT CCAAAGAT        48

(2) INFORMATION FOR SEQ ID NO:110:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA"

(xi) SEQUENCE DESCRIPTION: SEQ ID NO:110:

TTGGAATCTT CACCTGGTGG TACTGGAGCC ATGGCAGGTA        40

(2) INFORMATION FOR SEQ ID NO:111:

(i) SEQUENCE CHARACTERISTICS:
        (A) LENGTH: 26 base pairs (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA"

(xi) SEQUENCE DESCRIPTION: SEQ ID NO:111:

AGCTTCCATG GCTACCCCCC TGGGCC                                          26

(2) INFORMATION FOR SEQ ID NO:112:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA"

(xi) SEQUENCE DESCRIPTION: SEQ ID NO:112:

CAGGGGGTA GCCATGGA                                                    18

(2) INFORMATION FOR SEQ ID NO:113:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA"

(xi) SEQUENCE DESCRIPTION: SEQ ID NO:113:

CATGGCTACA CCATTGGGCC                                                 20

(2) INFORMATION FOR SEQ ID NO:114:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA"

(xi) SEQUENCE DESCRIPTION: SEQ ID NO:114:

CAATGGTGTA GC                                                         12

(2) INFORMATION FOR SEQ ID NO:115:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA"

(xi) SEQUENCE DESCRIPTION: SEQ ID NO:115:

CATGGCTACA CCATTAGGAC                                                 20

(2) INFORMATION FOR SEQ ID NO:116:

(i) SEQUENCE CHARACTERISTICS:

(A) LENGTH: 12 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "synthetic DNA"

(xi) SEQUENCE DESCRIPTION: SEQ ID NO:116:

TAATGGTGTA GC                                                               12

(2) INFORMATION FOR SEQ ID NO:117:

(i) SEQUENCE CHARACTERISTICS:
            (A) LENGTH: 30 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "synthetic DNA"

(xi) SEQUENCE DESCRIPTION: SEQ ID NO:117:

CCTGTCAACC CGGGCGGCGG CTCTGGTGGT                                             30

(2) INFORMATION FOR SEQ ID NO:118:

(i) SEQUENCE CHARACTERISTICS:
            (A) LENGTH: 31 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "synthetic DNA"

(xi) SEQUENCE DESCRIPTION: SEQ ID NO:118:

TCATAATACA TGTTACCGGA ACGGAGCCGC C                                           31

(2) INFORMATION FOR SEQ ID NO:119:

(i) SEQUENCE CHARACTERISTICS:
            (A) LENGTH: 34 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "synthetic DNA"

(xi) SEQUENCE DESCRIPTION: SEQ ID NO:119:

ATCGTCTGAC CTCCCGGGAC CTCCTGTCAA TGCT                                        34

(2) INFORMATION FOR SEQ ID NO:120:

(i) SEQUENCE CHARACTERISTICS:
            (A) LENGTH: 30 base pairs
            (B) TYPE: nucleic acid
            (C) STRANDEDNESS: single
            (D) TOPOLOGY: linear (ii) MOLECULE TYPE: other nucleic acid
            (A) DESCRIPTION: /desc = "synthetic DNA"

(xi) SEQUENCE DESCRIPTION: SEQ ID NO:120:

AGCGTTTGAC ATGTTTTCAT AATCAAAATC                                             30

(2) INFORMATION FOR SEQ ID NO:121:

(i) SEQUENCE CHARACTERISTICS:
    (A) LENGTH: 307 amino acids
    (B) TYPE: amino acid
    (C) STRANDEDNESS:
    (D) TOPOLOGY: linear (ii) MOLECULE TYPE: protein (xi) SEQUENCE DESCRIPTION: SEQ ID NO:121:

Met Ala Asn Cys Ser Ile Met Ile Asp Glu Ile Ile His His Leu Lys
1               5                   10                  15

Arg Pro Pro Asn Pro Leu Leu Asp Pro Asn Asn Leu Asn Ser Glu Asp
            20                  25                  30

Met Asp Ile Leu Met Glu Arg Asn Leu Arg Thr Pro Asn Leu Leu Ala
        35                  40                  45

Phe Val Arg Ala Val Lys His Leu Glu Asn Ala Ser Gly Ile Glu Ala
    50                  55                  60

Ile Leu Arg Asn Leu Gln Pro Cys Leu Pro Ser Ala Thr Ala Ala Pro
65                  70                  75                  80

Ser Arg His Pro Ile Ile Ile Lys Ala Gly Asp Trp Gln Glu Phe Arg
                85                  90                  95

Glu Lys Leu Thr Phe Tyr Leu Val Thr Leu Glu Gln Ala Gln Glu Gln
            100                 105                 110

Gln Tyr Val Ile Glu Gly Arg Ile Ser Pro Gly Gly Ser Gly Gly
        115                 120                 125

Gly Ser Asn Met Ala Thr Pro Leu Gly Pro Ala Ser Ser Leu Pro Gln
130                 135                 140

Ser Phe Leu Leu Lys Cys Leu Glu Gln Val Arg Lys Ile Gln Gly Asp
145                 150                 155                 160

Gly Ala Ala Leu Gln Glu Lys Leu Cys Ala Thr Tyr Lys Leu Cys His
                165                 170                 175

Pro Glu Glu Leu Val Leu Leu Gly His Ser Leu Gly Ile Pro Trp Ala
            180                 185                 190

Pro Leu Ser Ser Cys Pro Ser Gln Ala Leu Gln Leu Ala Gly Cys Leu
        195                 200                 205

Ser Gln Leu His Ser Gly Leu Phe Leu Tyr Gln Gly Leu Leu Gln Ala
210                 215                 220

Leu Glu Gly Ile Ser Pro Glu Leu Gly Pro Thr Leu Asp Thr Leu Gln
225                 230                 235                 240

Leu Asp Val Ala Asp Phe Ala Thr Thr Ile Trp Gln Gln Met Glu Glu
                245                 250                 255

Leu Gly Met Ala Pro Ala Leu Gln Pro Thr Gln Gly Ala Met Pro Ala
            260                 265                 270

Phe Ala Ser Ala Phe Gln Arg Arg Ala Gly Gly Val Leu Val Ala Ser
        275                 280                 285

His Leu Gln Ser Phe Leu Glu Val Ser Tyr Arg Val Leu Arg His Leu
290                 295                 300

Ala Gln Pro
305

(2) INFORMATION FOR SEQ ID NO:122:

(i) SEQUENCE CHARACTERISTICS:
        (A) LENGTH: 307 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:122:

```
Met Ala Asn Cys Ser Ile Met Ile Asp Glu Ile Ile His His Leu Lys
1               5                   10                  15

Arg Pro Pro Asn Pro Leu Leu Asp Pro Asn Asn Leu Asn Ser Glu Asp
                20                  25                  30

Met Asp Ile Leu Met Glu Arg Asn Leu Arg Thr Pro Asn Leu Leu Ala
            35                  40                  45

Phe Val Arg Ala Val Lys His Leu Glu Asn Ala Ser Gly Ile Glu Ala
        50                  55                  60

Ile Leu Arg Asn Leu Gln Pro Cys Leu Pro Ser Ala Thr Ala Ala Pro
65                  70                  75                  80

Ser Arg His Pro Ile Ile Ile Lys Ala Gly Asp Trp Gln Glu Phe Arg
                85                  90                  95

Glu Lys Leu Thr Phe Tyr Leu Val Thr Leu Glu Gln Ala Gln Glu Gln
                100                 105                 110

Gln Tyr Val Ile Glu Gly Arg Ile Ser Pro Gly Gly Gly Ser Gly Gly
            115                 120                 125

Gly Ser Asn Met Ala Thr Pro Leu Gly Pro Ala Ser Ser Leu Pro Gln
130                 135                 140

Ser Phe Leu Leu Lys Ser Leu Glu Gln Val Arg Lys Ile Gln Gly Asp
145                 150                 155                 160

Gly Ala Ala Leu Gln Glu Lys Leu Cys Ala Thr Tyr Lys Leu Cys His
                165                 170                 175

Pro Glu Glu Leu Val Leu Leu Gly His Ser Leu Gly Ile Pro Trp Ala
                180                 185                 190

Pro Leu Ser Ser Cys Pro Ser Gln Ala Leu Gln Leu Ala Gly Cys Leu
                195                 200                 205

Ser Gln Leu His Ser Gly Leu Phe Leu Tyr Gln Gly Leu Leu Gln Ala
                210                 215                 220

Leu Glu Gly Ile Ser Pro Glu Leu Gly Pro Thr Leu Asp Thr Leu Gln
225                 230                 235                 240

Leu Asp Val Ala Asp Phe Ala Thr Thr Ile Trp Gln Gln Met Glu Glu
                245                 250                 255

Leu Gly Met Ala Pro Ala Leu Gln Pro Thr Gln Gly Ala Met Pro Ala
                260                 265                 270

Phe Ala Ser Ala Phe Gln Arg Arg Ala Gly Gly Val Leu Val Ala Ser
                275                 280                 285

His Leu Gln Ser Phe Leu Glu Val Ser Tyr Arg Val Leu Arg His Leu
                290                 295                 300

Ala Gln Pro
305
```

(2) INFORMATION FOR SEQ ID NO:123:

(i) SEQUENCE CHARACTERISTICS:
        (A) LENGTH: 307 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:123:

```
Met Ala Asn Cys Ser Ile Met Ile Asp Glu Ile Ile His His Leu Lys
1               5                   10                  15
```

-continued

```
Arg Pro Pro Asn Pro Leu Leu Asp Pro Asn Asn Leu Asn Ser Glu Asp
             20                  25                  30

Met Asp Ile Leu Met Glu Arg Asn Leu Arg Thr Pro Asn Leu Leu Ala
         35                  40                  45

Phe Val Arg Ala Val Lys His Leu Glu Asn Ala Ser Gly Ile Glu Ala
     50                  55                  60

Ile Leu Arg Asn Leu Gln Pro Cys Leu Pro Ser Ala Thr Ala Ala Pro
 65                  70                  75                  80

Ser Arg His Pro Ile Ile Ile Lys Ala Gly Asp Trp Gln Glu Phe Arg
                 85                  90                  95

Glu Lys Leu Thr Phe Tyr Leu Val Thr Leu Glu Gln Ala Gln Glu Gln
            100                 105                 110

Gln Tyr Val Ile Glu Gly Lys Ile Ser Pro Gly Gly Gly Ser Gly Gly
            115                 120                 125

Gly Ser Asn Met Ala Thr Pro Leu Gly Pro Ala Ser Ser Leu Pro Gln
        130                 135                 140

Ser Phe Leu Leu Lys Ser Leu Glu Gln Val Arg Lys Ile Gln Gly Asp
145                 150                 155                 160

Gly Ala Ala Leu Gln Glu Lys Leu Cys Ala Thr Tyr Lys Leu Cys His
                165                 170                 175

Pro Glu Glu Leu Val Leu Leu Gly His Ser Leu Gly Ile Pro Trp Ala
            180                 185                 190

Pro Leu Ser Ser Cys Pro Ser Gln Ala Leu Gln Leu Ala Gly Cys Leu
            195                 200                 205

Ser Gln Leu His Ser Gly Leu Phe Leu Tyr Gln Gly Leu Leu Gln Ala
            210                 215                 220

Leu Glu Gly Ile Ser Pro Glu Leu Gly Pro Thr Leu Asp Thr Leu Gln
225                 230                 235                 240

Leu Asp Val Ala Asp Phe Ala Thr Thr Ile Trp Gln Gln Met Glu Glu
                245                 250                 255

Leu Gly Met Ala Pro Ala Leu Gln Pro Thr Gln Gly Ala Met Pro Ala
            260                 265                 270

Phe Ala Ser Ala Phe Gln Arg Arg Ala Gly Gly Val Leu Val Ala Ser
            275                 280                 285

His Leu Gln Ser Phe Leu Glu Val Ser Tyr Arg Val Leu Arg His Leu
            290                 295                 300

Ala Gln Pro
305

(2) INFORMATION FOR SEQ ID NO:124:

(i) SEQUENCE CHARACTERISTICS:
        (A) LENGTH: 307 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:124:

Met Ala Asn Cys Ser Ile Met Ile Asp Glu Ile Ile His His Leu Lys
  1               5                  10                  15

Arg Pro Pro Asn Pro Leu Leu Asp Pro Asn Asn Leu Asn Ser Glu Asp
             20                  25                  30

Met Asp Ile Leu Met Glu Arg Asn Leu Arg Thr Pro Asn Leu Leu Ala
         35                  40                  45
```

```
Phe Val Arg Ala Val Lys His Leu Glu Asn Ala Ser Gly Ile Glu Ala
 50                  55                  60

Ile Leu Arg Asn Leu Gln Pro Cys Leu Pro Ser Ala Thr Ala Ala Pro
 65                  70                  75                  80

Ser Arg His Pro Ile Ile Ile Lys Ala Gly Asp Trp Gln Glu Phe Arg
                 85                  90                  95

Glu Lys Leu Thr Phe Tyr Leu Val Thr Leu Glu Gln Ala Gln Glu Gln
                100                 105                 110

Gln Tyr Val Glu Gly Gly Gly Ser Pro Gly Gly Ser Gly Gly
            115                 120                 125

Gly Ser Asn Met Ala Thr Pro Leu Gly Pro Ala Ser Ser Leu Pro Gln
130                 135                 140

Ser Phe Leu Leu Lys Ser Leu Glu Gln Val Arg Lys Ile Gln Gly Asp
145                 150                 155                 160

Gly Ala Ala Leu Gln Glu Lys Leu Cys Ala Thr Tyr Lys Leu Cys His
                165                 170                 175

Pro Glu Glu Leu Val Leu Leu Gly His Ser Leu Gly Ile Pro Trp Ala
                180                 185                 190

Pro Leu Ser Ser Cys Pro Ser Gln Ala Leu Gln Leu Ala Gly Cys Leu
                195                 200                 205

Ser Gln Leu His Ser Gly Leu Phe Leu Tyr Gln Gly Leu Leu Gln Ala
210                 215                 220

Leu Glu Gly Ile Ser Pro Glu Leu Gly Pro Thr Leu Asp Thr Leu Gln
225                 230                 235                 240

Leu Asp Val Ala Asp Phe Ala Thr Thr Ile Trp Gln Gln Met Glu Glu
                245                 250                 255

Leu Gly Met Ala Pro Ala Leu Gln Pro Thr Gln Gly Ala Met Pro Ala
                260                 265                 270

Phe Ala Ser Ala Phe Gln Arg Arg Ala Gly Gly Val Leu Val Ala Ser
                275                 280                 285

His Leu Gln Ser Phe Leu Glu Val Ser Tyr Arg Val Leu Arg His Leu
    290                 295                 300

Ala Gln Pro
305

(2) INFORMATION FOR SEQ ID NO:125:

(i) SEQUENCE CHARACTERISTICS:
        (A) LENGTH: 244 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:125:

Met Ala Asn Cys Ser Ile Met Ile Asp Glu Ile Ile His His Leu Lys
 1               5                  10                  15

Arg Pro Pro Asn Pro Leu Leu Asp Pro Asn Asn Leu Asn Ser Glu Asp
                20                  25                  30

Met Asp Ile Leu Met Glu Arg Asn Leu Arg Thr Pro Asn Leu Leu Ala
            35                  40                  45

Phe Val Arg Ala Val Lys His Leu Glu Asn Ala Ser Gly Ile Glu Ala
 50                  55                  60

Ile Leu Arg Asn Leu Gln Pro Cys Leu Pro Ser Ala Thr Ala Ala Pro
65                   70                  75                  80
```

```
Ser Arg His Pro Ile Ile Ile Lys Ala Gly Asp Trp Gln Glu Phe Arg
             85                  90                  95

Glu Lys Leu Thr Phe Tyr Leu Val Thr Leu Glu Gln Ala Gln Glu Gln
            100                 105                 110

Gln Tyr Val Ile Glu Gly Arg Ile Ser Pro Gly Gly Gly Ser Gly Gly
            115                 120                 125

Gly Ser Asn Met Ala Asn Cys Ser Ile Met Ile Asp Glu Ile Ile His
            130                 135                 140

His Leu Lys Arg Pro Pro Asn Pro Leu Leu Asp Pro Asn Asn Leu Asn
145                 150                 155                 160

Ser Glu Asp Met Asp Ile Leu Met Glu Arg Asn Leu Arg Thr Pro Asn
            165                 170                 175

Leu Leu Ala Phe Val Arg Ala Val Lys His Leu Glu Asn Ala Ser Gly
            180                 185                 190

Ile Glu Ala Ile Leu Arg Asn Leu Gln Pro Cys Leu Pro Ser Ala Thr
            195                 200                 205

Ala Ala Pro Ser Arg His Pro Ile Ile Ile Lys Ala Gly Asp Trp Gln
            210                 215                 220

Glu Phe Arg Glu Lys Leu Thr Phe Tyr Leu Val Thr Leu Glu Gln Ala
225                 230                 235                 240

Gln Glu Gln Gln (2) INFORMATION FOR SEQ ID NO:126:

(i) SEQUENCE CHARACTERISTICS:
        (A) LENGTH: 244 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:126:

Met Ala Asn Cys Ser Ile Met Ile Asp Glu Ile Ile His His Leu Lys
1               5                   10                  15

Arg Pro Pro Asn Pro Leu Leu Asp Pro Asn Asn Leu Asn Ser Glu Asp
            20                  25                  30

Met Asp Ile Leu Met Glu Arg Asn Leu Arg Thr Pro Asn Leu Leu Ala
            35                  40                  45

Phe Val Arg Ala Val Lys His Leu Glu Asn Ala Ser Gly Ile Glu Ala
            50                  55                  60

Ile Leu Arg Asn Leu Gln Pro Cys Leu Pro Ser Ala Thr Ala Ala Pro
65                  70                  75                  80

Ser Arg His Pro Ile Ile Ile Lys Ala Gly Asp Trp Gln Glu Phe Arg
             85                  90                  95

Glu Lys Leu Thr Phe Tyr Leu Val Thr Leu Glu Gln Ala Gln Glu Gln
            100                 105                 110

Gln Tyr Val Ile Glu Gly Lys Ile Ser Pro Gly Gly Gly Ser Gly Gly
            115                 120                 125

Gly Ser Asn Met Ala Asn Cys Ser Ile Met Ile Asp Glu Ile Ile His
            130                 135                 140

His Leu Lys Arg Pro Pro Asn Pro Leu Leu Asp Pro Asn Asn Leu Asn
145                 150                 155                 160

Ser Glu Asp Met Asp Ile Leu Met Glu Arg Asn Leu Arg Thr Pro Asn
            165                 170                 175
```

```
Leu Leu Ala Phe Val Arg Ala Val Lys His Leu Glu Asn Ala Ser Gly
            180                 185                 190

Ile Glu Ala Ile Leu Arg Asn Leu Gln Pro Cys Leu Pro Ser Ala Thr
            195                 200                 205

Ala Ala Pro Ser Arg His Pro Ile Ile Ile Lys Ala Gly Asp Trp Gln
            210                 215                 220

Glu Phe Arg Glu Lys Leu Thr Phe Tyr Leu Val Thr Leu Glu Gln Ala
225                 230                 235                 240

Gln Glu Gln Gln (2) INFORMATION FOR SEQ ID NO:127:

(i) SEQUENCE CHARACTERISTICS:
        (A) LENGTH: 244 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:127:

Met Ala Asn Cys Ser Ile Met Ile Asp Glu Ile Ile His His Leu Lys
1               5                   10                  15

Arg Pro Pro Asn Pro Leu Leu Asp Pro Asn Asn Leu Asn Ser Glu Asp
            20                  25                  30

Met Asp Ile Leu Met Glu Arg Asn Leu Arg Thr Pro Asn Leu Leu Ala
            35                  40                  45

Phe Val Arg Ala Val Lys His Leu Glu Asn Ala Ser Gly Ile Glu Ala
            50                  55                  60

Ile Leu Arg Asn Leu Gln Pro Cys Leu Pro Ser Ala Thr Ala Ala Pro
65                  70                  75                  80

Ser Arg His Pro Ile Ile Ile Lys Ala Gly Asp Trp Gln Glu Phe Arg
            85                  90                  95

Glu Lys Leu Thr Phe Tyr Leu Val Thr Leu Glu Gln Ala Gln Glu Gln
            100                 105                 110

Gln Tyr Val Glu Gly Gly Gly Ser Pro Gly Gly Gly Ser Gly Gly
            115                 120                 125

Gly Ser Asn Met Ala Asn Cys Ser Ile Met Ile Asp Glu Ile Ile His
            130                 135                 140

His Leu Lys Arg Pro Pro Asn Pro Leu Leu Asp Pro Asn Asn Leu Asn
145                 150                 155                 160

Ser Glu Asp Met Asp Ile Leu Met Glu Arg Asn Leu Arg Thr Pro Asn
            165                 170                 175

Leu Leu Ala Phe Val Arg Ala Val Lys His Leu Glu Asn Ala Ser Gly
            180                 185                 190

Ile Glu Ala Ile Leu Arg Asn Leu Gln Pro Cys Leu Pro Ser Ala Thr
            195                 200                 205

Ala Ala Pro Ser Arg His Pro Ile Ile Ile Lys Ala Gly Asp Trp Gln
            210                 215                 220

Glu Phe Arg Glu Lys Leu Thr Phe Tyr Leu Val Thr Leu Glu Gln Ala
225                 230                 235                 240

Gln Glu Gln Gln (2) INFORMATION FOR SEQ ID NO:128:

(i) SEQUENCE CHARACTERISTICS:
        (A) LENGTH: 322 amino acids
```

(B) TYPE: amino acid
            (C) STRANDEDNESS:
            (D) TOPOLOGY: linear (ii) MOLECULE TYPE: protein (xi) SEQUENCE DESCRIPTION: SEQ ID NO:128:

Met Ala Asn Cys Ser Ile Met Ile Asp Glu Ile Ile His His Leu Lys
1               5                   10                  15

Arg Pro Pro Asn Pro Leu Leu Asp Pro Asn Asn Leu Asn Ser Glu Asp
                20                  25                  30

Met Asp Ile Leu Met Glu Arg Asn Leu Arg Thr Pro Asn Leu Leu Ala
            35                  40                  45

Phe Val Arg Ala Val Lys His Leu Glu Asn Ala Ser Gly Ile Glu Ala
    50                  55                  60

Ile Leu Arg Asn Leu Gln Pro Cys Leu Pro Ser Ala Thr Ala Ala Pro
65                  70                  75                  80

Ser Arg His Pro Ile Ile Ile Lys Ala Gly Asp Trp Gln Glu Phe Arg
                85                  90                  95

Glu Lys Leu Thr Phe Tyr Leu Val Thr Leu Glu Gln Ala Gln Glu Gln
            100                 105                 110

Gln Tyr Val Ile Glu Gly Arg Ile Ser Pro Gly Glu Pro Ser Gly Pro
        115                 120                 125

Ile Ser Thr Ile Asn Pro Ser Pro Pro Ser Lys Glu Ser His Lys Ser
130                 135                 140

Pro Asn Met Ala Thr Pro Leu Gly Pro Ala Ser Ser Leu Pro Gln Ser
145                 150                 155                 160

Phe Leu Leu Lys Cys Leu Glu Gln Val Arg Lys Ile Gln Gly Asp Gly
                165                 170                 175

Ala Ala Leu Gln Glu Lys Leu Cys Ala Thr Tyr Lys Leu Cys His Pro
            180                 185                 190

Glu Glu Leu Val Leu Leu Gly His Ser Leu Gly Ile Pro Trp Ala Pro
        195                 200                 205

Leu Ser Ser Cys Pro Ser Gln Ala Leu Gln Leu Ala Gly Cys Leu Ser
210                 215                 220

Gln Leu His Ser Gly Leu Phe Leu Tyr Gln Gly Leu Leu Gln Ala Leu
225                 230                 235                 240

Glu Gly Ile Ser Pro Glu Leu Gly Pro Thr Leu Asp Thr Leu Gln Leu
                245                 250                 255

Asp Val Ala Asp Phe Ala Thr Thr Ile Trp Gln Gln Met Glu Glu Leu
            260                 265                 270

Gly Met Ala Pro Ala Leu Gln Pro Thr Gln Gly Ala Met Pro Ala Phe
        275                 280                 285

Ala Ser Ala Phe Gln Arg Arg Ala Gly Gly Val Leu Val Ala Ser His
290                 295                 300

Leu Gln Ser Phe Leu Glu Val Ser Tyr Arg Val Leu Arg His Leu Ala
305                 310                 315                 320

Gln Pro (2) INFORMATION FOR SEQ ID NO:129:

(i) SEQUENCE CHARACTERISTICS:
        (A) LENGTH: 322 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:129:

```
Met Ala Asn Cys Ser Ile Met Ile Asp Glu Ile Ile His His Leu Lys
1               5                   10                  15

Arg Pro Pro Asn Pro Leu Leu Asp Pro Asn Asn Leu Asn Ser Glu Asp
                20                  25                  30

Met Asp Ile Leu Met Glu Arg Asn Leu Arg Thr Pro Asn Leu Leu Ala
            35                  40                  45

Phe Val Arg Ala Val Lys His Leu Glu Asn Ala Ser Gly Ile Glu Ala
        50                  55                  60

Ile Leu Arg Asn Leu Gln Pro Cys Leu Pro Ser Ala Thr Ala Ala Pro
65                  70                  75                  80

Ser Arg His Pro Ile Ile Ile Lys Ala Gly Asp Trp Gln Glu Phe Arg
                85                  90                  95

Glu Lys Leu Thr Phe Tyr Leu Val Thr Leu Glu Gln Ala Gln Glu Gln
                100                 105                 110

Gln Tyr Val Ile Glu Gly Lys Ile Ser Pro Gly Glu Pro Ser Gly Pro
            115                 120                 125

Ile Ser Thr Ile Asn Pro Ser Pro Pro Ser Lys Glu Ser His Lys Ser
130                 135                 140

Pro Asn Met Ala Thr Pro Leu Gly Pro Ala Ser Ser Leu Pro Gln Ser
145                 150                 155                 160

Phe Leu Leu Lys Cys Leu Glu Gln Val Arg Lys Ile Gln Gly Asp Gly
                165                 170                 175

Ala Ala Leu Gln Glu Lys Leu Cys Ala Thr Tyr Lys Leu Cys His Pro
            180                 185                 190

Glu Glu Leu Val Leu Leu Gly His Ser Leu Gly Ile Pro Trp Ala Pro
                195                 200                 205

Leu Ser Ser Cys Pro Ser Gln Ala Leu Gln Leu Ala Gly Cys Leu Ser
210                 215                 220

Gln Leu His Ser Gly Leu Phe Leu Tyr Gln Gly Leu Leu Gln Ala Leu
225                 230                 235                 240

Glu Gly Ile Ser Pro Glu Leu Gly Pro Thr Leu Asp Thr Leu Gln Leu
                245                 250                 255

Asp Val Ala Asp Phe Ala Thr Thr Ile Trp Gln Gln Met Glu Glu Leu
            260                 265                 270

Gly Met Ala Pro Ala Leu Gln Pro Thr Gln Gly Ala Met Pro Ala Phe
            275                 280                 285

Ala Ser Ala Phe Gln Arg Arg Ala Gly Gly Val Leu Val Ala Ser His
        290                 295                 300

Leu Gln Ser Phe Leu Glu Val Ser Tyr Arg Val Leu Arg His Leu Ala
305                 310                 315                 320

Gln Pro
```

(2) INFORMATION FOR SEQ ID NO:130:

(i) SEQUENCE CHARACTERISTICS:
        (A) LENGTH: 322 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:130:

```
Met Ala Asn Cys Ser Ile Met Ile Asp Glu Ile Ile His His Leu Lys
1               5                   10                  15

Arg Pro Pro Asn Pro Leu Leu Asp Pro Asn Asn Leu Asn Ser Glu Asp
                20                  25                  30

Met Asp Ile Leu Met Glu Arg Asn Leu Arg Thr Pro Asn Leu Leu Ala
            35                  40                  45

Phe Val Arg Ala Val Lys His Leu Glu Asn Ala Ser Gly Ile Glu Ala
        50                  55                  60

Ile Leu Arg Asn Leu Gln Pro Cys Leu Pro Ser Ala Thr Ala Ala Pro
65                  70                  75                  80

Ser Arg His Pro Ile Ile Ile Lys Ala Gly Asp Trp Gln Glu Phe Arg
                85                  90                  95

Glu Lys Leu Thr Phe Tyr Leu Val Thr Leu Glu Gln Ala Gln Glu Gln
                100                 105                 110

Gln Tyr Val Glu Gly Gly Gly Ser Pro Gly Glu Pro Ser Gly Pro
                115                 120                 125

Ile Ser Thr Ile Asn Pro Ser Pro Pro Ser Lys Glu Ser His Lys Ser
    130                 135                 140

Pro Asn Met Ala Thr Pro Leu Gly Pro Ala Ser Ser Leu Pro Gln Ser
145                 150                 155                 160

Phe Leu Leu Lys Cys Leu Glu Gln Val Arg Lys Ile Gln Gly Asp Gly
                165                 170                 175

Ala Ala Leu Gln Glu Lys Leu Cys Ala Thr Tyr Lys Leu Cys His Pro
            180                 185                 190

Glu Glu Leu Val Leu Leu Gly His Ser Leu Gly Ile Pro Trp Ala Pro
        195                 200                 205

Leu Ser Ser Cys Pro Ser Gln Ala Leu Gln Leu Ala Gly Cys Leu Ser
    210                 215                 220

Gln Leu His Ser Gly Leu Phe Leu Tyr Gln Gly Leu Leu Gln Ala Leu
225                 230                 235                 240

Glu Gly Ile Ser Pro Glu Leu Gly Pro Thr Leu Asp Thr Leu Gln Leu
                245                 250                 255

Asp Val Ala Asp Phe Ala Thr Thr Ile Trp Gln Gln Met Glu Glu Leu
                260                 265                 270

Gly Met Ala Pro Ala Leu Gln Pro Thr Gln Gly Ala Met Pro Ala Phe
            275                 280                 285

Ala Ser Ala Phe Gln Arg Arg Ala Gly Gly Val Leu Val Ala Ser His
        290                 295                 300

Leu Gln Ser Phe Leu Glu Val Ser Tyr Arg Val Leu Arg His Leu Ala
305                 310                 315                 320

Gln Pro (2) INFORMATION FOR SEQ ID NO:131:

(i) SEQUENCE CHARACTERISTICS:
        (A) LENGTH: 259 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:131:

Met Ala Asn Cys Ser Ile Met Ile Asp Glu Ile Ile His His Leu Lys
1               5                   10                  15

Arg Pro Pro Asn Pro Leu Leu Asp Pro Asn Asn Leu Asn Ser Glu Asp
```

-continued

```
                20                  25                  30
Met Asp Ile Leu Met Glu Arg Asn Leu Arg Thr Pro Asn Leu Leu Ala
            35                  40                  45
Phe Val Arg Ala Val Lys His Leu Glu Asn Ala Ser Gly Ile Glu Ala
    50                  55                  60
Ile Leu Arg Asn Leu Gln Pro Cys Leu Pro Ser Ala Thr Ala Ala Pro
65                  70                  75                  80
Ser Arg His Pro Ile Ile Ile Lys Ala Gly Asp Trp Gln Glu Phe Arg
                85                  90                  95
Glu Lys Leu Thr Phe Tyr Leu Val Thr Leu Glu Gln Ala Gln Glu Gln
            100                 105                 110
Gln Tyr Val Ile Glu Gly Arg Ile Ser Pro Gly Glu Pro Ser Gly Pro
            115                 120                 125
Ile Ser Thr Ile Asn Pro Ser Pro Ser Lys Glu Ser His Lys Ser
    130                 135                 140
Pro Asn Met Ala Asn Cys Ser Ile Met Ile Asp Glu Ile Ile His His
145                 150                 155                 160
Leu Lys Arg Pro Pro Asn Pro Leu Leu Asp Pro Asn Asn Leu Asn Ser
                165                 170                 175
Glu Asp Met Asp Ile Leu Met Glu Arg Asn Leu Arg Thr Pro Asn Leu
            180                 185                 190
Leu Ala Phe Val Arg Ala Val Lys His Leu Glu Asn Ala Ser Gly Ile
        195                 200                 205
Glu Ala Ile Leu Arg Asn Leu Gln Pro Cys Leu Pro Ser Ala Thr Ala
    210                 215                 220
Ala Pro Ser Arg His Pro Ile Ile Ile Lys Ala Gly Asp Trp Gln Glu
225                 230                 235                 240
Phe Arg Glu Lys Leu Thr Phe Tyr Leu Val Thr Leu Glu Gln Ala Gln
                245                 250                 255
Glu Gln Gln (2) INFORMATION FOR SEQ ID NO:132:

(i) SEQUENCE CHARACTERISTICS:
        (A) LENGTH: 259 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:132:

Met Ala Asn Cys Ser Ile Met Ile Asp Glu Ile Ile His His Leu Lys
1               5                   10                  15
Arg Pro Pro Asn Pro Leu Leu Asp Pro Asn Asn Leu Asn Ser Glu Asp
            20                  25                  30
Met Asp Ile Leu Met Glu Arg Asn Leu Arg Thr Pro Asn Leu Leu Ala
            35                  40                  45
Phe Val Arg Ala Val Lys His Leu Glu Asn Ala Ser Gly Ile Glu Ala
    50                  55                  60
Ile Leu Arg Asn Leu Gln Pro Cys Leu Pro Ser Ala Thr Ala Ala Pro
65                  70                  75                  80
Ser Arg His Pro Ile Ile Ile Lys Ala Gly Asp Trp Gln Glu Phe Arg
                85                  90                  95
Glu Lys Leu Thr Phe Tyr Leu Val Thr Leu Glu Gln Ala Gln Glu Gln
            100                 105                 110
```

```
Gln Tyr Val Ile Glu Gly Lys Ile Ser Pro Gly Pro Ser Gly Pro
            115                 120                 125

Ile Ser Thr Ile Asn Pro Ser Pro Pro Ser Lys Glu Ser His Lys Ser
            130                 135                 140

Pro Asn Met Ala Asn Cys Ser Ile Met Ile Asp Glu Ile Ile His His
145                 150                 155                 160

Leu Lys Arg Pro Pro Asn Pro Leu Leu Asp Pro Asn Asn Leu Asn Ser
                165                 170                 175

Glu Asp Met Asp Ile Leu Met Glu Arg Asn Leu Arg Thr Pro Asn Leu
            180                 185                 190

Leu Ala Phe Val Arg Ala Val Lys His Leu Glu Asn Ala Ser Gly Ile
            195                 200                 205

Glu Ala Ile Leu Arg Asn Leu Gln Pro Cys Leu Pro Ser Ala Thr Ala
210                 215                 220

Ala Pro Ser Arg His Pro Ile Ile Ile Lys Ala Gly Asp Trp Gln Glu
225                 230                 235                 240

Phe Arg Glu Lys Leu Thr Phe Tyr Leu Val Thr Leu Glu Gln Ala Gln
                245                 250                 255

Glu Gln Gln (2) INFORMATION FOR SEQ ID NO:133:

(i) SEQUENCE CHARACTERISTICS:
        (A) LENGTH: 259 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:133:

Met Ala Asn Cys Ser Ile Met Ile Asp Glu Ile Ile His His Leu Lys
1               5                   10                  15

Arg Pro Pro Asn Pro Leu Leu Asp Pro Asn Asn Leu Asn Ser Glu Asp
            20                  25                  30

Met Asp Ile Leu Met Glu Arg Asn Leu Arg Thr Pro Asn Leu Leu Ala
        35                  40                  45

Phe Val Arg Ala Val Lys His Leu Glu Asn Ala Ser Gly Ile Glu Ala
    50                  55                  60

Ile Leu Arg Asn Leu Gln Pro Cys Leu Pro Ser Ala Thr Ala Ala Pro
65                  70                  75                  80

Ser Arg His Pro Ile Ile Ile Lys Ala Gly Asp Trp Gln Glu Phe Arg
            85                  90                  95

Glu Lys Leu Thr Phe Tyr Leu Val Thr Leu Glu Gln Ala Gln Glu Gln
                100                 105                 110

Gln Tyr Val Glu Gly Gly Gly Ser Pro Gly Glu Pro Ser Gly Pro
            115                 120                 125

Ile Ser Thr Ile Asn Pro Ser Pro Pro Ser Lys Glu Ser His Lys Ser
            130                 135                 140

Pro Asn Met Ala Asn Cys Ser Ile Met Ile Asp Glu Ile Ile His His
145                 150                 155                 160

Leu Lys Arg Pro Pro Asn Pro Leu Leu Asp Pro Asn Asn Leu Asn Ser
                165                 170                 175

Glu Asp Met Asp Ile Leu Met Glu Arg Asn Leu Arg Thr Pro Asn Leu
            180                 185                 190
```

```
Leu Ala Phe Val Arg Ala Val Lys His Leu Glu Asn Ala Ser Gly Ile
        195                 200                 205

Glu Ala Ile Leu Arg Asn Leu Gln Pro Cys Leu Pro Ser Ala Thr Ala
        210                 215                 220

Ala Pro Ser Arg His Pro Ile Ile Ile Lys Ala Gly Asp Trp Gln Glu
225                 230                 235                 240

Phe Arg Glu Lys Leu Thr Phe Tyr Leu Val Thr Leu Glu Gln Ala Gln
                245                 250                 255

Glu Gln Gln (2) INFORMATION FOR SEQ ID NO:134:

(i) SEQUENCE CHARACTERISTICS:
        (A) LENGTH: 307 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:134:

Met Ala Asn Cys Ser Ile Met Ile Asp Glu Ile Ile His His Leu Lys
1               5                   10                  15

Arg Pro Pro Ala Pro Leu Leu Asp Pro Asn Asn Leu Asn Asp Glu Asp
                20                  25                  30

Val Ser Ile Leu Met Asp Arg Asn Leu Arg Leu Pro Asn Leu Glu Ser
            35                  40                  45

Phe Val Arg Ala Val Lys Asn Leu Glu Asn Ala Ser Gly Ile Glu Ala
        50                  55                  60

Ile Leu Arg Asn Leu Gln Pro Cys Leu Pro Ser Ala Thr Ala Ala Pro
65                  70                  75                  80

Ser Arg His Pro Ile Ile Ile Lys Ala Gly Asp Trp Gln Glu Phe Arg
                85                  90                  95

Glu Lys Leu Thr Phe Tyr Leu Val Thr Leu Glu Gln Ala Gln Glu Gln
                100                 105                 110

Gln Tyr Val Ile Glu Gly Arg Ile Ser Pro Gly Gly Gly Ser Gly Gly
            115                 120                 125

Gly Ser Asn Met Ala Thr Pro Leu Gly Pro Ala Ser Ser Leu Pro Gln
    130                 135                 140

Ser Phe Leu Leu Lys Cys Leu Glu Gln Val Arg Lys Ile Gln Gly Asp
145                 150                 155                 160

Gly Ala Ala Leu Gln Glu Lys Leu Cys Ala Thr Tyr Lys Leu Cys His
                165                 170                 175

Pro Glu Glu Leu Val Leu Leu Gly His Ser Leu Gly Ile Pro Trp Ala
                180                 185                 190

Pro Leu Ser Ser Cys Pro Ser Gln Ala Leu Gln Leu Ala Gly Cys Leu
            195                 200                 205

Ser Gln Leu His Ser Gly Leu Phe Leu Tyr Gln Gly Leu Leu Gln Ala
        210                 215                 220

Leu Glu Gly Ile Ser Pro Glu Leu Gly Pro Thr Leu Asp Thr Leu Gln
225                 230                 235                 240

Leu Asp Val Ala Asp Phe Ala Thr Thr Ile Trp Gln Gln Met Glu Glu
                245                 250                 255

Leu Gly Met Ala Pro Ala Leu Gln Pro Thr Gln Gly Ala Met Pro Ala
                260                 265                 270

Phe Ala Ser Ala Phe Gln Arg Arg Ala Gly Gly Val Leu Val Ala Ser
```

```
                275                 280                 285
His Leu Gln Ser Phe Leu Glu Val Ser Tyr Arg Val Leu Arg His Leu
    290                 295                 300
Ala Gln Pro
305
```

(2) INFORMATION FOR SEQ ID NO:135:

(i) SEQUENCE CHARACTERISTICS:
        (A) LENGTH: 307 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:135:

```
Met Ala Asn Cys Ser Ile Met Ile Asp Glu Ile His His Leu Lys
1               5                   10                  15
Arg Pro Ala Pro Leu Leu Asp Pro Asn Asn Leu Asn Asp Glu Asp
                20                  25                  30
Val Ser Ile Leu Met Asp Arg Asn Leu Arg Leu Pro Asn Leu Glu Ser
                35                  40                  45
Phe Val Arg Ala Val Lys Asn Leu Glu Asn Ala Ser Gly Ile Glu Ala
    50                  55                  60
Ile Leu Arg Asn Leu Gln Pro Cys Leu Pro Ser Ala Thr Ala Ala Pro
65                  70                  75                  80
Ser Arg His Pro Ile Ile Ile Lys Ala Gly Asp Trp Gln Glu Phe Arg
                85                  90                  95
Glu Lys Leu Thr Phe Tyr Leu Val Thr Leu Glu Gln Ala Gln Glu Gln
                100                 105                 110
Gln Tyr Val Ile Glu Gly Arg Ile Ser Pro Gly Gly Gly Ser Gly Gly
                115                 120                 125
Gly Ser Asn Met Ala Thr Pro Leu Gly Pro Ala Ser Ser Leu Pro Gln
130                 135                 140
Ser Phe Leu Leu Lys Ser Leu Glu Gln Val Arg Lys Ile Gln Gly Asp
145                 150                 155                 160
Gly Ala Ala Leu Gln Glu Lys Leu Cys Ala Thr Tyr Lys Leu Cys His
                165                 170                 175
Pro Glu Glu Leu Val Leu Leu Gly His Ser Leu Gly Ile Pro Trp Ala
                180                 185                 190
Pro Leu Ser Ser Cys Pro Ser Gln Ala Leu Gln Leu Ala Gly Cys Leu
                195                 200                 205
Ser Gln Leu His Ser Gly Leu Phe Leu Tyr Gln Gly Leu Leu Gln Ala
    210                 215                 220
Leu Glu Gly Ile Ser Pro Glu Leu Gly Pro Thr Leu Asp Thr Leu Gln
225                 230                 235                 240
Leu Asp Val Ala Asp Phe Ala Thr Thr Ile Trp Gln Gln Met Glu Glu
                245                 250                 255
Leu Gly Met Ala Pro Ala Leu Gln Pro Thr Gln Gly Ala Met Pro Ala
                260                 265                 270
Phe Ala Ser Ala Phe Gln Arg Arg Ala Gly Gly Val Leu Val Ala Ser
                275                 280                 285
His Leu Gln Ser Phe Leu Glu Val Ser Tyr Arg Val Leu Arg His Leu
    290                 295                 300
Ala Gln Pro
```

(2) INFORMATION FOR SEQ ID NO:136:

(i) SEQUENCE CHARACTERISTICS:
        (A) LENGTH: 244 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:136:

```
Met Ala Asn Cys Ser Ile Met Ile Asp Glu Ile Ile His His Leu Lys
1               5                   10                  15

Arg Pro Pro Ala Pro Leu Leu Asp Pro Asn Asn Leu Asn Asp Glu Asp
            20                  25                  30

Val Ser Ile Leu Met Asp Arg Asn Leu Arg Leu Pro Asn Leu Glu Ser
        35                  40                  45

Phe Val Arg Ala Val Lys Asn Leu Glu Asn Ala Ser Gly Ile Glu Ala
    50                  55                  60

Ile Leu Arg Asn Leu Gln Pro Cys Leu Pro Ser Ala Thr Ala Ala Pro
65                  70                  75                  80

Ser Arg His Pro Ile Ile Ile Lys Ala Gly Asp Trp Gln Glu Phe Arg
                85                  90                  95

Glu Lys Leu Thr Phe Tyr Leu Val Thr Leu Glu Gln Ala Gln Glu Gln
            100                 105                 110

Gln Tyr Val Ile Glu Gly Arg Ile Ser Pro Gly Gly Ser Gly Gly Gly
        115                 120                 125

Gly Ser Asn Met Ala Asn Cys Ser Ile Met Ile Asp Glu Ile Ile His
    130                 135                 140

His Leu Lys Arg Pro Pro Ala Pro Leu Leu Asp Pro Asn Asn Leu Asn
145                 150                 155                 160

Asp Glu Asp Val Ser Ile Leu Met Asp Arg Asn Leu Arg Leu Pro Asn
                165                 170                 175

Leu Glu Ser Phe Val Arg Ala Val Lys Asn Leu Glu Asn Ala Ser Gly
            180                 185                 190

Ile Glu Ala Ile Leu Arg Asn Leu Gln Pro Cys Leu Pro Ser Ala Thr
        195                 200                 205

Ala Ala Pro Ser Arg His Pro Ile Ile Ile Lys Ala Gly Asp Trp Gln
    210                 215                 220

Glu Phe Arg Glu Lys Leu Thr Phe Tyr Leu Val Thr Leu Glu Gln Ala
225                 230                 235                 240

Gln Glu Gln Gln
```

(2) INFORMATION FOR SEQ ID NO:137:

(i) SEQUENCE CHARACTERISTICS:
        (A) LENGTH: 259 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:137:

```
Met Ala Asn Cys Ser Ile Met Ile Asp Glu Ile Ile His His Leu Lys
1               5                   10                  15

Arg Pro Pro Ala Pro Leu Leu Asp Pro Asn Asn Leu Asn Asp Glu Asp
```

```
            20                  25                  30
Val Ser Ile Leu Met Asp Arg Asn Leu Arg Leu Pro Asn Leu Glu Ser
         35                  40                  45
Phe Val Arg Ala Val Lys Asn Leu Glu Asn Ala Ser Gly Ile Glu Ala
 50                  55                  60
Ile Leu Arg Asn Leu Gln Pro Cys Leu Pro Ser Ala Thr Ala Ala Pro
65                  70                  75                  80
Ser Arg His Pro Ile Ile Ile Lys Ala Gly Asp Trp Gln Glu Phe Arg
                 85                  90                  95
Glu Lys Leu Thr Phe Tyr Leu Val Thr Leu Glu Gln Ala Gln Glu Gln
                100                 105                 110
Gln Tyr Val Ile Glu Gly Arg Ile Ser Pro Gly Glu Pro Ser Gly Pro
             115                 120                 125
Ile Ser Thr Ile Asn Pro Ser Pro Ser Lys Glu Ser His Lys Ser
    130                 135                 140
Pro Asn Met Ala Asn Cys Ser Ile Met Ile Asp Glu Ile Ile His His
145                 150                 155                 160
Leu Lys Arg Pro Pro Ala Pro Leu Leu Asp Pro Asn Asn Leu Asn Asp
                165                 170                 175
Glu Asp Val Ser Ile Leu Met Asp Arg Asn Leu Arg Leu Pro Asn Leu
            180                 185                 190
Glu Ser Phe Val Arg Ala Val Lys Asn Leu Glu Asn Ala Ser Gly Ile
        195                 200                 205
Glu Ala Ile Leu Arg Asn Leu Gln Pro Cys Leu Pro Ser Ala Thr Ala
    210                 215                 220
Ala Pro Ser Arg His Pro Ile Ile Ile Lys Ala Gly Asp Trp Gln Glu
225                 230                 235                 240
Phe Arg Glu Lys Leu Thr Phe Tyr Leu Val Thr Leu Glu Gln Ala Gln
                245                 250                 255
Glu Gln Gln (2) INFORMATION FOR SEQ ID NO:138:

(i) SEQUENCE CHARACTERISTICS:
        (A) LENGTH: 322 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:138:

Met Ala Asn Cys Ser Ile Met Ile Asp Glu Ile Ile His His Leu Lys
 1               5                  10                  15
Arg Pro Pro Ala Pro Leu Leu Asp Pro Asn Asn Leu Asn Asp Glu Asp
                20                  25                  30
Val Ser Ile Leu Met Asp Arg Asn Leu Arg Leu Pro Asn Leu Glu Ser
             35                  40                  45
Phe Val Arg Ala Val Lys Asn Leu Glu Asn Ala Ser Gly Ile Glu Ala
 50                  55                  60
Ile Leu Arg Asn Leu Gln Pro Cys Leu Pro Ser Ala Thr Ala Ala Pro
65                  70                  75                  80
Ser Arg His Pro Ile Ile Ile Lys Ala Gly Asp Trp Gln Glu Phe Arg
                 85                  90                  95
Glu Lys Leu Thr Phe Tyr Leu Val Thr Leu Glu Gln Ala Gln Glu Gln
                100                 105                 110
```

```
Gln Tyr Val Ile Glu Gly Arg Ile Ser Pro Gly Pro Ser Gly Pro
            115                 120                 125

Ile Ser Thr Ile Asn Pro Ser Pro Ser Lys Glu Ser His Lys Ser
        130                 135                 140

Pro Asn Met Ala Thr Pro Leu Gly Pro Ala Ser Ser Leu Pro Gln Ser
145                 150                 155                 160

Phe Leu Leu Lys Ser Leu Glu Gln Val Arg Lys Ile Gln Gly Asp Gly
                165                 170                 175

Ala Ala Leu Gln Glu Lys Leu Cys Ala Thr Tyr Lys Leu Cys His Pro
                180                 185                 190

Glu Glu Leu Val Leu Leu Gly His Ser Leu Gly Ile Pro Trp Ala Pro
                195                 200                 205

Leu Ser Ser Cys Pro Ser Gln Ala Leu Gln Leu Ala Gly Cys Leu Ser
210                 215                 220

Gln Leu His Ser Gly Leu Phe Leu Tyr Gln Gly Leu Leu Gln Ala Leu
225                 230                 235                 240

Glu Gly Ile Ser Pro Glu Leu Gly Pro Thr Leu Asp Thr Leu Gln Leu
                245                 250                 255

Asp Val Ala Asp Phe Ala Thr Thr Ile Trp Gln Gln Met Glu Glu Leu
                260                 265                 270

Gly Met Ala Pro Ala Leu Gln Pro Thr Gln Gly Ala Met Pro Ala Phe
            275                 280                 285

Ala Ser Ala Phe Gln Arg Arg Ala Gly Gly Val Leu Val Ala Ser His
            290                 295                 300

Leu Gln Ser Phe Leu Glu Val Ser Tyr Arg Val Leu Arg His Leu Ala
305                 310                 315                 320

Gln Pro (2) INFORMATION FOR SEQ ID NO:139:

(i) SEQUENCE CHARACTERISTICS:
        (A) LENGTH: 349 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:139:

Met Ala Asn Cys Ser Ile Met Ile Asp Glu Ile Ile His His Leu Lys
1               5                   10                  15

Arg Pro Pro Asn Pro Leu Leu Asp Pro Asn Asn Leu Asn Ser Glu Asp
                20                  25                  30

Met Asp Ile Leu Met Glu Arg Asn Leu Arg Thr Pro Asn Leu Leu Ala
            35                  40                  45

Phe Val Arg Ala Val Lys His Leu Glu Asn Ala Ser Gly Ile Glu Ala
        50                  55                  60

Ile Leu Arg Asn Leu Gln Pro Cys Leu Pro Ser Ala Thr Ala Ala Pro
65                  70                  75                  80

Ser Arg His Pro Ile Ile Ile Lys Ala Gly Asp Trp Gln Glu Phe Arg
                85                  90                  95

Glu Lys Leu Thr Phe Tyr Leu Val Thr Leu Glu Gln Ala Gln Glu Gln
                100                 105                 110

Gln Tyr Val Ile Glu Gly Arg Ile Ser Pro Gln Pro Pro Val Asn Ala
            115                 120                 125
```

```
Gly Gly Gly Ser Gly Gly Gly Ser Gly Gly Ser Glu Gly Gly
        130                 135                 140

Ser Glu Gly Gly Gly Ser Glu Gly Gly Ser Glu Gly Gly Gly Ser
145                 150                 155                 160

Gly Gly Gly Ser Gly Ser Gly Asp Phe Asp Tyr Glu Asn Met Ala Thr
                165                 170                 175

Pro Leu Gly Pro Ala Ser Ser Leu Pro Gln Ser Phe Leu Leu Lys Ser
            180                 185                 190

Leu Glu Gln Val Arg Lys Ile Gln Gly Asp Gly Ala Ala Leu Gln Glu
        195                 200                 205

Lys Leu Cys Ala Thr Tyr Lys Leu Cys His Pro Glu Glu Leu Val Leu
    210                 215                 220

Leu Gly His Ser Leu Gly Ile Pro Trp Ala Pro Leu Ser Ser Cys Pro
225                 230                 235                 240

Ser Gln Ala Leu Gln Leu Ala Gly Cys Leu Ser Gln Leu His Ser Gly
                245                 250                 255

Leu Phe Leu Tyr Gln Gly Leu Leu Gln Ala Leu Glu Gly Ile Ser Pro
            260                 265                 270

Glu Leu Gly Pro Thr Leu Asp Thr Leu Gln Leu Asp Val Ala Asp Phe
        275                 280                 285

Ala Thr Thr Ile Trp Gln Gln Met Glu Glu Leu Gly Met Ala Pro Ala
    290                 295                 300

Leu Gln Pro Thr Gln Gly Ala Met Pro Ala Phe Ala Ser Ala Phe Gln
305                 310                 315                 320

Arg Arg Ala Gly Gly Val Leu Val Ala Ser His Leu Gln Ser Phe Leu
                325                 330                 335

Glu Val Ser Tyr Arg Val Leu Arg His Leu Ala Gln Pro
            340                 345

(2) INFORMATION FOR SEQ ID NO:140:

(i) SEQUENCE CHARACTERISTICS:
        (A) LENGTH: 64 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA"

(xi) SEQUENCE DESCRIPTION: SEQ ID NO:140:

GGATCCACCA TGAGCCGCCT GCCCGTCCTG CTCCTGCTCC AACTCCTGGT CCGCCCCGCC      60

ATGG                                                                  64

(2) INFORMATION FOR SEQ ID NO:141:

(i) SEQUENCE CHARACTERISTICS:
        (A) LENGTH: 259 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:141:

Met Ala Asn Cys Ser Ile Met Ile Asp Glu Ile Ile His His Leu Lys
1               5                   10                  15

Arg Pro Pro Asn Pro Leu Leu Asp Pro Asn Asn Leu Asn Ser Glu Asp
            20                  25                  30
```

```
Met Asp Ile Leu Met Glu Arg Asn Leu Arg Thr Pro Asn Leu Leu Ala
        35                  40                  45

Phe Val Arg Ala Val Lys His Leu Glu Asn Ala Ser Gly Ile Glu Ala
    50                  55                  60

Ile Leu Arg Asn Leu Gln Pro Cys Leu Pro Ser Ala Thr Ala Ala Pro
65                  70                  75                  80

Ser Arg His Pro Ile Ile Ile Lys Ala Gly Asp Trp Gln Glu Phe Arg
                85                  90                  95

Glu Lys Leu Thr Phe Tyr Leu Val Thr Leu Glu Gln Ala Gln Glu Gln
            100                 105                 110

Gln Tyr Val Ile Glu Gly Arg Ile Ser Pro Gly Gly Ser Gly Gly
            115                 120                 125

Gly Ser Asn Met Ala Pro Ala Arg Ser Pro Ser Pro Ser Thr Gln Pro
    130                 135                 140

Trp Glu His Val Asn Ala Ile Gln Glu Ala Arg Arg Leu Leu Asn Leu
145                 150                 155                 160

Ser Arg Asp Thr Ala Ala Glu Met Asn Glu Thr Val Glu Val Ile Ser
                165                 170                 175

Glu Met Phe Asp Leu Gln Glu Pro Thr Cys Leu Gln Thr Arg Leu Glu
            180                 185                 190

Leu Tyr Lys Gln Gly Leu Arg Gly Ser Leu Thr Lys Leu Lys Gly Pro
        195                 200                 205

Leu Thr Met Met Ala Ser His Tyr Lys Gln His Cys Pro Pro Thr Pro
210                 215                 220

Glu Thr Ser Cys Ala Thr Gln Ile Ile Thr Phe Glu Ser Phe Lys Glu
225                 230                 235                 240

Asn Leu Lys Asp Phe Leu Leu Val Ile Pro Phe Asp Cys Trp Glu Pro
                245                 250                 255

Val Gln Glu (2) INFORMATION FOR SEQ ID NO:142:

(i) SEQUENCE CHARACTERISTICS:
        (A) LENGTH: 301 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:142:

Met Ala Asn Cys Ser Ile Met Ile Asp Glu Ile Ile His His Leu Lys
1               5                   10                  15

Arg Pro Pro Asn Pro Leu Leu Asp Pro Asn Asn Leu Asn Ser Glu Asp
            20                  25                  30

Met Asp Ile Leu Met Glu Arg Asn Leu Arg Thr Pro Asn Leu Leu Ala
        35                  40                  45

Phe Val Arg Ala Val Lys His Leu Glu Asn Ala Ser Gly Ile Glu Ala
    50                  55                  60

Ile Leu Arg Asn Leu Gln Pro Cys Leu Pro Ser Ala Thr Ala Ala Pro
65                  70                  75                  80

Ser Arg His Pro Ile Ile Ile Lys Ala Gly Asp Trp Gln Glu Phe Arg
                85                  90                  95

Glu Lys Leu Thr Phe Tyr Leu Val Thr Leu Glu Gln Ala Gln Glu Gln
            100                 105                 110

Gln Tyr Val Ile Glu Gly Arg Ile Ser Pro Gln Pro Pro Val Asn Ala
```

```
                115                 120                     125
Gly Gly Gly Ser Gly Gly Gly Ser Gly Gly Gly Ser Glu Gly Gly Gly
            130                 135                 140
Ser Glu Gly Gly Gly Ser Glu Gly Gly Gly Ser Glu Gly Gly Gly Ser
145                 150                     155                 160
Gly Gly Gly Ser Gly Ser Gly Asp Phe Asp Tyr Glu Asn Met Ala Pro
                165                 170                 175
Ala Arg Ser Pro Ser Pro Ser Thr Gln Pro Trp Glu His Val Asn Ala
            180                 185                 190
Ile Gln Glu Ala Arg Arg Leu Leu Asn Leu Ser Arg Asp Thr Ala Ala
            195                 200                 205
Glu Met Asn Glu Thr Val Glu Val Ile Ser Glu Met Phe Asp Leu Gln
    210                 215                 220
Glu Pro Thr Cys Leu Gln Thr Arg Leu Glu Leu Tyr Lys Gln Gly Leu
225                 230                 235                 240
Arg Gly Ser Leu Thr Lys Leu Lys Gly Pro Leu Thr Met Met Ala Ser
                245                 250                 255
His Tyr Lys Gln His Cys Pro Pro Thr Pro Glu Thr Ser Cys Ala Thr
            260                 265                 270
Gln Ile Ile Thr Phe Glu Ser Phe Lys Glu Asn Leu Lys Asp Phe Leu
            275                 280                 285
Leu Val Ile Pro Phe Asp Cys Trp Glu Pro Val Gln Glu
    290                 295                 300

(2) INFORMATION FOR SEQ ID NO:143:

(i) SEQUENCE CHARACTERISTICS:
        (A) LENGTH: 335 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:143:

Met Ala Asn Cys Ser Ile Met Ile Asp Glu Ile Ile His His Leu Lys
1               5                   10                  15
Arg Pro Pro Asn Pro Leu Leu Asp Pro Asn Asn Leu Asn Ser Glu Asp
            20                  25                  30
Met Asp Ile Leu Met Glu Arg Asn Leu Arg Thr Pro Asn Leu Leu Ala
        35                  40                  45
Phe Val Arg Ala Val Lys His Leu Glu Asn Ala Ser Gly Ile Glu Ala
    50                  55                  60
Ile Leu Arg Asn Leu Gln Pro Cys Leu Pro Ser Ala Thr Ala Ala Pro
65                  70                  75                  80
Ser Arg His Pro Ile Ile Ile Lys Ala Gly Asp Trp Gln Glu Phe Arg
                85                  90                  95
Glu Lys Leu Thr Phe Tyr Leu Val Thr Leu Glu Gln Ala Gln Glu Gln
            100                 105                 110
Gln Tyr Val Pro Val Asn Ala Gly Gly Ser Gly Gly Gly Ser Gly
            115                 120                 125
Gly Gly Ser Glu Gly Gly Gly Ser Glu Gly Gly Gly Ser Glu Gly Gly
            130                 135                 140
Gly Ser Glu Gly Gly Gly Ser Gly Gly Gly Ser Gly Ser Gly Asn Met
145                 150                 155                 160
Ala Thr Pro Leu Gly Pro Ala Ser Ser Leu Pro Gln Ser Phe Leu Leu
```

-continued

```
                165                 170                 175
Lys Cys Leu Glu Gln Val Arg Lys Ile Gln Gly Asp Gly Ala Ala Leu
                    180                 185                 190

Gln Glu Lys Leu Cys Ala Thr Tyr Lys Leu Cys His Pro Glu Glu Leu
        195                 200                 205

Val Leu Leu Gly His Ser Leu Gly Ile Pro Trp Ala Pro Leu Ser Ser
    210                 215                 220

Cys Pro Ser Gln Ala Leu Gln Leu Ala Gly Cys Leu Ser Gln Leu His
225                 230                 235                 240

Ser Gly Leu Phe Leu Tyr Gln Gly Leu Leu Gln Ala Leu Glu Gly Ile
                245                 250                 255

Ser Pro Glu Leu Gly Pro Thr Leu Asp Thr Leu Gln Leu Asp Val Ala
                    260                 265                 270

Asp Phe Ala Thr Thr Ile Trp Gln Gln Met Glu Glu Leu Gly Met Ala
            275                 280                 285

Pro Ala Leu Gln Pro Thr Gln Gly Ala Met Pro Ala Phe Ala Ser Ala
290                 295                 300

Phe Gln Arg Arg Ala Gly Gly Val Leu Val Ala Ser His Leu Gln Ser
305                 310                 315                 320

Phe Leu Glu Val Ser Tyr Arg Val Leu Arg His Leu Ala Gln Pro
                325                 330                 335
```

(2) INFORMATION FOR SEQ ID NO:144:

(i) SEQUENCE CHARACTERISTICS:
        (A) LENGTH: 274 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:144:

```
Met Ala Asn Cys Ser Ile Met Ile Asp Glu Ile Ile His His Leu Lys
1               5                   10                  15

Arg Pro Pro Asn Pro Leu Leu Asp Pro Asn Asn Leu Asn Ser Glu Asp
                20                  25                  30

Met Asp Ile Leu Met Glu Arg Asn Leu Arg Thr Pro Asn Leu Leu Ala
            35                  40                  45

Phe Val Arg Ala Val Lys His Leu Glu Asn Ala Ser Gly Ile Glu Ala
    50                  55                  60

Ile Leu Arg Asn Leu Gln Pro Cys Leu Pro Ser Ala Thr Ala Ala Pro
65                  70                  75                  80

Ser Arg His Pro Ile Ile Ile Lys Ala Gly Asp Trp Gln Glu Phe Arg
                85                  90                  95

Glu Lys Leu Thr Phe Tyr Leu Val Thr Leu Glu Gln Ala Gln Glu Gln
            100                 105                 110

Gln Tyr Val Ile Glu Gly Arg Ile Ser Pro Gly Glu Pro Ser Gly Pro
        115                 120                 125

Ile Ser Thr Ile Asn Pro Ser Pro Ser Lys Glu Ser His Lys Ser
    130                 135                 140

Pro Asn Met Ala Pro Ala Arg Ser Pro Ser Pro Ser Thr Gln Pro Trp
145                 150                 155                 160

Glu His Val Asn Ala Ile Gln Glu Ala Arg Arg Leu Leu Asn Leu Ser
                165                 170                 175

Arg Asp Thr Ala Ala Glu Met Asn Glu Thr Val Glu Val Ile Ser Glu
```

```
                    180                 185                 190
Met Phe Asp Leu Gln Glu Pro Thr Cys Leu Gln Thr Arg Leu Glu Leu
            195                 200                 205

Tyr Lys Gln Gly Leu Arg Gly Ser Leu Thr Lys Leu Lys Gly Pro Leu
        210                 215                 220

Thr Met Met Ala Ser His Tyr Lys Gln His Cys Pro Pro Thr Pro Glu
225                 230                 235                 240

Thr Ser Cys Ala Thr Gln Ile Ile Thr Phe Glu Ser Phe Lys Glu Asn
                245                 250                 255

Leu Lys Asp Phe Leu Leu Val Ile Pro Phe Asp Cys Trp Glu Pro Val
            260                 265                 270

Gln Glu
```

(2) INFORMATION FOR SEQ ID NO:145:

(i) SEQUENCE CHARACTERISTICS:
        (A) LENGTH: 317 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:145:

```
Met Ala Asn Cys Ser Ile Met Ile Asp Glu Ile Ile His His Leu Lys
1               5                  10                  15

Arg Pro Pro Asn Pro Leu Leu Asp Pro Asn Asn Leu Asn Ser Glu Asp
            20                  25                  30

Met Asp Ile Leu Met Glu Arg Asn Leu Arg Thr Pro Asn Leu Leu Ala
        35                  40                  45

Phe Val Arg Ala Val Lys His Leu Glu Asn Ala Ser Gly Ile Glu Ala
    50                  55                  60

Ile Leu Arg Asn Leu Gln Pro Cys Leu Pro Ser Ala Thr Ala Ala Pro
65                  70                  75                  80

Ser Arg His Pro Ile Ile Ile Lys Ala Gly Asp Trp Gln Glu Phe Arg
                85                  90                  95

Glu Lys Leu Thr Phe Tyr Leu Val Thr Leu Glu Gln Ala Gln Glu Gln
            100                 105                 110

Gln Tyr Val Ile Glu Gly Arg Ile Ser Pro Gly Gly Gly Ser Gly Gly
        115                 120                 125

Gly Ser Asn Met Ala Pro Val Pro Pro Gly Glu Asp Ser Lys Asp Val
    130                 135                 140

Ala Ala Pro His Arg Gln Pro Leu Thr Ser Ser Glu Arg Ile Asp Lys
145                 150                 155                 160

Gln Ile Arg Tyr Ile Leu Asp Gly Ile Ser Ala Leu Arg Lys Glu Thr
                165                 170                 175

Cys Asn Lys Ser Asn Met Cys Glu Ser Ser Lys Glu Ala Leu Ala Glu
            180                 185                 190

Asn Asn Leu Asn Leu Pro Lys Met Ala Glu Lys Asp Gly Cys Phe Gln
        195                 200                 205

Ser Gly Phe Asn Glu Glu Thr Cys Leu Val Lys Ile Ile Thr Gly Leu
    210                 215                 220

Leu Glu Phe Glu Val Tyr Leu Glu Tyr Leu Gln Asn Arg Phe Glu Ser
225                 230                 235                 240

Ser Glu Glu Gln Ala Arg Ala Val Gln Met Ser Thr Lys Val Leu Ile
                245                 250                 255
```

```
Gln Phe Leu Gln Lys Lys Ala Lys Asn Leu Asp Ala Ile Thr Thr Pro
                260                 265                 270

Asp Pro Thr Thr Asn Ala Ser Leu Leu Thr Lys Leu Gln Ala Gln Asn
        275                 280                 285

Gln Trp Leu Gln Asp Met Thr Thr His Leu Ile Leu Arg Ser Phe Lys
        290                 295                 300

Glu Phe Leu Gln Ser Ser Leu Arg Ala Leu Arg Gln Met
305                 310                 315
```

(2) INFORMATION FOR SEQ ID NO:146:

(i) SEQUENCE CHARACTERISTICS:
        (A) LENGTH: 307 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:146:

```
Met Ala Thr Pro Leu Gly Pro Ala Ser Ser Leu Pro Gln Ser Phe Leu
1               5                   10                  15

Leu Lys Cys Leu Glu Gln Val Arg Lys Ile Gln Gly Asp Gly Ala Ala
                20                  25                  30

Leu Gln Glu Lys Leu Cys Ala Thr Tyr Lys Leu Cys His Pro Glu Glu
            35                  40                  45

Leu Val Leu Leu Gly His Ser Leu Gly Ile Pro Trp Ala Pro Leu Ser
        50                  55                  60

Ser Cys Pro Ser Gln Ala Leu Gln Leu Ala Gly Cys Leu Ser Gln Leu
65                  70                  75                  80

His Ser Gly Leu Phe Leu Tyr Gln Gly Leu Leu Gln Ala Leu Glu Gly
                85                  90                  95

Ile Ser Pro Glu Leu Gly Pro Thr Leu Asp Thr Leu Gln Leu Asp Val
                100                 105                 110

Ala Asp Phe Ala Thr Thr Ile Trp Gln Gln Met Glu Glu Leu Gly Met
            115                 120                 125

Ala Pro Ala Leu Gln Pro Thr Gln Gly Ala Met Pro Ala Phe Ala Ser
130                 135                 140

Ala Phe Gln Arg Arg Ala Gly Gly Val Leu Val Ala Ser His Leu Gln
145                 150                 155                 160

Ser Phe Leu Glu Val Ser Tyr Arg Val Leu Arg His Leu Ala Gln Pro
                165                 170                 175

Tyr Val Ile Glu Gly Arg Ile Ser Pro Gly Gly Gly Ser Gly Gly Gly
            180                 185                 190

Ser Asn Met Ala Asn Cys Ser Ile Met Ile Asp Glu Ile Ile His His
        195                 200                 205

Leu Lys Arg Pro Pro Asn Pro Leu Leu Asp Pro Asn Asn Leu Asn Ser
210                 215                 220

Glu Asp Met Asp Ile Leu Met Glu Arg Asn Leu Arg Thr Pro Asn Leu
225                 230                 235                 240

Leu Ala Phe Val Arg Ala Val Lys His Leu Glu Asn Ala Ser Gly Ile
                245                 250                 255

Glu Ala Ile Leu Arg Asn Leu Gln Pro Cys Leu Pro Ser Ala Thr Ala
            260                 265                 270

Ala Pro Ser Arg His Pro Ile Ile Lys Ala Gly Asp Trp Gln Glu
        275                 280                 285
```

```
Phe Arg Glu Lys Leu Thr Phe Tyr Leu Val Thr Leu Glu Gln Ala Gln
    290                 295                 300

Glu Gln Gln
305

(2) INFORMATION FOR SEQ ID NO:147:

(i) SEQUENCE CHARACTERISTICS:
        (A) LENGTH: 307 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:147:

Met Ala Thr Pro Leu Gly Pro Ala Ser Ser Leu Pro Gln Ser Phe Leu
1               5                   10                  15

Leu Lys Cys Leu Glu Gln Val Arg Lys Ile Gln Gly Asp Gly Ala Ala
            20                  25                  30

Leu Gln Glu Lys Leu Cys Ala Thr Tyr Lys Leu Cys His Pro Glu Glu
        35                  40                  45

Leu Val Leu Leu Gly His Ser Leu Gly Ile Pro Trp Ala Pro Leu Ser
    50                  55                  60

Ser Cys Pro Ser Gln Ala Leu Gln Leu Ala Gly Cys Leu Ser Gln Leu
65                  70                  75                  80

His Ser Gly Leu Phe Leu Tyr Gln Gly Leu Leu Gln Ala Leu Glu Gly
                85                  90                  95

Ile Ser Pro Glu Leu Gly Pro Thr Leu Asp Thr Leu Gln Leu Asp Val
            100                 105                 110

Ala Asp Phe Ala Thr Thr Ile Trp Gln Gln Met Glu Glu Leu Gly Met
        115                 120                 125

Ala Pro Ala Leu Gln Pro Thr Gln Gly Ala Met Pro Ala Phe Ala Ser
    130                 135                 140

Ala Phe Gln Arg Arg Ala Gly Gly Val Leu Val Ala Ser His Leu Gln
145                 150                 155                 160

Ser Phe Leu Glu Val Ser Tyr Arg Val Leu Arg His Leu Ala Gln Pro
                165                 170                 175

Tyr Val Ile Glu Gly Arg Ile Ser Pro Gly Gly Gly Ser Gly Gly Gly
            180                 185                 190

Ser Asn Met Ala Asn Cys Ser Ile Met Ile Asp Glu Ile Ile His His
        195                 200                 205

Leu Lys Arg Pro Pro Ala Pro Leu Leu Asp Pro Asn Asn Leu Asn Asp
    210                 215                 220

Glu Asp Val Ser Ile Leu Met Asp Arg Asn Leu Arg Leu Pro Asn Leu
225                 230                 235                 240

Glu Ser Phe Val Arg Ala Val Lys Asn Leu Glu Asn Ala Ser Gly Ile
                245                 250                 255

Glu Ala Ile Leu Arg Asn Leu Gln Pro Cys Leu Pro Ser Ala Thr Ala
            260                 265                 270

Ala Pro Ser Arg His Pro Ile Ile Ile Lys Ala Gly Asp Trp Gln Glu
        275                 280                 285

Phe Arg Glu Lys Leu Thr Phe Tyr Leu Val Thr Leu Glu Gln Ala Gln
    290                 295                 300

Glu Gln Gln
305
```

(2) INFORMATION FOR SEQ ID NO:148:

(i) SEQUENCE CHARACTERISTICS:
        (A) LENGTH: 337 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:148:

```
Met Ala Thr Pro Leu Gly Pro Ala Ser Ser Leu Pro Gln Ser Phe Leu
 1               5                  10                  15

Leu Lys Cys Leu Glu Gln Val Arg Lys Ile Gln Gly Asp Gly Ala Ala
            20                  25                  30

Leu Gln Glu Lys Leu Cys Ala Thr Tyr Lys Leu Cys His Pro Glu Glu
        35                  40                  45

Leu Val Leu Leu Gly His Ser Leu Gly Ile Pro Trp Ala Pro Leu Ser
    50                  55                  60

Ser Cys Pro Ser Gln Ala Leu Gln Leu Ala Gly Cys Leu Ser Gln Leu
65                  70                  75                  80

His Ser Gly Leu Phe Leu Tyr Gln Gly Leu Leu Gln Ala Leu Glu Gly
                85                  90                  95

Ile Ser Pro Glu Leu Gly Pro Thr Leu Asp Thr Leu Gln Leu Asp Val
            100                 105                 110

Ala Asp Phe Ala Thr Thr Ile Trp Gln Gln Met Glu Glu Leu Gly Met
        115                 120                 125

Ala Pro Ala Leu Gln Pro Thr Gln Gly Ala Met Pro Ala Phe Ala Ser
    130                 135                 140

Ala Phe Gln Arg Arg Ala Gly Gly Val Leu Val Ala Ser His Leu Gln
145                 150                 155                 160

Ser Phe Leu Glu Val Ser Tyr Arg Val Leu Arg His Leu Ala Gln Pro
                165                 170                 175

Tyr Val Pro Gln Pro Pro Val Asn Ala Gly Gly Gly Ser Gly Gly Gly
            180                 185                 190

Ser Gly Gly Gly Ser Glu Gly Gly Ser Glu Gly Gly Ser Glu
        195                 200                 205

Gly Gly Gly Ser Glu Gly Gly Ser Gly Gly Ser Gly Ser Gly
    210                 215                 220

Asp Phe Asp Tyr Glu Asn Met Ala Asn Cys Ser Ile Met Ile Asp Glu
225                 230                 235                 240

Ile Ile His His Leu Lys Arg Pro Pro Ala Pro Leu Leu Asp Pro Asn
                245                 250                 255

Asn Leu Asn Asp Glu Asp Val Ser Ile Leu Met Asp Arg Asn Leu Arg
            260                 265                 270

Leu Val Arg Ala Val Lys Asn Leu Glu Asn Ala Ser Gly Ile Glu Ala
        275                 280                 285

Ile Leu Arg Asn Leu Gln Pro Cys Leu Pro Ser Ala Thr Ala Ala Pro
    290                 295                 300

Ser Arg His Pro Ile Ile Ile Lys Ala Gly Asp Trp Gln Glu Phe Arg
305                 310                 315                 320

Glu Lys Leu Thr Phe Tyr Leu Val Thr Leu Glu Gln Ala Gln Glu Gln
                325                 330                 335

Gln
```

(2) INFORMATION FOR SEQ ID NO:149:

(i) SEQUENCE CHARACTERISTICS:
        (A) LENGTH: 322 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:149:

```
Met Ala Thr Pro Leu Gly Pro Ala Ser Ser Leu Pro Gln Ser Phe Leu
 1               5                  10                  15

Leu Lys Cys Leu Glu Gln Val Arg Lys Ile Gln Gly Asp Gly Ala Ala
            20                  25                  30

Leu Gln Glu Lys Leu Cys Ala Thr Tyr Lys Leu Cys His Pro Glu Glu
        35                  40                  45

Leu Val Leu Leu Gly His Ser Leu Gly Ile Pro Trp Ala Pro Leu Ser
    50                  55                  60

Ser Cys Pro Ser Gln Ala Leu Gln Leu Ala Gly Cys Leu Ser Gln Leu
65                  70                  75                  80

His Ser Gly Leu Phe Leu Tyr Gln Gly Leu Leu Gln Ala Leu Glu Gly
                85                  90                  95

Ile Ser Pro Glu Leu Gly Pro Thr Leu Asp Thr Leu Gln Leu Asp Val
            100                 105                 110

Ala Asp Phe Ala Thr Thr Ile Trp Gln Gln Met Glu Glu Leu Gly Met
        115                 120                 125

Ala Pro Ala Leu Gln Pro Thr Gln Gly Ala Met Pro Ala Phe Ala Ser
    130                 135                 140

Ala Phe Gln Arg Arg Ala Gly Gly Val Leu Val Ala Ser His Leu Gln
145                 150                 155                 160

Ser Phe Leu Glu Val Ser Tyr Arg Val Leu Arg His Leu Ala Gln Pro
                165                 170                 175

Tyr Val Ile Glu Gly Arg Ile Ser Pro Gly Glu Pro Ser Gly Pro Ile
            180                 185                 190

Ser Thr Ile Asn Pro Ser Pro Pro Ser Lys Glu Ser His Lys Ser Pro
        195                 200                 205

Asn Met Ala Asn Cys Ser Ile Met Ile Asp Glu Ile Ile His His Leu
    210                 215                 220

Lys Arg Pro Pro Ala Pro Leu Leu Asp Pro Asn Asn Leu Asn Asp Glu
225                 230                 235                 240

Asp Val Ser Ile Leu Met Asp Arg Asn Leu Arg Leu Pro Asn Leu Glu
                245                 250                 255

Ser Phe Val Arg Ala Val Lys Asn Leu Glu Asn Ala Ser Gly Ile Glu
            260                 265                 270

Ala Ile Leu Arg Asn Leu Gln Pro Cys Leu Pro Ser Ala Thr Ala Ala
        275                 280                 285

Pro Ser Arg His Pro Ile Ile Ile Lys Ala Gly Asp Trp Gln Glu Phe
    290                 295                 300

Arg Glu Lys Leu Thr Phe Tyr Leu Val Thr Leu Glu Gln Ala Gln Glu
305                 310                 315                 320

Gln Gln
```

(2) INFORMATION FOR SEQ ID NO:150:

(i) SEQUENCE CHARACTERISTICS:

(A) LENGTH: 322 amino acids
    (B) TYPE: amino acid
    (C) STRANDEDNESS:
    (D) TOPOLOGY: linear (ii) MOLECULE TYPE: protein (xi) SEQUENCE DESCRIPTION: SEQ ID NO:150:

Met Ala Thr Pro Leu Gly Pro Ala Ser Ser Leu Pro Gln Ser Phe Leu
1               5                   10                  15

Leu Lys Cys Leu Glu Gln Val Arg Lys Ile Gln Gly Asp Gly Ala Ala
            20                  25                  30

Leu Gln Glu Lys Leu Cys Ala Thr Tyr Lys Leu Cys His Pro Glu Glu
            35                  40                  45

Leu Val Leu Leu Gly His Ser Leu Gly Ile Pro Trp Ala Pro Leu Ser
    50                  55                  60

Ser Cys Pro Ser Gln Ala Leu Gln Leu Ala Gly Cys Leu Ser Gln Leu
65                  70                  75                  80

His Ser Gly Leu Phe Leu Tyr Gln Gly Leu Leu Gln Ala Leu Glu Gly
                85                  90                  95

Ile Ser Pro Glu Leu Gly Pro Thr Leu Asp Thr Leu Gln Leu Asp Val
            100                 105                 110

Ala Asp Phe Ala Thr Thr Ile Trp Gln Gln Met Glu Glu Leu Gly Met
            115                 120                 125

Ala Pro Ala Leu Gln Pro Thr Gln Gly Ala Met Pro Ala Phe Ala Ser
130                 135                 140

Ala Phe Gln Arg Arg Ala Gly Gly Val Leu Val Ala Ser His Leu Gln
145                 150                 155                 160

Ser Phe Leu Glu Val Ser Tyr Arg Val Leu Arg His Leu Ala Gln Pro
                165                 170                 175

Tyr Val Ile Glu Gly Arg Ile Ser Pro Gly Glu Pro Ser Gly Pro Ile
            180                 185                 190

Ser Thr Ile Asn Pro Ser Pro Pro Ser Lys Glu Ser His Lys Ser Pro
            195                 200                 205

Asn Met Ala Asn Cys Ser Ile Met Ile Asp Glu Ile Ile His His Leu
210                 215                 220

Lys Arg Pro Pro Asn Pro Leu Leu Asp Pro Asn Asn Leu Asn Ser Glu
225                 230                 235                 240

Asp Met Asp Ile Leu Met Glu Arg Asn Leu Arg Thr Pro Asn Leu Leu
                245                 250                 255

Ala Phe Val Arg Ala Val Lys His Leu Glu Asn Ala Ser Gly Ile Glu
            260                 265                 270

Ala Ile Leu Arg Asn Leu Gln Pro Cys Leu Pro Ser Ala Thr Ala Ala
            275                 280                 285

Pro Ser Arg His Pro Ile Ile Ile Lys Ala Gly Asp Trp Gln Glu Phe
    290                 295                 300

Arg Glu Lys Leu Thr Phe Tyr Leu Val Thr Leu Glu Gln Ala Gln Glu
305                 310                 315                 320

Gln Gln (2) INFORMATION FOR SEQ ID NO:151:

(i) SEQUENCE CHARACTERISTICS:
    (A) LENGTH: 349 amino acids
    (B) TYPE: amino acid
    (C) STRANDEDNESS:
    (D) TOPOLOGY: linear (ii) MOLECULE TYPE: protein (xi) SEQUENCE DESCRIPTION: SEQ ID NO:151:

| Met | Ala | Thr | Pro | Leu | Gly | Pro | Ala | Ser | Ser | Leu | Pro | Gln | Ser | Phe | Leu |
|---|---|---|---|---|---|---|---|---|---|---|---|---|---|---|---|
| 1 | | | | 5 | | | | | 10 | | | | | 15 | |

| Leu | Lys | Cys | Leu | Glu | Gln | Val | Arg | Lys | Ile | Gln | Gly | Asp | Gly | Ala | Ala |
|---|---|---|---|---|---|---|---|---|---|---|---|---|---|---|---|
| | | | 20 | | | | | 25 | | | | | 30 | | |

| Leu | Gln | Glu | Lys | Leu | Cys | Ala | Thr | Tyr | Lys | Leu | Cys | His | Pro | Glu | Glu |
|---|---|---|---|---|---|---|---|---|---|---|---|---|---|---|---|
| | | 35 | | | | | 40 | | | | | 45 | | | |

| Leu | Val | Leu | Leu | Gly | His | Ser | Leu | Gly | Ile | Pro | Trp | Ala | Pro | Leu | Ser |
|---|---|---|---|---|---|---|---|---|---|---|---|---|---|---|---|
| | 50 | | | | | 55 | | | | | 60 | | | | |

| Ser | Cys | Pro | Ser | Gln | Ala | Leu | Gln | Leu | Ala | Gly | Cys | Leu | Ser | Gln | Leu |
|---|---|---|---|---|---|---|---|---|---|---|---|---|---|---|---|
| 65 | | | | 70 | | | | | 75 | | | | | 80 | |

| His | Ser | Gly | Leu | Phe | Leu | Tyr | Gln | Gly | Leu | Leu | Gln | Ala | Leu | Glu | Gly |
|---|---|---|---|---|---|---|---|---|---|---|---|---|---|---|---|
| | | | 85 | | | | | 90 | | | | | 95 | | |

| Ile | Ser | Pro | Glu | Leu | Gly | Pro | Thr | Leu | Asp | Thr | Leu | Gln | Leu | Asp | Val |
|---|---|---|---|---|---|---|---|---|---|---|---|---|---|---|---|
| | | | 100 | | | | | 105 | | | | | 110 | | |

| Ala | Asp | Phe | Ala | Thr | Thr | Ile | Trp | Gln | Gln | Met | Glu | Glu | Leu | Gly | Met |
|---|---|---|---|---|---|---|---|---|---|---|---|---|---|---|---|
| | | | 115 | | | | | 120 | | | | | 125 | | |

| Ala | Pro | Ala | Leu | Gln | Pro | Thr | Gln | Gly | Ala | Met | Pro | Ala | Phe | Ala | Ser |
|---|---|---|---|---|---|---|---|---|---|---|---|---|---|---|---|
| | 130 | | | | | 135 | | | | | 140 | | | | |

| Ala | Phe | Gln | Arg | Arg | Ala | Gly | Gly | Val | Leu | Val | Ala | Ser | His | Leu | Gln |
|---|---|---|---|---|---|---|---|---|---|---|---|---|---|---|---|
| 145 | | | | | 150 | | | | | 155 | | | | | 160 |

| Ser | Phe | Leu | Glu | Val | Ser | Tyr | Arg | Val | Leu | Arg | His | Leu | Ala | Gln | Pro |
|---|---|---|---|---|---|---|---|---|---|---|---|---|---|---|---|
| | | | | 165 | | | | | 170 | | | | | 175 | |

| Tyr | Val | Ile | Glu | Gly | Arg | Ile | Ser | Pro | Gln | Pro | Pro | Val | Asn | Ala | Gly |
|---|---|---|---|---|---|---|---|---|---|---|---|---|---|---|---|
| | | | | 180 | | | | | 185 | | | | | 190 | |

| Gly | Gly | Ser | Gly | Gly | Gly | Ser | Gly | Gly | Ser | Glu | Gly | Gly | Gly | Ser |
|---|---|---|---|---|---|---|---|---|---|---|---|---|---|---|---|
| | | 195 | | | | | 200 | | | | | 205 | | | |

| Glu | Gly | Gly | Gly | Ser | Glu | Gly | Gly | Ser | Glu | Gly | Gly | Ser | Gly |
|---|---|---|---|---|---|---|---|---|---|---|---|---|---|---|---|
| | 210 | | | | | 215 | | | | | 220 | | | | |

| Gly | Gly | Ser | Gly | Ser | Gly | Asp | Phe | Asp | Tyr | Glu | Asn | Met | Ala | Asn | Cys |
|---|---|---|---|---|---|---|---|---|---|---|---|---|---|---|---|
| 225 | | | | | 230 | | | | | 235 | | | | | 240 |

| Ser | Ile | Met | Ile | Asp | Glu | Ile | Ile | His | His | Leu | Lys | Arg | Pro | Pro | Asn |
|---|---|---|---|---|---|---|---|---|---|---|---|---|---|---|---|
| | | | | 245 | | | | | 250 | | | | | 255 | |

| Pro | Leu | Leu | Asp | Pro | Asn | Asn | Leu | Asn | Ser | Glu | Asp | Met | Asp | Ile | Leu |
|---|---|---|---|---|---|---|---|---|---|---|---|---|---|---|---|
| | | 260 | | | | | 265 | | | | | 270 | | | |

| Met | Glu | Arg | Asn | Leu | Arg | Thr | Pro | Asn | Leu | Leu | Ala | Phe | Val | Arg | Ala |
|---|---|---|---|---|---|---|---|---|---|---|---|---|---|---|---|
| | 275 | | | | | 280 | | | | | 285 | | | | |

| Val | Lys | His | Leu | Glu | Asn | Ala | Ser | Gly | Ile | Glu | Ala | Ile | Leu | Arg | Asn |
|---|---|---|---|---|---|---|---|---|---|---|---|---|---|---|---|
| | 290 | | | | | 295 | | | | | 300 | | | | |

| Leu | Gln | Pro | Cys | Leu | Pro | Ser | Ala | Thr | Ala | Ala | Pro | Ser | Arg | His | Pro |
|---|---|---|---|---|---|---|---|---|---|---|---|---|---|---|---|
| 305 | | | | | 310 | | | | | 315 | | | | | 320 |

| Ile | Ile | Ile | Lys | Ala | Gly | Asp | Trp | Gln | Glu | Phe | Arg | Glu | Lys | Leu | Thr |
|---|---|---|---|---|---|---|---|---|---|---|---|---|---|---|---|
| | | | 325 | | | | | 330 | | | | | 335 | | |

| Phe | Tyr | Leu | Val | Thr | Leu | Glu | Gln | Ala | Gln | Glu | Gln | Gln |
|---|---|---|---|---|---|---|---|---|---|---|---|---|
| | | | 340 | | | | | 345 | | | | |

(2) INFORMATION FOR SEQ ID NO:152:

(i) SEQUENCE CHARACTERISTICS:
        (A) LENGTH: 307 amino acids
        (B) TYPE: amino acid
        (C) STRANDEDNESS:
        (D) TOPOLOGY: linear

```
    (ii) MOLECULE TYPE: protein (xi) SEQUENCE DESCRIPTION: SEQ ID NO:152:

Met Ala Asn Cys Ser Ile Met Ile Asp Glu Ile Ile His His Leu Lys
1               5                   10                  15

Arg Pro Pro Ala Pro Leu Leu Asp Pro Asn Asn Leu Asn Asp Glu Asp
                20                  25                  30

Val Ser Ile Leu Met Asp Arg Asn Leu Arg Leu Pro Asn Leu Glu Ser
            35                  40                  45

Phe Val Arg Ala Val Lys Asn Leu Glu Asn Ala Ser Gly Ile Glu Ala
        50                  55                  60

Ile Leu Arg Asn Leu Gln Pro Cys Leu Pro Ser Ala Thr Ala Ala Pro
65                  70                  75                  80

Ser Arg His Pro Ile Ile Ile Lys Ala Gly Asp Trp Gln Glu Phe Arg
                85                  90                  95

Glu Lys Leu Thr Phe Tyr Leu Val Thr Leu Glu Gln Ala Gln Glu Gln
                100                 105                 110

Gln Tyr Val Glu Gly Gly Gly Ser Pro Gly Gly Ser Gly Gly
            115                 120                 125

Gly Ser Asn Met Ala Thr Pro Leu Gly Pro Ala Ser Ser Leu Pro Gln
130                 135                 140

Ser Phe Leu Leu Lys Ser Leu Glu Gln Val Arg Lys Ile Gln Gly Asp
145                 150                 155                 160

Gly Ala Ala Leu Gln Glu Lys Leu Cys Ala Thr Tyr Lys Leu Cys His
                165                 170                 175

Pro Glu Glu Leu Val Leu Leu Gly His Ser Leu Gly Ile Pro Trp Ala
                180                 185                 190

Pro Leu Ser Ser Cys Pro Ser Gln Ala Leu Gln Leu Ala Gly Cys Leu
                195                 200                 205

Ser Gln Leu His Ser Gly Leu Phe Leu Tyr Gln Gly Leu Leu Gln Ala
210                 215                 220

Leu Glu Gly Ile Ser Pro Glu Leu Gly Pro Thr Leu Asp Thr Leu Gln
225                 230                 235                 240

Leu Asp Val Ala Asp Phe Ala Thr Thr Ile Trp Gln Gln Met Glu Glu
                245                 250                 255

Leu Gly Met Ala Pro Ala Leu Gln Pro Thr Gln Gly Ala Met Pro Ala
                260                 265                 270

Phe Ala Ser Ala Phe Gln Arg Arg Ala Gly Gly Val Leu Val Ala Ser
                275                 280                 285

His Leu Gln Ser Phe Leu Glu Val Ser Tyr Arg Val Leu Arg His Leu
    290                 295                 300

Ala Gln Pro
305

(2) INFORMATION FOR SEQ ID NO:153:

(i) SEQUENCE CHARACTERISTICS:
        (A) LENGTH: 244 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:153:

Met Ala Asn Cys Ser Ile Met Ile Asp Glu Ile Ile His His Leu Lys
```

```
1               5                  10                 15
Arg Pro Pro Ala Pro Leu Leu Asp Pro Asn Asn Leu Asn Asp Glu Asp
             20                 25                 30
Val Ser Ile Leu Met Asp Arg Asn Leu Arg Leu Pro Asn Leu Glu Ser
             35                 40                 45
Phe Val Arg Ala Val Lys Asn Leu Glu Asn Ala Ser Gly Ile Glu Ala
 50                 55                 60
Ile Leu Arg Asn Leu Gln Pro Cys Leu Pro Ser Ala Thr Ala Ala Pro
 65                 70                 75                 80
Ser Arg His Pro Ile Ile Ile Lys Ala Gly Asp Trp Gln Glu Phe Arg
                 85                 90                 95
Glu Lys Leu Thr Phe Tyr Leu Val Thr Leu Glu Gln Ala Gln Glu Gln
                100                105                110
Gln Tyr Val Glu Gly Gly Gly Ser Pro Gly Gly Ser Gly Gly
                115                120                125
Gly Ser Asn Met Ala Asn Cys Ser Ile Met Ile Asp Glu Ile Ile His
            130                135                140
His Leu Lys Arg Pro Pro Ala Pro Leu Leu Asp Pro Asn Asn Leu Asn
145                150                155                160
Asp Glu Asp Val Ser Ile Leu Met Asp Arg Asn Leu Arg Leu Pro Asn
                165                170                175
Leu Glu Ser Phe Val Arg Ala Val Lys Asn Leu Glu Asn Ala Ser Gly
                180                185                190
Ile Glu Ala Ile Leu Arg Asn Leu Gln Pro Cys Leu Pro Ser Ala Thr
            195                200                205
Ala Ala Pro Ser Arg His Pro Ile Ile Ile Lys Ala Gly Asp Trp Gln
210                215                220
Glu Phe Arg Glu Lys Leu Thr Phe Tyr Leu Val Thr Leu Glu Gln Ala
225                230                235                240
Gln Glu Gln Gln (2) INFORMATION FOR SEQ ID NO:154:

(i) SEQUENCE CHARACTERISTICS:
        (A) LENGTH: 322 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:154:

Met Ala Asn Cys Ser Ile Met Ile Asp Glu Ile Ile His His Leu Lys
 1               5                 10                 15
Arg Pro Pro Ala Pro Leu Leu Asp Pro Asn Asn Leu Asn Asp Glu Asp
             20                 25                 30
Val Ser Ile Leu Met Asp Arg Asn Leu Arg Leu Pro Asn Leu Glu Ser
             35                 40                 45
Phe Val Arg Ala Val Lys Asn Leu Glu Asn Ala Ser Gly Ile Glu Ala
 50                 55                 60
Ile Leu Arg Asn Leu Gln Pro Cys Leu Pro Ser Ala Thr Ala Ala Pro
 65                 70                 75                 80
Ser Arg His Pro Ile Ile Ile Lys Ala Gly Asp Trp Gln Glu Phe Arg
                 85                 90                 95
Glu Lys Leu Thr Phe Tyr Leu Val Thr Leu Glu Gln Ala Gln Glu Gln
                100                105                110
```

-continued

Gln Tyr Val Ile Glu Gly Gly Gly Ser Pro Gly Glu Pro Ser Gly Pro
            115                 120                 125

Ile Ser Thr Ile Asn Pro Ser Pro Ser Lys Glu Ser His Lys Ser
        130                 135                 140

Pro Asn Met Ala Thr Pro Leu Gly Pro Ala Ser Ser Leu Pro Gln Ser
145                 150                 155                 160

Phe Leu Leu Lys Ser Leu Glu Gln Val Arg Lys Ile Gln Gly Asp Gly
                165                 170                 175

Ala Ala Leu Gln Glu Lys Leu Cys Ala Thr Tyr Lys Leu Cys His Pro
            180                 185                 190

Glu Glu Leu Val Leu Leu Gly His Ser Leu Gly Ile Pro Trp Ala Pro
            195                 200                 205

Leu Ser Ser Cys Pro Ser Gln Ala Leu Gln Leu Ala Gly Cys Leu Ser
210                 215                 220

Gln Leu His Ser Gly Leu Phe Leu Tyr Gln Gly Leu Leu Gln Ala Leu
225                 230                 235                 240

Glu Gly Ile Ser Pro Glu Leu Gly Pro Thr Leu Asp Thr Leu Gln Leu
                245                 250                 255

Asp Val Ala Asp Phe Ala Thr Thr Ile Trp Gln Gln Met Glu Glu Leu
            260                 265                 270

Gly Met Ala Pro Ala Leu Gln Pro Thr Gln Gly Ala Met Pro Ala Phe
        275                 280                 285

Ala Ser Ala Phe Gln Arg Arg Ala Gly Gly Val Leu Val Ala Ser His
            290                 295                 300

Leu Gln Ser Phe Leu Glu Val Ser Tyr Arg Val Leu Arg His Leu Ala
305                 310                 315                 320

Gln Pro (2) INFORMATION FOR SEQ ID NO:155:

(i) SEQUENCE CHARACTERISTICS:
        (A) LENGTH: 259 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:155:

Met Ala Asn Cys Ser Ile Met Ile Asp Glu Ile Ile His His Leu Lys
1               5                   10                  15

Arg Pro Pro Ala Pro Leu Leu Asp Pro Asn Asn Leu Asn Asp Glu Asp
            20                  25                  30

Val Ser Ile Leu Met Asp Arg Asn Leu Arg Leu Pro Asn Leu Glu Ser
        35                  40                  45

Phe Val Arg Ala Val Lys Asn Leu Glu Asn Ala Ser Gly Ile Glu Ala
    50                  55                  60

Ile Leu Arg Asn Leu Gln Pro Cys Leu Pro Ser Ala Thr Ala Ala Pro
65                  70                  75                  80

Ser Arg His Pro Ile Ile Ile Lys Ala Gly Asp Trp Gln Glu Phe Arg
                85                  90                  95

Glu Lys Leu Thr Phe Tyr Leu Val Thr Leu Glu Gln Ala Gln Glu Gln
            100                 105                 110

Gln Tyr Val Glu Gly Gly Gly Ser Pro Gly Glu Pro Ser Gly Pro
            115                 120                 125

-continued

```
Ile Ser Thr Ile Asn Pro Ser Pro Ser Lys Glu Ser His Lys Ser
        130                 135                 140

Pro Asn Met Ala Asn Cys Ser Ile Met Ile Asp Glu Ile Ile His His
145                 150                 155                 160

Leu Lys Arg Pro Pro Ala Pro Leu Leu Asp Pro Asn Asn Leu Asn Asp
                165                 170                 175

Glu Asp Val Ser Ile Leu Met Asp Arg Asn Leu Arg Leu Pro Asn Leu
            180                 185                 190

Glu Ser Phe Val Arg Ala Val Lys Asn Leu Glu Asn Ala Ser Gly Ile
        195                 200                 205

Glu Ala Ile Leu Arg Asn Leu Gln Pro Cys Leu Pro Ser Ala Thr Ala
    210                 215                 220

Ala Pro Ser Arg His Pro Ile Ile Ile Lys Ala Gly Asp Trp Gln Glu
225                 230                 235                 240

Phe Arg Glu Lys Leu Thr Phe Tyr Leu Val Thr Leu Glu Gln Ala Gln
                245                 250                 255

Glu Gln Gln
```

(2) INFORMATION FOR SEQ ID NO:156:

(i) SEQUENCE CHARACTERISTICS:
        (A) LENGTH: 322 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:156:

```
Met Ala Thr Pro Leu Gly Pro Ala Ser Ser Leu Pro Gln Ser Phe Leu
1               5                   10                  15

Leu Lys Cys Leu Glu Gln Val Arg Lys Ile Gln Gly Asp Gly Ala Ala
            20                  25                  30

Leu Gln Glu Lys Leu Cys Ala Thr Tyr Lys Leu Cys His Pro Glu Glu
        35                  40                  45

Leu Val Leu Leu Gly His Ser Leu Gly Ile Pro Trp Ala Pro Leu Ser
    50                  55                  60

Ser Cys Pro Ser Gln Ala Leu Gln Leu Ala Gly Cys Leu Ser Gly Leu
65                  70                  75                  80

His Ser Gly Leu Phe Leu Tyr Gln Gly Leu Leu Gln Ala Leu Glu Gly
                85                  90                  95

Ile Ser Pro Glu Leu Gly Pro Thr Leu Asp Thr Leu Gln Leu Asp Val
            100                 105                 110

Ala Asp Phe Ala Thr Thr Ile Trp Gln Gln Met Glu Glu Leu Gly Met
        115                 120                 125

Ala Pro Ala Leu Gln Pro Thr Gln Gly Ala Met Pro Ala Phe Ala Ser
    130                 135                 140

Ala Phe Gln Arg Arg Ala Gly Gly Val Leu Val Ala Ser His Leu Gln
145                 150                 155                 160

Ser Phe Leu Glu Val Ser Tyr Arg Val Leu Arg His Leu Ala Gln Pro
                165                 170                 175

Tyr Val Glu Gly Gly Gly Gly Ser Pro Gly Glu Pro Ser Gly Pro Ile
            180                 185                 190

Ser Thr Ile Asn Pro Ser Pro Ser Lys Glu Ser His Lys Ser Pro
        195                 200                 205

Asn Met Ala Asn Cys Ser Ile Met Ile Asp Glu Ile Ile His His Leu
```

-continued

```
            210                 215                 220
Lys Arg Pro Pro Ala Pro Leu Leu Asp Pro Asn Asn Leu Asn Asp Glu
225                 230                 235                 240

Asp Val Ser Ile Leu Met Asp Arg Asn Leu Arg Leu Pro Asn Leu Glu
                245                 250                 255

Ser Phe Val Arg Ala Val Lys Asn Leu Glu Asn Ala Ser Gly Ile Glu
                260                 265                 270

Ala Ile Leu Arg Asn Leu Gln Pro Cys Leu Pro Ser Ala Thr Ala Ala
                275                 280                 285

Pro Ser Arg His Pro Ile Ile Ile Lys Ala Gly Asp Trp Gln Glu Phe
            290                 295                 300

Arg Glu Lys Leu Thr Phe Tyr Leu Val Thr Leu Glu Gln Ala Gln Glu
305                 310                 315                 320

Gln Gln (2) INFORMATION FOR SEQ ID NO:157:

(i) SEQUENCE CHARACTERISTICS:
        (A) LENGTH: 322 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:157:

Met Ala Thr Pro Leu Gly Pro Ala Ser Ser Leu Pro Gln Ser Phe Leu
1               5                   10                  15

Leu Lys Ser Leu Glu Gln Val Arg Lys Ile Gln Gly Asp Gly Ala Ala
                20                  25                  30

Leu Gln Glu Lys Leu Cys Ala Thr Tyr Lys Leu Cys His Pro Glu Glu
            35                  40                  45

Leu Val Leu Leu Gly His Ser Leu Gly Ile Pro Trp Ala Pro Leu Ser
        50                  55                  60

Ser Cys Pro Ser Gln Ala Leu Gln Leu Ala Gly Cys Leu Ser Gly Leu
65                  70                  75                  80

His Ser Gly Leu Phe Leu Tyr Gln Gly Leu Leu Gln Ala Leu Glu Gly
                85                  90                  95

Ile Ser Pro Glu Leu Gly Pro Thr Leu Asp Thr Leu Gln Leu Asp Val
                100                 105                 110

Ala Asp Phe Ala Thr Thr Ile Trp Gln Gln Met Glu Glu Leu Gly Met
            115                 120                 125

Ala Pro Ala Leu Gln Pro Thr Gln Gly Ala Met Pro Ala Phe Ala Ser
            130                 135                 140

Ala Phe Gln Arg Arg Ala Gly Gly Val Leu Val Ala Ser His Leu Gln
145                 150                 155                 160

Ser Phe Leu Glu Val Ser Tyr Arg Val Leu Arg His Leu Ala Gln Pro
                165                 170                 175

Tyr Val Glu Gly Gly Gly Gly Ser Pro Gly Glu Pro Ser Gly Pro Ile
                180                 185                 190

Ser Thr Ile Asn Pro Ser Pro Ser Lys Glu Ser His Lys Ser Pro
            195                 200                 205

Asn Met Ala Asn Cys Ser Ile Met Ile Asp Glu Ile Ile His Leu
            210                 215                 220

Lys Arg Pro Pro Ala Pro Leu Leu Asp Pro Asn Asn Leu Asn Asp Glu
225                 230                 235                 240
```

```
Asp Val Ser Ile Leu Met Asp Arg Asn Leu Arg Leu Pro Asn Leu Glu
                245                 250                 255

Ser Phe Val Arg Ala Val Lys Asn Leu Glu Asn Ala Ser Gly Ile Glu
                260                 265                 270

Ala Ile Leu Arg Asn Leu Gln Pro Cys Leu Pro Ser Ala Thr Ala Ala
                275                 280                 285

Pro Ser Arg His Pro Ile Ile Ile Lys Ala Gly Asp Trp Gln Glu Phe
                290                 295                 300

Arg Glu Lys Leu Thr Phe Tyr Leu Val Thr Leu Glu Gln Ala Gln Glu
305                 310                 315                 320

Gln Gln (2) INFORMATION FOR SEQ ID NO:158:

(i) SEQUENCE CHARACTERISTICS:
        (A) LENGTH: 307 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:158:

Met Ala Thr Pro Leu Gly Pro Ala Ser Ser Leu Pro Gln Ser Phe Leu
1               5                   10                  15

Leu Lys Cys Leu Glu Gln Val Arg Lys Ile Gln Gly Asp Gly Ala Ala
                20                  25                  30

Leu Gln Glu Lys Leu Cys Ala Thr Tyr Lys Leu Cys His Pro Glu Glu
                35                  40                  45

Leu Val Leu Leu Gly His Ser Leu Gly Ile Pro Trp Ala Pro Leu Ser
            50                  55                  60

Ser Cys Pro Ser Gln Ala Leu Gln Leu Ala Gly Cys Leu Ser Gly Leu
65                  70                  75                  80

His Ser Gly Leu Phe Leu Tyr Gln Gly Leu Leu Gln Ala Leu Glu Gly
                85                  90                  95

Ile Ser Pro Glu Leu Gly Pro Thr Leu Asp Thr Leu Gln Leu Asp Val
                100                 105                 110

Ala Asp Phe Ala Thr Thr Ile Trp Gln Gln Met Glu Glu Leu Gly Met
                115                 120                 125

Ala Pro Ala Leu Gln Pro Thr Gln Gly Ala Met Pro Ala Phe Ala Ser
                130                 135                 140

Ala Phe Gln Arg Arg Ala Gly Gly Val Leu Val Ala Ser His Leu Gln
145                 150                 155                 160

Ser Phe Leu Glu Val Ser Tyr Arg Val Leu Arg His Leu Ala Gln Pro
                165                 170                 175

Tyr Val Glu Gly Gly Gly Ser Pro Gly Gly Ser Gly Gly Gly
                180                 185                 190

Ser Asn Met Ala Asn Cys Ser Ile Met Ile Asp Glu Ile Ile His His
                195                 200                 205

Leu Lys Arg Pro Pro Ala Pro Leu Leu Asp Pro Asn Asn Leu Asn Asp
                210                 215                 220

Glu Asp Val Ser Ile Leu Met Asp Arg Asn Leu Arg Leu Pro Asn Leu
225                 230                 235                 240

Glu Ser Phe Val Arg Ala Val Lys Asn Leu Glu Asn Ala Ser Gly Ile
                245                 250                 255
```

-continued

```
Glu Ala Ile Leu Arg Asn Leu Gln Pro Cys Leu Pro Ser Ala Thr Ala
            260                 265                 270

Ala Pro Ser Arg His Pro Ile Ile Ile Lys Ala Gly Asp Trp Gln Glu
            275                 280                 285

Phe Arg Glu Lys Leu Thr Phe Tyr Leu Val Thr Leu Glu Gln Ala Gln
290                 295                 300

Glu Gln Gln
305

(2) INFORMATION FOR SEQ ID NO:159:

(i) SEQUENCE CHARACTERISTICS:
        (A) LENGTH: 307 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:159:

Met Ala Thr Pro Leu Gly Pro Ala Ser Ser Leu Pro Gln Ser Phe Leu
1               5                   10                  15

Leu Lys Ser Leu Glu Gln Val Arg Lys Ile Gln Gly Asp Gly Ala Ala
            20                  25                  30

Leu Gln Glu Lys Leu Cys Ala Thr Tyr Lys Leu Cys His Pro Glu Glu
        35                  40                  45

Leu Val Leu Leu Gly His Ser Leu Gly Ile Pro Trp Ala Pro Leu Ser
    50                  55                  60

Ser Cys Pro Ser Gln Ala Leu Gln Leu Ala Gly Cys Leu Ser Gly Leu
65                  70                  75                  80

His Ser Gly Leu Phe Leu Tyr Gln Gly Leu Leu Gln Ala Leu Glu Gly
            85                  90                  95

Ile Ser Pro Glu Leu Gly Pro Thr Leu Asp Thr Leu Gln Leu Asp Val
            100                 105                 110

Ala Asp Phe Ala Thr Thr Ile Trp Gln Gln Met Glu Glu Leu Gly Met
        115                 120                 125

Ala Pro Ala Leu Gln Pro Thr Gln Gly Ala Met Pro Ala Phe Ala Ser
    130                 135                 140

Ala Phe Gln Arg Arg Ala Gly Gly Val Leu Val Ala Ser His Leu Gln
145                 150                 155                 160

Ser Phe Leu Glu Val Ser Tyr Arg Val Leu Arg His Leu Ala Gln Pro
                165                 170                 175

Tyr Val Glu Gly Gly Gly Ser Pro Gly Gly Ser Gly Gly Gly
            180                 185                 190

Ser Asn Met Ala Asn Cys Ser Ile Met Ile Asp Glu Ile Ile His His
            195                 200                 205

Leu Lys Arg Pro Pro Ala Pro Leu Leu Asp Pro Asn Asn Leu Asn Asp
        210                 215                 220

Glu Asp Val Ser Ile Leu Met Asp Arg Asn Leu Arg Leu Pro Asn Leu
225                 230                 235                 240

Glu Ser Phe Val Arg Ala Val Lys Asn Leu Glu Asn Ala Ser Gly Ile
                245                 250                 255

Glu Ala Ile Leu Arg Asn Leu Gln Pro Cys Leu Pro Ser Ala Thr Ala
            260                 265                 270

Ala Pro Ser Arg His Pro Ile Ile Ile Lys Ala Gly Asp Trp Gln Glu
            275                 280                 285
```

```
Phe Arg Glu Lys Leu Thr Phe Tyr Leu Val Thr Leu Glu Gln Ala Gln
    290                 295                 300

Glu Gln Gln
305
```

(2) INFORMATION FOR SEQ ID NO:160:

(i) SEQUENCE CHARACTERISTICS:
        (A) LENGTH: 128 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:160:

```
Met Ala Pro Ala Arg Ser Pro Ser Pro Ser Thr Gln Pro Trp Glu His
1                   5                   10                  15

Val Asn Ala Ile Gln Glu Ala Arg Arg Leu Leu Asn Leu Ser Arg Asp
                20                  25                  30

Thr Ala Ala Glu Met Asn Glu Thr Val Glu Val Ile Ser Glu Met Phe
            35                  40                  45

Asp Leu Gln Glu Pro Thr Cys Leu Gln Thr Arg Leu Glu Leu Tyr Lys
        50                  55                  60

Gln Gly Leu Arg Gly Ser Leu Thr Lys Leu Lys Gly Pro Leu Thr Met
65                  70                  75                  80

Met Ala Ser His Tyr Lys Gln His Cys Pro Pro Thr Pro Glu Thr Ser
                85                  90                  95

Cys Ala Thr Gln Ile Ile Thr Phe Glu Ser Phe Lys Glu Asn Leu Lys
            100                 105                 110

Asp Phe Leu Leu Val Ile Pro Phe Asp Cys Trp Glu Pro Val Gln Glu
        115                 120                 125
```

(2) INFORMATION FOR SEQ ID NO:161:

(i) SEQUENCE CHARACTERISTICS:
        (A) LENGTH: 176 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:161:

```
Met Ala Thr Pro Leu Gly Pro Ala Ser Ser Leu Pro Gln Ser Phe Leu
1                   5                   10                  15

Leu Lys Cys Leu Glu Gln Val Arg Lys Ile Gln Gly Asp Gly Ala Ala
                20                  25                  30

Leu Gln Glu Lys Leu Cys Ala Thr Tyr Lys Leu Cys His Pro Glu Glu
            35                  40                  45

Leu Val Leu Leu Gly His Ser Leu Gly Ile Pro Trp Ala Pro Leu Ser
        50                  55                  60

Ser Cys Pro Ser Gln Ala Leu Gln Leu Ala Gly Cys Leu Ser Gln Leu
65                  70                  75                  80

His Ser Gly Leu Phe Leu Tyr Gln Gly Leu Leu Gln Ala Leu Glu Gly
                85                  90                  95

Ile Ser Pro Glu Leu Gly Pro Thr Leu Asp Thr Leu Gln Leu Asp Val
            100                 105                 110

Ala Asp Phe Ala Thr Thr Ile Trp Gln Gln Met Glu Glu Leu Gly Met
        115                 120                 125
```

```
Ala Pro Ala Leu Gln Pro Thr Gln Gly Ala Met Pro Ala Phe Ala Ser
        130                 135                 140

Ala Phe Gln Arg Arg Ala Gly Gly Val Leu Val Ala Ser His Leu Gln
145                 150                 155                 160

Ser Phe Leu Glu Val Ser Tyr Arg Val Leu Arg His Leu Ala Gln Pro
                165                 170                 175
```

(2) INFORMATION FOR SEQ ID NO:162:

(i) SEQUENCE CHARACTERISTICS:
      (A) LENGTH: 176 amino acids
      (B) TYPE: amino acid
      (C) STRANDEDNESS:
      (D) TOPOLOGY: linear (ii) MOLECULE TYPE: protein (xi) SEQUENCE DESCRIPTION: SEQ ID NO:162:

```
Met Ala Thr Pro Leu Gly Pro Ala Ser Ser Leu Pro Gln Ser Phe Leu
1               5                   10                  15

Leu Lys Ser Leu Glu Gln Val Arg Lys Ile Gln Gly Asp Gly Ala Ala
                20                  25                  30

Leu Gln Glu Lys Leu Cys Ala Thr Tyr Lys Leu Cys His Pro Glu Glu
        35                  40                  45

Leu Val Leu Leu Gly His Ser Leu Gly Ile Pro Trp Ala Pro Leu Ser
50                  55                  60

Ser Cys Pro Ser Gln Ala Leu Gln Leu Ala Gly Cys Leu Ser Gln Leu
65                  70                  75                  80

His Ser Gly Leu Phe Leu Tyr Gln Gly Leu Leu Gln Ala Leu Glu Gly
                85                  90                  95

Ile Ser Pro Glu Leu Gly Pro Thr Leu Asp Thr Leu Gln Leu Asp Val
            100                 105                 110

Ala Asp Phe Ala Thr Thr Ile Trp Gln Gln Met Glu Glu Leu Gly Met
        115                 120                 125

Ala Pro Ala Leu Gln Pro Thr Gln Gly Ala Met Pro Ala Phe Ala Ser
        130                 135                 140

Ala Phe Gln Arg Arg Ala Gly Gly Val Leu Val Ala Ser His Leu Gln
145                 150                 155                 160

Ser Phe Leu Glu Val Ser Tyr Arg Val Leu Arg His Leu Ala Gln Pro
                165                 170                 175
```

(2) INFORMATION FOR SEQ ID NO:163:

(i) SEQUENCE CHARACTERISTICS:
      (A) LENGTH: 186 amino acids
      (B) TYPE: amino acid
      (C) STRANDEDNESS:
      (D) TOPOLOGY: linear (ii) MOLECULE TYPE: protein (xi) SEQUENCE DESCRIPTION: SEQ ID NO:163:

```
Met Ala Pro Val Pro Pro Gly Glu Asp Ser Lys Asp Val Ala Ala Pro
1               5                   10                  15

His Arg Gln Pro Leu Thr Ser Ser Glu Arg Ile Asp Lys Gln Ile Arg
                20                  25                  30

Tyr Ile Leu Asp Gly Ile Ser Ala Leu Arg Lys Glu Thr Cys Asn Lys
        35                  40                  45

Ser Asn Met Cys Glu Ser Ser Lys Glu Ala Leu Ala Glu Asn Asn Leu
```

```
                50                  55                  60
Asn Leu Pro Lys Met Ala Glu Lys Asp Gly Cys Phe Gln Ser Gly Phe
 65                  70                  75                  80

Asn Glu Glu Thr Cys Leu Val Lys Ile Ile Thr Gly Leu Leu Glu Phe
                 85                  90                  95

Glu Val Tyr Leu Glu Tyr Leu Gln Asn Arg Phe Glu Ser Ser Glu Glu
                100                 105                 110

Gln Ala Arg Ala Val Gln Met Ser Thr Lys Val Leu Ile Gln Phe Leu
                115                 120                 125

Gln Lys Lys Ala Lys Asn Leu Asp Ala Ile Thr Thr Pro Asp Pro Thr
130                 135                 140

Thr Asn Ala Ser Leu Leu Thr Lys Leu Gln Ala Gln Asn Gln Trp Leu
145                 150                 155                 160

Gln Asp Met Thr Thr His Leu Ile Leu Arg Ser Phe Lys Glu Phe Leu
                165                 170                 175

Gln Ser Ser Leu Arg Ala Leu Arg Gln Met
                180                 185
```

(2) INFORMATION FOR SEQ ID NO:164:

(i) SEQUENCE CHARACTERISTICS:
        (A) LENGTH: 155 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:164:

```
Met Ala Ser Pro Ala Pro Pro Ala Cys Asp Leu Arg Val Leu Ser Lys
 1               5                  10                  15

Leu Leu Arg Asp Ser His Val Leu His Ser Arg Leu Ser Gln Cys Pro
                 20                  25                  30

Glu Val His Pro Leu Pro Thr Pro Val Leu Leu Pro Ala Val Asp Phe
                 35                  40                  45

Ser Leu Gly Glu Trp Lys Thr Gln Met Glu Glu Thr Lys Ala Gln Asp
 50                  55                  60

Ile Leu Gly Ala Val Thr Leu Leu Leu Glu Gly Val Met Ala Ala Arg
 65                  70                  75                  80

Gln Gln Leu Gly Pro Thr Cys Leu Ser Ser Leu Leu Gly Gln Leu Ser
                 85                  90                  95

Gly Gln Val Arg Leu Leu Leu Gly Ala Leu Gln Ser Leu Leu Gly Thr
                100                 105                 110

Gln Leu Pro Pro Gln Gly Arg Thr Thr Ala His Lys Asp Pro Asn Ala
                115                 120                 125

Ile Phe Leu Ser Phe Gln His Leu Leu Arg Gly Lys Val Arg Phe Leu
                130                 135                 140

Met Leu Val Gly Gly Ser Thr Leu Cys Val Arg
145                 150                 155
```

(2) INFORMATION FOR SEQ ID NO:165:

(i) SEQUENCE CHARACTERISTICS:
        (A) LENGTH: 286 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:165:

```
Met Ala Asn Cys Ser Ile Met Ile Asp Glu Ile Ile His His Leu Lys
1               5                   10                  15

Arg Pro Pro Asn Pro Leu Leu Asp Pro Asn Asn Leu Asn Ser Glu Asp
                20                  25                  30

Met Asp Ile Leu Met Glu Arg Asn Leu Arg Thr Pro Asn Leu Leu Ala
            35                  40                  45

Phe Val Arg Ala Val Lys His Leu Glu Asn Ala Ser Gly Ile Glu Ala
        50                  55                  60

Ile Leu Arg Asn Leu Gln Pro Cys Leu Pro Ser Ala Thr Ala Ala Pro
65                  70                  75                  80

Ser Arg His Pro Ile Ile Lys Ala Gly Asp Trp Gln Glu Phe Arg
                85                  90                  95

Glu Lys Leu Thr Phe Tyr Leu Val Thr Leu Glu Gln Ala Gln Glu Gln
                100                 105                 110

Gln Tyr Val Ile Glu Gly Arg Ile Ser Pro Gly Gly Gly Ser Gly Gly
            115                 120                 125

Gly Ser Asn Met Ala Ser Pro Ala Pro Pro Ala Cys Asp Leu Arg Val
    130                 135                 140

Leu Ser Lys Leu Leu Arg Asp Ser His Val Leu His Ser Arg Leu Ser
145                 150                 155                 160

Gln Cys Pro Glu Val His Pro Leu Pro Thr Pro Val Leu Leu Pro Ala
                165                 170                 175

Val Asp Phe Ser Leu Gly Glu Trp Lys Thr Gln Met Glu Glu Thr Lys
            180                 185                 190

Ala Gln Asp Ile Leu Gly Ala Val Thr Leu Leu Leu Glu Gly Val Met
        195                 200                 205

Ala Ala Arg Gln Gln Leu Gly Pro Thr Cys Leu Ser Ser Leu Leu Gly
    210                 215                 220

Gln Leu Ser Gly Gln Val Arg Leu Leu Leu Gly Ala Leu Gln Ser Leu
225                 230                 235                 240

Leu Gly Thr Gln Leu Pro Pro Gln Gly Arg Thr Thr Ala His Lys Asp
                245                 250                 255

Pro Asn Ala Ile Phe Leu Ser Phe Gln His Leu Leu Arg Gly Lys Val
            260                 265                 270

Arg Phe Leu Met Leu Val Gly Gly Ser Thr Leu Cys Val Arg
        275                 280                 285
```

(2) INFORMATION FOR SEQ ID NO:166:

(i) SEQUENCE CHARACTERISTICS:
        (A) LENGTH: 286 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:166:

```
Met Ala Asn Cys Ser Ile Met Ile Asp Glu Ile Ile His His Leu Lys
1               5                   10                  15

Arg Pro Pro Asn Pro Leu Leu Asp Pro Asn Asn Leu Asn Ser Glu Asp
                20                  25                  30

Met Asp Ile Leu Met Glu Arg Asn Leu Arg Thr Pro Asn Leu Leu Ala
            35                  40                  45
```

```
Phe Val Arg Ala Val Lys His Leu Glu Asn Ala Ser Gly Ile Glu Ala
 50                  55                  60

Ile Leu Arg Asn Leu Gln Pro Cys Leu Pro Ser Ala Thr Ala Ala Pro
 65                  70                  75                  80

Ser Arg His Pro Ile Ile Lys Ala Gly Asp Trp Gln Glu Phe Arg
                 85                  90                  95

Glu Lys Leu Thr Phe Tyr Leu Val Thr Leu Glu Gln Ala Gln Glu Gln
                100                 105                 110

Gln Tyr Val Glu Gly Gly Gly Ser Pro Gly Gly Ser Gly Gly
        115                 120                 125

Gly Ser Asn Met Ala Ser Pro Ala Pro Pro Ala Cys Asp Leu Arg Val
        130                 135                 140

Leu Ser Lys Leu Leu Arg Asp Ser His Val Leu His Ser Arg Leu Ser
145                 150                 155                 160

Gln Cys Pro Glu Val His Pro Leu Pro Thr Pro Val Leu Leu Pro Ala
                165                 170                 175

Val Asp Phe Ser Leu Gly Glu Trp Lys Thr Gln Met Glu Glu Thr Lys
                180                 185                 190

Ala Gln Asp Ile Leu Gly Ala Val Thr Leu Leu Glu Gly Val Met
        195                 200                 205

Ala Ala Arg Gln Gln Leu Gly Pro Thr Cys Leu Ser Ser Leu Leu Gly
        210                 215                 220

Gln Leu Ser Gly Gln Val Arg Leu Leu Leu Gly Ala Leu Gln Ser Leu
225                 230                 235                 240

Leu Gly Thr Gln Leu Pro Pro Gln Gly Arg Thr Thr Ala His Lys Asp
                245                 250                 255

Pro Asn Ala Ile Phe Leu Ser Phe Gln His Leu Leu Arg Gly Lys Val
                260                 265                 270

Arg Phe Leu Met Leu Val Gly Gly Ser Thr Leu Cys Val Arg
                275                 280                 285

(2) INFORMATION FOR SEQ ID NO:167:

(i) SEQUENCE CHARACTERISTICS:
        (A) LENGTH: 286 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:167:

Met Ala Ser Pro Ala Pro Pro Ala Cys Asp Leu Arg Val Leu Ser Lys
  1               5                  10                  15

Leu Leu Arg Asp Ser His Val Leu His Ser Arg Leu Ser Gln Cys Pro
                 20                  25                  30

Glu Val His Pro Leu Pro Thr Pro Val Leu Leu Pro Ala Val Asp Phe
                 35                  40                  45

Ser Leu Gly Glu Trp Lys Thr Gln Met Glu Glu Thr Lys Ala Gln Asp
                 50                  55                  60

Ile Leu Gly Ala Val Thr Leu Leu Glu Gly Val Met Ala Ala Arg
 65                  70                  75                  80

Gln Gln Leu Gly Pro Thr Cys Leu Ser Ser Leu Leu Gly Gln Leu Ser
                 85                  90                  95

Gly Gln Val Arg Leu Leu Leu Gly Ala Leu Gln Ser Leu Leu Gly Thr
                100                 105                 110
```

```
Gln Leu Pro Pro Gln Gly Arg Thr Thr Ala His Lys Asp Pro Asn Ala
        115                 120                 125

Ile Phe Leu Ser Phe Gln His Leu Leu Arg Gly Lys Val Arg Phe Leu
130                 135                 140

Met Leu Val Gly Gly Ser Thr Leu Cys Val Arg Tyr Val Ile Glu Gly
145                 150                 155                 160

Arg Ile Ser Pro Gly Gly Gly Ser Gly Gly Ser Asn Met Ala Asn
                165                 170                 175

Cys Ser Ile Met Ile Asp Glu Ile Ile His His Leu Lys Arg Pro Pro
                180                 185                 190

Asn Pro Leu Leu Asp Pro Asn Asn Leu Asn Ser Glu Asp Met Asp Ile
                195                 200                 205

Leu Met Glu Arg Asn Leu Arg Thr Pro Asn Leu Leu Ala Phe Val Arg
        210                 215                 220

Ala Val Lys His Leu Glu Asn Ala Ser Gly Ile Glu Ala Ile Leu Arg
225                 230                 235                 240

Asn Leu Gln Pro Cys Leu Pro Ser Ala Thr Ala Ala Pro Ser Arg His
                245                 250                 255

Pro Ile Ile Ile Lys Ala Gly Asp Trp Gln Glu Phe Arg Glu Lys Leu
                260                 265                 270

Thr Phe Tyr Leu Val Thr Leu Glu Gln Ala Gln Glu Gln Gln
        275                 280                 285
```

(2) INFORMATION FOR SEQ ID NO:168:

(i) SEQUENCE CHARACTERISTICS:
        (A) LENGTH: 290 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:168:

```
Met Ala Ser Pro Ala Pro Ala Cys Asp Leu Arg Val Leu Ser Lys
1               5                  10                  15

Leu Leu Arg Asp Ser His Val Leu His Ser Arg Leu Ser Gln Cys Pro
            20                  25                  30

Glu Val His Pro Leu Pro Thr Pro Val Leu Leu Pro Ala Val Asp Phe
        35                  40                  45

Ser Leu Gly Glu Trp Lys Thr Gln Met Glu Glu Thr Lys Ala Gln Asp
    50                  55                  60

Ile Leu Gly Ala Val Thr Leu Leu Leu Glu Gly Val Met Ala Ala Arg
65                  70                  75                  80

Gln Gln Leu Gly Pro Thr Cys Leu Ser Ser Leu Leu Gly Gln Leu Ser
                85                  90                  95

Gly Gln Val Arg Leu Leu Leu Gly Ala Leu Gln Ser Leu Leu Gly Thr
                100                 105                 110

Gln Leu Pro Pro Gln Gly Arg Thr Thr Ala His Lys Asp Pro Asn Ala
        115                 120                 125

Ile Phe Leu Ser Phe Gln His Leu Leu Arg Gly Lys Val Arg Phe Leu
130                 135                 140

Met Leu Val Gly Gly Ser Thr Leu Cys Val Arg Glu Phe His Ala Tyr
145                 150                 155                 160

Val Glu Gly Gly Gly Ser Pro Gly Gly Ser Gly Gly Ser
                165                 170                 175
```

```
Asn Met Ala Asn Cys Ser Ile Met Ile Asp Glu Ile Ile His His Leu
            180                 185                 190
Lys Arg Pro Pro Asn Pro Leu Leu Asp Pro Asn Asn Leu Asn Ser Glu
            195                 200                 205
Asp Met Asp Ile Leu Met Glu Arg Asn Leu Arg Thr Pro Asn Leu Leu
            210                 215                 220
Ala Phe Val Arg Ala Val Lys His Leu Glu Asn Ala Ser Gly Ile Glu
225                 230                 235                 240
Ala Ile Leu Arg Asn Leu Gln Pro Cys Leu Pro Ser Ala Thr Ala Ala
                245                 250                 255
Pro Ser Arg His Pro Ile Ile Ile Lys Ala Gly Asp Trp Gln Glu Phe
            260                 265                 270
Arg Glu Lys Leu Thr Phe Tyr Leu Val Thr Leu Glu Gln Ala Gln Glu
            275                 280                 285
Gln Gln
    290
```

(2) INFORMATION FOR SEQ ID NO:169:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA"

(xi) SEQUENCE DESCRIPTION: SEQ ID NO:169:

ACGTCCATGG CNTCNCCNGC NCCNCCTGCT TGTGACCTCC GAGTC          45

(2) INFORMATION FOR SEQ ID NO:170:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA"

(xi) SEQUENCE DESCRIPTION: SEQ ID NO:170:

AATAGCTGAA TTCTTACCCT TCCTGAGACA GATT          34

(2) INFORMATION FOR SEQ ID NO:171:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA"

(xi) SEQUENCE DESCRIPTION: SEQ ID NO:171:

TGACAAGCTT ACCTGACGCA GAGGGTGGAC CCT          33

(2) INFORMATION FOR SEQ ID NO:172:

(i) SEQUENCE CHARACTERISTICS:
        (A) LENGTH: 30 base pairs
        (B) TYPE: nucleic acid
        (C) STRANDEDNESS: single (D) TOPOLOGY: linear (ii) MOLECULE TYPE: other nucleic acid
        (A) DESCRIPTION: /desc = "synthetic DNA"

(xi) SEQUENCE DESCRIPTION: SEQ ID NO:172:

ATGCACGAAT TCCCTGACGC AGAGGGTGGA                                    30

(2) INFORMATION FOR SEQ ID NO:173:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA"

(xi) SEQUENCE DESCRIPTION: SEQ ID NO:173:

AATTCCATGC ATAC                                                     14

(2) INFORMATION FOR SEQ ID NO:174:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "synthetic DNA"

(xi) SEQUENCE DESCRIPTION: SEQ ID NO:174:

GGTACGTATG                                                          10

(2) INFORMATION FOR SEQ ID NO:175:

(i) SEQUENCE CHARACTERISTICS:
        (A) LENGTH: 561 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:175:

ATGGCTCCAG TACCACCAGG TGAAGATTCC AAAGATGTGG CCGCCCCACA CAGACAGCCA    60

CTCACCTCTT CAGAACGAAT TGACAAACAA ATTCGGTACA TCCTCGACGG GATATCAGCC   120

CTGAGAAAGG AGACATGTAA CAAGAGTAAC ATGTGTGAAA GCAGCAAAGA GGCGCTAGCA   180

GAAAACAACC TGAACCTTCC AAAGATGGCT GAAAAGATG GATGCTTCCA ATCCGGATTC    240

AATGAGGAGA CTTGCCTGGT GAAAATCATC ACTGGTCTTT TGGAGTTTGA GGTATACCTC   300

GAGTACCTCC AGAACAGATT TGAGAGTAGT GAGGAACAAG CCAGAGCTGT GCAGATGTCG   360

ACAAAAGTCC TGATCCAGTT CCTGCAGAAA AAGGCAAAGA ATCTAGATGC AATAACCACC   420

CCTGACCCAA CCACAAATGC ATCCCTGCTG ACGAAGCTGC AGGCACAGAA CCAGTGGCTG   480

CAGGACATGA CAACTCATCT CATTCTGCGC AGCTTTAAGG AGTTCCTGCA GTCCAGCCTG   540

AGGGCTCTTC GGCAAATGTA G                                            561

(2) INFORMATION FOR SEQ ID NO:176:

(i) SEQUENCE CHARACTERISTICS:
        (A) LENGTH: 402 base pairs

```
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:176:

ATGGCACCGG CTCGTTCCCC GTCCCCGTCT ACCCAGCCGT GGGAACACGT GAATGCCATC      60

CAGGAGGCCC GGCGTCTCCT GAACCTGAGT AGAGACACTG CTGCTGAGAT GAATGAAACA     120

GTAGAAGTGA TATCAGAAAT GTTTGACCTC CAGGAGCCGA CTTGCCTACA GACCCGCCTG     180

GAGCTGTACA AGCAGGGCCT GCGGGGCAGC CTCACCAAGC TCAAGGGCCC CTTGACCATG     240

ATGGCCAGCC ACTACAAGCA GCACTGCCCT CCAACCCCGG AAACTTCCTG TGCAACCCAG     300

ATTATCACCT TTGAAAGTTT CAAAGAGAAC CTGAAGGACT TCCTGCTTGT CATCCCCTTT     360

GACTGCTGGG AGCCAGTCCA GGAGTGATAA GGATCCGAAT TC                        402

(2) INFORMATION FOR SEQ ID NO:177:

(i) SEQUENCE CHARACTERISTICS:
        (A) LENGTH: 546 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:177:

ATGGCTACAC CATTAGGCCC TGCCAGCTCC CTGCCCCAGA GCTTCCTGCT CAAGTGCTTA      60

GAGCAAGTGA GGAAGATCCA GGGCGATGGC GCAGCGCTCC AGGAGAAGCT GTGTGCCACC     120

TACAAGCTGT GCCACCCCGA GGAGCTGGTG CTGCTCGGAC ACTCTCTGGG CATCCCCTGG     180

GCTCCCCTGA GCTCCTGCCC CAGCCAGGCC CTGCAGCTGG CAGGCTGCTT GAGCCAACTC     240

CATAGCGGCC TTTTCCTCTA CCAGGGGCTC CTGCAGGCCC TGGAAGGGAT ATCCCCCGAG     300

TTGGGTCCCA CCTTGGACAC ACTGCAGCTG GACGTCGCCG ACTTTGCCAC CACCATCTGG     360

CAGCAGATGG AAGAACTGGG AATGGCCCCT GCCCTGCAGC CCACCCAGGG TGCCATGCCG     420

GCCTTCGCCT CTGCTTTCCA GCGCCGGGCA GGAGGGGTCC TGGTTGCTAG CCATCTGCAG     480

AGCTTCCTGG AGGTGTCGTA CCGCGTTCTA CGCCACCTTG CGCAGCCCTG ATAAGGATCC     540

GAATTC                                                                546

(2) INFORMATION FOR SEQ ID NO:178:

(i) SEQUENCE CHARACTERISTICS:
        (A) LENGTH: 546 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:178:

ATGGCTACAC CATTAGGACC TGCCAGCTCC CTGCCCCAGA GCTTCCTGCT CAAGTGCTTA      60

GAGCAAGTGA GGAAGATCCA GGGCGATGGC GCAGCGCTCC AGGAGAAGCT GTGTGCCACC     120

TACAAGCTGT GCCACCCCGA GGAGCTGGTG CTGCTCGGAC ACTCTCTGGG CATCCCCTGG     180

GCTCCCCTGA GCTCCTGCCC CAGCCAGGCC CTGCAGCTGG CAGGCTGCTT GAGCCAACTC     240

CATAGCGGCC TTTTCCTCTA CCAGGGGCTC CTGCAGGCCC TGGAAGGGAT ATCCCCCGAG     300

TTGGGTCCCA CCTTGGACAC ACTGCAGCTG GACGTCGCCG ACTTTGCCAC CACCATCTGG     360
```

| CAGCAGATGG AAGAACTGGG AATGGCCCCT GCCCTGCAGC CCACCCAGGG TGCCATGCCG | 420 |
| GCCTTCGCCT CTGCTTTCCA GCGCCGGGCA GGAGGGGTCC TGGTTGCTAG CCATCTGCAG | 480 |
| AGCTTCCTGG AGGTGTCGTA CCGCGTTCTA CGCCACCTTG CGCAGCCCTG ATAAGGATCC | 540 |
| GAATTC | 546 |

(2) INFORMATION FOR SEQ ID NO:179:

(i) SEQUENCE CHARACTERISTICS:
        (A) LENGTH: 546 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:179:

| ATGGCTACAC CATTGGGCCC TGCCAGCTCC CTGCCCCAGA GCTTCCTGCT CAAGTCTTTA | 60 |
| GAGCAAGTGA GGAAGATCCA GGGCGATGGC GCAGCGCTCC AGGAGAAGCT GTGTGCCACC | 120 |
| TACAAGCTGT GCCACCCCGA GGAGCTGGTG CTGCTCGGAC ACTCTCTGGG CATCCCCTGG | 180 |
| GCTCCCCTGA GCTCCTGCCC CAGCCAGGCC CTGCAGCTGG CAGGCTGCTT GAGCCAACTC | 240 |
| CATAGCGGCC TTTTCCTCTA CCAGGGGCTC CTGCAGGCCC TGGAAGGGAT ATCCCCCGAG | 300 |
| TTGGGTCCCA CCTTGGACAC ACTGCAGCTG GACGTCGCCG ACTTTGCCAC CACCATCTGG | 360 |
| CAGCAGATGG AAGAACTGGG AATGGCCCCT GCCCTGCAGC CCACCCAGGG TGCCATGCCG | 420 |
| GCCTTCGCCT CTGCTTTCCA GCGCCGGGCA GGAGGGGTCC TGGTTGCTAG CCATCTGCAG | 480 |
| AGCTTCCTGG AGGTGTCGTA CCGCGTTCTA CGCCACCTTG CGCAGCCCTG ATAAGGATCC | 540 |
| GAATTC | 546 |

(2) INFORMATION FOR SEQ ID NO:180:

(i) SEQUENCE CHARACTERISTICS:
        (A) LENGTH: 465 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:180:

| ATGGCGTCTC CGGCGCCGCC TGCTTGTGAC CTCCGAGTCC TCAGTAAACT GCTTCGTGAC | 60 |
| TCCCATGTCC TTCACAGCAG ACTGAGCCAG TGCCCAGAGG TTCACCCTTT GCCTACACCT | 120 |
| GTCCTGCTGC CTGCTGTGGA CTTTAGCTTG GGAGAATGGA AAACCCAGAT GGAGGAGACC | 180 |
| AAGGCACAGG ACATTCTGGG AGCAGTGACC CTTCTGCTGG AGGGAGTGAT GGCAGCACGG | 240 |
| GGACAACTGG GACCCACTTG CCTCTCATCC CTCCTGGGGC AGCTTTCTGG ACAGGTCCGT | 300 |
| CTCCTCCTTG GGGCCCTGCA GAGCCTCCTT GGAACCCAGC TTCCTCCACA GGGCAGGACC | 360 |
| ACAGCTCACA AGGATCCCAA TGCCATCTTC CTGAGCTTCC AACACCTGCT CCGAGGAAAG | 420 |
| GTGCGTTTCC TGATGCTTGT AGGAGGGTCC ACCCTCTGCG TCAGG | 465 |

(2) INFORMATION FOR SEQ ID NO:181:

(i) SEQUENCE CHARACTERISTICS:
        (A) LENGTH: 143 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:181:

CCTGTCAACC CGGGCGGCGG CTCTGGTGGT GGTTCTGGTG GCGGCTCTGA GGGTGGCGGC    60

TCTGAGGGTG GCGGTTCTGA GGGTGGCGGC TCTGAGGGTG GCGGTTCCGG TGGCGGCTCC   120

GGTTCCGGTA ACATGTATTA TGA                                          143

(2) INFORMATION FOR SEQ ID NO:182:

(i) SEQUENCE CHARACTERISTICS:
            (A) LENGTH: 180 base pairs
            (B) TYPE: nucleic acid
            (C) STRANDEDNESS: double
            (D) TOPOLOGY: linear (ii) MOLECULE TYPE: DNA (genomic)

(xi) SEQUENCE DESCRIPTION: SEQ ID NO:182:

ATCGTCTGAC CTCCCGGGCC TCCTGTCAAT GCTGGCGGCG GCTCTGGTGG TGGTTCTGGT    60

GGCGGCTCTG AGGGTGGCGG CTCTGAGGGT GGCGGTTCTG AGGGTGGCGG CTCTGAGGGT   120

GGCGGTTCCG GTGGCGGCTC CGGTTCCGGT GATTTTGATT ATGAAAACAT GTCAAACGCT   180

(2) INFORMATION FOR SEQ ID NO:183:

(i) SEQUENCE CHARACTERISTICS:
            (A) LENGTH: 858 base pairs
            (B) TYPE: nucleic acid
            (C) STRANDEDNESS: double
            (D) TOPOLOGY: linear (ii) MOLECULE TYPE: DNA (genomic)

(xi) SEQUENCE DESCRIPTION: SEQ ID NO:183:

ATGGCTAACT GCTCTATAAT GATCGATGAA ATTATACATC ACTTAAAGAG ACCACCTAAC    60

CCTTTGCTGG ACCCGAACAA CCTCAATTCT GAAGACATGG ATATCCTGAT GGAACGAAAC   120

CTTCGAACTC CAAACCTGCT CGCATTCGTA AGGGCTGTCA AGCACTTAGA AAATGCATCA   180

GGTATTGAGG CAATTCTTCG TAATCTCCAA CCATGTCTGC CCTCTGCCAC GGCCGCACCC   240

TCTCGACATC CAATCATCAT CAAGGCAGGT GACTGGCAAG AATTCCGGGA AAAACTGACG   300

TTCTATCTGG TTACCCTTGA GCAAGCGCAG GAACAACAGT ACGTAATCGA GGGAAGGATT   360

TCCCCGGGTG GTGGTTCTGG CGGCGGCTCC AACATGGCGT CTCCGGCGCC GCCTGCTTGT   420

GACCTCCGAG TCCTCAGTAA ACTGCTTCGT GACTCCCATG TCCTTCACAG CAGACTGAGC   480

CAGTGCCCAG AGGTTCACCC TTTGCCTACA CCTGTCCTGC TGCCTGCTGT GGACTTTAGC   540

TTGGGAGAAT GGAAAACCCA GATGGAGGAG ACCAAGGCAC AGGACATTCT GGGAGCAGTG   600

ACCCTTCTGC TGGAGGGAGT GATGGCAGCA CGGGGACAAC TGGGACCCAC TTGCCTCTCA   660

TCCCTCCTGG GGCAGCTTTC TGGACAGGTC CGTCTCCTCC TTGGGGCCCT GCAGAGCCTC   720

CTTGAACCC AGCTTCCTCC ACAGGGCAGG ACCACAGCTC ACAAGGATCC CAATGCCATC   780

TTCCTGAGCT TCCAACACCT GCTCCGAGGA AAGGTGCGTT TCCTGATGCT TGTAGGAGGG   840

TCCACCCTCT GCGTCAGG                                                858

(2) INFORMATION FOR SEQ ID NO:184:

(i) SEQUENCE CHARACTERISTICS:
            (A) LENGTH: 858 base pairs
            (B) TYPE: nucleic acid

```
        (C) STRANDEDNESS: double
        (D) TOPOLOGY: linear (ii) MOLECULE TYPE: DNA (genomic)

(xi) SEQUENCE DESCRIPTION: SEQ ID NO:184:

ATGGCTAACT GCTCTATAAT GATCGATGAA ATTATACATC ACTTAAAGAG ACCACCTAAC      60

CCTTTGCTGG ACCCGAACAA CCTCAATTCT GAAGACATGG ATATCCTGAT GGAACGAAAC     120

CTTCGAACTC CAAACCTGCT CGCATTCGTA AGGGCTGTCA AGCACTTAGA AAATGCATCA     180

GGTATTGAGG CAATTCTTCG TAATCTCCAA CCATGTCTGC CCTCTGCCAC GGCCGCACCC     240

TCTCGACATC CAATCATCAT CAAGGCAGGT GACTGGCAAG AATTCCGGGA AAAACTGACG     300

TTCTATCTGG TTACCCTTGA GCAAGCGCAG GAACAACAGT ACGTAGAGGG CGGTGGAGGC     360

TCCCCGGGTG GTGGTTCTGG CGGCGGCTCC AACATGGCGT CTCCGGCGCC GCCTGCTTGT     420

GACCTCCGAG TCCTCAGTAA ACTGCTTCGT GACTCCCATG TCCTTCACAG CAGACTGAGC     480

CAGTGCCCAG AGGTTCACCC TTTGCCTACA CCTGTCCTGC TGCCTGCTGT GGACTTTAGC     540

TTGGGAGAAT GGAAAACCCA GATGGAGGAG ACCAAGGCAC AGGACATTCT GGGAGCAGTG     600

ACCCTTCTGC TGGAGGGAGT GATGGCAGCA CGGGGACAAC TGGGACCCAC TTGCCTCTCA     660

TCCCTCCTGG GGCAGCTTTC TGGACAGGTC CGTCTCCTCC TTGGGGCCCT GCAGAGCCTC     720

CTTGGAACCC AGCTTCCTCC ACAGGGCAGG ACCACAGCTC ACAAGGATCC AATGCCATC     780

TTCCTGAGCT TCCAACACCT GCTCCGAGGA AAGGTGCGTT TCCTGATGCT TGTAGGAGGG     840

TCCACCCTCT GCGTCAGG                                                   858

(2) INFORMATION FOR SEQ ID NO:185:

(i) SEQUENCE CHARACTERISTICS:
        (A) LENGTH: 852 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:185:

ATGGCGTCTC CGGCGCCGCC TGCTTGTGAC CTCCGAGTCC TCAGTAAACT GCTTCGTGAC      60

TCCCATGTCC TTCACAGCAG ACTGAGCCAG TGCCCAGAGG TTCACCCTTT GCCTACACCT     120

GTCCTGCTGC CTGCTGTGGA CTTTAGCTTG GGAGAATGGA AAACCCAGAT GGAGGAGACC     180

AAGGCACAGG ACATTCTGGG AGCAGTGACC CTTCTGCTGG AGGGAGTGAT GGCAGCACGG     240

GGACAACTGG GACCCACTTG CCTCTCATCC TCCTGGGGC AGCTTTCTGG ACAGGTCCGT     300

CTCCTCCTTG GGGCCCTGCA GAGCCTCCTT GGAACCCAGC TTCCTCCACA GGGCAGGACC     360

ACAGCTCACA AGGATCCCAA TGCCATCTTC CTGAGCTTCC AACACCTGCT CCGAGGAAAG     420

GTGCGTTTCC TGATGCTTGT AGGAGGGTCC ACCCTCTGCG TCAGGATCGA GGGAAGGATT     480

TCCCCGGGTG GTGGTTCTGG CGGCGGCTCC AACATGGCTA ACTGCTCTAT AATGATCGAT     540

GAAATTATAC ATCACTTAAA GAGACCACCT AACCCTTTGC TGGACCCGAA CAACCTCAAT     600

TCTGAAGACA TGGATATCCT GATGGAACGA AACCTTCGAA CTCCAAACCT GCTCGCATTC     660

GTAAGGGCTG TCAAGCACTT AGAAAATGCA TCAGGTATTG AGGCAATTCT TCGTAATCTC     720

CAACCATGTC TGCCCTCTGC CACGGCCGCA CCCTCTCGAC ATCCAATCAT CATCAAGGCA     780

GGTGACTGGC AAGAATTCCG GGAAAAACTG ACGTTCTATC TGGTTACCCT TGAGCAAGCG     840

CAGGAACAAC AG                                                         852
```

(2) INFORMATION FOR SEQ ID NO:186:

(i) SEQUENCE CHARACTERISTICS:
        (A) LENGTH: 870 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:186:

```
ATGGCGTCTC CGGCGCCGCC TGCTTGTGAC CTCCGAGTCC TCAGTAAACT GCTTCGTGAC    60
TCCCATGTCC TTCACAGCAG ACTGAGCCAG TGCCCAGAGG TTCACCCTTT GCCTACACCT   120
GTCCTGCTGC CTGCTGTGGA CTTTAGCTTG GGAGAATGGA AAACCCAGAT GGAGGAGACC   180
AAGGCACAGG ACATTCTGGG AGCAGTGACC CTTCTGCTGG AGGGAGTGAT GGCAGCACGG   240
GGACAACTGG GACCCACTTG CCTCTCATCC CTCCTGGGGC AGCTTTCTGG ACAGGTCCGT   300
CTCCTCCTTG GGGCCCTGCA GAGCCTCCTT GGAACCCAGC TTCCTCCACA GGGCAGGACC   360
ACAGCTCACA AGGATCCCAA TGCCATCTTC CTGAGCTTCC AACACCTGCT CCGAGGAAAG   420
GTGCGTTTCC TGATGCTTGT AGGAGGGTCC ACCCTCTGCG TCAGGGAATT CCATGCATAC   480
GTAGAGGGCG GTGGAGGCTC CCCGGGTGGT GGTTCTGGCG GCGGCTCCAA CATGGCTAAC   540
TGCTCTATAA TGATCGATGA AATTATACAT CACTTAAAGA GACCACCTAA CCCTTTGCTG   600
GACCCGAACA ACCTCAATTC TGAAGACATG GATATCCTGA TGGAACGAAA CCTTCGAACT   660
CCAAACCTGC TCGCATTCGT AAGGGCTGTC AAGCACTTAG AAAATGCATC AGGTATTGAG   720
GCAATTCTTC GTAATCTCCA ACCATGTCTG CCCTCTGCCA CGGCCGCACC CTCTCGACAT   780
CCAATCATCA TCAAGGCAGG TGACTGGCAA GAATTCCGGG AAAAACTGAC GTTCTATCTG   840
GTTACCCTTG AGCAAGCGCA GGAACAACAG                                   870
```

(2) INFORMATION FOR SEQ ID NO:187:

(i) SEQUENCE CHARACTERISTICS:
        (A) LENGTH: 18 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:187:

```
Met Ser Arg Leu Pro Val Leu Leu Leu Gln Leu Leu Val Arg Pro
1               5                   10                  15
Ala Met
```

(2) INFORMATION FOR SEQ ID NO:188:

(i) SEQUENCE CHARACTERISTICS:
        (A) LENGTH: 18 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:188:

```
Tyr Val Ile Glu Gly Arg Ile Ser Pro Gly Gly Gly Ser Gly Gly
1               5                   10                  15
Ser Asn
```

(2) INFORMATION FOR SEQ ID NO:189:

(i) SEQUENCE CHARACTERISTICS:
        (A) LENGTH: 18 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:189:

```
Tyr Val Ile Glu Gly Lys Ile Ser Pro Gly Gly Ser Gly Gly Gly
1               5                   10                  15

Ser Asn
```

(2) INFORMATION FOR SEQ ID NO:190:

(i) SEQUENCE CHARACTERISTICS:
        (A) LENGTH: 18 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:190:

```
Tyr Val Glu Gly Gly Gly Gly Ser Pro Gly Gly Ser Gly Gly Gly
1               5                   10                  15

Ser Asn
```

(2) INFORMATION FOR SEQ ID NO:191:

(i) SEQUENCE CHARACTERISTICS:
        (A) LENGTH: 33 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:191:

```
Tyr Val Ile Glu Gly Arg Ile Ser Pro Gly Glu Pro Ser Gly Pro Ile
1               5                   10                  15

Ser Thr Ile Asn Pro Ser Pro Pro Ser Lys Glu Ser His Lys Ser Pro
                20                  25                  30

Asn
```

(2) INFORMATION FOR SEQ ID NO:192:

(i) SEQUENCE CHARACTERISTICS:
        (A) LENGTH: 33 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:192:

```
Tyr Val Ile Glu Gly Lys Ile Ser Pro Gly Glu Pro Ser Gly Pro Ile
1               5                   10                  15

Ser Thr Ile Asn Pro Ser Pro Pro Ser Lys Glu Ser His Lys Ser Pro
                20                  25                  30

Asn
```

(2) INFORMATION FOR SEQ ID NO:193:

(i) SEQUENCE CHARACTERISTICS:
        (A) LENGTH: 33 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:193:

```
Tyr Val Glu Gly Gly Gly Gly Ser Pro Gly Glu Pro Ser Gly Pro Ile
1               5                   10                  15

Ser Thr Ile Asn Pro Ser Pro Pro Ser Lys Glu Ser His Lys Ser Pro
            20                  25                  30

Asn
```

(2) INFORMATION FOR SEQ ID NO:194:

(i) SEQUENCE CHARACTERISTICS:
        (A) LENGTH: 49 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:194:

```
Tyr Val Ile Glu Gly Arg Ile Ser Pro Gly Gly Ser Gly Gly Gly
1               5                   10                  15

Ser Gly Gly Gly Ser Glu Gly Gly Ser Glu Gly Gly Ser Glu
            20                  25                  30

Gly Gly Gly Ser Glu Gly Gly Gly Ser Gly Gly Ser Gly Ser Gly
        35                  40                  45

Asn
```

(2) INFORMATION FOR SEQ ID NO:195:

(i) SEQUENCE CHARACTERISTICS:
        (A) LENGTH: 60 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:195:

```
Tyr Val Ile Glu Gly Arg Ile Ser Pro Gln Pro Pro Val Asn Ala Gly
1               5                   10                  15

Gly Gly Ser Gly Gly Gly Ser Gly Gly Gly Ser Glu Gly Gly Gly Ser
            20                  25                  30

Glu Gly Gly Ser Glu Gly Gly Gly Ser Glu Gly Gly Ser Gly
        35                  40                  45

Gly Gly Ser Gly Ser Gly Asp Phe Asp Tyr Glu Asn
    50                  55                  60
```

(2) INFORMATION FOR SEQ ID NO:196:

(i) SEQUENCE CHARACTERISTICS:
        (A) LENGTH: 22 amino acids
        (B) TYPE: amino acid
        (C) STRANDEDNESS:
        (D) TOPOLOGY: linear -continued (ii) MOLECULE TYPE: peptide (xi) SEQUENCE DESCRIPTION: SEQ ID NO:196:

Glu Phe His Ala Tyr Val Glu Gly Gly Gly Ser Pro Gly Gly Gly
1               5                   10                  15

Ser Gly Gly Gly Ser Asn
            20

What is claimed is:

1. A method for ex vivo expansion of stem cells, comprising the steps of;

(a) culturing said stem cells with a growth medium comprising a chimera protein having the formula selected from the group consisting of:

$R_1$-L-$R_2$, $R_2$-L-$R_1$, $R_1$-$R_2$, $R_2$-$R_1$, $R_1$-L-$R_1$, $R_1$-$R_1$,

Met-Ala-$R_1$-L-$R_2$, Met-Ala-$R_2$-L-$R_1$, Met-Ala-$R_1$-$R_2$, Met-Ala-$R_2$-$R_1$, Met-$R_1$-L-$R_2$, Met-$R_2$-L-$R_1$, Met-$R_1$-$R_2$, Met-$R_2$-$R_1$,

Ala-$R_1$-L-$R_2$, Ala-$R_2$-L-$R_1$, Ala-$R_1$-$R_2$ and Ala-$R_2$-$R_1$;

wherein $R_1$ is a human interleukin-3 mutant polypeptide of SEQ ID NO:1 wherein

Xaa at position 17 is Ser, Lys, Gly, Asp, Met, Gln, or Arg;
Xaa at position 18 is Asn, His, Leu, le, Phe, Arg, or Gln;
Xaa at position 19 is Met, Phe, Ile, Arg, Gly, Ala, or Cys;
Xaa at position 20 is Ile, Cys, Gln, Glu, Arg, Pro, or Ala;
Xaa at position 21 is Asp, Phe, Lys, Arg, Ala, Gly, Glu, Gln, Asn, Thr, Ser or Val;
Xaa at position 22 is Glu, Trp, Pro, Ser, Ala, His, Asp, Asn, GLn, Leu, Val or Gly;
Xaa at position 23 is Ile, Val, Ala, Leu, Gly, Trp, Lys, Phe, Ser, or Arg;
Xaa at position 24 is Ile, Gly, Val, Arg, Ser, Phe, or Leu;
Xaa at position 25 is Thr, His, Gly, Gln, Arg, Pro, or Ala;
Xaa at position 26 is His, Thr, Phe, Gly, Arg, Ala, or Trp;
Xaa at position 27 is Leu, Gly, Arg, Thr, Ser, or Ala;
Xaa at position 28 is Lys, Arg, Leu, Gln, Gly, Pro, Val or Trp;
Xaa at position 29 is Gln, Asn, Leu, Pro, Arg, or Val;
Xaa at position 30 is Pro, His, Thr, Gly, Asp, Gln, Ser, Leu, or Lys;
Xaa at position 31 is Pro, Asp, Gly, Ala, Arg, Leu, or Gln;
Xaa at position 32 is Leu, Val, Arg, Gln, Asn, Gly, Ala, or Glu;
Xaa at position 33 is Pro, Leu, Gln, Ala, Thr, or Glu;
Xaa at position 34 is Leu, Val, Gly, Ser, Lys, Glu, Gln, Thr, Arg, Ala, Phe, Ile or Met;
Xaa at position 35 is Leu, Ala, Gly, Asn, Pro, Gln, or Val;
Xaa at position 36 is Asp, Leu, or Val;
Xaa at position 37 is Phe, Ser, Pro, Trp, or Ile;
Xaa at position 38 is Asn, or Ala;
Xaa at position 40 is Leu, Trp, or Arg;
Xaa at position 41 is Asn, Cys, Arg, Leu, His, Met, or Pro;
Xaa at position 42 is Gly, Asp, Ser, Cys, Asn, Lys, Thr, Leu, Val, Glu, Phe, Tyr, Ile, Met or Ala;
Xaa at position 43 is Glu, Asn, Tyr, Leu, Phe, Asp, Ala, Cys, Gln, Arg, Thr, Gly or Ser;
Xaa at position 44 is Asp, Ser, Leu, Arg, Lys, Thr, Met, Trp, Glu, Asn, Gln, Ala or Pro;
Xaa at position 45 is Gln, Pro, Phe, Val, Met, Leu, Thr, Lys, Trp, Asp, Asn, Arg, Ser, Ala, Ile, Glu or His;
Xaa at position 46 is Asp, Phe, Ser, Thr, Cys, Glu, Asn, Gln, Lys, His, Ala, Tyr, Ile, Val or Gly;
Xaa at position 47 is Ile, Gly, Val, Ser, Arg, Pro, or His;
Xaa at position 48 is Leu, Ser, Cys, Arg, Ile, His, Phe, Glu, Lys, Thr, Ala, Met, Val or Asn;
Xaa at position 49 is Met, Arg, Ala, Gly, Pro, Asn, His, or Asp;
Xaa at position 50 is Glu, Leu, Thr, Asp, Tyr, Lys, Asn, Ser, Ala, Ile, Val, His, Phe, Met or Gln;
Xaa at position 51 is Asn, Arg, Met, Pro, Ser, Thr, or His;
Xaa at position 52 is Asn, His, Arg, Leu, Gly, Ser, or Thr;
Xaa at position 53 is Leu, Thr, Ala, Gly, Glu, Pro, Lys, Ser, or Met;
Xaa at position 54 is Arg, Asp, Ile, Ser, Val, Thr, Gln, Asn, Lys, His, Ala or Leu;
Xaa at position 55 is Arg, Thr, Val, Ser, Leu, or Gly;
Xaa at position 56 is Pro, Gly, Cys, Ser, Gln, Glu, Arg, His, Thr, Ala, Tyr, Phe, Leu, Val or Lys;
Xaa at position 57 is Asn or Gly;
Xaa at position 58 is Leu, Ser, Asp, Arg, Gln, Val, or Cys;
Xaa at position 59 is Glu, Tyr, His, Leu, Pro, or Arg;
Xaa at position 60 is Ala, Ser, Pro, Tyr, Asn, or Thr;
Xaa at position 61 is Phe, Asn, Glu, Pro, Lys, Arg, or Ser;
Xaa at position 62 is Asn, His, Val, Arg, Pro, Thr, Asp, or Ile;
Xaa at position 63 is Arg, Tyr, Trp, Ser, His, Pro, or Val;
Xaa at position 64 is Ala, Asn, Pro, Ser, or Lys;
Xaa at position 65 is Val, Thr, Pro, His, Leu, Phe, or Ser;
Xaa at position 66 is Lys, Ile, Arg, Val, Asn, Glu, or Ser;
Xaa at position 67 is Ser, Ala, Phe, Val, Gly, Asn, Ile, Pro, or His;
Xaa at position 68 is Leu, Val, Trp, Ser, Ile, Phe, Thr, or His;
Xaa at position 69 is Gln, Ala, Pro, Thr, Glu, Arg, Trp, Gly, or Leu;
Xaa at position 70 is Asn, Leu, Val, Trp, Pro, or Ala;
Xaa at position 71 is Ala, Met, Leu, Pro, Arg, Glu, Thr, Gln, Trp, or Asn;
Xaa at position 72 is Ser, Glu, Met, Ala, His, Asn, Arg, or Asp;
Xaa at position 73 is Ala, Glu, Asp, Leu, Ser, Gly, Thr, or Arg;
Xaa at position 74 is Ile, Met, Thr, Pro, Arg, Gly, Ala;
Xaa at position 75 is Glu, Lys, Gly, Asp, Pro, Trp, Arg, Ser, Gln, or Leu;
Xaa at position 76 is Ser, Val, Ala, Asn, Trp, Glu, Pro, Gly, or Asp;
Xaa at position 77 is Ile, Ser, Arg, Thr, or Leu;
Xaa at position 78 is Leu, Ala, Ser, Glu, Phe, Gly, or Arg;
Xaa at position 79 is Lys, Thr, Asn, Met, Arg, Ile, Gly, or Asp;
Xaa at position 80 is Asn, Trp, Val, Gly, Thr, Leu, Glu, or Arg;
Xaa at position 81 is Leu, Gln, Gly, Ala, Trp, Arg, Val, or Lys;
Xaa at position 82 is Leu, Gln, Lys, Trp, Arg, Asp, Glu, Asn, His, Thr, Ser, Ala, Tyr, Phe, Ile, Met or Val;
Xaa at position 83 is Pro, Ala, Thr, Trp, Arg, or Met;
Xaa at position 84 is Cys, Glu, Gly, Arg, Met, or Val;

Xaa at position 85 is Leu, Asn, Val, or Gln;
Xaa at position 86 is Pro, Cys, Arg, Ala, or Lys;
Xaa at position 87 is Leu, Ser, Trp, or Gly;
Xaa at position 88 is Ala, Lys, Arg, Val, or Trp;
Xaa at position 89 is Thr, Asp, Cys, Leu, Val, Glu, His, Asn, or Ser;
Xaa at position 90 is Ala, Pro, Ser, Thr, Gly, Asp, Ile, or Met;
Xaa at position 91 is Ala, Pro, Ser, Thr, Phe, Leu, Asp, or His;
Xaa at position 92 is Pro, Phe, Arg, Ser, Lys, His, Ala, Gly, Ile or Leu;
Xaa at position 93 is Thr, Asp, Ser, Asn, Pro, Ala, Leu, or Arg;
Xaa at position 94 is Arg, Ile, Ser, Glu, Leu, Val, Gln, Lys, His, Ala, or Pro;
Xaa at position 95 is His, Gln, Pro, Arg, Val, Leu, Gly, Thr, Asn, Lys, Ser, Ala, Trp, Phe, Ile, or Tyr;
Xaa at position 96 is Pro, Lys, Tyr, Gly, Ile, or Thr;
Xaa at position 97 is Ile, Val, Lys, Ala, or Asn;
Xaa at position 98 is His, Ile, Asn, Leu, Asp, Ala, Thr, Glu, Gln, Ser, Phe, Met, Val, Lys, Tyr or Pro;
Xaa at position 99 is Ile, Leu, Arg, Asp, Val, Pro, Gln, Gly, Ser, Phe, or His;
Xaa at position 100 is Lys, Tyr, Leu, His, Arg, Ile, Ser, Gln, or Pro;
Xaa at position 101 is Asp, Pro, Met, Lys, His, Thr, Val, Tyr, Glu, Asn, Ser, Ala, Gly, Ile, Leu, or Gln;
Xaa at position 102 is Gly, Leu, Glu, Lys, Ser, Tyr, or Pro;
Xaa at position 103 is Asp, or Ser;
Xaa at position 104 is Trp, Val, Cys, Tyr, Thr, Met, Pro, Leu, Gln, Lys, Ala, Phe, or Gly;
Xaa at position 105 is Asn, Pro, Ala, Phe, Ser, Trp, Gln, Tyr, Leu, Lys, Ile, Asp, or His;
Xaa at position 106 is Glu, Ser, Ala, Lys, Thr, Ile, Gly, or Pro;
Xaa at position 108 is Arg, Lys, Asp, Leu, Thr, Ile, Gln, His, Ser, Ala or Pro;
Xaa at position 109 is Arg, Thr, Pro, Glu, Tyr, Leu, Ser, or Gly;
Xaa at position 110 is Lys, Ala, Asn, Thr, Leu, Arg, Gln, His, Glu, Ser, or Trp;
Xaa at position 111 is Leu, Ile, Arg, Asp, or Met;
Xaa at position 112 is Thr, Val, Gln, Tyr, Glu, His, Ser, or Phe;
Xaa at position 113 is Phe, Ser, Cys, His, Gly, Trp, Tyr, Asp, Lys, Leu, Ile, Val or Asn;
Xaa at position 114 is Tyr, Cys, His, Ser, Trp, Arg, or Leu;
Xaa at position 115 is Leu, Asn, Val, Pro, Arg, Ala, His, Thr, Trp, or Met;
Xaa at position 116 is Lys, Leu, Pro, Thr, Met, Asp, Val, Glu, Arg, Trp, Ser, Asn, His, Ala, Tyr, Phe, Gln, or Ile;
Xaa at position 117 is Thr, Ser, Asn, Ile, Trp, Lys, or Pro;
Xaa at position 118 is Leu, Ser, Pro, Ala, Glu, Cys, Asp, or Tyr;
Xaa at position 119 is Glu, Ser, Lys, Pro, Leu, Thr, Tyr, or Arg;
Xaa at position 120 is Asn, Ala, Pro, Leu, His, Val, or Gln;
Xaa at position 121 is Ala, Ser, Ile, Asn, Pro, Lys, Asp, or Gly;
Xaa at position 122 is Gln, Ser, Met, Trp, Arg, Phe, Pro, His, Ile, Tyr, or Cys;
Xaa at position 123 is Ala, Met, Glu, His, Ser, Pro, Tyr, or Leu;
wherein from 1 to 14 amino acids are optionally deleted from the N-terminus and/or from 1 to 15 amino acids are optionally deleted from the C-terminus of said human interleukin-3 mutant polypeptide; and wherein from 4 to about 44 of the amino acids designated by Xaa are different from the corresponding amino acids of native (1–133) human interleukin-3; with the proviso that no more than one of the amino acids at positions 63, 82, 87, 98, 112, and 121 are different from the corresponding amino acids in native human interleukin-3; and wherein said modified human interleukin-3 (hIL-3) amino acid sequence has increased activity, relative to native human interleukin-3, in at least one assay selected from the group consisting of: AML cell proliferation, TF-1 cell proliferation and Methylcellulose assay;

$R_2$ is a hematopoietic growth factor; and

L is a linker capable of Linking $R_1$ to $R_2$; and (b) harvesting said cultured stem cells.

2. A method for ex vivo expansion of stem cells, comprising the steps of;

(a) culturing said stem cells with a growth medium comprising a chimera protein having the formula selected from the group consisting of:

$R_1$-L-$R_2$, $R_2$-L-$R_1$, $R_1$-$R_2$, $R_2$-$R_1$, $R_1$-L-$R_1$, $R_1$-$R_1$,

Met-Ala-$R_1$-L-$R_2$, Met-Ala-$R_2$-L-$R_1$, Met-Ala-$R_1$-$R_2$, Met-Ala-$R_2$-$R_1$, Met-$R_1$-L-$R_2$, Met-$R_2$-L-$R_1$, Met-$R_1$-$R_2$, Met-$R_2$-$R_1$,

Ala-$R_1$-L-$R_2$, Ala-$R_2$-L-$R_1$, -Ala-$R_1$-$R_2$ and Ala-$R_2$-$R_1$;

wherein $R_1$ is a human interleukin-3 mutant polypeptide of SEQ ID NO:4 wherein

Xaa at position 3 is Ser, Lys, Gly, Asp, Met, Gln, or Arg;
Xaa at position 4 is Asn, His, Leu, Ile, Phe, Arg, or Gln;
Xaa at position 5 is Met, Phe, Ile, Arg, Gly, Ala, or Cys;
Xaa at position 6 is Ile, Cys, Gln, Glu, Arg, Pro, or Ala;
Xaa at position 7 is Asp, Phe, Lys, Arg, Ala, Gly, Glu, Gln, Asn, Thr, Ser or Val;
Xaa at position 8 is Glu, Trp, Pro, Ser, Ala, His, Asp, Asn, Gln, Leu, Val, or Gly;
Xaa at position 9 is Ile, Val, Ala, Gly, Trp, Lys, Phe, Ser, or Arg;
Xaa at position 10 is Ile, Gly, Val, Arg, Ser, Phe, or Leu;
Xaa at position 11 is Thr, His, Gly, Gln, Arg, Pro, or Ala;
Xaa at position 12 is His, Thr, Phe, Gly, Arg, Ala, or Trp;
Xaa at position 13 is Leu, Gly, Arg, Thr, Ser, or Ala;
Xaa at position 14 is Lys, Arg, Leu, Gln, Gly, Pro, Val or Trp;
Xaa at position 15 is Gln, Asn, Leu, Pro, Arg, or Val;
Xaa at position 16 is Pro, His, Thr, Gly, Asp, Gln, Ser, Leu, or Lys;
Xaa at position 17 is Pro, Asp, Gly, Ala, Arg, Leu, or Gln;
Xaa at position 18 is Leu, Val, Arg, Gln, Asn, Gly, Ala, or Glu;
Xaa at position 19 is Pro, Leu, Gln, Ala, Thr, or Glu;
Xaa at position 20 is Leu, Val, Gly, Ser, Lys, Glu, Gln, Thr, Arg, Ala, Phe, Ile or Met;
Xaa at position 21 is Leu, Ala, Gly, Asn, Pro, Gln, or Val;
Xaa at position 22 is Asp, Leu, or Val;
Xaa at position 23 is Phe, Ser, Pro, Trp, or Ile;
Xaa at position 24 is Asn, or Ala;
Xaa at position 26 is Leu, Trp, or Arg;
Xaa at position 27 is Asn, Cys, Arg, Leu, His, Met, Pro;
Xaa at position 28 is Gly, Asp, Ser, Cys, Ala, Lys, Asn, Thr, Leu, Val, Glu, Phe, Tyr, Ile or Met;
Xaa at position 29 is Glu, Asn, Tyr, Leu, Phe, Asp, Ala, Cys, Gln, Arg, Thr, Gly or Ser;
Xaa at position 30 is Asp, Ser, Leu, Arg, Lys, Thr, Met, Trp, Glu, Asn, Gln, Ala or Pro;
Xaa at position 31 is Gln, Pro, Phe, Val, Met, Leu, Thr, Lys, Asp, Asn, Arg, Ser, Ala, Ile, Glu, His or Trp;

Xaa at position 32 is Asp, Phe, Ser, Thr, Cys, Glu, Asn, Gln, Lys, His, Ala, Tyr, Ile, Val or Gly;
Xaa at position 33 is Ile, Gly, Val, Ser, Arg, Pro, or His;
Xaa at position 34 is Leu, Ser, Cys, Arg, Ile, His, Phe, Glu, Lys, Thr, Ala, Met, Val or Asn;
Xaa at position 35 is Met, Arg, Ala, Gly, Pro, Asn, His, or Asp;
Xaa at position 36 is Glu, Leu, Thr, Asp, Tyr, Lys, Asn, Ser, Ala, Ile, Val, His, Phe, Met or Gln;
Xaa at position 37 is Asn, Arg, Met, Pro, Ser, Thr, or His;
Xaa at position 38 is Asn, His, Arg, Leu, Gly, Ser, or Thr;
Xaa at position 39 is Leu, Thr, Ala, Gly, Glu, Pro, Lys, Ser, or Met;
Xaa at position 40 is Arg, Asp, Ile, Ser, Val, Thr, Gln, Asn, Lys, His, Ala or Leu;
Xaa at position 41 is Arg, Thr, Val, Ser, Leu, or Gly;
Xaa at position 42 is Pro, Gly, Cys, Ser, Gln, Glu, Arg, His, Thr, Ala, Tyr, Phe, Leu, Val or Lys;
Xaa at position 43 is Asn or Gly;
Xaa at position 44 is Leu, Ser, Asp, Arg, Gln, Val, or Cys;
Xaa at position 45 is Glu, Tyr, His, Leu, Pro, or Arg;
Xaa at position 46 is Ala, Ser, Pro, Tyr, Asn, or Thr;
Xaa at position 47 is Phe, Asn, Glu, Pro, Lys, Arg, or Ser;
Xaa at position 48 is Asn, His, Val, Arg, Pro, Thr, Asp, or Ile;
Xaa at position 49 is Arg, Tyr, Trp, Ser, His, Pro, or Val;
Xaa at position 50 is Ala, Asn, Pro, Ser, or Lys;
Xaa at position 51 is Val, Thr, Pro, His, Leu, Phe, or Ser;
Xaa at position 52 is Lys, Ile, Arg, Val, Asn, Glu, or Ser;
Xaa at position 53 is Ser, Ala, Phe, Val, Gly, Asn, Ile, Pro, or His;
Xaa at position 54 is Leu, Val, Trp, Ser, Ile, Phe, Thr, or His;
Xaa at position 55 is Gln, Ala, Pro, Thr, Glu, Arg, Trp, Gly, or Leu;
Xaa at position 56 is Asn, Leu, Val, Trp, Pro, or Ala;
Xaa at position 57 is Ala, Met, Leu, Pro, Arg, Glu, Thr, Gln, Trp, or Asn;
Xaa at position 58 is Ser, Glu, Met, Ala, His, Asn, Arg, or Asp;
Xaa at position 59 is Ala, Glu, Asp, Leu, Ser, Gly, Thr, or Arg;
Xaa at position 60 is Ile, Met, Thr, Pro, Arg, Gly, Ala;
Xaa at position 61 is Glu, Lys, Gly, Asp, Pro, Trp, Arg, Ser, Gln, or Leu;
Xaa at position 62 is Ser, Val, Ala, Asn, Trp, Glu, Pro, Gly, or Asp;
Xaa at position 63 is Ile, Ser, Arg, Thr, or Leu;
Xaa at position 64 is Leu, Ala, Ser, Glu, Phe, Gly, or Arg;
Xaa at position 65 is Lys, Thr, Gly, Asn, Met, Arg, Ile, or Asp;
Xaa at position 66 is Asn, Trp, Val, Gly, Thr, Leu, Glu, or Arg;
Xaa at position 67 is Leu, Gln, Gly, Ala, Trp, Arg, Val, or Lys;
Xaa at position 68 is Leu, Gln, Lys, Trp, Arg, Asp, Glu, Asn, His, Thr, Ser, Ala, Tyr, Phe, Ile, Met or Val;
Xaa at position 69 is Pro, Ala, Thr, Trp, Arg, or Met;
Xaa at position 70 is Cys, Glu, Gly, Arg, Met, or Val;
Xaa at position 71 is Leu, Asn, Val, or Gln;
Xaa at position 72 is Pro, Cys, Arg, Ala, or Lys;
Xaa at position 73 is Leu, Ser, Trp, or Gly;
Xaa at position 74 is Ala, Lys, Arg, Val, or Trp;
Xaa at position 75 is Thr, Asp, Cys, Leu, Val, Glu, His, Asn, or Ser;
Xaa at position 76 is Ala, Pro, Ser, Thr, Gly, Asp, Ile, or Met;
Xaa at position 77 is Ala, Pro, Ser, Thr, Phe, Leu, Asp, or His;
Xaa at position 78 is Pro, Phe, Arg, Ser, Lys, His, Ala, Gly, Ile or Leu;

Xaa at position 79 is Thr, Asp, Ser, Asn, Pro, Ala, Leu, or Arg;
Xaa at position 80 is Arg, Ile, Ser, Glu, Leu, Val, Gln, Lys, His, Ala or Pro;
Xaa at position 81 is His, Gln, Pro, Arg, Val, Leu, Gly, Thr, Asn, Lys, Ser, Ala, Trp, Phe, Ile or Tyr;
Xaa at position 82 is Pro, Lys, Tyr, Gly, Ile, or Thr;
Xaa at position 83 is Ile, Val, Lys, Ala, or Asn;
Xaa at position 84 is His, Ile, Asn, Leu, Asp, Ala, Thr, Glu, Gln, Ser, Phe, Met, Val, Lys, Tyr or Pro;
Xaa at position 85 is Ile, Leu, Arg, Asp, Val, Pro, Gln, Gly, Ser, Phe, or His;
Xaa at position 86 is Lys, Tyr, Leu, His, Arg, Ile, Ser, Gln, Pro;
Xaa at position 87 is Asp, Pro, Met, Lys, His, Thr, Val, Tyr, Glu, Asn, Ser, Ala, Gly, Ile, Leu or Gln;
Xaa at position 88 is Gly, Leu, Glu, Lys, Ser, Tyr, or Pro;
Xaa at position 89 is Asp, or Ser;
Xaa at position 90 is Trp, Val, Cys, Tyr, Thr, Met, Pro, Leu, Gln, Lys, Ala, Phe, or Gly;
Xaa at position 91 is Asn, Pro, Ala, Phe, Ser, Trp, Gln, Tyr, Leu, Lys, Ile, Asp, or His;
Xaa at position 92 is Glu, Ser, Ala, Lys, Thr, Ile, Gly, or Pro;
Xaa at position 94 is Arg, Lys, Asp, Leu, Thr, Ile, Gln, His, Ser, Ala, or Pro;
Xaa at position 95 is Arg, Thr, Pro, Glu, Tyr, Leu, Ser, or Gly;
Xaa at position 96 is Lys, Asn, Thr, Leu, Gln, Arg, His, Glu, Ser, Ala or Trp;
Xaa at position 97 is Leu, Ile, Arg, Asp, or Met;
Xaa at position 98 is Thr, Val, Gln, Tyr, Glu, His, Ser, or Phe;
Xaa at position 99 is Phe, Ser, Cys, His, Gly, Trp, Tyr, Asp, Lys, Leu, Ile, Val or Asn;
Xaa at position 100 is Tyr, Cys, His, Ser, Trp, Arg, or Leu;
Xaa at position 101 is Leu, Asn, Val, Pro, Arg, Ala, His, Thr, Trp, or Met;
Xaa at position 102 is Lys, Leu, Pro, Thr, Met, Asp, Val, Glu, Arg, Trp, Ser, Asn, His, Ala, Tyr, Phe, Gln, or Ile;
Xaa at position 103 is Thr, Ser, Asn, Ile, Trp, Lys, or Pro;
Xaa at position 104 is Leu, Ser, Pro, Ala, Glu, Cys, Asp, or Tyr;
Xaa at position 105 is Glu, Ser, Lys, Pro, Leu, Thr, Tyr, or Arg;
Xaa at position 106 is Asn, Ala, Pro, Leu, His, Val, or Gln;
Xaa at position 107 is Ala, Ser, Ile, Asn, Pro, Lys, Asp, or Gly;
Xaa at position 108 is Gln, Ser, Met, Trp, Arg, Phe, Pro, His, Ile, Tyr, or Cys;
Xaa at position 109 is Ala, Met, Glu, His, Ser, Pro, Tyr, or Leu;

wherein from 4 to about 44 of the amino acids designated by Xaa are different from the corresponding amino acids of native (1–133) human interleukin-3; with the proviso that no more than one of the amino acids at positions 49, 68, 73. 84, 98, and 107 are different from the corresponding amino acids in native human interleukin-3; and wherein said modified human interleukin-3 (hIL-3) amino acid sequence has increased activity, relative to native human interleukin-3, in at least one assay selected from the group consisting of: AML cell proliferation, TF-1 cell proliferation and Methylcellulose assay;

$R_2$ is a hematopoietic growth factor; and

L is a linker capable of Linking $R_1$ to $R_2$; and (b) harvesting said cultured stem cells.

3. A method for ex vivo expansion of stem cells, comprising the steps of;

(a) culturing said stem cells with a growth medium comprising a chimera protein having the formula selected from the group consisting of:

$R_1$-L-$R_2$, $R_2$-L-$R_1$, $R_1$-$R_2$, $R_2$-$R_1$, $R_1$-L-$R_1$, $R_1$-$R_1$,

Met-Ala-$R_1$-L-$R_2$, Met-Ala-$R_2$-L-$R_1$, Met-Ala-$R_1$-$R_2$, Met-Ala-$R_2$-$R_1$,

Met-$R_1$-L-$R_2$, Met-$R_2$-L-$R_1$, Met-$R_1$-$R_2$, Met-$R_2$-$R_1$, Ala-$R_1$-L-$R_2$, Ala-$R_2$-L-$R_1$, Ala-$R_1$-$R_2$ and Ala-$R_2$-$R_1$;

wherein $R_1$ is a human interleukin-3 mutant polypeptide of SEQ ID NO:7
wherein; Xaa at position 18 is Asn or Ile; Xaa at position 19 is Met, Ala or Ile; Xaa at position 20 is Ile, Pro or Leu; Xaa at position 23 is Ile, Ala or Leu; Xaa at position 25 is Thr or His; Xaa at position 29 is Gln, Arg, Val or Leu; Xaa at position 32 is Leu, Ala, Asn or Arg; Xaa at position 34 is Leu or Ser; Xaa at position 37 is Phe, Pro, or Ser; Xaa at position 38 is Asn or Ala; Xaa at position 42 is Gly, Ala, Ser, Asp or Asn; Xaa at position 45 is Gln, Val, or Met; Xaa at position 46 is Asp or Ser; Xaa at position 49 is Met, Ile, Leu or Asp; Xaa at position 50 is Glu or Asp; Xaa at position 51 is Asn Arg or Ser; Xaa at position 55 is Arg, Leu, or Thr; Xaa at position 56 is Pro or Ser; Xaa at position 59 is Glu or Leu; Xaa at position 60 is Ala or Ser; Xaa at position 62 is Asn, Val or Pro; Xaa at position 63 is Arg or His; Xaa at position 65 is Val or Ser; Xaa at position 67 is Ser, Asn, His or Gly; Xaa at position 69 is Gln or Glu; Xaa at position 73 is Ala or Gly; Xaa at position 76 is Ser, Ala or Pro; Xaa at position 79 is Lys, Arg or Ser; Xaa at position 82 is Leu, Glu, Val or Trp; Xaa at position 85 is Leu or Val; Xaa at position 87 is Leu, Ser, Trp; Xaa at position 88 is Ala or Trp; Xaa at position 91 is Ala or Pro; Xaa at position 93 is Pro or Ser; Xaa at position 95 is His or Thr; Xaa at position 98 is His, Ile, or Thr; Xaa at position 100 is Lys or Arg; Xaa at position 101 is Asp, Ala or Met; Xaa at position 105 is Asn or Gln; Xaa at position 109 is Arg, Glu or Leu; Xaa at position 112 is Thr or Gln; Xaa at position 116 is Lys, Val, Trp or Ser; Xaa at position 117 is Thr or Ser; Xaa at position 120 is Asn, Gln, or His; Xaa at position 123 is Ala or Glu; wherein from four to about forty-four of the amino acids designated by Xaa are different from the corresponding amino acids of native human interleukin-3; and wherein said modified human interleukin-3 (hIL-3) amino acid sequence has increased activity, relative to native human interleukin-3, in at least one assay selected from the group consisting of: AML cell proliferation, TF-1 cell proliferation and Methylcellulose assay;

$R_2$ is a hematopoietic growth factor; and

L is a linker capable of Linking $R_1$ to $R_2$; and (b) harvesting said cultured stem cells.

4. A method for ex vivo expansion of stem cells, comprising the steps of;
(a) culturing said stem cells with a growth medium comprising a chimera protein having the formula selected from the group consisting of:

$R_1$-L-$R_2$, $R_2$-L-$R_1$, $R_1$-$R_2$, $R_2$-$R_1$, $R_1$-L-$R_1$, $R_1$-$R_1$,

Met-Ala-$R_1$-L-$R_2$, Met-Ala-$R_2$-L-$R_1$, Met-Ala-$R_1$-$R_2$, Met-Ala-$R_2$-$R_1$, Met-$R_1$-L-$R_2$, Met-$R_2$-L-$R_1$, Met-$R_1$-$R_2$,

Met-$R_2$-$R_1$, Ala-$R_1$-L-$R_2$, Ala-$R_2$-L-$R_1$, -Ala-$R_1$-$R_2$ and Ala-$R_2$-$R_1$;

wherein $R_1$ is a human interleukin-3 mutant polypeptide of SEQ ID NO:8
wherein; Xaa at position 4 is Asn or Ile; Xaa at position 5 is Met, Ala or Ile: Xaa at position 6 is Ile, Pro or Leu; Xaa at position 9 is Ile, Ala or Leu; Xaa at position 11 is Thr or His; Xaa at position 15 is Gln, Arg, Val or Leu; Xaa at position 18 is Leu, Ala, Asn or Arg; Xaa at position 20 is Leu or Ser; Xaa at position 23 is Phe, Pro, or Ser; Xaa at position 24 is Asn or Ala; Xaa at position 28 is Gly, Ala, Ser, Asp or Asn; Xaa at position 31 is Gln, Val, or Met; Xaa at position 32 is Asp or Ser; Xaa at position 35 is Met, Ile, Leu or Asp; Xaa at position 36 is Glu or Asp; Xaa at position 37 is Asn, Arg or Ser; Xaa at position 41 is Arg, Leu, or Thr; Xaa at position 42 is Pro or Ser; Xaa at position 45 is Glu or Leu; Xaa at position 46 is Ala or Ser; Xaa at position 48 is Asn, Val or Pro; Xaa at position 49 is Arg or His; Xaa at position 51 is Val or Ser; Xaa at position 53 is Ser, Asn, His or Gly; Xaa at position 55 is Gln or Glu; Xaa at position 59 is Ala or Gly; Xaa at position 62 is Ser, Ala or Pro; Xaa at position 65 is Lys, Arg or Ser; Xaa at position 67 is Leu, Glu, or Val; Xaa at position 68 is Leu, Glu, Val or Trp; Xaa at position 71 is Leu or Val; Xaa at position 73 is Leu, Ser or Trp; Xaa at position 74 is Ala or Trp; Xaa at position 77 is Ala or Pro; Xaa at position 79 is Pro or Ser; Xaa at position 81 is His or Thr; Xaa at position 84 is His, Ile, or Thr; Xaa at position 86 is Lys or Arg; Xaa at position 87 is Asp, Ala or Met; Xaa at position 91 is Asn or Glu; Xaa at position 95 is Arg, Glu, Leu; Xaa at position 98 Thr or Gln; Xaa at position 102 is Lys, Val, Trp or Ser; Xaa at position 103 is Thr or Ser; Xaa at position 106 is Asn, Gln, or His; Xaa at position 109 is Ala or Glu; wherein from four to about forty-four of the amino acids designated by Xaa are different from the corresponding amino acids of native (15–125)human interleukin-3; and wherein said modified human interleukin-3 (hIL-3) amino acid sequence has increased activity, relative to native human interleukin-3, in at least one assay selected from the group consisting of: AML cell proliferation. TF-1 cell Proliferation and Methylcellulose assay;

$R_2$ is a hematopoietic growth factor; and

L is a linker capable of Linking $R_1$ to $R_2$; and (b) harvesting said cultured stem cells.

5. The method according to claim 2 wherein $R_1$ is selected from the group consisting of:

Asn Cys Ser Ile Met Ile Asp Glu Ile Ile His His Leu Lys    SEQ ID NO:9;

Arg Pro Pro Ala Pro Leu Leu Asp Pro Asn Asn Leu Asn Ala

Glu Asp Val Asp Ile Leu Met Glu Asn Asn Leu Arg Arg Pro

Asn Leu Glu Ala Phe Asn Arg Ala Val Lys Ser Leu Gln Asn

Ala Ser Ala Ile Glu Ser Ile Leu Lys Asn Leu Leu Pro Cys

Leu Pro Leu Ala Thr Ala Ala Pro Thr Arg His Pro Ile His

```
Ile Lys Asp Gly Asp Trp Asn Glu Phe Arg Arg Lys Leu Thr
Phe Tyr Leu Lys Thr Leu Glu Asn Ala Gln Ala Gln Gln

Asn Cys Ser Ile Met Ile Asp Glu Ile Ile His His Leu Lys    SEQ ID NO:10;
Arg Pro Pro Asn Pro Leu Leu Asp Pro Asn Asn Leu Asn Ser
Glu Asp Met Asp Ile Leu Met Glu Asn Asn Leu Arg Arg Pro
Asn Leu Glu Ala Phe Asn Arg Ala Val Lys Ser Leu Gln Asn
Ala Ser Ala Ile Glu Ser Ile Leu Lys Asn Leu Leu Pro Cys
Leu Pro Leu Ala Thr Ala Ala Pro Thr Arg His Pro Ile His
Ile Lys Asp Gly Asp Trp Asn Glu Phe Arg Arg Lys Leu Thr
Phe Tyr Leu Lys Thr Leu Glu Asn Ala Gln Ala Gln Gln

Asn Cys Ser Ile Met Ile Asp Glu Ile Ile His His Leu Lys    SEQ ID NO:11;
Val Pro Pro Ala Pro Leu Leu Asp Ser Asn Asn Leu Asn Ser
Glu Asp Met Asp Ile Leu Met Glu Asn Asn Leu Arg Arg Pro
Asn Leu Glu Ala Phe Asn Arg Ala Val Lys Ser Leu Gln Asn
Ala Ser Ala Ile Glu Ser Ile Leu Lys Asn Leu Leu Pro Cys
Leu Pro Leu Ala Thr Ala Ala Pro Thr Arg His Pro Ile His
Ile Lys Asp Gly Asp Trp Asn Glu Phe Arg Arg Lys Leu Thr
Phe Tyr Leu Lys Thr Leu Glu Asn Ala Gln Ala Gln Gln

Asn Cys Ser Asn Met Ile Asp Glu Ile Ile Thr His Leu Lys    SEQ ID NO:12;
Gln Pro Pro Leu Pro Leu Leu Asp Phe Asn Asn Leu Asn Gly
Glu Asp Gln Asp Ile Leu Met Glu Arg Asn Leu Arg Leu Pro
Asn Leu Leu Ala Phe Val Arg Ala Val Lys Asn Leu Glu Asn
Ala Ser Ala Ile Glu Ser Ile Leu Lys Asn Leu Leu Pro Cys
Leu Pro Leu Ala Thr Ala Ala Pro Thr Arg His Pro Ile His
Ile Lys Asp Gly Asp Trp Asn Glu Phe Arg Arg Lys Leu Thr
Phe Tyr Leu Lys Thr Leu Glu Asn Ala Gln Ala Gln Gln

Asn Cys Ser Asn Met Ile Asp Glu Ile Ile Thr His Leu Lys    SEQ ID NO:13;
Gln Pro Pro Leu Pro Leu Leu Asp Phe Asn Asn Leu Asn Gly
Glu Asp Gln Asp Ile Leu Met Glu Arg Asn Leu Arg Leu Pro
Asn Leu Glu Ser Phe Val Arg Ala Val Lys Asn Leu Glu Asn
Ala Ser Ala Ile Glu Ser Ile Leu Lys Asn Leu Leu Pro Cys
Leu Pro Leu Ala Thr Ala Ala Pro Thr Arg His Pro Ile His
Ile Lys Asp Gly Asp Trp Asn Glu Phe Arg Arg Lys Leu Thr
Phe Tyr Leu Lys Thr Leu Glu Asn Ala Gln Ala Gln Gln

Asn Cys Ser Asn Met Ile Asp Glu Ile Ile Thr His Leu Lys    SEQ ID NO:14;
Gln Pro Pro Leu Pro Leu Leu Asp Phe Asn Asn Leu Asn Gly
Glu Asp Gln Asp Ile Leu Met Glu Arg Asn Leu Arg Thr Pro
Asn Leu Leu Ala Phe Val Arg Ala Val Lys His Leu Glu Asn
```

-continued

```
Ala Ser Ala Ile Glu Ser Ile Leu Lys Asn Leu Leu Pro Cys
Leu Pro Leu Ala Thr Ala Ala Pro Thr Arg His Pro Ile His
Ile Lys Asp Gly Asp Trp Asn Glu Phe Arg Arg Lys Leu Thr
Phe Tyr Leu Lys Thr Leu Glu Asn Ala Gln Ala Gln Gln

Asn Cys Ser Asn Met Ile Asp Glu Ile Ile Thr His Leu Lys    SEQ ID NO:15;
Gln Pro Pro Leu Pro Leu Leu Asp Phe Asn Asn Leu Asn Gly
Glu Asp Gln Asp Ile Leu Met Glu Asn Asn Leu Arg Arg Pro
Asn Leu Glu Ala Phe Asn Arg Ala Val Lys Ser Leu Gln Asn
Ala Ser Gly Ile Glu Ala Ile Leu Arg Asn Leu Gln Pro Cys
Leu Pro Ser Ala Thr Ala Ala Pro Ser Arg His Pro Ile Ile
Ile Lys Ala Gly Asp Trp Gln Glu Phe Arg Arg Lys Leu Thr
Phe Tyr Leu Lys Thr Leu Glu Asn Ala Gln Ala Gln Gln

Asn Cys Ser Asn Met Ile Asp Glu Ile Ile Thr His Leu Lys    SEQ ID NO:16;
Gln Pro Pro Leu Pro Leu Leu Asp Phe Asn Asn Leu Asn Gly
Glu Asp Gln Asp Ile Leu Met Glu Asn Asn Leu Arg Arg Pro
Asn Leu Glu Ala Phe Asn Arg Ala Val Lys Ser Leu Gln Asn
Ala Ser Gly Ile Glu Ala Ile Leu Arg Asn Leu Val Pro Cys
Leu Pro Ser Ala Thr Ala Ala Pro Ser Arg His Pro Ile Thr
Ile Lys Ala Gly Asp Trp Gln Glu Phe Arg Arg Lys Leu Thr
Phe Tyr Leu Lys Thr Leu Glu Asn Ala Gln Ala Gln Gln

Asn Cys Ser Asn Met Ile Asp Glu Ile Ile Thr His Leu Lys    SEQ ID NO:17;
Gln Pro Pro Leu Pro Leu Leu Asp Phe Asn Asn Leu Asn Gly
Glu Asp Gln Asp Ile Leu Met Glu Asn Asn Leu Arg Arg Pro
Asn Leu Glu Ala Phe Asn Arg Ala Val Lys Ser Leu Gln Asn
Ala Ser Ala Ile Glu Ser Ile Leu Lys Asn Leu Leu Pro Cys
Leu Pro Leu Ala Thr Ala Ala Pro Thr Arg His Pro Ile His
Ile Lys Asp Gly Asp Trp Asn Glu Phe Arg Glu Lys Leu Thr
Phe Tyr Leu Val Thr Leu Glu Gln Ala Gln Glu Gln Gln

Asn Cys Ser Asn Met Ile Asp Glu Ile Ile Thr His Leu Lys    SEQ ID NO:18;
Gln Pro Pro Leu Pro Leu Leu Asp Phe Asn Asn Leu Asn Gly
Glu Asp Gln Asp Ile Leu Met Glu Asn Asn Leu Arg Arg Pro
Asn Leu Glu Ala Phe Asn Arg Ala Val Lys Ser Leu Gln Asn
Ala Ser Ala Ile Glu Ser Ile Leu Lys Asn Leu Leu Pro Cys
Leu Pro Leu Ala Thr Ala Ala Pro Thr Arg His Pro Ile His
Ile Lys Asp Gly Asp Trp Asn Glu Phe Arg Glu Lys Leu Thr
Phe Tyr Leu Val Ser Leu Glu His Ala Gln Glu Gln Gln

Asn Cys Ser Asn Met Ile Asp Glu Ile Ile Thr His Leu Lys    SEQ ID NO:19;
```

-continued

```
Gln Pro Pro Leu Pro Leu Leu Asp Phe Asn Asn Leu Asn Gly
Glu Asp Gln Asp Ile Leu Met Glu Asn Asn Leu Arg Arg Pro
Asn Leu Glu Ala Phe Asn Arg Ala Val Lys Ser Leu Gln Asn
Ala Ser Gly Ile Glu Ala Ile Leu Arg Asn Leu Gln Pro Cys
Leu Pro Ser Ala Thr Ala Ala Pro Ser Arg His Pro Ile Ile
Ile Lys Ala Gly Asp Trp Gln Glu Phe Arg Glu Lys Leu Thr
Phe Tyr Leu Val Thr Leu Glu Gln Ala Gln Glu Gln Gln

Asn Cys Ser Asn Met Ile Asp Glu Ile Ile Thr His Leu Lys   SEQ ID NO:20;
Gln Pro Pro Leu Pro Leu Leu Asp Phe Asn Asn Leu Asn Gly
Glu Asp Gln Asp Ile Leu Met Glu Asn Asn Leu Arg Arg Pro
Asn Leu Glu Ala Phe Asn Arg Ala Val Lys Ser Leu Gln Asn
Ala Ser Gly Ile Glu Ala Ile Leu Arg Asn Leu Val Pro Cys
Leu Pro Ser Ala Thr Ala Ala Pro Ser Arg His Pro Ile Thr
Ile Lys Ala Gly Asp Trp Gln Glu Phe Arg Glu Lys Leu Thr
Phe Tyr Leu Val Thr Leu Glu Gln Ala Gln Glu Gln Gln

Asn Cys Ser Asn Met Ile Asp Glu Ile Ile Thr His Leu Lys   SEQ ID NO:21;
Gln Pro Pro Leu Pro Leu Leu Asp Phe Asn Asn Leu Asn Gly
Glu Asp Gln Asp Ile Leu Met Glu Asn Asn Leu Arg Arg Pro
Asn Leu Glu Ala Phe Asn Arg Ala Val Lys Ser Leu Gln Asn
Ala Ser Gly Ile Glu Ala Ile Leu Arg Asn Leu Val Pro Cys
Leu Pro Ser Ala Thr Ala Ala Pro Ser Arg His Pro Ile Thr
Ile Lys Ala Gly Asp Trp Gln Glu Phe Arg Glu Lys Leu Thr
Phe Tyr Leu Val Ser Leu Glu His Ala Gln Glu Gln Gln

Asn Cys Ser Ile Met Ile Asp Glu Ile Ile His His Leu Lys   SEQ ID NO:22;
Arg Pro Pro Ala Pro Leu Leu Asp Pro Asn Asn Leu Asn Ala
Glu Asp Val Asp Ile Leu Met Glu Arg Asn Leu Arg Leu Pro
Asn Leu Glu Ser Phe Val Arg Ala Val Lys Asn Leu Glu Asn
Ala Ser Ala Ile Glu Ser Ile Leu Lys Asn Leu Leu Pro Cys
Leu Pro Leu Ala Thr Ala Ala Pro Thr Arg His Pro Ile His
Ile Lys Asp Gly Asp Trp Asn Glu Phe Arg Arg Lys Leu Thr
Phe Tyr Leu Lys Thr Leu Glu Asn Ala Gln Ala Gln Gln

Asn Cys Ser Ile Met Ile Asp Glu Ile Ile His His Leu Lys   SEQ ID NO:23;
Arg Pro Pro Asn Pro Leu Leu Asp Pro Asn Asn Leu Asn Ser
Glu Asp Met Asp Ile Leu Met Glu Arg Asn Leu Arg Thr Pro
Asn Leu Leu Ala Phe Val Arg Ala Val Lys His Leu Glu Asn
Ala Ser Ala Ile Glu Ser Ile Leu Lys Asn Leu Leu Pro Cys
Leu Pro Leu Ala Thr Ala Ala Pro Thr Arg His Pro Ile His
Ile Lys Asp Gly Asp Trp Asn Glu Phe Arg Arg Lys Leu Thr
```

```
Phe Tyr Leu Lys Thr Leu Glu Asn Ala Gln Ala Gln Gln

Asn Cys Ser Ile Met Ile Asp Glu Ile Ile His His Leu Lys    SEQ ID NO:24;
Val Pro Pro Ala Pro Leu Leu Asp Ser Asn Asn Leu Asn Ser
Glu Asp Met Asp Ile Leu Met Glu Arg Asn Leu Arg Leu Pro
Asn Leu Leu Ala Phe Val Arg Ala Val Lys Asn Leu Glu Asn
Ala Ser Ala Ile Glu Ser Ile Leu Lys Asn Leu Leu Pro Cys
Leu Pro Leu Ala Thr Ala Ala Pro Thr Arg His Pro Ile His
Ile Lys Asp Gly Asp Trp Asn Glu Phe Arg Arg Lys Leu Thr
Phe Tyr Leu Lys Thr Leu Glu Asn Ala Gln Ala Gln Gln

Met Ala Asn Cys Ser Asn Met Ile Asp Glu Ile Ile Thr His    SEQ ID NO:25;
Leu Lys Gln Pro Pro Leu Pro Leu Leu Asp Phe Asn Asn Leu
Asn Gly Glu Asp Gln Asp Ile Leu Met Glu Asn Asn Leu Arg
Arg Pro Asn Leu Glu Ala Phe Asn Arg Ala Val Lys Ser Leu
Gln Asn Ala Ser Gly Ile Glu Ala Ile Leu Arg Asn Leu Gln
Pro Cys Leu Pro Ser Ala Thr Ala Ala Pro Ser Arg His Pro
Ile Ile Ile Lys Ala Gly Asp Trp Gln Glu Phe Arg Glu Lys
Leu Thr Phe Tyr Leu Val Thr Leu Glu Gln Ala Gln Glu Gln
Gln

Met Ala Asn Cys Ser Asn Met Ile Asp Glu Ile Ile Thr His    SEQ ID NO:26;
Leu Lys Gln Pro Pro Leu Pro Leu Leu Asp Phe Asn Asn Leu
Asn Gly Glu Asp Gln Asp Ile Leu Met Glu Asn Asn Leu Arg
Arg Pro Asn Leu Glu Ala Phe Asn Arg Ala Val Lys Ser Leu
Gln Asn Ala Ser Gly Ile Glu Ala Ile Leu Arg Asn Leu Val
Pro Cys Leu Pro Ser Ala Thr Ala Ala Pro Ser Arg His Pro
Ile Thr Ile Lys Ala Gly Asp Trp Gln Glu Phe Arg Glu Lys
Leu Thr Phe Tyr Leu Val Thr Leu Glu Gln Ala Gln Glu Gln
Gln

Met Ala Asn Cys Ser Asn Met Ile Asp Glu Ile Ile Thr His    SEQ ID NO:27;
Leu Lys Gln Pro Pro Leu Pro Leu Leu Asp Phe Asn Asn Leu
Asn Gly Glu Asp Gln Asp Ile Leu Met Glu Asn Asn Leu Arg
Arg Pro Asn Leu Glu Ala Phe Asn Arg Ala Val Lys Ser Leu
Gln Asn Ala Ser Gly Ile Glu Ala Ile Leu Arg Asn Leu Val
Pro Cys Leu Pro Ser Ala Thr Ala Ala Pro Ser Arg His Pro
Ile Thr Ile Lys Ala Gly Asp Trp Gln Glu Phe Arg Glu Lys
Leu Thr Phe Tyr Leu Val Ser Leu Glu His Ala Gln Glu Gln
Gln

Met Ala Asn Cys Ser Ile Met Ile Asp Glu Ile Ile His His    SEQ ID NO:28;
Leu Lys Arg Pro Pro Ala Pro Leu Leu Asp Pro Asn Asn Leu
```

-continued

Asn Ala Glu Asp Val Asp Ile Leu Met Glu Arg Asn Leu Arg
Leu Pro Asn Leu Glu Ser Phe Val Arg Ala Val Lys Asn Leu
Glu Asn Ala Ser Ala Ile Glu Ser Ile Leu Lys Asn Leu Leu
Pro Cys Leu Pro Leu Ala Thr Ala Ala Pro Thr Arg His Pro
Ile His Ile Lys Asp Gly Asp Trp Asn Glu Phe Arg Arg Lys
Leu Thr Phe Tyr Leu Lys Thr Leu Glu Asn Ala Gln Ala Gln
Gln

Met Ala Asn Cys Ser Ile Met Ile Asp Glu Ile Ile His His    SEQ ID NO:29;
Leu Lys Arg Pro Pro Asn Pro Leu Leu Asp Pro Asn Asn Leu
Asn Ser Glu Asp Met Asp Ile Leu Met Glu Arg Asn Leu Arg
Thr Pro Asn Leu Leu Ala Phe Val Arg Ala Val Lys His Leu
Glu Asn Ala Ser Ala Ile Glu Ser Ile Leu Lys Asn Leu Leu
Pro Cys Leu Pro Leu Ala Thr Ala Ala Pro Thr Arg His Pro
Ile His Ile Lys Asp Gly Asp Trp Asn Glu Phe Arg Arg Lys
Leu Thr Phe Tyr Leu Lys Thr Leu Glu Asn Ala Gln Ala Gln
Gln

Met Ala Asn Cys Ser Ile Met Ile Asp Glu Ile Ile His His    SEQ ID NO:30;
Leu Lys Val Pro Pro Ala Pro Leu Leu Asp Ser Asn Asn Leu
Asn Ser Glu Asp Met Asp Ile Leu Met Glu Arg Asn Leu Arg
Leu Pro Asn Leu Leu Ala Phe Val Arg Ala Val Lys Asn Leu
Glu Asn Ala Ser Ala Ile Glu Ser Ile Leu Lys Asn Leu Leu
Pro Cys Leu Pro Leu Ala Thr Ala Ala Pro Thr Arg His Pro
Ile His Ile Lys Asp Gly Asp Trp Asn Glu Phe Arg Arg Lys
Leu Thr Phe Tyr Leu Lys Thr Leu Glu Asn Ala Gln Ala Gln
Gln

Met Ala Asn Cys Ser Ile Met Ile Asp Glu Ile Ile His His    SEQ ID NO:31;
Leu Lys Arg Pro Pro Ala Pro Leu Leu Asp Pro Asn Asn Leu
Asn Ala Glu Asp Val Asp Ile Leu Met Glu Arg Asn Leu Arg
Leu Pro Asn Leu Glu Ser Phe Val Arg Ala Val Lys Asn Leu
Glu Asn Ala Ser Gly Ile Glu Ala Ile Leu Arg Asn Leu Gln
Pro Cys Leu Pro Ser Ala Thr Ala Ala Pro Ser Arg His Pro
Ile Ile Ile Lys Ala Gly Asp Trp Gln Glu Phe Arg Glu Lys
Leu Thr Phe Tyr Leu Val Thr Leu Glu Gln Ala Gln Glu Gln
Gln

Met Ala Asn Cys Ser Ile Met Ile Asp Glu Ile Ile His His    SEQ ID NO:32;
Leu Lys Arg Pro Pro Asn Pro Leu Leu Asp Pro Asn Asn Leu
Asn Ser Glu Asp Met Asp Ile Leu Met Glu Arg Asn Leu Arg
Thr Pro Asn Leu Leu Ala Phe Val Arg Ala Val Lys His Leu

-continued

```
Glu Asn Ala Ser Gly Ile Glu Ala Ile Leu Arg Asn Leu Gln
Pro Cys Leu Pro Ser Ala Thr Ala Ala Pro Ser Arg His Pro
Ile Ile Ile Lys Ala Gly Asp Trp Gln Glu Phe Arg Glu Lys
Leu Thr Phe Tyr Leu Val Thr Leu Glu Gln Ala Gln Glu Gln
Gln

Met Ala Asn Cys Ser Ile Met Ile Asp Glu Ile Ile His His    SEQ ID NO:33;
Leu Lys Val Pro Pro Ala Pro Leu Leu Asp Ser Asn Asn Leu
Asn Ser Glu Asp Met Asp Ile Leu Met Glu Arg Asn Leu Arg
Leu Pro Asn Leu Leu Ala Phe Val Arg Ala Val Lys Asn Leu
Glu Asn Ala Ser Gly Ile Glu Ala Ile Leu Arg Asn Leu Gln
Pro Cys Leu Pro Ser Ala Thr Ala Ala Pro Ser Arg His Pro
Ile Ile Ile Lys Ala Gly Asp Trp Gln Glu Phe Arg Glu Lys
Leu Thr Phe Tyr Leu Val Thr Leu Glu Gln Ala Gln Glu Gln
Gln

Met Ala Asn Cys Ser Ile Met Ile Asp Glu Ile Ile His His    SEQ ID NO:34;
Leu Lys Arg Pro Pro Ala Pro Leu Leu Asp Pr6 Asn Asn Leu
Asn Ala Glu Asp Val Asp Ile Leu Met Glu Arg Asn Leu Arg
Leu Pro Asn Leu Glu Ser Phe Val Arg Ala Val Lys Asn Leu
Glu Asn Ala Ser Gly Ile Glu Ala Ile Leu Arg Asn Leu Val
Pro Cys Leu Pro Ser Ala Thr Ala Ala Pro Ser Arg His Pro
Ile Thr Ile Lys Ala Gly Asp Trp Gln Glu Phe Arg Glu Lys
Leu Thr Phe Tyr Leu Val Thr Leu Glu Gln Ala Gln Glu Gln
Gln

Met Ala Asn Cys Ser Ile Met Ile Asp Glu Ile Ile His His    SEQ ID NO:35;
Leu Lys Val Pro Pro Ala Pro Leu Leu Asp Ser Asn Asn Leu
Asn Ser Glu Asp Met Asp Ile Leu Met Glu Arg Asn Leu Arg
Leu Pro Asn Leu Leu Ala Phe Val Arg Ala Val Lys Asn Leu
Glu Asn Ala Ser Gly Ile Glu Ala Ile Leu Arg Asn Leu Val
Pro Cys Leu Pro Ser Ala Thr Ala Ala Pro Ser Arg His Pro
Ile Thr Ile Lys Ala Gly Asp Trp Gln Glu Phe Arg Glu Lys
Leu Thr Phe Tyr Leu Val Thr Leu Glu Gln Ala Gln Glu Gln
Gln

Met Ala Asn Cys Ser Ile Met Ile Asp Glu Ile Ile His His    SEQ ID NO:36;
Leu Lys Arg Pro Pro Asn Pro Leu Leu Asp Pro Asn Asn Leu
Asn Ser Glu Asp Met Asp Ile Leu Met Glu Arg Asn Leu Arg
Thr Pro Asn Leu Leu Ala Phe Val Arg Ala Val Lys His Leu
Glu Asn Ala Ser Gly Ile Glu Ala Ile Leu Arg Asn Leu Val
Pro Cys Leu Pro Ser Ala Thr Ala Ala Pro Ser Arg His Pro
```

-continued

```
Ile Thr Ile Lys Ala Gly Asp Trp Gln Glu Phe Arg Glu Lys

Leu Thr Phe Tyr Leu Val Ser Leu Glu His Ala Gln Glu Gln

Gln

Met Ala Asn Cys Ser Ile Met Ile Asp Glu Ile Ile His His    SEQ ID NO:37;

Leu Lys Val Pro Pro Ala Pro Leu Leu Asp Ser Asn Asn Leu

Asn Ser Glu Asp Met Asp Ile Leu Met Glu Arg Asn Leu Arg

Leu Pro Asn Leu Leu Ala Phe Val Arg Ala Val Lys Asn Leu

Glu Asn Ala Ser Gly Ile Glu Ala Ile Leu Arg Asn Leu Val

Pro Cys Leu Pro Ser Ala Thr Ala Ala Pro Ser Arg His Pro

Ile Thr Ile Lys Ala Gly Asp Trp Gln Glu Phe Arg Glu Lys

Leu Thr Phe Tyr Leu Val Ser Leu Glu His Ala Gln Glu Gln

Gln

Met Ala Asn Cys Ser Ile Met Ile Asp Glu Ile Ile His His    SEQ ID NO:38;

Leu Lys Arg Pro Pro Asn Pro Leu Leu Asp Pro Asn Asn Leu

Asn Ser Glu Asp Met Asp Ile Leu Met Glu Arg Asn Leu Arg

Thr Pro Asn Leu Leu Ala Phe Val Arg Ala Val Lys His Leu

Glu Asn Ala Ser Gly Ile Glu Ala Ile Leu Arg Asn Leu Val

Pro Cys Leu Pro Ser Ala Thr Ala Ala Pro Ser Arg His Pro

Ile Thr Ile Lys Ala Gly Asp Trp Gln Glu Phe Arg Glu Lys

Leu Thr Phe Tyr Leu Val Thr Leu Glu Gln Ala Gln Glu Gln

Gln

Met Ala Asn Cys Ser Ile Met Ile Asp Glu Ile Ile His His    SEQ ID NO:39;

Leu Lys Arg Pro Pro Ala Pro Leu Leu Asp Pro Asn Asn Leu

Asn Ala Glu Asp Val Asp Ile Leu Met Glu Arg Asn Leu Arg

Leu Pro Asn Leu Glu Ser Phe Val Arg Ala Val Lys Asn Leu

Glu Asn Ala Ser Gly Ile Glu Ala Ile Leu Arg Asn Leu Val

Pro Cys Leu Pro Ser Ala Thr Ala Ala Pro Ser Arg His Pro

Ile Thr Ile Lys Ala Gly Asp Trp Gln Glu Phe Arg Glu Lys

Leu Thr Phe Tyr Leu Val Ser Leu Glu His Ala Gln Glu Gln

Gln

Met Ala Asn Cys Ser Ile Met Ile Asp Glu Ile Ile His His    SEQ ID NO:40;

Leu Lys Arg Pro Pro Ala Pro Leu Leu Asp Pro Asn Asn Leu

Asn Ala Glu Asp Val Asp Ile Leu Met Asp Arg Asn Leu Arg

Leu Ser Asn Leu Glu Ser Phe Val Arg Ala Val Lys Asn Leu

Glu Asn Ala Ser Gly Ile Glu Ala Ile Leu Arg Asn Leu Gln

Pro Cys Leu Pro Ser Ala Thr Ala Ala Pro Ser Arg His Pro

Ile Ile Ile Lys Ala Gly Asp Trp Gln Glu Phe Arg Glu Lys

Leu Thr Phe Tyr Leu Val Thr Leu Glu Gln Ala Gln Glu Gln
```

-continued

Gln

```
Met Ala Asn Cys Ser Ile Met Ile Asp Glu Ala Ile His His    SEQ ID NO:41;
Leu Lys Arg Pro Pro Ala Pro Ser Leu Asp Pro Asn Asn Leu
Asn Asp Glu Asp Met Ser Ile Leu Met Glu Arg Asn Leu Arg
Leu Pro Asn Leu Glu Ser Phe Val Arg Ala Val Lys Asn Leu
Glu Asn Ala Ser Gly Ile Glu Ala Ile Leu Arg Asn Leu Gln
Pro Cys Leu Pro Ser Ala Thr Ala Ala Pro Ser Arg His Pro
Ile Ile Ile Lys Ala Gly Asp Trp Gln Glu Phe Arg Glu Lys
Leu Thr Phe Tyr Leu Val Thr Leu Glu Gln Ala Gln Glu Gln
Gln

Met Ala Asn Cys Ser Ile Met Ile Asp Glu Ile Ile His His    SEQ ID NO:42;
Leu Lys Arg Pro Pro Ala Pro Leu Leu Asp Pro Asn Asn Leu
Asn Asp Glu Asp Met Ser Ile Leu Met Glu Arg Asn Leu Arg
Leu Pro Asn Leu Glu Ser Phe Val Arg Ala Val Lys Asn Leu
Glu Asn Ala Ser Gly Ile Glu Ala Ile Leu Arg Asn Leu Gln
Pro Cys Leu Pro Ser Ala Thr Ala Ala Pro Ser Arg His Pro
Ile Ile Ile Lys Ala Gly Asp Trp Gln Glu Phe Arg Glu Lys
Leu Thr Phe Tyr Leu Val Thr Leu Glu Gln Ala Gln Glu Gln
Gln

Met Ala Asn Cys Ser Ile Met Ile Asp Glu Ile Ile His His    SEQ ID NO:43;
Leu Lys Arg Pro Pro Ala Pro Leu Leu Asp Pro Asn Asn Leu
Asn Ala Glu Asp Val Asp Ile Leu Met Asp Arg Asn Leu Arg
Leu Pro Asn Leu Glu Ser Phe Val Arg Ala Val Lys Asn Leu
Glu Asn Ala Ser Gly Ile Glu Ala Ile Leu Arg Asn Leu Gln
Pro Cys Leu Pro Ser Ala Thr Ala Ala Pro Ser Arg His Pro
Ile Ile Ile Lys Ala Gly Asp Trp Gln Glu Phe Arg Glu Lys
Leu Thr Phe Tyr Leu Val Thr Leu Glu Gln Ala Gln Glu Gln
Gln

Met Ala Asn Cys Ser Ile Met Ile Asp Glu Ile Ile His His    SEQ ID NO:44;
Leu Lys Arg Pro Pro Ala Pro Leu Leu Asp Pro Asn Asn Leu
Asn Asp Glu Asp Val Ser Ile Leu Met Glu Arg Asn Leu Arg
Leu Pro Asn Leu Glu Ser Phe Val Arg Ala Val Lys Asn Leu
Glu Asn Ala Ser Gly Ile Glu Ala Ile Leu Arg Asn Leu Gln
Pro Cys Leu Pro Ser Ala Thr Ala Ala Pro Ser Arg His Pro
Ile Ile Ile Lys Ala Gly Asp Trp Gln Glu Phe Arg Glu Lys
Leu Thr Phe Tyr Leu Val Thr Leu Glu Gln Ala Gln Glu Gln
Gln
```

```
Met Ala Asn Cys Ser Ile Met Ile Asp Glu Ile Ile His His    SEQ ID NO:45;

Leu Lys Arg Pro Pro Ala Pro Leu Leu Asp Pro Asn Asn Leu

Asn Asp Glu Asp Met Ser Ile Leu Met Glu Arg Asn Leu Arg

Leu Pro Asn Leu Glu Ser Phe Val Arg Ala Val Lys Asn Leu

Glu Asn Ala Ser Gly Ile Glu Ala Ile Leu Arg Asn Leu Gln

Pro Cys Leu Pro Ser Ala Thr Ala Ala Pro Ser Arg His Pro

Ile Ile Ile Lys Ala Gly Asp Trp Gln Glu Phe Arg Glu Lys

Leu Thr Phe Tyr Leu Val Thr Leu Glu Gln Ala Gln Glu Gln

Gln

Met Ala Tyr Pro Glu Thr Asp Tyr Lys Asp Asp Asp Asp Lys    SEQ ID NO:46;

Asn Cys Ser Ile Met Ile Asp Glu Ile Ile His His Leu Lys

Arg Pro Pro Ala Pro Leu Leu Asp Pro Asn Asn Leu Asn Ala

Glu Asp Val Asp Ile Leu Met Glu Arg Asn Leu Arg Leu Pro

Asn Leu Glu Ser Phe Val Arg Ala Val Lys Asn Leu Glu Asn

Ala Ser Gly Ile Glu Ala Ile Leu Arg Asn Leu Gln Pro Cys

Leu Pro Ser Ala Thr Ala Ala Pro Ser Arg His Pro Ile Ile

Ile Lys Ala Gly Asp Trp Gln Glu Phe Arg Glu Lys Leu Thr

Phe Tyr Leu Val Thr Leu Glu Gln Ala Gln Glu Gln Gln

Met Ala Tyr Pro Glu Thr Asp Tyr Lys Asp Asp Asp Asp Lys    SEQ ID NO:47;

Asn Cys Ser Ile Met Ile Asp Glu Ile Ile His His Leu Lys

Arg Pro Pro Asn Pro Leu Leu Asp Pro Asn Asn Leu Asn Ser

Glu Asp Met Asp Ile Leu Met Glu Arg Asn Leu Arg Thr Pro

Asn Leu Leu Ala Phe Val Arg Ala Val Lys His Leu Glu Asn

Ala Ser Gly Ile Glu Ala Ile Leu Arg Asn Leu Gln Pro Cys

Leu Pro Ser Ala Thr Ala Ala Pro Ser Arg His Pro Ile Ile

Ile Lys Ala Gly Asp Trp Gln Glu Phe Arg Glu Lys Leu Thr

Phe Tyr Leu Val Thr Leu Glu Gln Ala Gln Glu Gln Gln and

Met Ala Asn Cys Ser Ile Met Ile Asp Glu Leu Ile His His    SEQ ID NO:48;

Leu Lys Ile Pro Pro Asn Pro Ser Leu Asp Ser Ala Asn Leu

Asn Ser Glu Asp Val Ser Ile Leu Met Glu Arg Asn Leu Arg

Thr Pro Asn Leu Leu Ala Phe Val Arg Ala Val Lys His Leu

Glu Asn Ala Ser Gly Ile Glu Ala Ile Leu Arg Asn Leu Gln

Pro Cys Leu Pro Ser Ala Thr Ala Ala Pro Ser Arg His Pro

Ile Ile Ile Lys Ala Gly Asp Trp Gln Glu Phe Arg Glu Lys

Leu Thr Phe Tyr Leu Val Thr Leu Glu Gln Ala Gln Glu Gln

Gln
```

6. The method of claim 1, 2, 3, 4 or 5 wherein is $R_2$ is $R_1$ or a hematopoietic growth factor selected from the group consisting of: GM-CSF, CSF-1, G-CSF, G-CSF Ser[17], c-mpl ligand (TPO), MGDF, M-CSF, erythropoietin (EPO), IL-1, IL-2, IL-3, IL-4, IL-5, IL-6, IL-7, IL-8, IL-9, IL-10, IL-11, IL-12, IL-13, IL-15, IL-16, LIF, flt3 ligand, human growth hormone, B-cell growth factor, B-cell differentiation factor, eosinophil differentiation factor and stem cell factor (SCF).

7. The method of claim 6 wherein is $R_2$ is selected from the group consisting of G-CSF, G-CSF Ser,[17] flt3 ligand and c-mpl ligand.

8. The method of claim 2 wherein said chimera protein is selected from group consisting of: SEQ ID NO:121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 165, 166, 167 and 168.

9. The method of claim 8 wherein said chimera protein is selected from group consisting of: SEQ ID NO:124, SEQ ID NO:133, SEQ ID NO:154 and SEQ ID NO:155.

10. The method of claim 1, 2, 3, 4, 5, 8 or 9 wherein said culture medium further comprises a hematopoietic growth factor selected from the group consisting of: GM-CSF, CSF-1, G-CSF, G-CSF Ser[17], c-mpl ligand (TPO), MGDF, M-CSF, erythropoietin (EPO), IL-1, IL-4, IL-2, IL-5, IL-6, IL-7, IL-8, IL-9, IL-10, IL-11, IL-12, IL-13, IL-15, IL-16, LIF, flt3 ligand, human growth hormone, B-cell growth factor, B-cell differentiation factor, eosinophil differentiation factor and stem cell factor (SCF).

11. The method of claim 6 wherein said culture medium further comprises a hematopoietic growth factor selected from the group consisting of: GM-CSF, CSF-1, G-CSF, G-CSF Ser[17], c-mpl ligand (TPO), MGDF, M-CSF, erythropoietin (EPO), IL-1, IL-4, IL-2, IL-5, IL-6, IL-7, IL-8, IL-9, IL-10, IL-11, IL-12, IL-13, IL-15, IL-16, LIF, flt3 ligand, human growth hormone, B-cell growth factor, B-cell differentiation factor, eosinophil differentiation factor and stem cell factor (SCF).

12. The method of claim 7 wherein said culture medium further comprises a hematopoietic growth factor selected from the group consisting of: GM-CSF, CSF-1, G-CSF, G-CSF Ser[17], c-mpl ligand (TPO), MGDF, M-CSF, erythropoietin (EPO), IL-1, IL-4, IL-2, IL-5, IL-6, IL-7, IL-8, IL-9, IL-10, IL-11, IL-12, IL-13, IL-15, IL-16, LIF, flt3 ligand, human growth hormone, B-cell growth factor, B-cell differentiation factor, eosinophil differentiation factor and stem cell factor (SCF).

13. The method of claim 1 wherein said mutant human interleukin-3 polypeptide has at least three times greater activity than native human interleukin-3, in at least one assay selected from the group consisting of: AML cell proliferation, TF-1 cell proliferation and Methylcellulose assay.

14. The method of claim 7 wherein said mutant human interleukin-3 polypeptide has at least three times greater activity than native human interleukin-3, in at least one assay selected from the group consisting of: AML cell proliferation, TF-1 cell proliferation and Methylcellulose assay.

15. The method of claim 1 further comprising the step of separating the stem cells from a mixed population of cells prior to culturing the stem cells.

16. The method of claim 15 wherein said stem cells are separated from a mixed population of cells based on the stem cells having CD34 surface antigen.

17. A method for treatment of a patient having a hematopoietic disorder, comprising the steps of;
  (a) removing stem cells from said patient or a donor;
  (b) culturing said stem cells with a growth medium comprising a chimera protein having the formula selected from the group consisting of:

$R_1$-L-$R_2$, $R_2$-L-$R_1$, $R_1$-$R_2$, $R_2$-$R_1$, $R_1$-L-$R_1$, $R_1$-$R_1$,

Met-Ala-$R_1$-L-$R_2$, Met-Ala-$R_2$-L-$R_1$, Met-Ala-$R_1$-$R_2$, Met-Ala-$R_2$-$R_1$, Met-$R_1$-L-$R_2$, Met-$R_2$-L-$R_1$, Met-$R_1$-$R_2$, Met-$R_2$-$R_1$,

Ala-$R_1$-L-$R_2$, Ala-$R_2$-L-$R_1$, -Ala-$R_1$-$R_2$ and Ala-$R_2$-$R_1$;

wherein $R_1$ is a human interleukin-3 mutant polypeptide of SEQ ID NO:1
wherein
Xaa at position 17 is Ser, Lys, Gly, Asp, Met, Gln, or Arg;
Xaa at position 18 is Asn, His, Leu, Ile, Phe, Arg, or Gln;
Xaa at position 19 is Met, Phe, Ile, Arg, Gly, Ala, or Cys;
Xaa at position 20 is Ile, Cys, Gln, Glu, Arg, Pro, or Ala;
Xaa at position 21 is Asp, Phe, Lys, Arg, Ala, Gly, Glu, Gln, Asn, Thr, Ser or Val;
Xaa at position 22 is Glu, Trp, Pro, Ser, Ala, His, Asp, Asn, Gln, Leu, Val or Gly;
Xaa at position 23 is Ile, Val, Ala, Leu, Gly, Trp, Lys, Phe, Ser, or Arg;
Xaa at position 24 is Ile, Gly, Val, Arg, Ser, Phe, or Leu;
Xaa at position 25 is Thr, His, Gly, Gln, Arg, Pro, or Ala;
Xaa at position 26 is His, Thr, Phe, Gly, Arg, Ala, or Trp;
Xaa at position 27 is Leu, Gly, Arg, Thr, Ser, or Ala;
Xaa at position 28 is Lys, Arg, Leu, Gln, Gly, Pro, Val or Trp;
Xaa at position 29 is Gln, Asn, Leu, Pro, Arg, or Val;
Xaa at position 30 is Pro, His, Thr, Gly, Asp, Gln, Ser, Leu, or Lys;
Xaa at position 31 is Pro, Asp, Gly, Ala, Arg, Leu, or Gln;
Xaa at position 32 is Leu, Val, Arg, Gln, Asn, Gly, Ala, or Glu;
Xaa at position 33 is Pro, Leu, Gln, Ala, Thr, or Glu;
Xaa at position 34 is Leu, Val, Gly, Ser, Lys, Glu, Gln, Thr, Arg, Ala, Phe, Ile or Met;
Xaa at position 35 is Leu, Ala, Gly, Asn, Pro, Gln, or Val;
Xaa at position 36 is Asp, Leu, or Val;
Xaa at position 37 is Phe, Ser, Pro, Trp, or Ile;
Xaa at position 38 is Asn, or Ala;
Xaa at position 40 is Leu, Trp, or Arg;
Xaa at position 41 is Asn, Cys, Ser, Arg, Leu, His, Met, or Pro;
Xaa at position 42 is Gly, Asp, Ser, Cys, Asn, Lys, Thr, Leu, Val, Glu, Phe, Tyr, Ile, Met or Ala;
Xaa at position 43 is Glu, Asn, Tyr, Leu, Phe, Asp, Ala, Cys, Gln, Arg, Thr, Gly or Ser;
Xaa at position 44 is Asp, Ser, Leu, Arg, Lys, Thr, Met, Trp, Glu, Asn, Gln, Ala or Pro;
Xaa at position 45 is Gln, Pro, Phe, Val, Met, Leu, Thr, Lys, Trp, Asp, Asn, Arg, Ser, Ala, Ile, Glu or His;
Xaa at position 46 is Asp, Phe, Ser, Thr, Cys, Glu, Asn, Gln, Lys, His, Ala, Tyr, Ile, Val or Gly;
Xaa at position 47 is Ile, Gly, Val, Ser, Arg, Pro, or His;
Xaa at position 48 is Leu, Ser, Cys, Arg, Ile, His, Phe, Glu, Lys, Thr, Ala, Met, Val or Asn;
Xaa at position 49 is Met, Arg, Ala, Gly, Pro, Asn, His, or Asp;
Xaa at position 50 is Glu, Leu, Thr, Asp, Tyr, Lys, Asn, Ser, Ala, Ile, Val, His, Phe, Met or Gln;
Xaa at position 51 is Asn, Arg, Met, Pro, Ser, Thr, or His;
Xaa at position 52 is Asn, His, Arg, Leu, Gly, Ser, or Thr;
Xaa at position 53 is Leu, Thr, Ala, Gly, Glu, Pro, Lys, Ser, or Met;
Xaa at position 54 is Arg, Asp, Ile, Ser, Val, Thr, Gln, Asn, Lys, His, Ala or Leu;
Xaa at position 55 is Arg, Thr, Val, Ser, Leu, or Gly;
Xaa at position 56 is Pro, Gly, Cys, Ser, Gln, Glu, Arg, His, Thr, Ala, Tyr, Phe, Leu, Val or Lys;
Xaa at position 57 is Asn or Gly;
Xaa at position 58 is Leu, Ser, Asp, Arg, Gln, Val, or Cys;

Xaa at position 59 is Glu, Tyr, His, Leu, Pro, or Arg;
Xaa at position 60 is Ala, Ser, Pro, Tyr, Asn, or Thr;
Xaa at position 61 is Phe, Asn, Glu, Pro, Lys, Arg, or Ser;
Xaa at position 62 is Asn, His, Val, Arg, Pro, Thr, Asp, or Ile;
Xaa at position 63 is Arg, Tyr, Trp, Ser, His, Pro, or Val;
Xaa at position 64 is Ala, Asn, Pro, Ser, or Lys;
Xaa at position 65 is Val, Thr, Pro, His, Leu, Phe, or Ser;
Xaa at position 66 is Lys, Ile, Arg, Val, Asn, Glu, or Ser;
Xaa at position 67 is Ser, Ala, Phe, Val, Gly, Asn, Ile, Pro, or His;
Xaa at position 68 is Leu, Val, Trp, Ser, Ile, Phe, Thr, or His;
Xaa at position 69 is Gln, Ala, Pro, Thr, Glu, Arg, Trp, Gly, or Leu;
Xaa at position 70 is Asn, Leu, Val, Trp, Pro, or Ala;
Xaa at position 71 is Ala, Met, Leu, Pro, Arg, Glu, Thr, Gln, Trp, or Asn;
Xaa at position 72 is Ser, Glu, Met, Ala, His, Asn, Arg, or Asp;
Xaa at position 73 is Ala, Glu, Asp, Leu, Ser, Gly, Thr, or Arg;
Xaa at position 74 is Ile, Met, Thr, Pro, Arg, Gly, Ala;
Xaa at position 75 is Glu, Lys, Gly, Asp, Pro, Trp, Arg, Ser, Gln, or Leu;
Xaa at position 76 is Ser, Val, Ala, Asn, Trp, Glu, Pro, Gly, or Asp;
Xaa at position 77 is Ile, Ser, Arg, Thr, or Leu;
Xaa at position 78 is Leu, Ala, Ser, Glu, Phe, Gly, or Arg;
Xaa at position 79 is Lys, Thr, Asn, Met, Arg, Ile, Gly, or Asp;
Xaa at position 80 is Asn, Trp, Val, Gly, Thr, Leu, Glu, or Arg;
Xaa at position 81 is Leu, Gln, Gly, Ala, Trp, Arg, Val, or Lys;
Xaa at position 82 is Leu, Gln, Lys, Trp, Arg, Asp, Glu, Asn, His, Thr, Ser, Ala, Tyr, Phe, Ile, Met or Val;
Xaa at position 83 is Pro, Ala, Thr, Trp, Arg, or Met;
Xaa at position 84 is Cys, Glu, Gly, Arg, Met, or Val;
Xaa at position 85 is Leu, Asn, Val, or Gln;
Xaa at position 86 is Pro, Cys, Arg, Ala, or Lys;
Xaa at position 87 is Leu, Ser, Trp, or Gly;
Xaa at position 88 is Ala, Lys, Arg, Val, or Trp;
Xaa at position 89 is Thr, Asp, Cys, Leu, Val, Glu, His, Asn, or Ser;
Xaa at position 90 is Ala, Pro, Ser, Thr, Gly, Asp, Ile, or Met;
Xaa at position 91 is Ala, Pro, Ser, Thr, Phe, Leu, Asp, or His;
Xaa at position 92 is Pro, Phe, Arg, Ser, Lys, His, Ala, Gly, Ile or Leu;
Xaa at position 93 is Thr, Asp, Ser, Asn, Pro, Ala, Leu, or Arg;
Xaa at position 94 is Arg, Ile, Ser, Glu, Leu, Val, Gln, Lys, His, Ala, or Pro;
Xaa at position 95 is His, Gln, Pro, Arg, Val, Leu, Gly, Thr, Asn, Lys, Ser, Ala, Trp, Phe, Ile, or Tyr;
Xaa at position 96 is Pro, Lys, Tyr, Gly, Ile, or Thr;
Xaa at position 97 is Ile, Val, Lys, Ala, or Asn;
Xaa at position 98 is His, Ile, Asn, Leu, Asp, Ala, Thr, Glu, Gln, Ser, Phe, Met, Val, Lys, Tyr or Pro;
Xaa at position 99 is Ile, Leu, Arg, Asp, Val, Pro, Gln, Gly, Ser, Phe, or His;
Xaa at position 100 is Lys, Tyr, Leu, His, Arg, Ile, Ser, Gln, or Pro;
Xaa at position 101 is Asp, Pro, Met, Lys, His, Thr, Val, Tyr, Glu, Asn, Ser, Ala, Gly, Ile, Leu, or Gln;
Xaa at position 102 is Gly, Leu, Glu, Lys, Ser, Tyr, or Pro;
Xaa at position 103 is Asp, or Ser;
Xaa at position 104 is Trp, Val, Cys, Tyr, Thr, Met, Pro, Leu, Gln, Lys, Ala, Phe, or Gly;
Xaa at position 105 is Asn, Pro, Ala, Phe, Ser, Trp, Gln, Tyr, Leu, Lys, Ile, Asp, or His;
Xaa at position 106 is Glu, Ser, Ala, Lys, Thr, Ile, Gly, or Pro;
Xaa at position 108 is Arg, Lys, Asp, Leu, Thr, Ile, Gln, His, Ser, Ala or Pro;
Xaa at position 109 is Arg, Thr, Pro, Glu, Tyr, Leu, Ser, or Gly;
Xaa at position 110 is Lys, Ala, Asn, Thr, Leu, Arg, Gln, His, Glu, Ser, or Trp;
Xaa at position 111 is Leu, Ile, Arg, Asp, or Met;
Xaa at position 112 is Thr, Val, Gln, Tyr, Glu, His, Ser, or Phe;
Xaa at position 113 is Phe, Ser, Cys, His, Gly, Trp, Tyr, Asp, Lys, Leu, Ile, Val or Asn;
Xaa at position 114 is Tyr, Cys, His, Ser, Trp, Arg, or Leu;
Xaa at position 115 is Leu, Asn, Val, Pro, Arg, Ala, His, Thr, Trp, or Met;
Xaa at position 116 is Lys, Leu, Pro, Thr, Met, Asp, Val, Glu, Arg, Trp, Ser, Asn, His, Ala, Tyr, Phe, Gln, or Ile;
Xaa at position 117 is Thr, Ser, Asn, Ile, Trp, Lys, or Pro;
Xaa at position 118 is Leu, Ser, Pro, Ala, Glu, Cys, Asp, or Tyr;
Xaa at position 119 is Glu, Ser, Lys, Pro, Leu, Thr, Tyr, or Arg;
Xaa at position 120 is Asn, Ala, Pro, Leu, His, Val, or Gln;
Xaa at position 121 is Ala, Ser, Ile, Asn, Pro, Lys, Asp, or Gly;
Xaa at position 122 is Gln, Ser, Met, Trp, Arg, Phe, Pro, His, Ile, Tyr, or Cys;
Xaa at position 123 is Ala, Met, Glu, His, Ser, Pro, Tyr, or Leu;

wherein from 1 to 14 amino acids are optionally deleted from the N-terminus and/or from 1 to 15 amino acids are optionally deleted from the C-terminus of said human interleukin-3 mutant polypeptide; and wherein from 4 to about 44 of the amino acids designated by Xaa are different from the corresponding amino acids of native (1–133) human interleukin-3; with the proviso that no more than one of the amino acids at positions 63, 82, 87, 98, 112 and 121 are different from the corresponding amino acids in native human interleukin-3; and wherein said modified human interleukin-3 (hIL-3) amino acid sequence has increased activity, relative to native human interleukin-3, in at least one assay selected from the group consisting of: AML cell proliferation, TF-1 cell proliferation and Methylcellulose assay;

$R_2$ is a hematopoietic growth factor; and

L is a linker capable of Linking $R_1$ to $R_2$;

(c) harvesting said cultured stem cells; and (d) transplanting said cultured stem cells into said patient.

18. A method for treatment of a patient having a hematopoietic disorder, comprising the steps of;

(a) removing stem cells from said patient or a donor;

(b) culturing said stem cells with a growth medium comprising a chimera protein having the formula selected from the group consisting of:

$R_1$-L-$R_2$, $R_2$-L-$R_1$, $R_1$-$R_2$, $R_2$-$R_1$, $R_1$-L-$R_1$, $R_1$-$R_1$,

Met-Ala-$R_1$-L-$R_2$, Met-Ala-$R_2$-L-$R_1$, Met-Ala-$R_1$-$R_2$, Met-Ala-$R_2$-$R_1$, Met-$R_1$-L-$R_2$, Met-$R_2$-L-$R_1$, Met-$R_1$-$R_2$, Met-$R_2$-$R_1$,

Ala-$R_1$-L-$R_2$, Ala-$R_2$-L-$R_1$, Ala-$R_1$-$R_2$ and Ala-$R_2$-$R_1$;

wherein $R_1$ is a human interleukin-3 mutant polypeptide of SEQ ID NO:4 wherein
Xaa at position 3 is Ser, Lys, Gly, Asp, Met, Gln, or Arg;
Xaa at position 4 is Asn, His, Leu, Ile, Phe, Arg, or Gln;
Xaa at position 5 is Met, Phe, Ile, Arg, Gly, Ala, or Cys;
Xaa at position 6 is Ile, Cys, Gln, Glu, Arg, Pro, or Ala;
Xaa at position 7 is Asp, Phe, Lys, Arg, Ala, Gly, Glu, Gln, Asn, Thr, Ser or Val;
Xaa at position 8 is Glu, Trp, Pro, Ser, Ala, His, Asp, Asn, Gln, Leu, Val, or Gly;
Xaa at position 9 is Ile, Val, Ala, Leu, Gly, Trp, Lys, Phe, Ser, or Arg;
Xaa at position 10 is Ile, Gly, Val, Arg, Ser, Phe, or Leu;
Xaa at position 11 is Thr, His, Gly, Gln, Arg, Pro, or Ala;
Xaa at position 12 is His, Thr, Phe, Gly, Arg, Ala, or Trp;
Xaa at position 13 is Leu, Gly, Arg, Thr, Ser, or Ala;
Xaa at position 14 is Lys, Arg, Leu, Gln, Gly, Pro, Val or Trp;
Xaa at position 15 is Gln, Asn, Leu, Pro, Arg, or Val;
Xaa at position 16 is Pro, His, Thr, Gly, Asp, Gln, Ser, Leu, or Lys;
Xaa at position 17 is Pro, Asp, Gly, Ala, Arg, Leu, or Gln;
Xaa at position 18 is Leu, Val, Arg, Gln, Asn, Gly, Ala, or Glu;
Xaa at position 19 is Pro, Leu, Gln, Ala, Thr, or Glu;
Xaa at position 20 is Leu, Val, Gly, Ser, Lys, Glu, Gln, Thr, Arg, Ala, Phe, Ile or Met;
Xaa at position 21 is Leu, Ala, Gly, Asn, Pro, Gln, or Val;
Xaa at position 22 is Asp, Leu, or Val;
Xaa at position 23 is Phe, Ser, Pro, Trp, or Ile;
Xaa at position 24 is Asn, or Ala;
Xaa at position 26 is Leu, Trp, or Arg;
Xaa at position 27 is Asn, Cys, Arg, Leu, His, Met, Pro;
Xaa at position 28 is Gly, Asp, Ser, Cys, Ala, Lys, Asn, Thr, Leu, Val, Glu, Phe, Tyr, Ile or Met;
Xaa at position 29 is Glu, Asn, Tyr, Leu, Phe, Asp, Ala, Cys, Gln, Arg, Thr, Gly or Ser;
Xaa at position 30 is Asp, Ser, Leu, Arg, Lys, Thr, Met, Trp, Glu, Asn, Gln, Ala or Pro;
Xaa at position 31 is Gln, Pro, Phe, Val, Met, Leu, Thr, Lys, Asp, Asn, Arg, Ser, Ala, Ile, Glu, His or Trp;
Xaa at position 32 is Asp, Phe, Ser, Thr, Cys, Glu, Asn, Gln, Lys, His, Ala, Tyr, Ile, Val or Gly;
Xaa at position 33 is Ile, Gly, Val, Ser, Arg, Pro, or His;
Xaa at position 34 is Leu, Ser, Cys, Arg, Ile, His, Phe, Glu, Lys, Thr, Ala, Met, Val or Asn;
Xaa at position 35 is Met, Arg, Ala, Gly, Pro, Asn, His, or Asp;
Xaa at position 36 is Glu, Leu, Thr, Asp, Tyr, Lys, Asn, Ser, Ala, Ile, Val, His, Phe, Met or Gln;
Xaa at position 37 is Asn, Arg, Met, Pro, Ser, Thr, or His;
Xaa at position 38 is Asn, His, Arg, Leu, Gly, Ser, or Thr;
Xaa at position 39 is Leu, Thr, Ala, Gly, Glu, Pro, Lys, Ser, or Met;
Xaa at position 40 is Arg, Asp, Ile, Ser, Val, Thr, Gln, Asn, Lys, His, Ala or Leu;
Xaa at position 41 is Arg, Thr, Val, Ser, Leu, or Gly;
Xaa at position 42 is Pro, Gly, Cys, Ser, Gln, Glu, Arg, His, Thr, Ala, Tyr, Phe, Leu, Val or Lys;
Xaa at position 43 is Asn or Gly;
Xaa at position 44 is Leu, Ser, Asp, Arg, Gln, Val, or Cys;
Xaa at position 45 is Glu, Tyr, His, Leu, Pro, or Arg;
Xaa at position 46 is Ala, Ser, Pro, Tyr, Asn, or Thr;
Xaa at position 47 is Phe, Asn, Glu, Pro, Lys, Arg, or Ser;
Xaa at position 48 is Asn, His, Val, Arg, Pro, Thr, Asp, or Ile;
Xaa at position 49 is Arg, Tyr, Trp, Ser, His, Pro, or Val;
Xaa at position 50 is Ala, Asn, Pro, Ser, or Lys;
Xaa at position 51 is Val, Thr, Pro, His, Leu, Phe, or Ser;
Xaa at position 52 is Lys, Ile, Arg, Val, Asn, Glu, or Ser;
Xaa at position 53 is Ser, Ala, Phe, Val, Gly, Asn, Ile, Pro, or His;
Xaa at position 54 is Leu, Val, Trp, Ser, Ile, Phe, Thr, or His;
Xaa at position 55 is Gln, Ala, Pro, Thr, Glu, Arg, Trp, Gly, or Leu;
Xaa at position 56 is Asn, Leu, Val, Trp, Pro, or Ala;
Xaa at position 57 is Ala, Met, Leu, Pro, Arg, Glu, Thr, Gln, Trp, or Asn;
Xaa at position 58 is Ser, Glu, Met, Ala, His, Asn, Arg, or Asp;
Xaa at position 59 is Ala, Glu, Asp, Leu, Ser, Gly, Thr, or Arg;
Xaa at position 60 is Ile, Met, Thr, Pro, Arg, Gly, Ala;
Xaa at position 61 is Glu, Lys, Gly, Asp, Pro, Trp, Arg, Ser, Gln, or Leu;
Xaa at position 62 is Ser, Val, Ala, Asn, Trp, Glu, Pro, Gly, or Asp;
Xaa at position 63 is Ile, Ser, Arg, Thr, or Leu;
Xaa at position 64 is Leu, Ala, Ser, Glu, Phe, Gly, or Arg;
Xaa at position 65 is Lys, Thr, Gly, Asn, Met, Arg, Ile, or Asp;
Xaa at position 66 is Asn, Trp, Val, Gly, Thr, Leu, Glu, or Arg;
Xaa at position 67 is Leu, Gln, Gly, Ala, Trp, Arg, Val, or Lys;
Xaa at position 68 is Leu, Gln, Lys, Trp, Arg, Asp, Glu, Asn, His, Thr, Ser, Ala, Tyr, Phe, Ile, Met or Val;
Xaa at position 69 is Pro, Ala, Thr, Trp, Arg, or Met;
Xaa at position 70 is Cys, Glu, Gly, Arg, Met, or Val;
Xaa at position 71 is Leu, Asn, Val, or Gln;
Xaa at position 72 is Pro, Cys, Arg, Ala, or Lys;
Xaa at position 73 is Leu, Ser, Trp, or Gly;
Xaa at position 74 is Ala, Lys, Arg, Val, or Trp;
Xaa at position 75 is Thr, Asp, Cys, Leu, Val, Glu, His, Asn, or Ser;
Xaa at position 76 is Ala, Pro, Ser, Thr, Gly, Asp, Ile, or Met;
Xaa at position 77 is Ala, Pro, Ser, Thr, Phe, Leu, Asp, or His;
Xaa at position 78 is Pro, Phe, Arg, Ser, Lys, His, Ala, Gly, Ile or Leu;
Xaa at position 79 is Thr, Asp, Ser, Asn, Pro, Ala, Leu, or Arg;
Xaa at position 80 is Arg, Ile, Ser, Glu, Leu, Val, Gln, Lys, His, Ala or Pro;
Xaa at position 81 is His, Gln, Pro, Arg, Val, Leu, Gly, Thr, Asn, Lys, Ser, Ala, Trp, Phe, Ile or Tyr;
Xaa at position 82 is Pro, Lys, Tyr, Gly, Ile, or Thr;
Xaa at position 83 is Ile, Val, Lys, Ala, or Asn;
Xaa at position 84 is His, Ile, Asn, Leu, Asp, Ala, Thr, Glu, Gln, Ser, Phe, Met, Val, Lys, Tyr or Pro;
Xaa at position 85 is Ile, Leu, Arg, Asp, Val, Pro, Gln, Gly, Ser, Phe, or His;
Xaa at position 86 is Lys, Tyr, Leu, His, Arg, Ile, Ser, Gln, Pro;
Xaa at position 87 is Asp, Pro, Met, Lys, His, Thr, Val, Tyr, Glu, Asn, Ser, Ala, Gly, Ile, Leu or Gln;
Xaa at position 88 is Gly, Leu, Glu, Lys, Ser, Tyr, or Pro;
Xaa at position 89 is Asp, or Ser;
Xaa at position 90 is Trp, Val, Cys, Tyr, Thr, Met, Pro, Leu, Gln, Lys, Ala, Phe, or Gly;
Xaa at position 91 is Asn, Pro, Ala, Phe, Ser, Trp, Gln, Tyr, Leu, Lys, Ile, Asp, or His;
Xaa at position 92 is Glu, Ser, Ala, Lys, Thr, Ile, Gly, or Pro;
Xaa at position 94 is Arg, Lys, Asp, Leu, Thr, Ile, Gln, His, Ser, Ala, or Pro;
Xaa at position 95 is Arg, Thr, Pro, Glu, Tyr, Leu, Ser, or Gly;

Xaa at position 96 is Lys, Asn, Thr, Leu, Gln, Arg, His, Glu, Ser, Ala or Trp;
Xaa at position 97 is Leu, Ile, Arg, Asp, or Met;
Xaa at position 98 is Thr, Val, Gln, Tyr, Glu, His, Ser, or Phe;
Xaa at position 99 is Phe, Ser, Cys, His, Gly, Trp, Tyr, Asp, Lys, Leu, Ile, Val or Asn;
Xaa at position 100 is Tyr, Cys, His, Ser, Trp, Arg, or Leu;
Xaa at position 101 is Leu, Asn, Val, Pro, Arg, Ala, His, Thr, Trp, or Met;
Xaa at position 102 is Lys, Leu, Pro, Thr, Met, Asp, Val, Glu, Arg, Trp, Ser, Asn, His, Ala, Tyr, Phe, Gln, or Ile;
Xaa at position 103 is Thr, Ser, Asn, Ile, Trp, Lys, or Pro;
Xaa at position 104 is Leu, Ser, Pro, Ala, Glu, Cys, Asp, or Tyr;
Xaa at position 105 is Glu, Ser, Lys, Pro, Leu, Thr, Tyr, or Arg;
Xaa at position 106 is Asn, Ala, Pro, Leu, His, Val, or Gln;
Xaa at position 107 is Ala, Ser, Ile, Asn, Pro, Lys, Asp, or Gly;
Xaa at position 108 is Gln, Ser, Met, Trp, Arg, Phe, Pro, His, Ile, Tyr, or Cys;
Xaa at position 109 is Ala, Met, Glu, His, Ser, Pro, Tyr, or Leu;
wherein from 4 to about 44 of the amino acids designated by Xaa are different from the corresponding amino acids of native (1–133) human interleukin-3; with the proviso that no more than one of the amino acids at positions 49, 68, 73, 84, 98, and 112 are different from the corresponding amino acids in native human interleukin-3; and wherein said modified human interleukin-3 (hIL-3) amino acid sequence has increased activity, relative to native human interleukin-3, in at least one assay selected from the group consisting of: AML cell proliferation, TF-1 cell proliferation and Methylcellulose assay;

$R_2$ is a hematopoietic growth factor; and

L is a linker capable of Linking $R_1$ to $R_2$;

(c) harvesting said cultured stem cells; and (d) transplanting said cultured stem cells into said patient.

19. A method for treatment of a patient having a hematopoietic disorder, comprising the steps of;

(a) removing stem cells from said patient or a donor;

(b) culturing said stem cells with a growth medium comprising a chimera protein having the formula selected from the group consisting of:

$R_1$-L-$R_2$, $R_2$-L-$R_1$, $R_1$-$R_2$, $R_2$-$R_1$, $R_1$-L-$R_1$, $R_1$-$R_1$,

Met-Ala-$R_1$-L-$R_2$, Met-Ala-$R_2$-L-$R_1$, Met-Ala-$R_1$-$R_2$, Met-Ala-$R_2$-$R_1$, Met-$R_1$-L-$R_2$, Met-$R_2$-L-$R_1$, Met-$R_1$-$R_2$, Met-$R_2$-$R_1$,

Ala-$R_1$-L-$R_2$, Ala-$R_2$-L-$R_1$, Ala-$R_1$-$R_2$ and Ala-$R_2$-$R_1$;

wherein $R_1$ is a human interleukin-3 mutant polypeptide of SEQ ID NO:7 wherein; Xaa at position 18 is Asn or Ile; Xaa at position 19 is Met, Ala or Ile; Xaa at position 20 is Ile, Pro or Leu; Xaa at position 23 is Ile, Ala or Leu; Xaa at position 25 is Thr or His; Xaa at position 29 is Gln, Arg, Val or Leu; Xaa at position 32 is Leu, Ala, Asn or Arg; Xaa at position 34 is Leu or Ser; Xaa at position 37 is Phe, Pro, or Ser; Xaa at position 38 is Asn or Ala; Xaa at position 42 is Gly, Ala, Ser, Asp or Asn; Xaa at position 45 is Gln, Val, or Met; Xaa at position 46 is Asp or Ser; Xaa at position 49 is Met, Ile, Leu or Asp; Xaa at position 50 is Glu or Asp; Xaa at position 51 is Asn Arg or Ser; Xaa at position 55 is Arg, Leu, or Thr; Xaa at position 56 is Pro or Ser; Xaa at position 59 is Glu or Leu; Xaa at position 60 is Ala or Ser; Xaa at position 62 is Asn, Val or Pro; Xaa at position 63 is Arg or His; Xaa at position 65 is Val or Ser; Xaa at position 67 is Ser, Asn, His or Gly; Xaa at position 69 is Gln or Glu; Xaa at position 73 is Ala or Gly; Xaa at position 76 is Ser, Ala or Pro; Xaa at position 79 is Lys, Arg or Ser; Xaa at position 82 is Leu, Glu, Val or Trp; Xaa at position 85 is Leu or Val; Xaa at position 87 is Leu, Ser, Trp; Xaa at position 88 is Ala or Trp; Xaa at position 91 is Ala or Pro; Xaa at position 93 is Pro or Ser; Xaa at position 95 is His or Thr; Xaa at position 98 is His, Ile, or Thr; Xaa at position 100 is Lys or Arg; Xaa at position 101 is Asp, Ala or Met; Xaa at position 105 is Asn or Gln; Xaa at position 109 is Arg, Glu or Leu; Xaa at position 112 is Thr or Gln; Xaa at position 116 is Lys, Val, Trp or Ser; Xaa at position 117 is Thr or Ser; Xaa at position 120 is Asn, Gln, or His; Xaa at position 123 is Ala or Glu; wherein from four to about forty-four of the amino acids designated by Xaa are different from the corresponding amino acids of native human interleukin-3); and wherein said modified human interleukin-3 (hIL-3) amino acid sequence has increased activity, relative to native human interleukin-3, in at least one assay selected from the group consisting of: AML cell proliferation, TF-1 cell proliferation and Methylcellulose assay;

$R_2$ is a hematopoietic growth factor; and

L is a linker capable of Linking $R_1$ to $R_2$;

(c) harvesting said cultured stem cells; and (d) transplanting said cultured stem cells into said patient.

20. A method for treatment of a patient having a hematopoietic disorder, comprising the steps of;

(a) removing stem cells from said patient or a donor;

(b) culturing said stem cells with a growth medium comprising a chimera protein having the formula selected from the group consisting of:

$R_1$-L-$R_2$, $R_2$-L-$R_1$, $R_1$-$R_2$, $R_2$-$R_1$, $R_1$-L-$R_1$, $R_1$-$R_1$,

Met-Ala-$R_1$-L-$R_2$, Met-Ala-$R_2$-L-$R_1$, Met-Ala-$R_1$-$R_2$, Met-Ala-$R_2$-$R_1$, Met-$R_1$-L-$R_2$, Met-$R_2$-L-$R_1$, Met-$R_1$-$R_2$, Met-$R_2$-$R_1$,

Ala-$R_1$-L-$R_2$, Ala-$R_2$-L-$R_1$, Ala-$R_1$-$R_2$ and Ala-$R_2$-$R_1$;

wherein $R_1$ is a human interleukin-3 mutant polypeptide of SEQ ID NO:8 wherein; Xaa at position 4 is Asn or Ile; Xaa at position 5 is Met, Ala or Ile: Xaa at position 6 is Ile, Pro or Leu; Xaa at position 9 is Ile, Ala or Leu; Xaa at position 11 is Thr or His; Xaa at position 15 is Gln, Arg, Val or Leu; Xaa at position 18 is Leu, Ala, Asn or Arg; Xaa at position 20 is Leu or Ser; Xaa at position 23 is Phe, Pro, or Ser; Xaa at position 24 is Asn or Ala; Xaa at position 28 is Gly, Ala, Ser, Asp or Asn; Xaa at position 31 is Gln, Val, or Met; Xaa at position 32 is Asp or Ser; Xaa at position 35 is Met, Ile, Leu or Asp; Xaa at position 36 is Glu or Asp; Xaa at position 37 is Asn, Arg or Ser; Xaa at position 41 is Arg, Leu, or Thr; Xaa at position 42 is Pro or Ser; Xaa at position 45 is Glu or Leu; Xaa at position 46 is Ala or Ser; Xaa at position 48 is Asn, Val or Pro; Xaa at position 49 is Arg or His; Xaa at position 51 is Val or Ser; Xaa at position 53 is Ser, Asn, His or Gly; Xaa at position 55 is Gln or Glu; Xaa at position 59 is Ala or Gly; Xaa at position 62 is Ser, Ala or Pro; Xaa at position 65 is Lys, Arg or Ser; Xaa at position 67 is Leu, Glu, or Val; Xaa at position 68 is Leu, Glu, Val or Trp; Xaa at position 71 is Leu or Val; Xaa at position 73 is Leu, Ser or Trp; Xaa at position 74 is Ala or Trp; Xaa at position 77 is Ala or Pro; Xaa at position 79 is Pro or Ser; Xaa at position 81 is His or Thr; Xaa at position 84 is His, Ile, or Thr; Xaa at position 86 is Lys or Arg; Xaa at position 87 is Asp, Ala or Met; Xaa at position 91 is Asn or Glu; Xaa at position 95 is Arg, Glu, Leu; Xaa at position 98 Thr or Gln; Xaa at position 102 is Lys, Val, Trp or Ser; Xaa at position 103 is Thr or Ser; Xaa at position 106 is Asn, Gln, or His; Xaa at position 109 is Ala or Glu; wherein from four to about forty-four of the amino acids designated by Xaa are different from the corresponding amino acids of native (15–125)human interleukin-3; and wherein said modified human interleukin-3 (hIL-3) amino acid sequence has increased activity, relative to native human interleukin-3, in at least one assay selected from the group consisting of: AML cell proliferation, TF-1 cell proliferation and Methylcellulose assay;

$R_2$ is a h

-continued

```
Asn Cys Ser Asn Met Ile Asp Glu Ile Ile Thr His Leu Lys    SEQ ID NO:13;
Gln Pro Pro Leu Pro Leu Leu Asp Phe Asn Asn Leu Asn Gly
Glu Asp Gln Asp Ile Leu Met Glu Arg Asn Leu Arg Leu Pro
Asn Leu Glu Ser Phe Val Arg Ala Val Lys Asn Leu Glu Asn
Ala Ser Ala Ile Glu Ser Ile Leu Lys Asn Leu Leu Pro Cys
Leu Pro Leu Ala Thr Ala Ala Pro Thr Arg His Pro Ile His
Ile Lys Asp Gly Asp Trp Asn Glu Phe Arg Arg Lys Leu Thr
Phe Tyr Leu Lys Thr Leu Glu Asn Ala Gln Ala Gln Gln

Asn Cys Ser Asn Met Ile Asp Glu Ile Ile Thr His Leu Lys    SEQ ID NO:14;
Gln Pro Pro Leu Pro Leu Leu Asp Phe Asn Asn Leu Asn Gly
Glu Asp Gln Asp Ile Leu Met Glu Arg Asn Leu Arg Thr Pro
Asn Leu Leu Ala Phe Val Arg Ala Val Lys His Leu Glu Asn
Ala Ser Ala Ile Glu Ser Ile Leu Lys Asn Leu Leu Pro Cys
Leu Pro Leu Ala Thr Ala Ala Pro Thr Arg His Pro Ile His
Ile Lys Asp Gly Asp Trp Asn Glu Phe Arg Arg Lys Leu Thr
Phe Tyr Leu Lys Thr Leu Glu Asn Ala Gln Ala Gln Gln

Asn Cys Ser Asn Met Ile Asp Glu Ile Ile Thr His Leu Lys    SEQ ID NO:15;
Gln Pro Pro Leu Pro Leu Leu Asp Phe Asn Asn Leu Asn Gly
Glu Asp Gln Asp Ile Leu Met Glu Asn Asn Leu Arg Arg Pro
Asn Leu Glu Ala Phe Asn Arg Ala Val Lys Ser Leu Gln Asn
Ala Ser Gly Ile Glu Ala Ile Leu Arg Asn Leu Gln Pro Cys
Leu Pro Ser Ala Thr Ala Ala Pro Ser Arg His Pro Ile Ile
Ile Lys Ala Gly Asp Trp Gln Glu Phe Arg Arg Lys Leu Thr
Phe Tyr Leu Lys Thr Leu Glu Asn Ala Gln Ala Gln Gln

Asn Cys Ser Asn Met Ile Asp Glu Ile Ile Thr His Leu Lys    SEQ ID NO:16;
Gln Pro Pro Leu Pro Leu Leu Asp Phe Asn Asn Leu Asn Gly
Glu Asp Gln Asp Ile Leu Met Glu Asn Asn Leu Arg Arg Pro
Asn Leu Glu Ala Phe Asn Arg Ala Val Lys Ser Leu Gln Asn
Ala Ser Gly Ile Glu Ala Ile Leu Arg Asn Leu Val Pro Cys
Leu Pro Ser Ala Thr Ala Ala Pro Ser Arg His Pro Ile Thr
Ile Lys Ala Gly Asp Trp Gln Glu Phe Arg Arg Lys Leu Thr
Phe Tyr Leu Lys Thr Leu Glu Asn Ala Gln Ala Gln Gln

Asn Cys Ser Asn Met Ile Asp Glu Ile Ile Thr His Leu Lys    SEQ ID NO:17;
Gln Pro Pro Leu Pro Leu Leu Asp Phe Asn Asn Leu Asn Gly
Glu Asp Gln Asp Ile Leu Met Glu Asn Asn Leu Arg Arg Pro
Asn Leu Glu Ala Phe Asn Arg Ala Val Lys Ser Leu Gln Asn
Ala Ser Ala Ile Glu Ser Ile Leu Lys Asn Leu Leu Pro Cys
```

-continued

```
Leu Pro Leu Ala Thr Ala Ala Pro Thr Arg His Pro Ile His
Ile Lys Asp Gly Asp Trp Asn Glu Phe Arg Glu Lys Leu Thr
Phe Tyr Leu Val Thr Leu Glu Gln Ala Gln Glu Gln Gln

Asn Cys Ser Asn Met Ile Asp Glu Ile Ile Thr His Leu Lys    SEQ ID NO:18;
Gln Pro Pro Leu Pro Leu Leu Asp Phe Asn Asn Leu Asn Gly
Glu Asp Gln Asp Ile Leu Met Glu Asn Asn Leu Arg Arg Pro
Asn Leu Glu Ala Phe Asn Arg Ala Val Lys Ser Leu Gln Asn
Ala Ser Ala Ile Glu Ser Ile Leu Lys Asn Leu Leu Pro Cys
Leu Pro Leu Ala Thr Ala Ala Pro Thr Arg His Pro Ile His
Ile Lys Asp Gly Asp Trp Asn Glu Phe Arg Glu Lys Leu Thr
Phe Tyr Leu Val Ser Leu Glu His Ala Gln Glu Gln Gln

Asn Cys Ser Asn Met Ile Asp Glu Ile Ile Thr His Leu Lys    SEQ ID NO:19;
Gln Pro Pro Leu Pro Leu Leu Asp Phe Asn Asn Leu Asn Gly
Glu Asp Gln Asp Ile Leu Met Glu Asn Asn Leu Arg Arg Pro
Asn Leu Glu Ala Phe Asn Arg Ala Val Lys Ser Leu Gln Asn
Ala Ser Gly Ile Glu Ala Ile Leu Arg Asn Leu Gln Pro Cys
Leu Pro Ser Ala Thr Ala Ala Pro Ser Arg His Pro Ile Ile
Ile Lys Ala Gly Asp Trp Gln Glu Phe Arg Glu Lys Leu Thr
Phe Tyr Leu Val Thr Leu Glu Gln Ala Gln Glu Gln Gln

Asn Cys Ser Asn Met Ile Asp Glu Ile Ile Thr His Leu Lys    SEQ ID NO:20;
Gln Pro Pro Leu Pro Leu Leu Asp Phe Asn Asn Leu Asn Gly
Glu Asp Gln Asp Ile Leu Met Glu Asn Asn Leu Arg Arg Pro
Asn Leu Glu Ala Phe Asn Arg Ala Val Lys Ser Leu Gln Asn
Ala Ser Gly Ile Glu Ala Ile Leu Arg Asn Leu Val Pro Cys
Leu Pro Ser Ala Thr Ala Ala Pro Ser Arg His Pro Ile Thr
Ile Lys Ala Gly Asp Trp Gln Glu Phe Arg Glu Lys Leu Thr
Phe Tyr Leu Val Thr Leu Glu Gln Ala Gln Glu Gln Gln

Asn Cys Ser Asn Met Ile Asp Glu Ile Ile Thr His Leu Lys    SEQ ID NO:21;
Gln Pro Pro Leu Pro Leu Leu Asp Phe Asn Asn Leu Asn Gly
Glu Asp Gln Asp Ile Leu Met Glu Asn Asn Leu Arg Arg Pro
Asn Leu Glu Ala Phe Asn Arg Ala Val Lys Ser Leu Gln Asn
Ala Ser Gly Ile Glu Ala Ile Leu Arg Asn Leu Val Pro Cys
Leu Pro Ser Ala Thr Ala Ala Pro Ser Arg His Pro Ile Thr
Ile Lys Ala Gly Asp Trp Gln Glu Phe Arg Glu Lys Leu Thr
Phe Tyr Leu Val Ser Leu Glu His Ala Gln Glu Gln Gln

Asn Cys Ser Ile Met Ile Asp Glu Ile Ile His His Leu Lys    SEQ ID NO:22;
Arg Pro Pro Ala Pro Leu Leu Asp Pro Asn Asn Leu Asn Ala
Glu Asp Val Asp Ile Leu Met Glu Arg Asn Leu Arg Leu Pro
```

```
Asn Leu Glu Ser Phe Val Arg Ala Val Lys Asn Leu Glu Asn
Ala Ser Ala Ile Glu Ser Ile Leu Lys Asn Leu Leu Pro Cys
Leu Pro Leu Ala Thr Ala Ala Pro Thr Arg His Pro Ile His
Ile Lys Asp Gly Asp Trp Asn Glu Phe Arg Arg Lys Leu Thr
Phe Tyr Leu Lys Thr Leu Glu Asn Ala Gln Ala Gln Gln

Asn Cys Ser Ile Met Ile Asp Glu Ile Ile His His Leu Lys    SEQ ID NO:23;
Arg Pro Pro Asn Pro Leu Leu Asp Pro Asn Asn Leu Asn Ser
Glu Asp Met Asp Ile Leu Met Glu Arg Asn Leu Arg Thr Pro
Asn Leu Leu Ala Phe Val Arg Ala Val Lys His Leu Glu Asn
Ala Ser Ala Ile Glu Ser Ile Leu Lys Asn Leu Leu Pro Cys
Leu Pro Leu Ala Thr Ala Ala Pro Thr Arg His Pro Ile His
Ile Lys Asp Gly Asp Trp Asn Glu Phe Arg Arg Lys Leu Thr
Phe Tyr Leu Lys Thr Leu Glu Asn Ala Gln Ala Gln Gln

Asn Cys Ser Ile Met Ile Asp Glu Ile Ile His His Leu Lys    SEQ ID NO:24;
Val Pro Pro Ala Pro Leu Leu Asp Ser Asn Asn Leu Asn Ser
Glu Asp Met Asp Ile Leu Met Glu Arg Asn Leu Arg Leu Pro
Asn Leu Leu Ala Phe Val Arg Ala Val Lys Asn Leu Glu Asn
Ala Ser Ala Ile Glu Ser Ile Leu Lys Asn Leu Leu Pro Cys
Leu Pro Leu Ala Thr Ala Ala Pro Thr Arg His Pro Ile His
Ile Lys Asp Gly Asp Trp Asn Glu Phe Arg Arg Lys Leu Thr
Phe Tyr Leu Lys Thr Leu Glu Asn Ala Gln Ala Gln Gln

Met Ala Asn Cys Ser Asn Met Ile Asp Glu Ile Ile Thr His    SEQ ID NO:25;
Leu Lys Gln Pro Pro Leu Pro Leu Leu Asp Phe Asn Asn Leu
Asn Gly Glu Asp Gln Asp Ile Leu Met Glu Asn Asn Leu Arg
Arg Pro Asn Leu Glu Ala Phe Asn Arg Ala Val Lys Ser Leu
Gln Asn Ala Ser Gly Ile Glu Ala Ile Leu Arg Asn Leu Gln
Pro Cys Leu Pro Ser Ala Thr Ala Ala Pro Ser Arg His Pro
Ile Ile Ile Lys Ala Gly Asp Trp Gln Glu Phe Arg Glu Lys
Leu Thr Phe Tyr Leu Val Thr Leu Glu Gln Ala Gln Glu Gln
Gln

Met Ala Asn Cys Ser Asn Met Ile Asp Glu Ile Ile Thr His    SEQ ID NO:26;
Leu Lys Gln Pro Pro Leu Pro Leu Leu Asp Phe Asn Asn Leu
Asn Gly Glu Asp Gln Asp Ile Leu Met Glu Asn Asn Leu Arg
Arg Pro Asn Leu Glu Ala Phe Asn Arg Ala Val Lys Ser Leu
Gln Asn Ala Ser Gly Ile Glu Ala Ile Leu Arg Asn Leu Val
Pro Cys Leu Pro Ser Ala Thr Ala Ala Pro Ser Arg His Pro
Ile Thr Ile Lys Ala Gly Asp Trp Gln Glu Phe Arg Glu Lys
Leu Thr Phe Tyr Leu Val Thr Leu Glu Gln Ala Gln Glu Gln
```

-continued

Gln

```
Met Ala Asn Cys Ser Asn Met Ile Asp Glu Ile Ile Thr His    SEQ ID NO:27;
Leu Lys Gln Pro Pro Leu Pro Leu Leu Asp Phe Asn Asn Leu
Asn Gly Glu Asp Gln Asp Ile Leu Met Glu Asn Asn Leu Arg
Arg Pro Asn Leu Glu Ala Phe Asn Arg Ala Val Lys Ser Leu
Gln Asn Ala Ser Gly Ile Glu Ala Ile Leu Arg Asn Leu Val
Pro Cys Leu Pro Ser Ala Thr Ala Pro Ser Arg His Pro
Ile Thr Ile Lys Ala Gly Asp Trp Gln Glu Phe Arg Glu Lys
Leu Thr Phe Tyr Leu Val Ser Leu Glu His Ala Gln Glu Gln
Gln

Met Ala Asn Cys Ser Ile Met Ile Asp Glu Ile Ile His His    SEQ ID NO:28;
Leu Lys Arg Pro Pro Ala Pro Leu Leu Asp Pro Asn Asn Leu
Asn Ala Glu Asp Val Asp Ile Leu Met Glu Arg Asn Leu Arg
Leu Pro Asn Leu Glu Ser Phe Val Arg Ala Val Lys Asn Leu
Glu Asn Ala Ser Ala Ile Glu Ser Ile Leu Lys Asn Leu Leu
Pro Cys Leu Pro Leu Ala Thr Ala Ala Pro Thr Arg His Pro
Ile His Ile Lys Asp Gly Asp Trp Asn Glu Phe Arg Arg Lys
Leu Thr Phe Tyr Leu Lys Thr Leu Glu Asn Ala Gln Ala Gln
Gln

Met Ala Asn Cys Ser Ile Met Ile Asp Glu Ile Ile His His    SEQ ID NO:29;
Leu Lys Arg Pro Pro Asn Pro Leu Leu Asp Pro Asn Asn Leu
Asn Ser Glu Asp Met Asp Ile Leu Met Glu Arg Asn Leu Arg
Thr Pro Asn Leu Leu Ala Phe Val Arg Ala Val Lys His Leu
Glu Asn Ala Ser Ala Ile Glu Ser Ile Leu Lys Asn Leu Leu
Pro Cys Leu Pro Leu Ala Thr Ala Ala Pro Thr Arg His Pro
Ile His Ile Lys Asp Gly Asp Trp Asn Glu Phe Arg Arg Lys
Leu Thr Phe Tyr Leu Lys Thr Leu Glu Asn Ala Gln Ala Gln
Gln

Met Ala Asn Cys Ser Ile Met Ile Asp Glu Ile Ile His His    SEQ ID NO:30;
Leu Lys Val Pro Pro Ala Pro Leu Leu Asp Ser Asn Asn Leu
Asn Ser Glu Asp Met Asp Ile Leu Met Glu Arg Asn Leu Arg
Leu Pro Asn Leu Leu Ala Phe Val Arg Ala Val Lys Asn Leu
Glu Asn Ala Ser Ala Ile Glu Ser Ile Leu Lys Asn Leu Leu
Pro Cys Leu Pro Leu Ala Thr Ala Ala Pro Thr Arg His Pro
Ile His Ile Lys Asp Gly Asp Trp Asn Glu Phe Arg Arg Lys
Leu Thr Phe Tyr Leu Lys Thr Leu Glu Asn Ala Gln Ala Gln
Gln
```

```
Met Ala Asn Cys Ser Ile Met Ile Asp Glu Ile Ile His His   SEQ ID NO:31;
Leu Lys Arg Pro Pro Ala Pro Leu Leu Asp Pro Asn Asn Leu
Asn Ala Glu Asp Val Asp Ile Leu Met Glu Arg Asn Leu Arg
Leu Pro Asn Leu Glu Ser Phe Val Arg Ala Val Lys Asn Leu
Glu Asn Ala Ser Gly Ile Glu Ala Ile Leu Arg Asn Leu Gln
Pro Cys Leu Pro Ser Ala Thr Ala Ala Pro Ser Arg His Pro
Ile Ile Ile Lys Ala Gly Asp Trp Gln Glu Phe Arg Glu Lys
Leu Thr Phe Tyr Leu Val Thr Leu Glu Gln Ala Gln Glu Gln
Gln

Met Ala Asn Cys Ser Ile Met Ile Asp Glu Ile Ile His His   SEQ ID NO:32;
Leu Lys Arg Pro Pro Asn Pro Leu Leu Asp Pro Asn Asn Leu
Asn Ser Glu Asp Met Asp Ile Leu Met Glu Arg Asn Leu Arg
Thr Pro Asn Leu Leu Ala Phe Val Arg Ala Val Lys His Leu
Glu Asn Ala Ser Gly Ile Glu Ala Ile Leu Arg Asn Leu Gln
Pro Cys Leu Pro Ser Ala Thr Ala Ala Pro Ser Arg His Pro
Ile Ile Ile Lys Ala Gly Asp Trp Gln Glu Phe Arg Glu Lys
Leu Thr Phe Tyr Leu Val Thr Leu Glu Gln Ala Gln Glu Gln
Gln

Met Ala Asn Cys Ser Ile Met Ile Asp Glu Ile Ile His His   SEQ ID NO:33;
Leu Lys Val Pro Pro Ala Pro Leu Leu Asp Ser Asn Asn Leu
Asn Ser Glu Asp Met Asp Ile Leu Met Glu Arg Asn Leu Arg
Leu Pro Asn Leu Leu Ala Phe Val Arg Ala Val Lys Asn Leu
Glu Asn Ala Ser Gly Ile Glu Ala Ile Leu Arg Asn Leu Gln
Pro Cys Leu Pro Ser Ala Thr Ala Ala Pro Ser Arg His Pro
Ile Ile Ile Lys Ala Gly Asp Trp Gln Glu Phe Arg Glu Lys
Leu Thr Phe Tyr Leu Val Thr Leu Glu Gln Ala Gln Glu Gln
Gln

Met Ala Asn Cys Ser Ile Met Ile Asp Glu Ile Ile His His   SEQ ID NO:34;
Leu Lys Arg Pro Pro Ala Pro Leu Leu Asp Pr6 Asn Asn Leu
Asn Ala Glu Asp Val Asp Ile Leu Met Glu Arg Asn Leu Arg
Leu Pro Asn Leu Glu Ser Phe Val Arg Ala Val Lys Asn Leu
Glu Asn Ala Ser Gly Ile Glu Ala Ile Leu Arg Asn Leu Val
Pro Cys Leu Pro Ser Ala Thr Ala Ala Pro Ser Arg His Pro
Ile Thr Ile Lys Ala Gly Asp Trp Gln Glu Phe Arg Glu Lys
Leu Thr Phe Tyr Leu Val Thr Leu Glu Gln Ala Gln Glu Gln
Gln

Met Ala Asn Cys Ser Ile Met Ile Asp Glu Ile Ile His His   SEQ ID NO:35;
Leu Lys Val Pro Pro Ala Pro Leu Leu Asp Ser Asn Asn Leu
```

```
Asn Ser Glu Asp Met Asp Ile Leu Met Glu Arg Asn Leu Arg
Leu Pro Asn Leu Leu Ala Phe Val Arg Ala Val Lys Asn Leu
Glu Asn Ala Ser Gly Ile Glu Ala Ile Leu Arg Asn Leu Val
Pro Cys Leu Pro Ser Ala Thr Ala Ala Pro Ser Arg His Pro
Ile Thr Ile Lys Ala Gly Asp Trp Gln Glu Phe Arg Glu Lys
Leu Thr Phe Tyr Leu Val Thr Leu Glu Gln Ala Gln Glu Gln
Gln

Met Ala Asn Cys Ser Ile Met Ile Asp Glu Ile Ile His His    SEQ ID NO:36;
Leu Lys Arg Pro Pro Asn Pro Leu Leu Asp Pro Asn Asn Leu
Asn Ser Glu Asp Met Asp Ile Leu Met Glu Arg Asn Leu Arg
Thr Pro Asn Leu Leu Ala Phe Val Arg Ala Val Lys His Leu
Glu Asn Ala Ser Gly Ile Glu Ala Ile Leu Arg Asn Leu Val
Pro Cys Leu Pro Ser Ala Thr Ala Ala Pro Ser Arg His Pro
Ile Thr Ile Lys Ala Gly Asp Trp Gln Glu Phe Arg Glu Lys
Leu Thr Phe Tyr Leu Val Ser Leu Glu His Ala Gln Glu Gln
Gln

Met Ala Asn Cys Ser Ile Met Ile Asp Glu Ile Ile His His    SEQ ID NO:37;
Leu Lys Val Pro Pro Ala Pro Leu Leu Asp Ser Asn Asn Leu
Asn Ser Glu Asp Met Asp Ile Leu Met Glu Arg Asn Leu Arg
Leu Pro Asn Leu Leu Ala Phe Val Arg Ala Val Lys Asn Leu
Glu Asn Ala Ser Gly Ile Glu Ala Ile Leu Arg Asn Leu Val
Pro Cys Leu Pro Ser Ala Thr Ala Ala Pro Ser Arg His Pro
Ile Thr Ile Lys Ala Gly Asp Trp Gln Glu Phe Arg Glu Lys
Leu Thr Phe Tyr Leu Val Ser Leu Glu His Ala Gln Glu Gln
Gln

Met Ala Asn Cys Ser Ile Met Ile Asp Glu Ile Ile His His    SEQ ID NO:38;
Leu Lys Arg Pro Pro Asn Pro Leu Leu Asp Pro Asn Asn Leu
Asn Ser Glu Asp Met Asp Ile Leu Met Glu Arg Asn Leu Arg
Thr Pro Asn Leu Leu Ala Phe Val Arg Ala Val Lys His Leu
Glu Asn Ala Ser Gly Ile Glu Ala Ile Leu Arg Asn Leu Val
Pro Cys Leu Pro Ser Ala Thr Ala Ala Pro Ser Arg His Pro
Ile Thr Ile Lys Ala Gly Asp Trp Gln Glu Phe Arg Glu Lys
Leu Thr Phe Tyr Leu Val Thr Leu Glu Gln Ala Gln Glu Gln
Gln

Met Ala Asn Cys Ser Ile Met Ile Asp Glu Ile Ile His His    SEQ ID NO:39;
Leu Lys Arg Pro Pro Ala Pro Leu Leu Asp Pro Asn Asn Leu
Asn Ala Glu Asp Val Asp Ile Leu Met Glu Arg Asn Leu Arg
Leu Pro Asn Leu Glu Ser Phe Val Arg Ala Val Lys Asn Leu
```

```
Glu Asn Ala Ser Gly Ile Glu Ala Ile Leu Arg Asn Leu Val

Pro Cys Leu Pro Ser Ala Thr Ala Ala Pro Ser Arg His Pro

Ile Thr Ile Lys Ala Gly Asp Trp Gln Glu Phe Arg Glu Lys

Leu Thr Phe Tyr Leu Val Ser Leu Glu His Ala Gln Glu Gln

Gln

Met Ala Asn Cys Ser Ile Met Ile Asp Glu Ile Ile His His   SEQ ID NO:40;

Leu Lys Arg Pro Pro Ala Pro Leu Leu Asp Pro Asn Asn Leu

Asn Ala Glu Asp Val Asp Ile Leu Met Asp Arg Asn Leu Arg

Leu Ser Asn Leu Glu Ser Phe Val Arg Ala Val Lys Asn Leu

Glu Asn Ala Ser Gly Ile Glu Ala Ile Leu Arg Asn Leu Gln

Pro Cys Leu Pro Ser Ala Thr Ala Ala Pro Ser Arg His Pro

Ile Ile Ile Lys Ala Gly Asp Trp Gln Glu Phe Arg Glu Lys

Leu Thr Phe Tyr Leu Val Thr Leu Glu Gln Ala Gln Glu Gln

Gln

Met Ala Asn Cys Ser Ile Met Ile Asp Glu Ala Ile His His   SEQ ID NO:41;

Leu Lys Arg Pro Pro Ala Pro Ser Leu Asp Pro Asn Asn Leu

Asn Asp Glu Asp Met Ser Ile Leu Met Glu Arg Asn Leu Arg

Leu Pro Asn Leu Glu Ser Phe Val Arg Ala Val Lys Asn Leu

Glu Asn Ala Ser Gly Ile Glu Ala Ile Leu Arg Asn Leu Gln

Pro Cys Leu Pro Ser Ala Thr Ala Ala Pro Ser Arg His Pro

Ile Ile Ile Lys Ala Gly Asp Trp Gln Glu Phe Arg Glu Lys

Leu Thr Phe Tyr Leu Val Thr Leu Glu Gln Ala Gln Glu Gln

Gln

Met Ala Asn Cys Ser Ile Met Ile Asp Glu Ile Ile His His   SEQ ID NO:42;

Leu Lys Arg Pro Pro Ala Pro Leu Leu Asp Pro Asn Asn Leu

Asn Asp Glu Asp Met Ser Ile Leu Met Glu Arg Asn Leu Arg

Leu Pro Asn Leu Glu Ser Phe Val Arg Ala Val Lys Asn Leu

Glu Asn Ala Ser Gly Ile Glu Ala Ile Leu Arg Asn Leu Gln

Pro Cys Leu Pro Ser Ala Thr Ala Ala Pro Ser Arg His Pro

Ile Ile Ile Lys Ala Gly Asp Trp Gln Glu Phe Arg Glu Lys

Leu Thr Phe Tyr Leu Val Thr Leu Glu Gln Ala Gln Glu Gln

Gln

Met Ala Asn Cys Ser Ile Met Ile Asp Glu Ile Ile His His   SEQ ID NO:43;

Leu Lys Arg Pro Pro Ala Pro Leu Leu Asp Pro Asn Asn Leu

Asn Ala Glu Asp Val Asp Ile Leu Met Asp Arg Asn Leu Arg

Leu Pro Asn Leu Glu Ser Phe Val Arg Ala Val Lys Asn Leu

Glu Asn Ala Ser Gly Ile Glu Ala Ile Leu Arg Asn Leu Gln

Pro Cys Leu Pro Ser Ala Thr Ala Ala Pro Ser Arg His Pro
```

```
Ile Ile Ile Lys Ala Gly Asp Trp Gln Glu Phe Arg Glu Lys
Leu Thr Phe Tyr Leu Val Thr Leu Glu Gln Ala Gln Glu Gln
Gln

Met Ala Asn Cys Ser Ile Met Ile Asp Glu Ile Ile His His    SEQ ID NO:44;
Leu Lys Arg Pro Pro Ala Pro Leu Leu Asp Pro Asn Asn Leu
Asn Asp Glu Asp Val Ser Ile Leu Met Glu Arg Asn Leu Arg
Leu Pro Asn Leu Glu Ser Phe Val Arg Ala Val Lys Asn Leu
Glu Asn Ala Ser Gly Ile Glu Ala Ile Leu Arg Asn Leu Gln
Pro Cys Leu Pro Ser Ala Thr Ala Ala Pro Ser Arg His Pro
Ile Ile Ile Lys Ala Gly Asp Trp Gln Glu Phe Arg Glu Lys
Leu Thr Phe Tyr Leu Val Thr Leu Glu Gln Ala Gln Glu Gln
Gln

Met Ala Asn Cys Ser Ile Met Ile Asp Glu Ile Ile His His    SEQ ID NO:45;
Leu Lys Arg Pro Pro Ala Pro Leu Leu Asp Pro Asn Asn Leu
Asn Asp Glu Asp Met Ser Ile Leu Met Glu Arg Asn Leu Arg
Leu Pro Asn Leu Glu Ser Phe Val Arg Ala Val Lys Asn Leu
Glu Asn Ala Ser Gly Ile Glu Ala Ile Leu Arg Asn Leu Gln
Pro Cys Leu Pro Ser Ala Thr Ala Ala Pro Ser Arg His Pro
Ile Ile Ile Lys Ala Gly Asp Trp Gln Glu Phe Arg Glu Lys
Leu Thr Phe Tyr Leu Val Thr Leu Glu Gln Ala Gln Glu Gln
Gln

Met Ala Tyr Pro Glu Thr Asp Tyr Lys Asp Asp Asp Asp Lys    SEQ ID NO:46;
Asn Cys Ser Ile Met Ile Asp Glu Ile Ile His His Leu Lys
Arg Pro Pro Ala Pro Leu Leu Asp Pro Asn Asn Leu Asn Ala
Glu Asp Val Asp Ile Leu Met Glu Arg Asn Leu Arg Leu Pro
Asn Leu Glu Ser Phe Val Arg Ala Val Lys Asn Leu Glu Asn
Ala Ser Gly Ile Glu Ala Ile Leu Arg Asn Leu Gln Pro Cys
Leu Pro Ser Ala Thr Ala Ala Pro Ser Arg His Pro Ile Ile
Ile Lys Ala Gly Asp Trp Gln Glu Phe Arg Glu Lys Leu Thr
Phe Tyr Leu Val Thr Leu Glu Gln Ala Gln Glu Gln Gln

Met Ala Tyr Pro Glu Thr Asp Tyr Lys Asp Asp Asp Asp Lys    SEQ ID NO:47;
Asn Cys Ser Ile Met Ile Asp Glu Ile Ile His His Leu Lys
Arg Pro Pro Asn Pro Leu Leu Asp Pro Asn Asn Leu Asn Ser
Glu Asp Met Asp Ile Leu Met Glu Arg Asn Leu Arg Thr Pro
Asn Leu Leu Ala Phe Val Arg Ala Val Lys His Leu Glu Asn
Ala Ser Gly Ile Glu Ala Ile Leu Arg Asn Leu Gln Pro Cys
Leu Pro Ser Ala Thr Ala Ala Pro Ser Arg His Pro Ile Ile
Ile Lys Ala Gly Asp Trp Gln Glu Phe Arg Glu Lys Leu Thr
```

```
                         -continued
Phe Tyr Leu Val Thr Leu Glu Gln Ala Gln Glu Gln Gln and Met Ala Asn Cys Ser Ile Met Ile Asp Glu Leu Ile His His    SEQ ID NO:48.

Leu Lys Ile Pro Pro Asn Pro Ser Leu Asp Ser Ala Asn Leu

Asn Ser Glu Asp Val Ser Ile Leu Met Glu Arg Asn Leu Arg

Thr Pro Asn Leu Leu Ala Phe Val Arg Ala Val Lys His Leu

Glu Asn Ala Ser Gly Ile Glu Ala Ile Leu Arg Asn Leu Gln

Pro Cys Leu Pro Ser Ala Thr Ala Ala Pro Ser Arg His Pro

Ile Ile Ile Lys Ala Gly Asp Trp Gln Glu Phe Arg Glu Lys

Leu Thr Phe Tyr Leu Val Thr Leu Glu Gln Ala Gln Glu Gln

Gln.
```

22. The method of claim 17, 18, 19, 20 or 21 wherein is $R_2$ is $R_1$ or a hematopoietic growth factor selected from the group consisting of: GM-CSF, CSF-1, G-CSF, G-CSF Ser[17], c-mpl ligand (TPO), MGDF, M-CSF, erythropoietin (EPO), IL-1, IL-2, IL-3, IL-4, IL-5, IL-6, IL-7, IL-8, IL-9, IL-10, IL-11, IL-12, IL-13, IL-15, IL-16, LIF, flt3 ligand, human growth hormone, B-cell growth factor, B-cell differentiation factor, eosinophil differentiation factor and stem cell factor (SCF).

23. The method of claim 22 wherein is $R_2$ is selected from the group consisting of G-CSF, G-CSF Ser,[17] flt3 ligand and c-mpl ligand.

24. The method of claim 18 wherein said chimera protein is selected from group consisting of: SEQ ID NO:121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 165, 166, 167 and 168.

25. The method of claim 24 wherein said chimera protein is selected from group consisting of: SEQ ID NO:124, SEQ ID NO:133, SEQ ID NO:154 and SEQ ID NO:155.

26. The method of claim 17, 18, 19, 20, 21, 24 or 25 wherein said culture medium further comprises a hematopoietic growth factor selected from the group consisting of: GM-CSF, CSF-1, G-CSF, G-CSF Ser[17], c-mpl ligand (TPO), MGDF, M-CSF, erythropoietin (EPO), IL-1, IL-4, IL-2, IL-5, IL-6, IL-7, IL-8, IL-9, IL-10, IL-11, IL-12, IL-13, IL-15, IL-16, LIF, flt3 ligand, human growth hormone, B-cell growth factor, B-cell differentiation factor, eosinophil differentiation factor and stem cell factor (SCF).

27. The method of claim 22 wherein said culture medium further comprises a hematopoietic growth factor selected from the group consisting of: GM-CSF, CSF-1, G-CSF, G-CSF Ser[17], c-mpl ligand (TPO), MGDF, M-CSF, erythropoietin (EPO), IL-1, IL-4, IL-2, IL-5, IL-6, IL-7, IL-8, IL-9, IL-10, IL-11, IL-12, IL-13, IL-15, IL-16, LIF, flt3 ligand, human growth hormone, B-cell growth factor, B-cell differentiation factor, eosinophil differentiation factor and stem cell factor (SCF).

28. The method of claim 23 wherein said culture medium further comprises a hematopoietic growth factor selected from the group consisting of: GM-CSF, CSF-1, G-CSF, G-CSF Ser[17], c-mpl ligand (TPO), MGDF, M-CSF, erythropoietin (EPO), IL-1, IL-4, IL-2, IL-5, IL-6, IL-7, IL-8, IL-9, IL-10, IL-11, IL-12, IL-13, IL-15, IL-16, LIF, flt3 ligand, human growth hormone, B-cell growth factor, B-cell differentiation factor, eosinophil differentiation factor and stem cell factor (SCF).

29. The method of claim 17 wherein said mutant human interleukin-3 polypeptide has at least three times greater activity than native human interleukin-3, in at least one assay selected from the group consisting of: AML cell proliferation, TF-1 cell proliferation and Methylcellulose assay.

30. The method of claim 23 wherein said mutant human interleukin-3 polypeptide has at least three times greater activity than native human interleukin-3, in at least one assay selected from the group consisting of: AML cell proliferation, TF-1 cell proliferation and Methylcellulose assay.

31. The method of claim 17 further comprising the step of separating the stem cells from a mixed population of cells prior to culturing the stem cells.

32. The method of claim 31 wherein said stem cells are separated from a mixed population of cells based on the stem cells having CD34 surface antigen.

33. A method of enhancing the efficiency of the transduction of cultured stem cells by a heterologous gene, comprising the steps of;

(a) removing stem cells from a patient or donor;

(b) culturing said stem cells with a growth medium comprising a chimera protein having the formula selected from the group consisting of:

$R_1$-L-$R_2$, $R_2$-L-$R_1$, $R_1$-$R_2$, $R_2$-$R_1$, $R_1$-L-$R_1$, $R_1$-$R_1$, Met-Ala-$R_1$-L-$R_2$,

Met-Ala-$R_2$-L-$R_1$, Met-Ala-$R_1$-$R_2$, Met-Ala-$R_2$-$R_1$, Met-$R_1$-L-$R_2$, Met-$R_2$-L-$R_1$, Met-$R_1$-$R_2$, Met-$R_2$-$R_1$, Ala-$R_1$-L-$R_2$,

Ala-$R_2$-L-$R_1$, Ala-$R_1$-$R_2$ and Ala-$R_2$-$R_1$;

wherein $R_1$ is a human interleukin-3 mutant polypeptide of SEQ ID NO:1
wherein
Xaa at position 17 is Ser, Lys, Gly, Asp, Met, Gln, or Arg;
Xaa at position 18 is Asn, His, Leu, Ile, Phe, Arg, or Gln;
Xaa at position 19 is Met, Phe, Ile, Arg, Gly, Ala, or Cys;
Xaa at position 20 is Ile, Cys, Gln, Glu, Arg, Pro, or Ala;
Xaa at position 21 is Asp, Phe, Lys, Arg, Ala, Gly, Glu, Gln, Asn, Thr, Ser or Val;
Xaa at position 22 is Glu, Trp, Pro, Ser, Ala, His, Asp, Asn, Gln, Leu, Val or Gly;

Xaa at position 23 is Ile, Val, Ala, Leu, Gly, Trp, Lys, Phe, Ser, or Arg;
Xaa at position 24 is Ile, Gly, Val, Arg, Ser, Phe, or Leu;
Xaa at position 25 is Thr, His, Gly, Gln, Arg, Pro, or Ala;
Xaa at position 26 is His, Thr, Phe, Gly, Arg, Ala, or Trp;
Xaa at position 27 is Leu, Gly, Arg, Thr, Ser, or Ala;
Xaa at position 28 is Lys, Arg, Leu, Gln, Gly, Pro, Val or Trp;
Xaa at position 29 is Gln, Asn, Leu, Pro, Arg, or Val;
Xaa at position 30 is Pro, His, Thr, Gly, Asp, Gln, Ser, Leu, or Lys;
Xaa at position 31 is Pro, Asp, Gly, Ala, Arg, Leu, or Gln;
Xaa at position 32 is Leu, Val, Arg, Gln, Asn, Gly, Ala, or Glu;
Xaa at position 33 is Pro, Leu, Gln, Ala, Thr, or Glu;
Xaa at position 34 is Leu, Val, Gly, Ser, Lys, Glu, Gln, Thr, Arg, Ala, Phe, Ile or Met;
Xaa at position 35 is Leu, Ala, Gly, Asn, Pro, Gln, or Val;
Xaa at position 36 is Asp, Leu, or Val;
Xaa at position 37 is Phe, Ser, Pro, Trp, or Ile;
Xaa at position 38 is Asn, or Ala;
Xaa at position 40 is Leu, Trp, or Arg;
Xaa at position 41 is Asn, Cys, Arg, Leu, His, Met, or Pro;
Xaa at position 42 is Gly, Asp, Ser, Cys, Asn, Lys, Thr, Leu, Val, Glu, Phe, Tyr, Ile, Met or Ala;
Xaa at position 43 is Glu, Asn, Tyr, Leu, Phe, Asp, Ala, Cys, Gln, Arg, Thr, Gly or Ser;
Xaa at position 44 is Asp, Ser, Leu, Arg, Lys, Thr, Met, Trp, Glu, Asn, Gln, Ala or Pro;
Xaa at position 45 is Gln, Pro, Phe, Val, Met, Leu, Thr, Lys, Trp, Asp, Asn, Arg, Ser, Ala, Ile, Glu or His;
Xaa at position 46 is Asp, Phe, Ser, Thr, Cys, Glu, Asn, Gln, Lys, His, Ala, Tyr, Ile, Val or Gly;
Xaa at position 47 is Ile, Gly, Val, Ser, Arg, Pro, or His;
Xaa at position 48 is Leu, Ser, Cys, Arg, Ile, His, Phe, Glu, Lys, Thr, Ala, Met, Val or Asn;
Xaa at position 49 is Met, Arg, Ala, Gly, Pro, Asn, His, or Asp;
Xaa at position 50 is Glu, Leu, Thr, Asp, Tyr, Lys, Asn, Ser, Ala, Ile, Val, His, Phe, Met or Gln;
Xaa at position 51 is Asn, Arg, Met, Pro, Ser, Thr, or His;
Xaa at position 52 is Asn, His, Arg, Leu, Gly, Ser, or Thr;
Xaa at position 53 is Leu, Thr, Ala, Gly, Glu, Pro, Lys, Ser, or Met;
Xaa at position 54 is Arg, Asp, Ile, Ser, Val, Thr, Gln, Asn, Lys, His, Ala or Leu;
Xaa at position 55 is Arg, Thr, Val, Ser, Leu, or Gly;
Xaa at position 56 is Pro, Gly, Cys, Ser, Gln, Glu, Arg, His, Thr, Ala, Tyr, Phe, Leu, Val or Lys;
Xaa at position 57 is Asn or Gly;
Xaa at position 58 is Leu, Ser, Asp, Arg, Gln, Val, or Cys;
Xaa at position 59 is Glu, Tyr, His, Leu, Pro, or Arg;
Xaa at position 60 is Ala, Ser, Pro, Tyr, Asn, or Thr;
Xaa at position 61 is Phe, Asn, Glu, Pro, Lys, Arg, or Ser;
Xaa at position 62 is Asn, His, Val, Arg, Pro, Thr, Asp, or Ile;
Xaa at position 63 is Arg, Tyr, Trp, Ser, His, Pro, or Val;
Xaa at position 64 is Ala, Asn, Pro, Ser, or Lys;
Xaa at position 65 is Val, Thr, Pro, His, Leu, Phe, or Ser;
Xaa at position 66 is Lys, Ile, Arg, Val, Asn, Glu, or Ser;
Xaa at position 67 is Ser, Ala, Phe, Val, Gly, Asn, Ile, Pro, or His;
Xaa at position 68 is Leu, Val, Trp, Ser, Ile, Phe, Thr, or His;
Xaa at position 69 is Gln, Ala, Pro, Thr, Glu, Arg, Trp, Gly, or Leu;
Xaa at position 70 is Asn, Leu, Val, Trp, Pro, or Ala;
Xaa at position 71 is Ala, Met, Leu, Pro, Arg, Glu, Thr, Gln, Trp, or Asn;
Xaa at position 72 is Ser, Glu, Met, Ala, His, Asn, Arg, or Asp;
Xaa at position 73 is Ala, Glu, Asp, Leu, Ser, Gly, Thr, or Arg;
Xaa at position 74 is Ile, Met, Thr, Pro, Arg, Gly, Ala;
Xaa at position 75 is Glu, Lys, Gly, Asp, Pro, Trp, Arg, Ser, Gln, or Leu;
Xaa at position 76 is Ser, Val, Ala, Asn, Trp, Glu, Pro, Gly, or Asp;
Xaa at position 77 is Ile, Ser, Arg, Thr, or Leu;
Xaa at position 78 is Leu, Ala, Ser, Glu, Phe, Gly, or Arg;
Xaa at position 79 is Lys, Thr, Asn, Met, Arg, Ile, Gly, or Asp;
Xaa at position 80 is Asn, Trp, Val, Gly, Thr, Leu, Glu, or Arg;
Xaa at position 81 is Leu, Gln, Gly, Ala, Trp, Arg, Val, or Lys;
Xaa at position 82 is Leu, Gln, Lys, Trp, Arg, Asp, Glu, Asn, His, Thr, Ser, Ala, Tyr, Phe, Ile, Met or Val;
Xaa at position 83 is Pro, Ala, Thr, Trp, Arg, or Met;
Xaa at position 84 is Cys, Glu, Gly, Arg, Met, or Val;
Xaa at position 85 is Leu, Asn, Val, or Gln;
Xaa at position 86 is Pro, Cys, Arg, Ala, or Lys;
Xaa at position 87 is Leu, Ser, Trp, or Gly;
Xaa at position 88 is Ala, Lys, Arg, Val, or Trp;
Xaa at position 89 is Thr, Asp, Cys, Leu, Val, Glu, His, Asn, or Ser;
Xaa at position 90 is Ala, Pro, Ser, Thr, Gly, Asp, Ile, or Met;
Xaa at position 91 is Ala, Pro, Ser, Thr, Phe, Leu, Asp, or His;
Xaa at position 92 is Pro, Phe, Arg, Ser, Lys, His, Ala, Gly, Ile or Leu;
Xaa at position 93 is Thr, Asp, Ser, Asn, Pro, Ala, Leu, or Arg;
Xaa at position 94 is Arg, Ile, Ser, Glu, Leu, Val, Gln, Lys, His, Ala, or Pro;
Xaa at position 95 is His, Gln, Pro, Arg, Val, Leu, Gly, Thr, Asn, Lys, Ser, Ala, Trp, Phe, Ile, or Tyr;
Xaa at position 96 is Pro, Lys, Tyr, Gly, Ile, or Thr;
Xaa at position 97 is Ile, Val, Lys, Ala, or Asn;
Xaa at position 98 is His, Ile, Asn, Leu, Asp, Ala, Thr, Glu, Gln, Ser, Phe, Met, Val, Lys, Tyr or Pro;
Xaa at position 99 is Ile, Leu, Arg, Asp, Val, Pro, Gln, Gly, Ser, Phe, or His;
Xaa at position 100 is Lys, Tyr, Leu, His, Arg, Ile, Ser, Gln, or Pro;
Xaa at position 101 is Asp, Pro, Met, Lys, His, Thr, Val, Tyr, Glu, Asn, Ser, Ala, Gly, Ile, Leu, or Gln;
Xaa at position 102 is Gly, Leu, Glu, Lys, Ser, Tyr, or Pro;
Xaa at position 103 is Asp, or Ser;
Xaa at position 104 is Trp, Val, Cys, Tyr, Thr, Met, Pro, Leu, Gln, Lys, Ala, Phe, or Gly;
Xaa at position 105 is Asn, Pro, Ala, Phe, Ser, Trp, Gln, Tyr, Leu, Lys, Ile, Asp, or His;
Xaa at position 106 is Glu, Ser, Ala, Lys, Thr, Ile, Gly, or Pro;
Xaa at position 108 is Arg, Lys, Asp, Leu, Thr, Ile, Gln, His, Ser, Ala or Pro;
Xaa at position 109 is Arg, Thr, Pro, Glu, Tyr, Leu, Ser, or Gly;
Xaa at position 110 is Lys, Ala, Asn, Thr, Leu, Arg, Gln, His, Glu, Ser, or Trp;
Xaa at position 111 is Leu, Ile, Arg, Asp, or Met;
Xaa at position 112 is Thr, Val, Gln, Tyr, Glu, His, Ser, or Phe;
Xaa at position 113 is Phe, Ser, Cys, His, Gly, Trp, Tyr, Asp, Lys, Leu, Ile, Val or Asn;
Xaa at position 114 is Tyr, Cys, His, Ser, Trp, Arg, or Leu;
Xaa at position 115 is Leu, Asn, Val, Pro, Arg, Ala, His, Thr, Trp, or Met;

Xaa at position 116 is Lys, Leu, Pro, Thr, Met, Asp, Val, Glu, Arg, Trp, Ser, Asn, His, Ala, Tyr, Phe, Gln, or Ile;
Xaa at position 117 is Thr, Ser, Asn, Ile, Trp, Lys, or Pro;
Xaa at position 118 is Leu, Ser, Pro, Ala, Glu, Cys, Asp, or Tyr;
Xaa at position 119 is Glu, Ser, Lys, Pro, Leu, Thr, Tyr, or Arg;
Xaa at position 120 is Asn, Ala, Pro, Leu, His, Val, or Gln;
Xaa at position 121 is Ala, Ser, le, Asn, Pro, Lys, Asp, or Gly;
Xaa at position 122 is Gln, Ser, Met, Trp, Arg, Phe, Pro, His, Ile, Tyr, or Cys;
Xaa at position 123 is Ala, Met, Glu, His, Ser, Pro, Tyr, or Leu;
wherein from 1 to 14 amino acids are optionally deleted from the N-terminus and/or from 1 to 15 amino acids are optionally deleted from the C-terminus of said human interleukin-3 mutant polypeptide; and wherein from 4 to about 44 of the amino acids designated by Xaa are different from the corresponding amino acids of native (1–133) human interleukin-3; with the proviso that no more than one of the amino acids at positions 63, 82, 87, 98, 112 and 121 are different from the corresponding amino acids in native human interleukin-3; and wherein said modified human interleukin-3 (hIL-3) amino acid sequence has increased activity, relative to native human interleukin-3, in at least one assay selected from the group consisting of: AML cell proliferation, TF-1 cell proliferation and Methylcellulose assay;

$R_2$ is a hematopoietic growth factor; and

L is a linker capable of Linking $R_1$ to $R_2$;

(c) traducing DNA into said cultured cells; and (d) harvesting said transduced cells.

34. A method of enhancing the efficiency of the transduction of cultured stem cells by a heterologous gene, comprising the steps of;

(a) removing stem cells from a patient or a donor;

(b) culturing said stem cells with a growth medium comprising a chimera protein having the formula selected from the group consisting of:

$R_1$-L-$R_2$, $R_2$-L-$R_1$, $R_1$-$R_2$, $R_2$-$R_1$, $R_1$-L-$R_1$, $R_1$-$R_1$,

Met-Ala-$R_1$-L-$R_2$, Met-Ala-$R_2$-L-$R_1$, Met-Ala-$R_1$-$R_2$, Met-Ala-$R_2$-$R_1$, Met-$R_1$-L-$R_2$, Met-$R_2$-L-$R_1$, Met-$R_1$-$R_2$, Met-$R_2$-$R_1$,

Ala-$R_1$-L-R2, Ala-$R_2$-L-$R_1$, Ala-$R_1$-$R_2$ and Ala-$R_2$-$R_1$;

wherein $R_1$ is a human interleukin-3 mutant polypeptide of SEQ ID NO:4 wherein

Xaa at position 3 is Ser, Lys, Gly, Asp, Met, Gln, or Arg;
Xaa at position 4 is Asn, His, Leu, Ile, Phe, Arg, or Gln;
Xaa at position 5 is Met, Phe, Ile, Arg, Gly, Ala, or Cys;
Xaa at position 6 is Ile, Cys, Gln, Glu, Arg, Pro, or Ala;
Xaa at position 7 is Asp, Phe, Lys, Arg, Ala, Gly, Glu, Gln, Asn, Thr, Ser or Val;
Xaa at position 8 is Glu, Trp, Pro, Ser, Ala, His, Asp, Asn, Gln, Leu, Val, or Gly;
Xaa at position 9 is Ile, Val, Ala, Leu, Gly, Trp, Lys, Phe, Ser, or Arg;
Xaa at position 10 is Ile, Gly, Val, Arg, Ser, Phe, or Leu;
Xaa at position 11 is Thr, His, Gly, Gln, Arg, Pro, or Ala;
Xaa at position 12 is His, Thr, Phe, Gly, Arg, Ala, or Trp;
Xaa at position 13 is Leu, Gly, Arg, Thr, Ser, or Ala;
Xaa at position 14 is Lys, Arg, Leu, Gln, Gly, Pro, Val or Trp;
Xaa at position 15 is Gln, Asn, Leu, Pro, Arg, or Val;
Xaa at position 16 is Pro, His, Thr, Gly, Asp, Gln, Ser, Leu, or Lys;
Xaa at position 17 is Pro, Asp, Gly, Ala, Arg, Leu, or Gln;
Xaa at position 18 is Leu, Val, Arg, Gln, Asn, Gly, Ala, or Glu;
Xaa at position 19 is Pro, Leu, Gln, Ala, Thr, or Glu;
Xaa at position 20 is Leu, Val, Gly, Ser, Lys, Glu, Gln, Thr, Arg, Ala, Phe, Ile or Met;
Xaa at position 21 is Leu, Ala, Gly, Asn, Pro, Gln, or Val;
Xaa at position 22 is Asp, Leu, or Val;
Xaa at position 23 is Phe, Ser, Pro, Trp, or Ile;
Xaa at position 24 is Asn, or Ala;
Xaa at position 26 is Leu, Trp, or Arg;
Xaa at position 27 is Asn, Cys, Arg, Leu, His, Met, Pro;
Xaa at position 28 is Gly, Asp, Ser, Cys, Ala, Lys, Asn, Thr, Leu, Val, Glu, Phe, Tyr, Ile or Met;
Xaa at position 29 is Glu, Asn, Tyr, Leu, Phe, Asp, Ala, Cys, Gln, Arg, Thr, Gly or Ser;
Xaa at position 30 is Asp, Ser, Leu, Arg, Lys, Thr, Met, Trp, Glu, Asn, Gln, Ala or Pro;
Xaa at position 31 is Gln, Pro, Phe, Val, Met, Leu, Thr, Lys, Asp, Asn, Arg, Ser, Ala, Ile, Glu, His or Trp;
Xaa at position 32 is Asp, Phe, Ser, Thr, Cys, Glu, Asn, Gln, Lys, His, Ala, Tyr, Ile, Val or Gly;
Xaa at position 33 is Ile, Gly, Val, Ser, Arg, Pro, or His;
Xaa at position 34 is Leu, Ser, Cys, Arg, Ile, His, Phe, Glu, Lys, Thr, Ala, Met, Val or Asn;
Xaa at position 35 is Met, Arg, Ala, Gly, Pro, Asn, His, or Asp;
Xaa at position 36 is Glu, Leu, Thr, Asp, Tyr, Lys, Asn, Ser, Ala, Ile, Val, His, Phe, Met or Gln;
Xaa at position 37 is Asn, Arg, Met, Pro, Ser, Thr, or His;
Xaa at position 38 is Asn, His, Arg, Leu, Gly, Ser, or Thr;
Xaa at position 39 is Leu, Thr, Ala, Gly, Glu, Pro, Lys, Ser, or Met;
Xaa at position 40 is Arg, Asp, Ile, Ser, Val, Thr, Gln, Asn, Lys, His, Ala or Leu;
Xaa at position 41 is Arg, Thr, Val, Ser, Leu, or Gly;
Xaa at position 42 is Pro, Gly, Cys, Ser, Gln, Glu, Arg, His, Thr, Ala, Tyr, Phe, Leu, Val or Lys;
Xaa at position 43 is Asn or Gly;
Xaa at position 44 is Leu, Ser, Asp, Arg, Gln, Val, or Cys;
Xaa at position 45 is Glu, Tyr, His, Leu, Pro, or Arg;
Xaa at position 46 is Ala, Ser, Pro, Tyr, Asn, or Thr;
Xaa at position 47 is Phe, Asn, Glu, Pro, Lys, Arg, or Ser;
Xaa at position 48 is Asn, His, Val, Arg, Pro, Thr, Asp, or Ile;
Xaa at position 49 is Arg, Tyr, Trp, Ser, His, Pro, or Val;
Xaa at position 50 is Ala, Asn, Pro, Ser, or Lys;
Xaa at position 51 is Val, Thr, Pro, His, Leu, Phe, or Ser;
Xaa at position 52 is Lys, Ile, Arg, Val, Asn, Glu, or Ser;
Xaa at position 53 is Ser, Ala, Phe, Val, Gly, Asn, Ile, Pro, or His;
Xaa at position 54 is Leu, Val, Trp, Ser, Ile, Phe, Thr, or His;
Xaa at position 55 is Gln, Ala, Pro, Thr, Glu, Arg, Trp, Gly, or Leu;
Xaa at position 56 is Asn, Leu, Val, Trp, Pro, or Ala;
Xaa at position 57 is Ala, Met, Leu, Pro, Arg, Glu, Thr, Gln, Trp, or Asn;
Xaa at position 58 is Ser, Glu, Met, Ala, His, Asn, Arg, or Asp;
Xaa at position 59 is Ala, Glu, Asp, Leu, Ser, Gly, Thr, or Arg;
Xaa at position 60 is Ile, Met, Thr, Pro, Arg, Gly, Ala;
Xaa at position 61 is Glu, Lys, Gly, Asp, Pro, Trp, Arg, Ser, Gln, or Leu;
Xaa at position 62 is Ser, Val, Ala, Asn, Trp, Glu, Pro, Gly, or Asp;

Xaa at position 63 is Ile, Ser, Arg, Thr, or Leu;
Xaa at position 64 is Leu, Ala, Ser, Glu, Phe, Gly, or Arg;
Xaa at position 65 is Lys, Thr, Gly, Asn, Met, Arg, Ile, or Asp;
Xaa at position 66 is Asn, Trp, Val, Gly, Thr, Leu, Glu, or Arg;
Xaa at position 67 is Leu, Gln, Gly, Ala, Trp, Arg, Val, or Lys;
Xaa at position 68 is Leu, Gln, Lys, Trp, Arg, Asp, Glu, Asn, His, Thr, Ser, Ala, Tyr, Phe, Ile, Met or Val;
Xaa at position 69 is Pro, Ala, Thr, Trp, Arg, or Met;
Xaa at position 70 is Cys, Glu, Gly, Arg, Met, or Val;
Xaa at position 71 is Leu, Asn, Val, or Gln;
Xaa at position 72 is Pro, Cys, Arg, Ala, or Lys;
Xaa at position 73 is Leu, Ser, Trp, or Gly;
Xaa at position 74 is Ala, Lys, Arg, Val, or Trp;
Xaa at position 75 is Thr, Asp, Cys, Leu, Val, Glu, His, Asn, or Ser;
Xaa at position 76 is Ala, Pro, Ser, Thr, Gly, Asp, Ile, or Met;
Xaa at position 77 is Ala, Pro, Ser, Thr, Phe, Leu, Asp, or His;
Xaa at position 78 is Pro, Phe, Arg, Ser, Lys, His, Ala, Gly, Ile or Leu;
Xaa at position 79 is Thr, Asp, Ser, Asn, Pro, Ala, Leu, or Arg;
Xaa at position 80 is Arg, Ile, Ser, Glu, Leu, Val, Gln, Lys, His, Ala or Pro;
Xaa at position 81 is His, Gln, Pro, Arg, Val, Leu, Gly, Thr, Asn, Lys, Ser, Ala, Trp, Phe, Ile or Tyr;
Xaa at position 82 is Pro, Lys, Tyr, Gly, Ile, or Thr;
Xaa at position 83 is Ile, Val, Lys, Ala, or Asn;
Xaa at position 84 is His, Ile, Asn, Leu, Asp, Ala, Thr, Glu, Gln, Ser, Phe, Met, Val, Lys, Tyr or Pro;
Xaa at position 85 is Ile, Leu, Arg, Asp, Val, Pro, Gln, Gly, Ser, Phe, or His;
Xaa at position 86 is Lys, Tyr, Leu, His, Arg, Ile, Ser, Gln, Pro;
Xaa at position 87 is Asp, Pro, Met, Lys, His, Thr, Val, Tyr, Glu, Asn, Ser, Ala, Gly, Ile, Leu or Gln;
Xaa at position 88 is Gly, Leu, Glu, Lys, Ser, Tyr, or Pro;
Xaa at position 89 is Asp, or Ser;
Xaa at position 90 is Trp, Val, Cys, Tyr, Thr, Met, Pro, Leu, Gln, Lys, Ala, Phe, or Gly;
Xaa at position 91 is Asn, Pro, Ala, Phe, Ser, Trp, Gln, Tyr, Leu, Lys, Ile, Asp, or His;
Xaa at position 92 is Glu, Ser, Ala, Lys, Thr, Ile, Gly, or Pro;
Xaa at position 94 is Arg, Lys, Asp, Leu, Thr, Ile, Gln, His, Ser, Ala, or Pro;
Xaa at position 95 is Arg, Thr, Pro, Glu, Tyr, Leu, Ser, or Gly;
Xaa at position 96 is Lys, Asn, Thr, Leu, Gln, Arg, His, Glu, Ser, Ala or Trp;
Xaa at position 97 is Leu, Ile, Arg, Asp, or Met;
Xaa at position 98 is Thr, Val, Gln, Tyr, Glu, His, Ser, or Phe;
Xaa at position 99 is Phe, Ser, Cys, His, Gly, Trp, Tyr, Asp, Lys, Leu, Ile, Val or Asn;
Xaa at position 100 is Tyr, Cys, His, Ser, Trp, Arg, or Leu;
Xaa at position 101 is Leu, Asn, Val, Pro, Arg, Ala, His, Thr, Trp, or Met;
Xaa at position 102 is Lys, Leu, Pro, Thr, Met, Asp, Val, Glu, Arg, Trp, Ser, Asn, His, Ala, Tyr, Phe, Gln, or Ile;
Xaa at position 103 is Thr, Ser, Asn, Ile, Trp, Lys, or Pro;
Xaa at position 104 is Leu, Ser, Pro, Ala, Glu, Cys, Asp, or Tyr;
Xaa at position 105 is Glu, Ser, Lys, Pro, Leu, Thr, Tyr, or Arg;
Xaa at position 106 is Asn, Ala, Pro, Leu, His, Val, or Gln;

Xaa at position 107 is Ala, Ser, Ile, Asn, Pro, Lys, Asp, or Gly;
Xaa at position 108 is Gln, Ser, Met, Trp, Arg, Phe, Pro, His, Ile, Tyr, or Cys;
Xaa at position 109 is Ala, Met, Glu, His, Ser, Pro, Tyr, or Leu;
wherein from 4 to about 44 of the amino acids designated by Xaa are different from the corresponding amino acids of native (1–133) human interleukin-3; with the proviso that no more than one of the amino acids at positions 49, 68, 73, 84, 98 and 107 are different from the corresponding amino acids in native human interleukin-3; and wherein said modified human interleukin-3 (hIL-3) amino acid sequence has increased activity, relative to native human interleukin-3, in at least one assay selected from the group consisting of: AML cell proliferation, TF-1 cell proliferation and Methylcellulose assay;

$R_2$ is a hematopoietic growth factor; and

L is a linker capable of Linking $R_1$ to $R_2$;

(c) transducing DNA into said cultured cells; and (d) harvesting said transduced cells.

35. A method of enhancing the efficiency of the transduction of cultured stem cells by a heterologous gene, comprising the steps of;

(a) removing stem cells from a patient or a donor;

(b) culturing said stem cells with a growth medium comprising a chimera protein having the formula selected from the group consisting of:

$R_1$-L-$R_2$, $R_2$-L-$R_1$, $R_1$-$R_2$, $R_2$-$R_1$, $R_1$-L-$R_1$, $R_1$-$R_1$, Met-Ala-$R_1$-L-$R_2$,

Met-Ala-$R_2$-L-$R_1$, Met-Ala-$R_1$-$R_2$, Met-Ala-$R_2$-$R_1$, Met-$R_1$-L-$R_2$, Met-$R_2$-L-$R_1$, Met-$R_1$-$R_2$, Met-$R_2$-$R_1$, Ala-$R_1$-L-$R_2$,

Ala-$R_2$-L-$R_1$, Ala-$R_1$-$R_2$ and Ala-$R_2$-$R_1$;

wherein $R_1$ is a human interleukin-3 mutant polypeptide of SEQ ID NO:7 wherein; Xaa at position 18 is Asn or Ile; Xaa at position 19 is Met, Ala or Ile; Xaa at position 20 is Ile, Pro or Leu; Xaa at position 23 is Ile, Ala or Leu; Xaa at position 25 is Thr or His; Xaa at position 29 is Gln, Arg, Val or Leu; Xaa at position 32 is Leu, Ala, Asn or Arg; Xaa at position 34 is Leu or Ser; Xaa at position 37 is Phe, Pro, or Ser; Xaa at position 38 is Asn or Ala; Xaa at position 42 is Gly, Ala, Ser, Asp or Asn; Xaa at position 45 is Gln, Val, or Met; Xaa at position 46 is Asp or Ser; Xaa at position 49 is Met, Ile, Leu or Asp; Xaa at position 50 is Glu or Asp; Xaa at position 51 is Asn Arg or Ser; Xaa at position 55 is Arg, Leu, or Thr; Xaa at position 56 is Pro or Ser; Xaa at position 59 is Glu or Leu; Xaa at position 60 is Ala or Ser; Xaa at position 62 is Asn, Val or Pro; Xaa at position 63 is Arg or His; Xaa at position 65 is Val or Ser; Xaa at position 67 is Ser, Asn, His or Gly; Xaa at position 69 is Gln or Glu; Xaa at position 73 is Ala or Gly; Xaa at position 76 is Ser, Ala or Pro; Xaa at position 79 is Lys, Arg or Ser; Xaa at position 82 is Leu, Glu, Val or Trp; Xaa at position 85 is Leu or Val; Xaa at position 87 is Leu, Ser, Trp; Xaa at position 88 is Ala or Trp; Xaa at position 91 is Ala or Pro; Xaa at position 93 is Pro or Ser; Xaa at position 95 is His or Thr; Xaa at position 98 is His, Ile, or Thr; Xaa at position 100 is Lys or Arg; Xaa at position 101 is Asp, Ala or Met; Xaa at position 105 is Asn or Gln; Xaa at position 109 is Arg, Glu or Leu; Xaa at position 112 is Thr or Gln; Xaa at position 116 is Lys, Val, Trp or Ser; Xaa at position 117 is Thr or Ser; Xaa at position 120 is Asn, Gln, or His; Xaa at position 123 is Ala or Glu; wherein from four to about forty-four of the amino acids designated by Xaa are different from the corresponding amino acids of native human interleukin-3; and wherein said modified human interleukin-3 (hIL-3) amino acid sequence has increased activity, relative to native human interleukin-3, in at least one assay selected from the group consisting of: AML cell proliferation, TF-1 cell proliferation and Methylcellulose assay;

$R_2$ is a hematopoietic growth factor; and

L is a linker capable of Linking $R_1$ to $R_2$;

(c) transducing DNA into said cultured cells; and (d) harvesting said transduced cells.

36. A method of enhancing the efficiency of the transduction of cultured stem cells by a heterologous gene, comprising the steps of;

(a) removing stem cells from a patient or a donor;

(b) culturing said stem cells with a growth medium comprising a chimera protein having the formula selected from the group consisting of:

$R_1$-L-$R_2$, $R_2$-L-$R_1$, $R_1$-$R_2$, $R_2$-$R_1$, $R_1$-L-$R_1$, $R_1$-$R_1$, Met-Ala-$R_1$-L-$R_2$,

Met-Ala-$R_2$-L-$R_1$, Met-Ala-$R_1$-$R_2$, Met-Ala-$R_2$-$R_1$, Met-$R_1$-L-$R_2$, Met-$R_2$-L-$R_1$, Met-$R_1$-$R_2$, Met-$R_2$-$R_1$, Ala-$R_1$-L-$R_2$, Ala-$R_2$-L-$R_1$, Ala-$R_1$-$R_2$ and Ala-$R_2$-$R_1$;

wherein $R_1$ is a human interleukin-3 mutant polypeptide of wherein $R_1$ is a human interleukin-3 mutant polypeptide of SEQ ID NO:8 wherein; Xaa at position 4 is Asn or Ile; Xaa at position 5 is Met, Ala or Ile: Xaa at position 6 is Ile, Pro or Leu; Xaa at position 9 is Ile, Ala or Leu; Xaa at position 11 is Thr or His; Xaa at position 15 is Gln, Arg, Val or Leu; Xaa at position 18 is Leu, Ala, Asn or Arg; Xaa at position 20 is Leu or Ser; Xaa at position 23 is Phe, Pro, or Ser; Xaa at position 24 is Asn or Ala; Xaa at position 28 is Gly, Ala, Ser, Asp or Asn; Xaa at position 31 is Gln, Val, or Met; Xaa at position 32 is Asp or Ser; Xaa at position 35 is Met, Ile, Leu or Asp; Xaa at position 36 is Glu or Asp; Xaa at position 37 is Asn, Arg or Ser; Xaa at position 41 is Arg, Leu, or Thr; Xaa at position 42 is Pro or Ser; Xaa at position 45 is Glu or Leu; Xaa at position 46 is Ala or Ser; Xaa at position 48 is Asn, Val or Pro; Xaa at position 49 is Arg or His; Xaa at position 51 is Val or Ser; Xaa at position 53 is Ser, Asn, His or Gly; Xaa at position 55 is Gln or Glu; Xaa at position 59 is Ala or Gly; Xaa at position 62 is Ser, Ala or Pro; Xaa at position 65 is Lys, Arg or Ser; Xaa at position 67 is Leu, Glu, or Val; Xaa at position 68 is Leu, Glu, Val or Trp; Xaa at position 71 is Leu or Val; Xaa at position 73 is Leu, Ser or Trp; Xaa at position 74 is Ala or Trp; Xaa at position 77 is Ala or Pro; Xaa at position 79 is Pro or Ser; Xaa at position 81 is His or Thr; Xaa at position 84 is His, Ile, or Thr; Xaa at position 86 is Lys or Arg; Xaa at position 87 is Asp, Ala or Met; Xaa at position 91 is Asn or Glu; Xaa at position 95 is Arg, Glu, Leu; Xaa at position 98 Thr or Gln; Xaa at position 102 is Lys, Val, Trp or Ser; Xaa at position 103 is Thr or Ser; Xaa at position 106 is Asn, Gln, or His; Xaa at position 109 is Ala or Glu; wherein from four to about forty-four of the amino acids designated by Xaa are different from the corresponding amino acids of native (15–125)human interleukin-3; and wherein said modified human interleukin-3 (hIL-3) amino acid sequence has increased activity, relative to native human interleukin-3, in at least one assay selected from the group consisting of: AML cell proliferation, TF-1 cell proliferation and Methylcellulose assay;

$R_2$ is a hematopoietic growth factor; and

L is a linker capable of Linking $R_1$ to $R_2$;

(c) transducing DNA into said cultured cells; and (d) harvesting said transduced cells.

37. The method according to claim 33 wherein $R_1$ is selected from the group consisting of:

```
Asn Cys Ser Ile Met Ile Asp Glu Ile Ile His His Leu Lys   SEQ ID NO:9;

Arg Pro Pro Ala Pro Leu Leu Asp Pro Asn Asn Leu Asn Ala

Glu Asp Val Asp Ile Leu Met Glu Asn Asn Leu Arg Arg Pro

Asn Leu Glu Ala Phe Asn Arg Ala Val Lys Ser Leu Gln Asn

Ala Ser Ala Ile Glu Ser Ile Leu Lys Asn Leu Leu Pro Cys

Leu Pro Leu Ala Thr Ala Ala Pro Thr Arg His Pro Ile His

Ile Lys Asp Gly Asp Trp Asn Glu Phe Arg Arg Lys Leu Thr

Phe Tyr Leu Lys Thr Leu Glu Asn Ala Gln Ala Gln Gln

Asn Cys Ser Ile Met Ile Asp Glu Ile Ile His His Leu Lys   SEQ ID NO:10;

Arg Pro Pro Asn Pro Leu Leu Asp Pro Asn Asn Leu Asn Ser

Glu Asp Met Asp Ile Leu Met Glu Asn Asn Leu Arg Arg Pro

Asn Leu Glu Ala Phe Asn Arg Ala Val Lys Ser Leu Gln Asn

Ala Ser Ala Ile Glu Ser Ile Leu Lys Asn Leu Leu Pro Cys

Leu Pro Leu Ala Thr Ala Ala Pro Thr Arg His Pro Ile His

Ile Lys Asp Gly Asp Trp Asn Glu Phe Arg Arg Lys Leu Thr

Phe Tyr Leu Lys Thr Leu Glu Asn Ala Gln Ala Gln Gln
```

-continued

```
Asn Cys Ser Ile Met Ile Asp Glu Ile Ile His His Leu Lys    SEQ ID NO:11;
Val Pro Pro Ala Pro Leu Leu Asp Ser Asn Asn Leu Asn Ser
Glu Asp Met Asp Ile Leu Met Glu Asn Asn Leu Arg Arg Pro
Asn Leu Glu Ala Phe Asn Arg Ala Val Lys Ser Leu Gln Asn
Ala Ser Ala Ile Glu Ser Ile Leu Lys Asn Leu Leu Pro Cys
Leu Pro Leu Ala Thr Ala Ala Pro Thr Arg His Pro Ile His
Ile Lys Asp Gly Asp Trp Asn Glu Phe Arg Arg Lys Leu Thr
Phe Tyr Leu Lys Thr Leu Glu Asn Ala Gln Ala Gln Gln

Asn Cys Ser Asn Met Ile Asp Glu Ile Ile Thr His Leu Lys    SEQ ID NO:12;
Gln Pro Pro Leu Pro Leu Leu Asp Phe Asn Asn Leu Asn Gly
Glu Asp Gln Asp Ile Leu Met Glu Arg Asn Leu Arg Leu Pro
Asn Leu Leu Ala Phe Val Arg Ala Val Lys Asn Leu Glu Asn
Ala Ser Ala Ile Glu Ser Ile Leu Lys Asn Leu Leu Pro Cys
Leu Pro Leu Ala Thr Ala Ala Pro Thr Arg His Pro Ile His
Ile Lys Asp Gly Asp Trp Asn Glu Phe Arg Arg Lys Leu Thr
Phe Tyr Leu Lys Thr Leu Glu Asn Ala Gln Ala Gln Gln

Asn Cys Ser Asn Met Ile Asp Glu Ile Ile Thr His Leu Lys    SEQ ID NO:13;
Gln Pro Pro Leu Pro Leu Leu Asp Phe Asn Asn Leu Asn Gly
Glu Asp Gln Asp Ile Leu Met Glu Arg Asn Leu Arg Leu Pro
Asn Leu Glu Ser Phe Val Arg Ala Val Lys Asn Leu Glu Asn
Ala Ser Ala Ile Glu Ser Ile Leu Lys Asn Leu Leu Pro Cys
Leu Pro Leu Ala Thr Ala Ala Pro Thr Arg His Pro Ile His
Ile Lys Asp Gly Asp Trp Asn Glu Phe Arg Arg Lys Leu Thr
Phe Tyr Leu Lys Thr Leu Glu Asn Ala Gln Ala Gln Gln

Asn Cys Ser Asn Met Ile Asp Glu Ile Ile Thr His Leu Lys    SEQ ID NO:14;
Gln Pro Pro Leu Pro Leu Leu Asp Phe Asn Asn Leu Asn Gly
Glu Asp Gln Asp Ile Leu Met Glu Arg Asn Leu Arg Thr Pro
Asn Leu Leu Ala Phe Val Arg Ala Val Lys His Leu Glu Asn
Ala Ser Ala Ile Glu Ser Ile Leu Lys Asn Leu Leu Pro Cys
Leu Pro Leu Ala Thr Ala Ala Pro Thr Arg His Pro Ile His
Ile Lys Asp Gly Asp Trp Asn Glu Phe Arg Arg Lys Leu Thr
Phe Tyr Leu Lys Thr Leu Glu Asn Ala Gln Ala Gln Gln

Asn Cys Ser Asn Met Ile Asp Glu Ile Ile Thr His Leu Lys    SEQ ID NO:15;
Gln Pro Pro Leu Pro Leu Leu Asp Phe Asn Asn Leu Asn Gly
Glu Asp Gln Asp Ile Leu Met Glu Asn Asn Leu Arg Arg Pro
Asn Leu Glu Ala Phe Asn Arg Ala Val Lys Ser Leu Gln Asn
Ala Ser Gly Ile Glu Ala Ile Leu Arg Asn Leu Gln Pro Cys
```

-continued

```
Leu Pro Ser Ala Thr Ala Ala Pro Ser Arg His Pro Ile Ile

Ile Lys Ala Gly Asp Trp Gln Glu Phe Arg Arg Lys Leu Thr

Phe Tyr Leu Lys Thr Leu Glu Asn Ala Gln Ala Gln Gln

Asn Cys Ser Asn Met Ile Asp Glu Ile Ile Thr His Leu Lys    SEQ ID NO:16;

Gln Pro Pro Leu Pro Leu Leu Asp Phe Asn Asn Leu Asn Gly

Glu Asp Gln Asp Ile Leu Met Glu Asn Asn Leu Arg Arg Pro

Asn Leu Glu Ala Phe Asn Arg Ala Val Lys Ser Leu Gln Asn

Ala Ser Gly Ile Glu Ala Ile Leu Arg Asn Leu Val Pro Cys

Leu Pro Ser Ala Thr Ala Ala Pro Ser Arg His Pro Ile Thr

Ile Lys Ala Gly Asp Trp Gln Glu Phe Arg Arg Lys Leu Thr

Phe Tyr Leu Lys Thr Leu Glu Asn Ala Gln Ala Gln Gln

Asn Cys Ser Asn Met Ile Asp Glu Ile Ile Thr His Leu Lys    SEQ ID NO:17;

Gln Pro Pro Leu Pro Leu Leu Asp Phe Asn Asn Leu Asn Gly

Glu Asp Gln Asp Ile Leu Met Glu Asn Asn Leu Arg Arg Pro

Asn Leu Glu Ala Phe Asn Arg Ala Val Lys Ser Leu Gln Asn

Ala Ser Ala Ile Glu Ser Ile Leu Lys Asn Leu Leu Pro Cys

Leu Pro Leu Ala Thr Ala Ala Pro Thr Arg His Pro Ile His

Ile Lys Asp Gly Asp Trp Asn Glu Phe Arg Glu Lys Leu Thr

Phe Tyr Leu Val Thr Leu Glu Gln Ala Gln Glu Gln Gln

Asn Cys Ser Asn Met Ile Asp Glu Ile Ile Thr His Leu Lys    SEQ ID NO:18;

Gln Pro Pro Leu Pro Leu Leu Asp Phe Asn Asn Leu Asn Gly

Glu Asp Gln Asp Ile Leu Met Glu Asn Asn Leu Arg Arg Pro

Asn Leu Glu Ala Phe Asn Arg Ala Val Lys Ser Leu Gln Asn

Ala Ser Ala Ile Glu Ser Ile Leu Lys Asn Leu Leu Pro Cys

Leu Pro Leu Ala Thr Ala Ala Pro Thr Arg His Pro Ile His

Ile Lys Asp Gly Asp Trp Asn Glu Phe Arg Glu Lys Leu Thr

Phe Tyr Leu Val Ser Leu Glu His Ala Gln Glu Gln Gln

Asn Cys Ser Asn Met Ile Asp Glu Ile Ile Thr His Leu Lys    SEQ ID NO:19;

Gln Pro Pro Leu Pro Leu Leu Asp Phe Asn Asn Leu Asn Gly

Glu Asp Gln Asp Ile Leu Met Glu Asn Asn Leu Arg Arg Pro

Asn Leu Glu Ala Phe Asn Arg Ala Val Lys Ser Leu Gln Asn

Ala Ser Gly Ile Glu Ala Ile Leu Arg Asn Leu Gln Pro Cys

Leu Pro Ser Ala Thr Ala Ala Pro Ser Arg His Pro Ile Ile

Ile Lys Ala Gly Asp Trp Gln Glu Phe Arg Glu Lys Leu Thr

Phe Tyr Leu Val Thr Leu Glu Gln Ala Gln Glu Gln Gln

Asn Cys Ser Asn Met Ile Asp Glu Ile Ile Thr His Leu Lys    SEQ ID NO:20;

Gln Pro Pro Leu Pro Leu Leu Asp Phe Asn Asn Leu Asn Gly

Glu Asp Gln Asp Ile Leu Met Glu Asn Asn Leu Arg Arg Pro
```

-continued

```
Asn Leu Glu Ala Phe Asn Arg Ala Val Lys Ser Leu Gln Asn
Ala Ser Gly Ile Glu Ala Ile Leu Arg Asn Leu Val Pro Cys
Leu Pro Ser Ala Thr Ala Ala Pro Ser Arg His Pro Ile Thr
Ile Lys Ala Gly Asp Trp Gln Glu Phe Arg Glu Lys Leu Thr
Phe Tyr Leu Val Thr Leu Glu Gln Ala Gln Glu Gln Gln

Asn Cys Ser Asn Met Ile Asp Glu Ile Ile Thr His Leu Lys    SEQ ID NO:21;
Gln Pro Pro Leu Pro Leu Leu Asp Phe Asn Asn Leu Asn Gly
Glu Asp Gln Asp Ile Leu Met Glu Asn Asn Leu Arg Arg Pro
Asn Leu Glu Ala Phe Asn Arg Ala Val Lys Ser Leu Gln Asn
Ala Ser Gly Ile Glu Ala Ile Leu Arg Asn Leu Val Pro Cys
Leu Pro Ser Ala Thr Ala Ala Pro Ser Arg His Pro Ile Thr
Ile Lys Ala Gly Asp Trp Gln Glu Phe Arg Glu Lys Leu Thr
Phe Tyr Leu Val Ser Leu Glu His Ala Gln Glu Gln Gln

Asn Cys Ser Ile Met Ile Asp Glu Ile Ile His His Leu Lys    SEQ ID NO:22;
Arg Pro Pro Ala Pro Leu Leu Asp Pro Asn Asn Leu Asn Ala
Glu Asp Val Asp Ile Leu Met Glu Arg Asn Leu Arg Leu Pro
Asn Leu Glu Ser Phe Val Arg Ala Val Lys Asn Leu Glu Asn
Ala Ser Ala Ile Glu Ser Ile Leu Lys Asn Leu Leu Pro Cys
Leu Pro Leu Ala Thr Ala Ala Pro Thr Arg His Pro Ile His
Ile Lys Asp Gly Asp Trp Asn Glu Phe Arg Arg Lys Leu Thr
Phe Tyr Leu Lys Thr Leu Glu Asn Ala Gln Ala Gln Gln

Asn Cys Ser Ile Met Ile Asp Glu Ile Ile His His Leu Lys    SEQ ID NO:23;
Arg Pro Pro Asn Pro Leu Leu Asp Pro Asn Asn Leu Asn Ser
Glu Asp Met Asp Ile Leu Met Glu Arg Asn Leu Arg Thr Pro
Asn Leu Leu Ala Phe Val Arg Ala Val Lys His Leu Glu Asn
Ala Ser Ala Ile Glu Ser Ile Leu Lys Asn Leu Leu Pro Cys
Leu Pro Leu Ala Thr Ala Ala Pro Thr Arg His Pro Ile His
Ile Lys Asp Gly Asp Trp Asn Glu Phe Arg Arg Lys Leu Thr
Phe Tyr Leu Lys Thr Leu Glu Asn Ala Gln Ala Gln Gln

Asn Cys Ser Ile Met Ile Asp Glu Ile Ile His His Leu Lys    SEQ ID NO:24;
Val Pro Pro Ala Pro Leu Leu Asp Ser Asn Asn Leu Asn Ser
Glu Asp Met Asp Ile Leu Met Glu Arg Asn Leu Arg Leu Pro
Asn Leu Leu Ala Phe Val Arg Ala Val Lys Asn Leu Glu Asn
Ala Ser Ala Ile Glu Ser Ile Leu Lys Asn Leu Leu Pro Cys
Leu Pro Leu Ala Thr Ala Ala Pro Thr Arg His Pro Ile His
Ile Lys Asp Gly Asp Trp Asn Glu Phe Arg Arg Lys Leu Thr
Phe Tyr Leu Lys Thr Leu Glu Asn Ala Gln Ala Gln Gln
```

-continued

```
Met Ala Asn Cys Ser Asn Met Ile Asp Glu Ile Ile Thr His   SEQ ID NO:25;
Leu Lys Gln Pro Pro Leu Pro Leu Leu Asp Phe Asn Asn Leu
Asn Gly Glu Asp Gln Asp Ile Leu Met Glu Asn Asn Leu Arg
Arg Pro Asn Leu Glu Ala Phe Asn Arg Ala Val Lys Ser Leu
Gln Asn Ala Ser Gly Ile Glu Ala Ile Leu Arg Asn Leu Gln
Pro Cys Leu Pro Ser Ala Thr Ala Ala Pro Ser Arg His Pto
Ile Ile Ile Lys Ala Gly Asp Trp Gln Glu Phe Arg Glu Lys
Leu Thr Phe Tyr Leu Val Thr Leu Glu Gln Ala Gln Glu Gln
Gln

Met Ala Asn Cys Ser Asn Met Ile Asp Glu Ile Ile Thr His   SEQ ID NO:26;
Leu Lys Gln Pro Pro Leu Pro Leu Leu Asp Phe Asn Asn Leu
Asn Gly Glu Asp Gln Asp Ile Leu Met Glu Asn Asn Leu Arg
Arg Pro Asn Leu Glu Ala Phe Asn Arg Ala Val Lys Ser Leu
Gln Asn Ala Ser Gly Ile Glu Ala Ile Leu Arg Asn Leu Val
Pro Cys Leu Pro Ser Ala Thr Ala Ala Pro Ser Arg His Pro
Ile Thr Ile Lys Ala Gly Asp Trp Gln Glu Phe Arg Glu Lys
Leu Thr Phe Tyr Leu Val Thr Leu Glu Gln Ala Gln Glu Gln
Gln

Met Ala Asn Cys Ser Asn Met Ile Asp Glu Ile Ile Thr His   SEQ ID NO:27;
Leu Lys Gln Pro Pro Leu Pro Leu Leu Asp Phe Asn Asn Leu
Asn Gly Glu Asp Gln Asp Ile Leu Met Glu Asn Asn Leu Arg
Arg Pro Asn Leu Glu Ala Phe Asn Arg Ala Val Lys Ser Leu
Gln Asn Ala Ser Gly Ile Glu Ala Ile Leu Arg Asn Leu Val
Pro Cys Leu Pro Ser Ala Thr Ala Ala Pro Ser Arg His Pro
Ile Thr Ile Lys Ala Gly Asp Trp Gln Glu Phe Arg Glu Lys
Leu Thr Phe Tyr Leu Val Ser Leu Glu His Ala Gln Glu Gln
Gln

Met Ala Asn Cys Ser Ile Met Ile Asp Glu Ile Ile His His   SEQ ID NO:28;
Leu Lys Arg Pro Pro Ala Pro Leu Leu Asp Pro Asn Asn Leu
Asn Ala Glu Asp Val Asp Ile Leu Met Glu Arg Asn Leu Arg
Leu Pro Asn Leu Glu Ser Phe Val Arg Ala Val Lys Asn Leu
Glu Asn Ala Ser Ala Ile Glu Ser Ile Leu Lys Asn Leu Leu
Pro Cys Leu Pro Leu Ala Thr Ala Ala Pro Thr Arg His Pro
Ile His Ile Lys Asp Gly Asp Trp Asn Glu Phe Arg Arg Lys
Leu Thr Phe Tyr Leu Lys Thr Leu Glu Asn Ala Gln Ala Gln
Gln

Met Ala Asn Cys Ser Ile Met Ile Asp Glu Ile Ile His His   SEQ ID NO:29;
Leu Lys Arg Pro Pro Asn Pro Leu Leu Asp Pro Asn Asn Leu
```

-continued

```
Asn Ser Glu Asp Met Asp Ile Leu Met Glu Arg Asn Leu Arg
Thr Pro Asn Leu Leu Ala Phe Val Arg Ala Val Lys His Leu
Glu Asn Ala Ser Ala Ile Glu Ser Ile Leu Lys Asn Leu Leu
Pro Cys Leu Pro Leu Ala Thr Ala Ala Pro Thr Arg His Pro
Ile His Ile Lys Asp Gly Asp Trp Asn Glu Phe Arg Arg Lys
Leu Thr Phe Tyr Leu Lys Thr Leu Glu Asn Ala Gln Ala Gln
Gln

Met Ala Asn Cys Ser Ile Met Ile Asp Glu Ile Ile His His   SEQ ID NO:30;
Leu Lys Val Pro Pro Ala Pro Leu Leu Asp Ser Asn Asn Leu
Asn Ser Glu Asp Met Asp Ile Leu Met Glu Arg Asn Leu Arg
Leu Pro Asn Leu Leu Ala Phe Val Arg Ala Val Lys Asn Leu
Glu Asn Ala Ser Ala Ile Glu Ser Ile Leu Lys Asn Leu Leu
Pro Cys Leu Pro Leu Ala Thr Ala Ala Pro Thr Arg His Pro
Ile His Ile Lys Asp Gly Asp Trp Asn Glu Phe Arg Arg Lys
Leu Thr Phe Tyr Leu Lys Thr Leu Glu Asn Ala Gln Ala Gln
Gln

Met Ala Asn Cys Ser Ile Met Ile Asp Glu Ile Ile His His   SEQ ID NO:31;
Leu Lys Arg Pro Pro Ala Pro Leu Leu Asp Pro Asn Asn Leu
Asn Ala Glu Asp Val Asp Ile Leu Met Glu Arg Asn Leu Arg
Leu Pro Asn Leu Glu Ser Phe Val Arg Ala Val Lys Asn Leu
Glu Asn Ala Ser Gly Ile Glu Ala Ile Leu Arg Asn Leu Gln
Pro Cys Leu Pro Ser Ala Thr Ala Ala Pro Ser Arg His Pro
Ile Ile Ile Lys Ala Gly Asp Trp Gln Glu Phe Arg Glu Lys
Leu Thr Phe Tyr Leu Val Thr Leu Glu Gln Ala Gln Glu Gln
Gln

Met Ala Asn Cys Ser Ile Met Ile Asp Glu Ile Ile His His   SEQ ID NO:32;
Leu Lys Arg Pro Pro Asn Pro Leu Leu Asp Pro Asn Asn Leu
Asn Ser Glu Asp Met Asp Ile Leu Met Glu Arg Asn Leu Arg
Thr Pro Asn Leu Leu Ala Phe Val Arg Ala Val Lys His Leu
Glu Asn Ala Ser Gly Ile Glu Ala Ile Leu Arg Asn Leu Gln
Pro Cys Leu Pro Ser Ala Thr Ala Ala Pro Ser Arg His Pro
Ile Ile Ile Lys Ala Gly Asp Trp Gln Glu Phe Arg Glu Lys
Leu Thr Phe Tyr Leu Val Thr Leu Glu Gln Ala Gln Glu Gln
Gln

Met Ala Asn Cys Ser Ile Met Ile Asp Glu Ile Ile His His   SEQ ID NO:33;
Leu Lys Val Pro Pro Ala Pro Leu Leu Asp Ser Asn Asn Leu
Asn Ser Glu Asp Met Asp Ile Leu Met Glu Arg Asn Leu Arg
Leu Pro Asn Leu Leu Ala Phe Val Arg Ala Val Lys Asn Leu
```

```
Glu Asn Ala Ser Gly Ile Glu Ala Ile Leu Arg Asn Leu Gln

Pro Cys Leu Pro Ser Ala Thr Ala Ala Pro Ser Arg His Pro

Ile Ile Ile Lys Ala Gly Asp Trp Gln Glu Phe Arg Glu Lys

Leu Thr Phe Tyr Leu Val Thr Leu Glu Gln Ala Gln Glu Gln

Gln

Met Ala Asn Cys Ser Ile Met Ile Asp Glu Ile Ile His His   SEQ ID NO:34;

Leu Lys Arg Pro Pro Ala Pro Leu Leu Asp Pro Asn Asn Leu

Asn Ala Glu Asp Val Asp Ile Leu Met Glu Arg Asn Leu Arg

Leu Pro Asn Leu Glu Ser Phe Val Arg Ala Val Lys Asn Leu

Glu Asn Ala Ser Gly Ile Glu Ala Ile Leu Arg Asn Leu Val

Pro Cys Leu Pro Ser Ala Thr Ala Ala Pro Ser Arg His Pro

Ile Thr Ile Lys Ala Gly Asp Trp Gln Glu Phe Arg Glu Lys

Leu Thr Phe Tyr Leu Val Thr Leu Glu Gln Ala Gln Glu Gln

Gln

Met Ala Asn Cys Ser Ile Met Ile Asp Glu Ile Ile His His   SEQ ID NO:35;

Leu Lys Val Pro Pro Ala Pro Leu Leu Asp Ser Asn Asn Leu

Asn Ser Glu Asp Met Asp Ile Leu Met Glu Arg Asn Leu Arg

Leu Pro Asn Leu Leu Ala Phe Val Arg Ala Val Lys Asn Leu

Glu Asn Ala Ser Gly Ile Glu Ala Ile Leu Arg Asn Leu Val

Pro Cys Leu Pro Ser Ala Thr Ala Ala Pro Ser Arg His Pro

Ile Thr Ile Lys Ala Gly Asp Trp Gln Glu Phe Arg Glu Lys

Leu Thr Phe Tyr Leu Val Thr Leu Glu Gln Ala Gln Glu Gln

Gln

Met Ala Asn Cys Ser Ile Met Ile Asp Glu Ile Ile His His   SEQ ID NO:36;

Leu Lys Arg Pro Pro Asn Pro Leu Leu Asp Pro Asn Asn Leu

Asn Ser Glu Asp Met Asp Ile Leu Met Glu Arg Asn Leu Arg

Thr Pro Asn Leu Leu Ala Phe Val Arg Ala Val Lys His Leu

Glu Asn Ala Ser Gly Ile Glu Ala Ile Leu Arg Asn Leu Val

Pro Cys Leu Pro Ser Ala Thr Ala Ala Pro Ser Arg His Pro

Ile Thr Ile Lys Ala Gly Asp Trp Gln Glu Phe Arg Glu Lys

Leu Thr Phe Tyr Leu Val Ser Leu Glu His Ala Gln Glu Gln

Gln

Met Ala Asn Cys Ser Ile Met Ile Asp Glu Ile Ile His His   SEQ ID NO:37;

Leu Lys Val Pro Pro Ala Pro Leu Leu Asp Ser Asn Asn Leu

Asn Ser Glu Asp Met Asp Ile Leu Met Glu Arg Asn Leu Arg

Leu Pro Asn Leu Leu Ala Phe Val Arg Ala Val Lys Asn Leu

Glu Asn Ala Ser Gly Ile Glu Ala Ile Leu Arg Asn Leu Val

Pro Cys Leu Pro Ser Ala Thr Ala Ala Pro Ser Arg His Pro
```

-continued

```
Ile Thr Ile Lys Ala Gly Asp Trp Gln Glu Phe Arg Glu Lys
Leu Thr Phe Tyr Leu Val Ser Leu Glu His Ala Gln Glu Gln
Gln

Met Ala Asn Cys Ser Ile Met Ile Asp Glu Ile Ile His His     SEQ ID NO:38;
Leu Lys Arg Pro Pro Asn Pro Leu Leu Asp Pro Asn Asn Leu
Asn Ser Glu Asp Met Asp Ile Leu Met Glu Arg Asn Leu Arg
Thr Pro Asn Leu Leu Ala Phe Val Arg Ala Val Lys His Leu
Glu Asn Ala Ser Gly Ile Glu Ala Ile Leu Arg Asn Leu Val
Pro Cys Leu Pro Ser Ala Thr Ala Ala Pro Ser Arg His Pro
Ile Thr Ile Lys Ala Gly Asp Trp Gln Glu Phe Arg Glu Lys
Leu Thr Phe Tyr Leu Val Thr Leu Glu Gln Ala Gln Glu Gln
Gln

Met Ala Asn Cys Ser Ile Met Ile Asp Glu Ile Ile His His     SEQ ID NO:39;
Leu Lys Arg Pro Pro Ala Pro Leu Leu Asp Pro Asn Asn Leu
Asn Ala Glu Asp Val Asp Ile Leu Met Glu Arg Asn Leu Arg
Leu Pro Asn Leu Glu Ser Phe Val Arg Ala Val Lys Asn Leu
Glu Asn Ala Ser Gly Ile Glu Ala Ile Leu Arg Asn Leu Val
Pro Cys Leu Pro Ser Ala Thr Ala Ala Pro Ser Arg His Pro
Ile Thr Ile Lys Ala Gly Asp Trp Gln Glu Phe Arg Glu Lys
Leu Thr Phe Tyr Leu Val Ser Leu Glu His Ala Gln Glu Gln
Gln

Met Ala Asn Cys Ser Ile Met Ile Asp Glu Ile Ile His His     SEQ ID NO:40;
Leu Lys Arg Pro Pro Ala Pro Leu Leu Asp Pro Asn Asn Leu
Asn Ala Glu Asp Val Asp Ile Leu Met Asp Arg Asn Leu Arg
Leu Ser Asn Leu Glu Ser Phe Val Arg Ala Val Lys Asn Leu
Glu Asn Ala Ser Gly Ile Glu Ala Ile Leu Arg Asn Leu Gln
Pro Cys Leu Pro Ser Ala Thr Ala Ala Pro Ser Arg His Pro
Ile Ile Ile Lys Ala Gly Asp Trp Gln Glu Phe Arg Glu Lys
Leu Thr Phe Tyr Leu Val Thr Leu Glu Gln Ala Gln Glu Gln
Gln

Met Ala Asn Cys Ser Ile Met Ile Asp Glu Ala Ile His His     SEQ ID NO:41;
Leu Lys Arg Pro Pro Ala Pro Ser Leu Asp Pro Asn Asn Leu
Asn Asp Glu Asp Met Ser Ile Leu Met Glu Arg Asn Leu Arg
Leu Pro Asn Leu Glu Ser Phe Val Arg Ala Val Lys Asn Leu
Glu Asn Ala Ser Gly Ile Glu Ala Ile Leu Arg Asn Leu Gln
Pro Cys Leu Pro Ser Ala Thr Ala Ala Pro Ser Arg His Pro
Ile Ile Ile Lys Ala Gly Asp Trp Gln Glu Phe Arg Glu Lys
Leu Thr Phe Tyr Leu Val Thr Leu Glu Gln Ala Gln Glu Gln
```

Gln

```
Met Ala Asn Cys Ser Ile Met Ile Asp Glu Ile Ile His His    SEQ ID NO:42;
Leu Lys Arg Pro Pro Ala Pro Leu Leu Asp Pro Asn Asn Leu
Asn Asp Glu Asp Met Ser Ile Leu Met Glu Arg Asn Leu Arg
Leu Pro Asn Leu Glu Ser Phe Val Arg Ala Val Lys Asn Leu
Glu Asn Ala Ser Gly Ile Glu Ala Ile Leu Arg Asn Leu Gln
Pro Cys Leu Pro Ser Ala Thr Ala Ala Pro Ser Arg His Pro
Ile Ile Ile Lys Ala Gly Asp Trp Gln Glu Phe Arg Glu Lys
Leu Thr Phe Tyr Leu Val Thr Leu Glu Gln Ala Gln Glu Gln
Gln

Met Ala Asn Cys Ser Ile Met Ile Asp Glu Ile Ile His His    SEQ ID NO:43;
Leu Lys Arg Pro Pro Ala Pro Leu Leu Asp Pro Asn Asn Leu
Asn Ala Glu Asp Val Asp Ile Leu Met Asp Arg Asn Leu Arg
Leu Pro Asn Leu Glu Ser Phe Val Arg Ala Val Lys Asn Leu
Glu Asn Ala Ser Gly Ile Glu Ala Ile Leu Arg Asn Leu Gln
Pro Cys Leu Pro Ser Ala Thr Ala Ala Pro Ser Arg His Pro
Ile Ile Ile Lys Ala Gly Asp Trp Gln Glu Phe Arg Glu Lys
Leu Thr Phe Tyr Leu Val Thr Leu Glu Gln Ala Gln Glu Gln
Gln

Met Ala Asn Cys Ser Ile Met Ile Asp Glu Ile Ile His His    SEQ ID NO:44;
Leu Lys Arg Pro Pro Ala Pro Leu Leu Asp Pro Asn Asn Leu
Asn Asp Glu Asp Val Ser Ile Leu Met Glu Arg Asn Leu Arg
Leu Pro Asn Leu Glu Ser Phe Val Arg Ala Val Lys Asn Leu
Glu Asn Ala Ser Gly Ile Glu Ala Ile Leu Arg Asn Leu Gln
Pro Cys Leu Pro Ser Ala Thr Ala Ala Pro Ser Arg His Pro
Ile Ile Ile Lys Ala Gly Asp Trp Gln Glu Phe Arg Glu Lys
Leu Thr Phe Tyr Leu Val Thr Leu Glu Gln Ala Gln Glu Gln
Gln

Met Ala Asn Cys Ser Ile Met Ile Asp Glu Ile Ile His His    SEQ ID NO:45;
Leu Lys Arg Pro Pro Ala Pro Leu Leu Asp Pro Asn Asn Leu
Asn Asp Glu Asp Met Ser Ile Leu Met Glu Arg Asn Leu Arg
Leu Pro Asn Leu Glu Ser Phe Val Arg Ala Val Lys Asn Leu
Glu Asn Ala Ser Gly Ile Glu Ala Ile Leu Arg Asn Leu Gln
Pro Cys Leu Pro Ser Ala Thr Ala Ala Pro Ser Arg His Pro
Ile Ile Ile Lys Ala Gly Asp Trp Gln Glu Phe Arg Glu Lys
Leu Thr Phe Tyr Leu Val Thr Leu Glu Gln Ala Gln Glu Gln
Gln

Met Ala Tyr Pro Glu Thr Asp Tyr Lys Asp Asp Asp Lys    SEQ ID NO:46;
```

-continued

Asn Cys Ser Ile Met Ile Asp Glu Ile Ile His His Leu Lys

Arg Pro Pro Ala Pro Leu Leu Asp Pro Asn Asn Leu Asn Ala

Glu Asp Val Asp Ile Leu Met Glu Arg Asn Leu Arg Leu Pro

Asn Leu Glu Ser Phe Val Arg Ala Val Lys Asn Leu Glu Asn

Ala Ser Gly Ile Glu Ala Ile Leu Arg Asn Leu Gln Pro Cys

Leu Pro Ser Ala Thr Ala Ala Pro Ser Arg His Pro Ile Ile

Ile Lys Ala Gly Asp Trp Gln Glu Phe Arg Glu Lys Leu Thr

Phe Tyr Leu Val Thr Leu Glu Gln Ala Gln Glu Gln Gln

Met Ala Tyr Pro Glu Thr Asp Tyr Lys Asp Asp Asp Lys   SEQ ID NO:47;

Asn Cys Ser Ile Met Ile Asp Glu Ile Ile His His Leu Lys

Arg Pro Pro Asn Pro Leu Leu Asp Pro Asn Asn Leu Asn Ser

Glu Asp Met Asp Ile Leu Met Glu Arg Asn Leu Arg Thr Pro

Asn Leu Leu Ala Phe Val Arg Ala Val Lys His Leu Glu Asn

Ala Ser Gly Ile Glu Ala Ile Leu Arg Asn Leu Gln Pro Cys

Leu Pro Ser Ala Thr Ala Ala Pro Ser Arg His Pro Ile Ile

Ile Lys Ala Gly Asp Trp Gln Glu Phe Arg Glu Lys Leu Thr

Phe Tyr Leu Val Thr Leu Glu Gln Ala Gln Glu Gln Gln and

Met Ala Asn Cys Ser Ile Met Ile Asp Glu Leu Ile His His   SEQ ID NO:48.

Leu Lys Ile Pro Pro Asn Pro Ser Leu Asp Ser Ala Asn Leu

Asn Ser Glu Asp Val Ser Ile Leu Met Glu Arg Asn Leu Arg

Thr Pro Asn Leu Leu Ala Phe Val Arg Ala Val Lys His Leu

Glu Asn Ala Ser Gly Ile Glu Ala Ile Leu Arg Asn Leu Gln

Pro Cys Leu Pro Ser Ala Thr Ala Ala Pro Ser Arg His Pro

Ile Ile Ile Lys Ala Gly Asp Trp Gln Glu Phe Arg Glu Lys

Leu Thr Phe Tyr Leu Val Thr Leu Glu Gln Ala Gln Glu Gln

Gln

38. The method of claim 33, 34, 35, 36 or 37 wherein is R$_2$ is R$_1$ or a hematopoietic growth factor selected from the group consisting of: GM-CSF, CSF-1, G-CSF, G-CSF Ser$^{17}$, c-mpl ligand (TPO), MGDF, M-CSF, erythropoietin (EPO), IL-1, IL-2, IL-3, IL-4, IL-5, IL-6, IL-7, IL-8, IL-9, IL-10, IL-11, IL-12, IL-13, IL-15, IL-16, LIF, flt3 ligand, human growth hormone, B-cell growth factor, B-cell differentiation factor, eosinophil differentiation factor and stem cell factor (SCF).

39. The method of claim 38 wherein is R$_2$ is selected from the group consisting of G-CSF, G-CSF Ser,$^{17}$ flt3 ligand or c-mpl ligand.

40. The method of claim 34 wherein said chimera protein is selected from group consisting of: SEQ ID NO:121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 165, 166, 167 and 168.

41. The method of claim 40 wherein said chimera protein is selected from group consisting of: SEQ ID NO:124, SEQ ID NO:133, SEQ ID NO:154 and SEQ ID NO:155.

42. The method of claim 33, 34, 35, 36 or 37 wherein said culture medium further comprises a hematopoietic growth factor selected from the group consisting of: GM-CSF, CSF-1, G-CSF, G-CSF Ser$^{17}$, c-mpl ligand (TPO), MGDF, M-CSF, erythropoietin (EPO), IL-1, IL-4, IL-2, IL-5, IL-6, IL-7, IL-8, IL-9, IL-10, IL-11, IL-12, IL-13, IL-15, IL-16, LIF, flt3 ligand, human growth hormone, B-cell growth factor, B-cell differentiation factor, eosinophil differentiation factor and stem cell factor (SCF).

43. The method of claim 38 wherein said culture medium further comprises a hematopoietic growth factor selected from the group consisting of: GM-CSF, CSF-1, G-CSF, G-CSF Ser$^{17}$, c-mpl ligand (TPO), MGDF, M-CSF, eryth ropoietin (EPO), IL-1, IL-4, IL-2, IL-5, IL-6, IL-7, IL-8, IL-9, IL-10, IL-11, IL-12, IL-13, IL-15, IL-16, LIF, flt3 ligand, human growth hormone, B-cell growth factor, B-cell differentiation factor, eosinophil differentiation factor and stem cell factor (SCF).

44. The method of claim 39 wherein said culture medium further comprises a hematopoietic growth factor selected from the group consisting of: GM-CSF, CSF-1, G-CSF, G-CSF Ser$^{17}$, c-mpl ligand (TPO), MGDF, M-CSF, erythropoietin (EPO), IL-1, IL-4, IL-2, IL-5, IL-6, IL-7, IL-8, IL-9, IL-10, IL-11, IL-12, IL-13, IL-15, IL-16, LIF, flt3 ligand, human growth hormone, B-cell growth factor, B-cell differentiation factor, eosinophil differentiation factor and stem cell factor (SCF).

45. The method of claim 33 wherein said mutant human interleukin-3 polypeptide has at least three times greater activity than native human interleukin-3, in at least one assay selected from the group consisting of: AML cell proliferation, TF-1 cell proliferation and Methylcellulose assay.

46. The method of claim 38 wherein said mutant human interleukin-3 polypeptide has at least three times greater activity than native human interleukin-3, in at least one assay selected from the group consisting of: AML cell proliferation, TF-1 cell proliferation and Methylcellulose assay.

47. The method of claim 33 further comprising the step of separating the stem cells from a mixed population of cells prior to culturing the stem cells.

48. The method of claim 47 wherein said stem cells are separated from a mixed population of cells based on the stem cells having CD34 surface antigen.

* * * * *